(12) United States Patent
Westh et al.

(10) Patent No.: US 10,676,769 B2
(45) Date of Patent: Jun. 9, 2020

(54) CELLOBIOHYDROLASE VARIANTS AND POLYNUCLEOTIDES ENCODING SAME

(71) Applicant: Novozymes A/S, Bagsvaerd (DK)

(72) Inventors: Peter Westh, Copenhagen (DK); Kim Borch, Birkerød (DK); Trine Soerensen, Copenhagen (DK); Michael Windahl, Stenløse (DK); Brett McBrayer, Sacramento, CA (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/509,659

(22) PCT Filed: Sep. 8, 2015

(86) PCT No.: PCT/US2015/048850
§ 371 (c)(1),
(2) Date: Mar. 8, 2017

(87) PCT Pub. No.: WO2016/040265
PCT Pub. Date: Mar. 17, 2016

(65) Prior Publication Data
US 2017/0292136 A1 Oct. 12, 2017

Related U.S. Application Data

(60) Provisional application No. 62/047,296, filed on Sep. 8, 2014.

(51) Int. Cl.
| | | |
|---|---|---|
| *C12P 19/14* | (2006.01) | |
| *C12N 9/42* | (2006.01) | |
| *C12N 9/24* | (2006.01) | |
| *C12N 15/82* | (2006.01) | |
| *C12P 7/14* | (2006.01) | |
| *C12P 19/02* | (2006.01) | |
| *C12P 19/12* | (2006.01) | |

(52) U.S. Cl.
CPC ............ *C12P 19/14* (2013.01); *C12N 9/2402* (2013.01); *C12N 9/2437* (2013.01); *C12N 15/8257* (2013.01); *C12P 7/14* (2013.01); *C12P 19/02* (2013.01); *C12P 19/12* (2013.01); *C12Y 302/01091* (2013.01); *C07K 2319/00* (2013.01); *C12P 2201/00* (2013.01); *C12P 2203/00* (2013.01)

(58) Field of Classification Search
CPC ............................... C12P 19/14; C12N 9/2437
USPC .......................................... 435/99, 106, 209
See application file for complete search history.

(56) References Cited

U.S. PATENT DOCUMENTS

| | | | |
|---|---|---|---|
| 7,375,197 B2 | 5/2008 | Adney et al. | |
| 8,637,293 B2 | 1/2014 | Adney et al. | |
| 2009/0162916 A1 | 6/2009 | Adney et al. | |
| 2013/0052694 A1* | 2/2013 | Montalibet | C12P 19/14 435/99 |

FOREIGN PATENT DOCUMENTS

| | | |
|---|---|---|
| WO | 2004016760 A2 | 2/2004 |
| WO | 2005001065 A2 | 1/2005 |
| WO | 2005028636 A2 | 3/2005 |
| WO | 2005030926 A2 | 4/2005 |
| WO | 2007118935 A1 | 10/2007 |
| WO | 2010060056 A2 | 5/2010 |
| WO | 2010096931 A1 | 9/2010 |
| WO | 2011050037 A1 | 4/2011 |
| WO | 2011097713 A1 | 8/2011 |
| WO | 2011098551 A2 | 8/2011 |
| WO | 2012048171 A2 | 4/2012 |
| WO | 2012051055 A2 | 4/2012 |
| WO | 2012104239 A2 | 9/2012 |
| WO | 2012135719 A1 | 10/2012 |
| WO | 2013029176 A1 | 3/2013 |
| WO | 2013091577 A1 | 6/2013 |
| WO | 2013138357 A1 | 9/2013 |
| WO | 2014064115 A1 | 5/2014 |
| WO | 2014093282 A1 | 6/2014 |
| WO | 2014093294 A1 | 6/2014 |
| WO | 2014138672 A1 | 9/2014 |

OTHER PUBLICATIONS

Le Costaoueca, 2013, Bioresource Technology, 143, 196-203.
Linder, 1995, Protein Science 4, 1056-1064.
Linder, 1999, FEBS Let 447, 13-16.
Nimols, 2007, Prot Engg esign Selection, 20(4), 179-187.
Pakarinen, 2014, Biotechnol Biofuels 7(27), 1-11.
Takashima, 2007, FEBS Lett 581, 5891-5896.
Varnai, 2013, Biotechnology for Biofuels 6(30), 1-11.
Voutilainen, 2013, Appl Microbiol Biotechnol, 98, 2991-3001.

* cited by examiner

*Primary Examiner* — Tekchand Saidha
(74) *Attorney, Agent, or Firm* — Kelly Reynolds; Elias Lambiris

(57) ABSTRACT

The present invention relates to cellobiohydrolase variants. The present invention also relates to polynucleotides encoding the variants; nucleic acid constructs, vectors, and host cells comprising the polynucleotides; and methods of using the variants.

29 Claims, 15 Drawing Sheets
Specification includes a Sequence Listing.

US 10,676,769 B2

CELLOBIOHYDROLASE VARIANTS AND POLYNUCLEOTIDES ENCODING SAME

CROSS-REFERENCE TO RELATED APPLICATIONS

This application is a 35 U.S.C. § 371 national application of PCT/US2015/048850 filed Sep. 8, 2015, which claims priority or the benefit under 35 U.S.C. § 119 from U.S. Provisional Patent Application Ser. No. 62/047,296 filed Sep. 8, 2014, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to cellobiohydrolase variants, polynucleotides encoding the variants, and methods of producing and using the variants.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars can easily be fermented by yeast into ethanol.

WO 2011/050037 discloses *Thielavia terrestris* cellobiohydrolase variants with improved thermostability. WO 2011/050037 discloses *Aspergillus fumigatus* cellobiohydrolase variants with improved thermostability. WO 2005/028636 discloses variants of *Hypocrea jecorina* Cel7A cellobiohydrolase I. WO 2005/001065 discloses variants of *Humicola grisea* Cel7A cellobiohydrolase I, *Hypocrea jecorina* cellobiohydrolase I, and *Scytalidium thermophilium* cellobiohydrolase I. WO 2004/016760 discloses variants of *Hypocrea jecorina* Cel7A cellobiohydrolase I. U.S. Pat. No. 7,375,197 discloses variants of *Trichoderma reesei* cellobiohydrolase I.

Hybrid polypeptides comprising a cellobiohydrolase catalytic domain and a carbohydrate binding module are described in e.g., WO 2010/060056, WO 2013/091577, and WO 2014/138672.

There is a need in the art for cellobiohydrolase variants with improved properties to increase the efficiency of the saccharification of lignocellulosic feedstocks.

The present invention provides cellobiohydrolase variants with increased specific performance, polynucleotides encoding the variants, and methods of producing and using the variants.

SUMMARY OF THE INVENTION

The present invention relates to cellobiohydrolase variants, comprising deletions at two or more consecutive positions of the B2-loop, wherein the variants have cellobiohydrolase activity.

The present also invention relates to cellobiohydrolase variants, comprising a deletion at one or more positions corresponding to positions 195, 196, 197, and 198 of SEQ ID NO: 2, and wherein the variants have cellobiohydrolase activity.

The present invention also relates to isolated polynucleotides encoding the variants; nucleic acid constructs, vectors, and host cells comprising the polynucleotides; and methods of producing the variants.

The present invention also relates to processes for degrading a cellulosic material, comprising: treating the cellulosic material with an enzyme composition in the presence of a cellobiohydrolase variant of the present invention. In one aspect, the processes further comprise recovering the degraded cellulosic material.

The present invention also relates to processes of producing a fermentation product, comprising: (a) saccharifying a cellulosic material with an enzyme composition in the presence of a cellobiohydrolase variant of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a cellobiohydrolase variant of the present invention. In one aspect, the fermenting of the cellulosic material produces a fermentation product. In another aspect, the processes further comprise recovering the fermentation product from the fermentation.

DEFINITIONS

Figure 1:
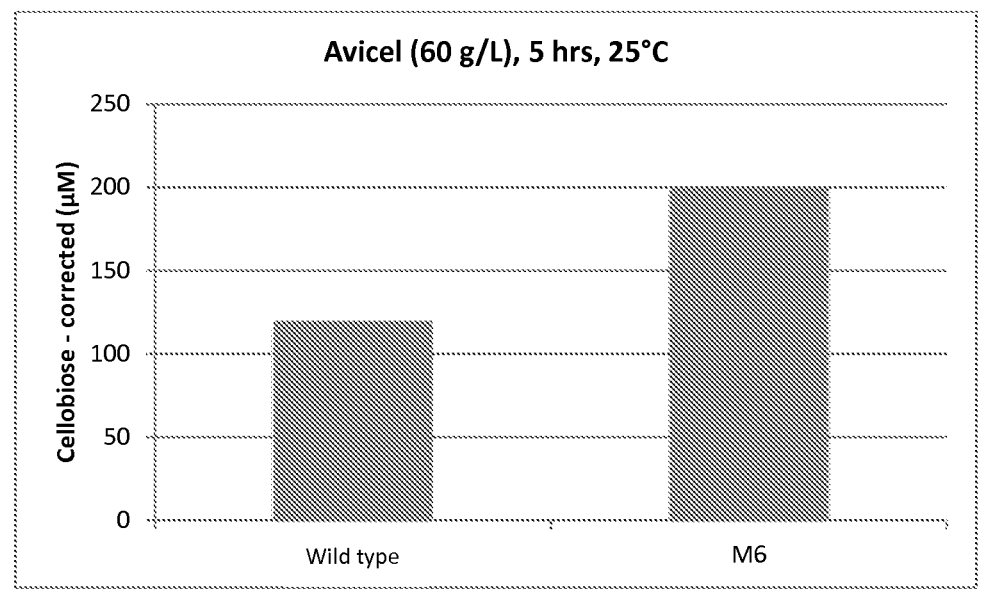
FIG. 1 shows saccharide production from microcrystalline cellulose by the *Trichoderma reesei* wild-type cellobiohydrolase I and the cellobiohydrolase I M6 variant thereof after 5 hours at pH 5 and 25° C. The results were corrected for background sugars determined in a control sample.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 µmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 µmole of glucuronic or 4-O-methylglucuronic acid per minute at pH 5, 40° C.

B2-loop: The term "B2-loop" means the amino acids corresponding to P194 to T201 of the *Trichoderma reesei* Cel7A cellobiohydrolase of SEQ ID NO: 2, as described in Payne et al., *Chem. Rev.* 115: 11308-1448.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, beta-xylosidase activity is determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

Carbohydrate binding module: The term "carbohydrate binding module" means a domain within a carbohydrate-active enzyme that provides carbohydrate-binding activity (Boraston et al., 2004, *Biochem. J.* 383: 769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. The term "carbohydrate binding module" is also used interchangedly herein with the term "carbohydrate binding domain".

Catalytic domain: The term "catalytic domain" means the region of an enzyme containing the catalytic machinery of the enzyme. In one aspect, the catalytic domain is amino acids 1 to 429 of SEQ ID NO: 2. In another aspect, the catalytic domain is amino acids 1 to 437 of SEQ ID NO: 8. In another aspect, the catalytic domain is amino acids 1 to 440 of SEQ ID NO: 10. In another aspect, the catalytic domain is amino acids 1 to 437 of SEQ ID NO: 12. In another aspect, the catalytic domain is amino acids 1 to 437 of SEQ ID NO: 14. In another aspect, the catalytic domain is amino acids 1 to 438 of SEQ ID NO: 16. In another aspect, the catalytic domain is amino acids 1 to 437 of SEQ ID NO: 18. In another aspect, the catalytic domain is amino acids 1 to 430 of SEQ ID NO: 20. In another aspect, the catalytic domain is amino acids 1 to 433 of SEQ ID NO: 22.

Catalytic domain coding sequence: The term "catalytic domain coding sequence" means a polynucleotide that encodes a domain catalyzing cellobiohydrolase activity. In one aspect, the catalytic domain coding sequence is nucleotides 52 to 1469 of SEQ ID NO: 1. In another aspect, the catalytic domain coding sequence is nucleotides 52 to 1389 of SEQ ID NO: 3. In another aspect, the catalytic domain coding sequence is nucleotides 52 to 1389 of SEQ ID NO: 4. In another aspect, the catalytic domain coding sequence is nucleotides 79 to 1389 of SEQ ID NO: 7. In another aspect, the catalytic domain coding sequence is nucleotides 52 to 1371 of SEQ ID NO: 9. In another aspect, the catalytic domain coding sequence is nucleotides 55 to 1482 of SEQ ID NO: 11. In another aspect, the catalytic domain coding sequence is nucleotides 76 to 1386 of SEQ ID NO: 13. In another aspect, the catalytic domain is nucleotides 76 to 1386 of SEQ ID NO: 15. In another aspect, the catalytic domain coding sequence is nucleotides 55 to 1504 of SEQ ID NO: 17. In another aspect, the catalytic domain coding sequence is nucleotides 61 to 1350 of SEQ ID NO: 19. In another aspect, the catalytic domain coding sequence is nucleotides 55 to 1353 of SEQ ID NO: 21.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al., 1988, *Eur. J. Biochem.* 170: 575-581. In the present invention, cellobiohydrolase activity is preferably determined according to Examples 8 and 9 herein.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature such as 25° C.-80° C., e.g., 30° C., 35° C., 40° C., 45° C., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one aspect, the cellulosic material is any biomass material. In another aspect, the cellulosic material is lignocellulose, which comprises cellulose, hemicelluloses, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is *arundo*, bagasse, bamboo, corn cob, corn fiber, corn stover, *miscanthus*, rice straw, switchgrass, or wheat straw.

In another embodiment, the cellulosic material is aspen, *eucalyptus*, fir, pine, poplar, spruce, or willow.

In another embodiment, the cellulosic material is algal cellulose, bacterial cellulose, cotton linter, filter paper, microcrystalline cellulose (e.g., AVICEL®), or phosphoric-acid treated cellulose.

In another embodiment, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Endoglucanase: The term "endoglucanase" means a 4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat, 1991, *Biochem. J.* 280: 309-316, and Henrissat, and Bairoch, 1996, *Biochem. J.* 316: 695-696. The GH61 polypeptides have recently been classified as lytic polysaccharide monooxygenases (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061) and are designated "Auxiliary Activity 9" or "AA9" polypeptides.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide; wherein the fragment has cellobiohydrolase activity. In one aspect, a fragment contains at least 420 amino acid residues, e.g., at least 445 amino acid residues or at least 470 amino acid residues of the mature polypeptide of SEQ ID NO: 2 or a variant thereof. In another aspect, a fragment contains at least 430 amino acid residues, e.g., at least 455 amino acid residues or at least 480 amino acid residues of the mature polypeptide of SEQ ID NO: 8 or a variant thereof. In another aspect, a fragment contains at least 380 amino acid residues, e.g., at least 400 amino acid residues or at least 420 amino acid residues of the mature polypeptide of SEQ ID NO: 10 or a variant thereof. In another aspect, a fragment contains at least 380 amino acid residues, e.g., at least 400 amino acid residues or at least 420 amino acid residues of the mature polypeptide of SEQ ID NO: 12 or a variant thereof. In another aspect, a fragment contains at least 430 amino acid residues, e.g., at least 455 amino acid residues or at least 480 amino acid residues of the mature polypeptide of SEQ ID NO: 14 or a variant thereof. In another aspect, a fragment contains at least 430 amino acid residues, e.g., at least 455 amino acid residues or at least 480 amino acid residues of the mature polypeptide of SEQ ID NO: 16 or a variant thereof. In another aspect, a fragment contains at least 380 amino acid residues, e.g., at least 400 amino acid residues or at least 420 amino acid residues of the mature polypeptide of SEQ ID NO: 18 or a variant thereof. In another aspect, a fragment contains at least 370 amino acid residues, e.g., at least 390 amino acid residues or at least 410 amino acid residues of the mature polypeptide of SEQ ID NO: 20 or a variant thereof. In another aspect, a fragment contains at least 435 amino acid residues, e.g., at least 460 amino acid residues or at least 485 amino acid residues of the mature polypeptide of SEQ ID NO: 22 or a variant thereof.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0.

High stringency conditions: The term "high stringency conditions" means for probes of at least 100 nucleotides in length, prehybridization and hybridization at 42° C. in 5× SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such an improved property is preferably increased specific performance.

Increased specific performance: The term "increased specific performance" by a variant of the present invention means improved conversion of a cellulosic material to a product, as compared to the same level of conversion by the parent. Increased specific performance is determined per unit protein (e.g., mg protein, or μmole protein). The increased specific performance of the variant relative to the parent can be assessed, for example, under one or more (e.g., several) conditions of pH, temperature, and substrate concentration. In one aspect, the product is glucose. In another aspect, the product is cellobiose. In another aspect, the product is glucose+cellobiose.

In one aspect, the condition is pH. For example, the pH can be any pH in the range of 3 to 7, e.g., 3.0, 3.5, 4.0, 4.5, 5.0, 5.5, 6.0, 6.5, or 7.0 (or in between). Any suitable buffer for achieving the desired pH can be used.

In another aspect, the condition is temperature. For example, the temperature can be any temperature in the range of 25° C. to 90° C., e.g., 25, 30, 35, 40, 45, 50, 55, 60, 65, 70, 75, 80, 85, or 90° C. (or in between).

In another aspect, the condition is substrate concentration. Any cellulosic material defined herein can be used as the substrate. In one aspect, the substrate concentration is measured as the dry solids content. The dry solids content is preferably in the range of about 1 to about 50 wt %, e.g., about 5 to about 45 wt %, about 10 to about 40 wt %, or about 20 to about 30 wt %. In another aspect, the substrate concentration is measured as the insoluble glucan content. The insoluble glucan content is preferably in the range of about 2.5 to about 25 wt %, e.g., about 5 to about 20 wt % or about 10 to about 15 wt %.

In another aspect, a combination of two or more (e.g., several) of the above conditions are used to determine the increased specific performance of the variant relative to the parent, such as any temperature in the range of 25° C. to 90° C., e.g., 25, 30, 35, 40, 45, 50, 55, 60, 65, 70, 75, 80, 85, or 90° C. (or in between) at a pH in the range of 3 to 7, e.g., 3.0, 3.5, 4.0, 4.5, 5.0, 5.5, 6.0, 6.5, or 7.0 (or in between).

The increased specific performance of the variant relative to the parent can be determined using any enzyme assay known in the art for cellobiohydrolases as described herein. Alternatively, the increased specific performance of the variant relative to the parent can be determined using the assays described in Examples 8 and 9.

In another aspect, the specific performance of the variant is at least 1.01-fold, e.g., at least 1.02-fold, at least 1.03-fold, at least 1.04-fold, at least 1.05-fold, at least 1.06-fold, at least 1.07-fold, at least 1.08-fold, at least 1.09-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, at least 5-fold, at least 10-fold, at least 15-fold, at least 20-fold, at least 25-fold, and at least 50-fold higher than the specific performance of the parent.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours.

The carrier material is finally washed three times each for 15 minutes using 0.2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 497 of SEQ ID NO: 2 based on the SignalP 3.0 program (Bendtsen et al., 2004, *J. Mol. Biol.* 340: 783-795) that predicts amino acids −1 to −17 of SEQ ID NO: 2 are a signal peptide. In another aspect, the mature polypeptide is amino acids 1 to 506 of SEQ ID NO: 8 (P3EX) based on the SignalP 3.0 program that predicts amino acids −1 to −26 of SEQ ID NO: 8 are a signal peptide. In another aspect, the mature polypeptide is amino acids 1 to 440 of SEQ ID NO: 10 (P57J) based on the SignalP 3.0 program that predicts amino acids −1 to −17 of SEQ ID NO: 10 are a signal peptide. In another aspect, the mature polypeptide is amino acids 1 to 437 of SEQ ID NO: 12 (P82PH) based on the SignalP 3.0 program that predicts amino acids −1 to −18 of SEQ ID NO: 12 are a signal peptide. In another aspect, the mature polypeptide is amino acids 1 to 507 of SEQ ID NO: 14 (P23YSY) based on the SignalP 3.0 program that predicts amino acids −1 to −25 of SEQ ID NO: 14 are a signal peptide. In another aspect, the mature polypeptide is amino acids 1 to 507 of SEQ ID NO: 16 (P23YSX) based on the SignalP 3.0 program that predicts amino acids −1 to −25 of SEQ ID NO: 16 are a signal peptide. In another aspect, the mature polypeptide is amino acids 1 to 437 of SEQ ID NO: 18 (P24765) based on the SignalP 3.0 program that predicts amino acids −1 to −18 of SEQ ID NO: 18 are a signal peptide. In another aspect, the mature polypeptide is amino acids 1 to 430 of SEQ ID NO: 20 (P66Z) based on the SignalP 3.0 program that predicts amino acids −1 to −20 of SEQ ID NO: 20 are a signal peptide. In another aspect, the mature polypeptide is amino acids 1 to 511 of SEQ ID NO: 22 (P57G) based on the SignalP 3.0 program that predicts amino acids −1 to −18 of SEQ ID NO: 22 are a signal peptide. It is known in the art that a host cell may produce a mixture of two of more different mature polypeptides (i.e., with a different C-terminal and/or N-terminal amino acid) expressed by the same polynucleotide. It is also known in the art that different host cells may process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having cellobiohydrolase activity. In one aspect, the mature polypeptide coding sequence is nucleotides 52 to 1673 of SEQ ID NO: 1 (without the stop codon) based on SignalP 3.0 program (Bendtsen et al., 2004, supra) that predicts nucleotides 1 to 51 of SEQ ID NO: 1 encode a signal peptide. In another aspect, the mature polypeptide coding sequence is nucleotides 52 to 1542 of SEQ ID NO: 3 (without the stop codon) based on SignalP 3.0 program that predicts nucleotides 1 to 51 of SEQ ID NO: 3 encode a signal peptide. In another aspect, the mature polypeptide coding sequence is nucleotides 52 to 1542 of SEQ ID NO: 4 (without the stop codon) based on SignalP 3.0 program that predicts nucleotides 1 to 51 of SEQ ID NO: 4 encode a signal peptide. In another aspect, the mature polypeptide coding sequence is nucleotides 79 to 1596 of SEQ ID NO: 7 (D1R9) (without the stop codon) based on SignalP 3.0 program that predicts nucleotides 1 to 78 of SEQ ID NO: 7 encode a signal peptide. In another aspect, the mature polypeptide coding sequence is nucleotides 52 to 1371 of SEQ ID NO: 9 (D3FQ) (without the stop codon) based on SignalP 3.0 program that predicts nucleotides 1 to 51 of SEQ ID NO: 9 encode a signal peptide. In another aspect, the mature polypeptide coding sequence is nucleotides 55 to 1482 of SEQ ID NO: 11 (D23Y2) (without the stop codon) based on SignalP 3.0 program that predicts nucleotides 1 to 54 of SEQ ID NO: 11 encode a signal peptide. In another aspect, the mature polypeptide coding sequence is nucleotides 76 to 1596 of SEQ ID NO: 13 (D72PP3) (without the stop codon) based on SignalP 3.0 program that predicts nucleotides 1 to 75 of SEQ ID NO: 13 encode a signal peptide. In another aspect, the mature polypeptide coding sequence is nucleotides 76 to 1596 of SEQ ID NO: 15 (D72PP2) (without the stop codon) based on SignalP 3.0 program that predicts nucleotides 1 to 75 of SEQ ID NO: 15 encode a signal peptide. In another aspect, the mature polypeptide coding sequence is nucleotides 55 to 1504 of SEQ ID NO: 17 (D82ACF) (without the stop codon) based on SignalP 3.0 program that predicts nucleotides 1 to 54 of SEQ ID NO: 17 encode a signal peptide. In another aspect, the mature polypeptide coding sequence is nucleotides 61 to 1350 of SEQ ID NO: 19 (D6CT) (without the stop codon) based on SignalP 3.0 program that predicts nucleotides 1 to 60 of SEQ ID NO: 19 encode a signal peptide. In another aspect, the mature polypeptide coding sequence is nucleotides 55 to 1587 of SEQ ID NO: 21 (D3FP) (without the stop codon) based on SignalP 3.0 program that predicts nucleotides 1 to 54 of SEQ ID NO: 21 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent cellobiohydrolase: The term "parent" or "parent cellobiohydrolase" means a polypeptide having cellobiohydrolase activity to which an alteration, i.e., a substitution, insertion, and/or deletion, at one or more (e.g., several) positions, is made to produce an enzyme variant of the present invention. The parent may be a naturally occurring (wild-type) polypeptide or a variant or fragment thereof.

Polypeptide having cellulolytic enhancing activity: The term "polypeptide having cellulolytic enhancing activity" means a GH61 polypeptide or variant thereof that catalyzes the enhancement of the hydrolysis of a cellulosic material by enzyme having cellulolytic activity, i.e., a cellulase. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of a GH61 polypeptide or variant thereof for 1-7 days at a suitable temperature, such as 25° C.-80° C., e.g., 30° C., 35° C., 40° C., 45° C., 50° C., 55° C., 60° C., 65° C., or 70° C., and a suitable pH, such as 4-9, e.g., 4.5, 5.0, 5.5, 6.0, 6.5, 7.0, 7.5, 8.0, or 8.5, compared to a control hydrolysis with equal total protein loading without cellulolytic enhancing activity (1-50 mg of cellulolytic protein/g of cellulose in PCS) In one aspect, GH61 polypeptide enhancing activity is determined using a mixture of CELLUCLAST® 1.5L (Novozymes A/S, Bagsvaerd, Denmark) in the presence of 2-3% of total protein weight Aspergillus oryzae beta-glucosidase (recombinantly produced in Aspergillus oryzae according to WO 02/095014) or 2-3% of total protein weight Aspergillus fumigatus beta-glucosidase (recombinantly produced in Aspergillus oryzae as described in WO 02/095014) of cellulase protein loading is used as the source of the cellulolytic activity.

Another assay for determining the cellulolytic enhancing activity of a GH61 polypeptide or variant thereof is to incubate the GH61 polypeptide or variant with 0.5% phosphoric acid swollen cellulose (PASC), 100 mM sodium acetate pH 5, 1 mM $MnSO_4$, 0.1% gallic acid, 0.025 mg/ml of Aspergillus fumigatus beta-glucosidase, and 0.01% TRITON® X100 (4-(1,1,3,3-tetramethylbutyl)phenyl-polyethylene glycol) for 24-96 hours at 40° C. followed by determination of the glucose released from the PASC.

The GH61 polypeptides or variants thereof having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are a gap open penalty of 10, a gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having cellobiohydrolase activity. In one aspect, a subsequence contains at least 1400 nucleotides, e.g., at least 1475 nucleotides or at least 1550 nucleotides of the mature polypeptide coding sequence of SEQ ID NO: 1 or a mutant thereof. In another aspect, a subsequence contains at least 1260 nucleotides, e.g., at least 1335 nucleotides or at least 1410 nucleotides of the mature polypeptide coding sequence of SEQ ID NO: 3 or a mutant thereof. In another aspect, a subsequence contains at least 1260 nucleotides, e.g., at least 1335 nucleotides or at least 1410 nucleotides of the mature polypeptide coding sequence of SEQ ID NO: 4 or a mutant thereof. In another aspect, a fragment contains at least 1290 nucleotides, e.g., at least 1365 nucleotides or at least 1440 nucleotides of the mature polypeptide of SEQ ID NO: 7 or a mutant thereof. In another aspect, a fragment contains at least 1140 nucleotides, e.g., at least 1200 nucleotides or at least 1260 nucleotides of the mature polypeptide of SEQ ID NO: 9 or a mutant thereof. In another aspect, a fragment contains at least 1140 nucleotides, e.g., at least 1200 nucleotides or at least 1260 nucleotides of the mature polypeptide of SEQ ID NO: 11 or a mutant thereof. In another aspect, a fragment contains at least 1290 nucleotides, e.g., at least 1365 nucleotides or at least 1440 nucleotides of the mature polypeptide of SEQ ID NO: 13 or a mutant thereof. In another aspect, a fragment contains at least 1290 nucleotides, e.g., at least 1365 nucleotides or at least 1440 nucleotides of the mature polypeptide of SEQ ID NO: 15 or a mutant thereof. In another aspect, a fragment contains at least 1140 nucleotides, e.g., at least 1200 nucleotides or at least 1260 nucleotides of the mature polypeptide of SEQ ID NO: 17 or a mutant thereof. In another aspect, a fragment contains at least 1110 nucleotides, e.g., at least 1170 nucleotides or at least 1230 nucleotides of the mature polypeptide of SEQ ID NO: 19 or a mutant thereof. In another aspect, a fragment contains at least 1305 nucleotides, e.g., at least 1380 nucleotides or at least 1455 nucleotides of the mature polypeptide of SEQ ID NO: 21 or a mutant thereof.

Variant: The term "variant" means a polypeptide having cellobiohydrolase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have a specific performance which is at least 1.01-fold higher than the specific performance of the parent.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

Wild-type cellobiohydrolase: The term "wild-type" cellobiohydrolase means a cellobiohydrolase naturally produced by a microorganism, such as a bacterium, yeast, or filamentous fungus found in nature.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrimann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Conventions for Designation of Variants

For purposes of the present invention, the sequence of SEQ ID NO: 2 is used to determine the corresponding amino acid residue in another cellobiohydrolase. The amino acid sequence of another cellobiohydrolase is aligned with SEQ ID NO: 2, and based on the alignment, the amino acid position number corresponding to any amino acid residue in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. Numbering of the amino acid positions is based on the full-length polypeptide (e.g., including the signal peptide) of SEQ ID NO: 2 wherein position −17 is the first amino acid of the signal peptide (i.e., Met) and position 1 is Gln of SEQ ID NO: 2. For example, the position corresponding to position 197 of the *Trichoderma reesei* cellobiohydrolase I (SEQ ID NO: 2) is position 194 of the *Rasamsonia emersonii* cellobiohydrolase I, and position 200 of the *Trichoderma reesei* cellobiohydrolase I is position 197 of the *Rasamsonia emersonii* cellobiohydrolase I.

Identification of the corresponding amino acid residue in another cellobiohydrolase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When another cellobiohydrolase has diverged from the sequence of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the cellobiohydrolase variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G-K-A    |

Multiple Alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Alterations.

Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:
"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to cellobiohydrolase variants, comprising deletions at two or more consecutive positions of the B2-loop, wherein the variants have cellobiohydrolase activity.

The present invention also relates to isolated cellobiohydrolase variants, comprising a deletion at one or more positions corresponding to positions 195, 196, 197, 198, and 199 of SEQ ID NO: 2, and wherein the variants have cellobiohydrolase activity.

Variants

In an embodiment, the variant has a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, to the amino acid sequence of the parent cellobiohydrolase or the mature polypeptide thereof.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 2.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 8.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 10.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 12.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 14.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 16.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 18.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 20.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 22.

In one aspect, the number of alterations (e.g., substitutions and/or deletions) in the variants of the present invention is 1-4, e.g., 1, 2, 3, or 4 alterations. In another aspect, the number of substitutions and/or deletions in the variants of the present invention is 1-3, e.g., 1, 2, or 3 substitutions. In another aspect, the number of deletions in the variants of the present invention is 1 deletion.

In one aspect, a variant comprises or consists of deletions at two or more consecutive positions of the B2-loop. In one embodiment, the variant comprises deletions at positions corresponding to positions 194 and 195 of SEQ ID NO: 2 (e.g., P194*+S195*). In another embodiment, the variant comprises deletions at positions corresponding to positions 195 and 196 of SEQ ID NO: 2 (e.g., S195*+S196*, or S195*+A196*). In another embodiment, the variant comprises deletions at positions corresponding to positions 196 and 197 of SEQ ID NO: 2 (e.g., S196*+N197*, or A196*+N197*). In another embodiment, the variant comprises deletions at positions corresponding to positions 197 and 198 of SEQ ID NO: 2 (e.g., N197*+N198*, N197*+D198*). In another embodiment, the variant comprises deletions at positions corresponding to positions 198 and 199 of SEQ ID NO: 2 (e.g., N198*+A199*, D198*+A199*, or D198*+P199*). In another embodiment, the variant comprises deletions at positions corresponding to positions 199 and 200 of SEQ ID NO: 2 (e.g., A199*+N200*, or P199*+N200*). In another embodiment, the variant comprises deletions at positions corresponding to positions 200 and 201 of SEQ ID NO: 2 (e.g., N200*+T201*, N200*+A201*, or N200*+S201*).

In another aspect, a variant comprises or consists of deletions at three or more consecutive positions of the B2-loop (e.g., deletions at positions corresponding to positions 194*+195*+196*, 195*+196*+197*, 196*+197*+198*, 197*+198*+199*, 198*+199*+200*, or 199*+200*+201* of SEQ ID NO: 2).

In another aspect, a variant comprises or consists of deletions at four or more consecutive positions of the B2-loop (e.g., deletions at positions corresponding to positions 194*+195*+196*+197*, 195*+196*+197*+198*, 196*+197*+198*+199*, 197*+198*+199*+200*, or 198*+199*+200*+201* of SEQ ID NO: 2).

In another aspect, a variant comprises or consists of deletions at five or more consecutive positions of the B2-loop (e.g., deletions at positions corresponding to positions 194*+195*+196*+197*+198*, 195*+196*+197*+198*+199*, 196*+197*+198*+199*+200*, or 197*+198*+199*+200*+201* of SEQ ID NO: 2).

In another aspect, a variant comprises or consists of deletions at six or more consecutive positions of the B2-loop. (e.g., deletions at positions corresponding to positions 194*+195*+196*+197*+198*+199*, 195*+196*+197*+198*+199*+200*, or 196*+197*+198*+199*+200*+201* of SEQ ID NO: 2).

In another aspect, a variant comprises or consists of deletions at seven or more consecutive positions of the B2-loop (e.g., deletions at positions corresponding to positions 194*+195*+196*+197*+198*+199*+200*, or 195*+196*+197*+198*+199*+200*+201* of SEQ ID NO: 2).

In one aspect, a variant comprises or consists of deletions at eight consecutive positions of the B2-loop (e.g., deletions at positions corresponding to positions 194*+195*+196*+197*+198*+199*+200*+201* of SEQ ID NO: 2).

In another aspect, a variant comprises a deletion at one or more (e.g., several) positions corresponding to positions 195, 196, 197, and 198 of SEQ ID NO: 2.

In one aspect, the variant comprises or consists of a deletion at one position corresponding to positions 195, 196, 197, and 198 of SEQ ID NO: 2. In one embodiment, the variant comprises or consists of a deletion at a position corresponding to position 195 of SEQ ID NO: 2. In one embodiment, the deletion is an S195* deletion. In another embodiment, the variant comprises or consists of a deletion at a position corresponding to position 196 of SEQ ID NO: 2. In one embodiment, the deletion is an S196* deletion. In another embodiment, the variant comprises or consists of a deletion at a position corresponding to position 197 of SEQ ID NO: 2. In one embodiment, the deletion is an N197* deletion. In another embodiment, the variant comprises or consists of a deletion at a position corresponding to position 198 of SEQ ID NO: 2. In one embodiment, the deletion is an N198* deletion. In any of these embodiments, the variant may further comprise a substitution at any position corresponding positions 197, 198, and 200, and/or a deletion at a position corresponding to position 199 of SEQ ID NO: 2, as described infra.

In another aspect, a variant comprises or consists of a deletion at two positions corresponding to any of positions 195, 196, 197, and 198 of SEQ ID NO: 2. In one embodiment, the variant comprises or consists of deletions at positions corresponding to positions 195 and 196 of SEQ ID NO: 2. In one embodiment, the deletions are S195*+S196* deletions. In one embodiment, the variant comprises or consists of deletions at positions corresponding to positions 195 and 197 of SEQ ID NO: 2. In one embodiment, the deletions are S195*+N197* deletions. In one embodiment, the variant comprises or consists of deletions at positions corresponding to positions 195 and 198 of SEQ ID NO: 2. In one embodiment, the deletions are S195*+N198* deletions. In one embodiment, the variant comprises or consists of deletions at positions corresponding to positions 196 and 197 of SEQ ID NO: 2. In one embodiment, the deletions are S196*+N197* deletions. In one embodiment, the variant comprises or consists of deletions at positions corresponding to positions 196 and 198 of SEQ ID NO: 2. In one embodiment, the deletions are S196*+N198* deletions. In one embodiment, the variant comprises or consists of deletions at positions corresponding to positions 197 and 198 of SEQ ID NO: 2. In one embodiment, the deletions are N197*+N198* deletions. In any of these embodiments, the variant may further comprise a substitution at any position corresponding positions 197, 198, and 200, and/or a deletion at a position corresponding to position 199 of SEQ ID NO: 2, as described infra.

In another aspect, a variant comprises a deletion at positions corresponding to positions 196, 197, and 198 of SEQ ID NO: 2. In one embodiment, the deletions are S196*+N197*+N198* deletions. In one embodiment, the variant may further comprise a substitution at a position corresponding position 200, and/or a deletion at a position corresponding to position 199 of SEQ ID NO: 2, as described infra.

In another aspect, a variant comprises a deletion at each position corresponding to positions 195, 196, 197, and 198 of SEQ ID NO: 2. In one embodiment, the deletions are S195*+S196*+N197*+N198* deletions. In one embodiment, the variant may further comprise a substitution at a position corresponding position 200, and/or a deletion at a position corresponding to position 199 of SEQ ID NO: 2, as described infra.

In one embodiment, the variant comprises or consists of amino acids 1-434 of SEQ ID NO: 78. In another embodiment, the variant comprises or consists of amino acids 1-495 of SEQ ID NO: 80. In another embodiment, the variant comprises or consists of amino acids 1-495 of SEQ ID NO: 82.

The variants may further comprise one or more additional alterations, e.g., substitutions, insertions, or deletions at one or more (e.g., several) other positions, such as a substitution, a deletion, and/or an insertion at one or more (e.g., several) other positions disclosed in PCT/US2014/022068, WO 2011/050037, WO 2005/028636, WO 2005/001065, WO 2004/016760, and U.S. Pat. No. 7,375,197, which are incorporated herein in their entireties.

For example, in one aspect, the variant comprises an alteration at one or more positions corresponding to positions 197, 198, 199, and 200 of SEQ ID NO: 2, wherein the alteration at the one or more positions corresponding to positions 197, 198, and 200 is a substitution and the alteration at the position corresponding to position 199 is a deletion. In another aspect, a variant comprises an alteration at two positions corresponding to any of positions 197, 198, 199, and 200 of SEQ ID NO: 2, wherein the alteration at the one or more positions corresponding to positions 197, 198, and 200 is a substitution and the alteration at the position corresponding to position 199 is a deletion. In another aspect, a variant comprises an alteration at three positions corresponding to any of positions 197, 198, 199, and 200 of SEQ ID NO: 2, wherein the alteration at the one or more positions corresponding to positions 197, 198, and 200 is a substitution and the alteration at the position corresponding to position 199 is a deletion. In another aspect, a variant comprises a substitution at each position corresponding to positions 197, 198, and 200 and a deletion at a position corresponding to position 199.

In another aspect, the variant comprises a substitution at a position corresponding to position 197. In another aspect, the amino acid at a position corresponding to position 197 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises the substitution N197A of SEQ ID NO: 2.

In another aspect, the variant comprises a substitution at a position corresponding to position 198. In another aspect, the amino acid at a position corresponding to position 198 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises the substitution N198A of SEQ ID NO: 2.

In another aspect, the variant comprises a deletion at a position corresponding to position 199. In another aspect, the amino acid at a position corresponding to position 199 is Ala, Arg, Asn, Asp, Cys, Gln, Glu, Gly, His, Ile, Leu, Lys, Met, Phe, Pro, Ser, Thr, Trp, Tyr, or Val, preferably Ala. In another aspect, the variant comprises the deletion A199* of SEQ ID NO: 2.

In another aspect, the variant comprises a substitution at a position corresponding to position 200. In another aspect, the amino acid at a position corresponding to position 200 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Gly, or Trp. In another aspect, the variant comprises the substitution N200A,G,W of SEQ ID NO: 2.

In another aspect, the variant comprises an alteration at positions corresponding to positions 197 and 198, such as those described above.

In another aspect, the variant comprises alterations at positions corresponding to positions 197 and 199, such as those described above.

In another aspect, the variant comprises alterations at positions corresponding to positions 197 and 200, such as those described above.

In another aspect, the variant comprises alterations at positions corresponding to positions 198 and 199, such as those described above.

In another aspect, the variant comprises alterations at positions corresponding to positions 198 and 200, such as those described above.

In another aspect, the variant comprises alterations at positions corresponding to positions 199 and 200, such as those described above.

In another aspect, the variant comprises alterations at positions corresponding to positions 197, 198, and 199, such as those described above.

In another aspect, the variant comprises alterations at positions corresponding to positions 197, 198, and 200, such as those described above.

In another aspect, the variant comprises alterations at positions corresponding to positions 197, 199, and 200, such as those described above.

In another aspect, the variant comprises alterations at positions corresponding to positions 198, 199, and 200, such as those described above.

In another aspect, the variant comprises alterations at positions corresponding to positions 197, 198, 199, and 200, such as those described above.

In another aspect, the variant comprises one or more alterations selected from the group consisting of N197A, N198A, A199*, and N200A,G,W.

In another aspect, the variant comprises the alterations N197A+N198A of SEQ ID NO: 2.

In another aspect, the variant comprises the alterations N197A+A199* of SEQ ID NO: 2.

In another aspect, the variant comprises the alterations N197A+N200A,G,W of SEQ ID NO: 2.

In another aspect, the variant comprises the alterations N198A+A199* of SEQ ID NO: 2.

In another aspect, the variant comprises the alterations N198A+N200A,G,W of SEQ ID NO: 2.

In another aspect, the variant comprises the alterations A199*+N200A,G,W of SEQ ID NO: 2.

In another aspect, the variant comprises the alterations N197A+N198A+A199* of SEQ ID NO: 2.

In another aspect, the variant comprises the alterations N197A+N198A+N200A,G,W of SEQ ID NO: 2.

In another aspect, the variant comprises the alterations N197A+A199*+N200A,G,W of SEQ ID NO: 2.

In another aspect, the variant comprises the alterations N198A+A199*+N200A,G,W of SEQ ID NO: 2.

In another aspect, the variant comprises the alterations N197A+N198A+A199*+N200A,G,W of SEQ ID NO: 2.

The variants may further comprise one or more additional alterations, e.g., substitutions, insertions, or deletions at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

The variants may even further comprise one or more (e.g., several) substitutions at positions corresponding to positions disclosed in WO 2011/050037, WO 2011/050037, WO 2005/02863, WO 2005/001065, WO 2004/016760, and U.S. Pat. No. 7,375,197, which are incorporated herein in their entireties.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellobiohydrolase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The variants may consist of 370 to 507 amino acids, e.g., 370 to 380, 380 to 390, 390 to 400, 400 to 410, 410 to 420, 420 to 430, 430 to 440, 450 to 460, 460 to 470, 470 to 480, 480 to 490, 490 to 500, or 500 to 507 amino acids.

In each of the embodiments described above, a variant of the present invention may be a hybrid polypeptide (chimera) in which a region of the variant is replaced with a region of another polypeptide. In one aspect, the region is a carbohydrate binding domain. The carbohydrate binding domain of a variant may be replaced with another (heterologous) carbohydrate binding domain.

In each of the embodiments described above, a variant of the present invention may be a fusion polypeptide or cleavable fusion polypeptide in which another polypeptide is fused at the N-terminus or the C-terminus of the variant. In one aspect, the other polypeptide is a carbohydrate binding domain. The catalytic domain of a variant of the present invention without a carbohydrate binding domain may be fused to a carbohydrate binding domain. A fusion polypeptide is produced by fusing a polynucleotide encoding another polypeptide to a polynucleotide encoding a variant of the present invention. Techniques for producing fusion polypeptides are known in the art, and include ligating the coding sequences encoding the polypeptides so that they are in frame and expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

In one embodiment, the variant is a hybrid or chimeric polypeptide in which the carbohydrate binding domain of the variant is replaced with a different carbohydrate binding domain. In another embodiment, the variant is a fusion protein in which a heterologous carbohydrate binding domain is fused to the variant. In one aspect, the carbohydrate binding domain is fused to the N-terminus of the variant. In another aspect, the carbohydrate binding domain is fused to the C-terminus of the variant. In another aspect, the fusion protein variant comprises or consists of SEQ ID NO: 78 or the mature polypeptide thereof. SEQ ID NO: 78 is encoded by SEQ ID NO: 77.

In an embodiment, the variant has increased specific performance compared to the parent enzyme.

Parent Cellobiohydrolases

The parent cellobiohydrolase may be any cellobiohydrolase I.

In one embodiment, the parent cellobiohydrolase may be (a) a polypeptide having at least 60% sequence identity to the mature polypeptide of SEQ ID NO: 2; (b) a polypeptide encoded by a polynucleotide that hybridizes under low stringency conditions with the mature polypeptide coding sequence of SEQ ID NO: 1, SEQ ID NO: 3, or SEQ ID NO: 4; or the full-length complement thereof; or (c) a polypeptide encoded by a polynucleotide having at least 60% sequence identity to the mature polypeptide coding sequence of SEQ ID NO: 1, SEQ ID NO: 3, or SEQ ID NO: 4.

In another embodiment, the parent cellobiohydrolase may also be (a) a polypeptide having at least 60% sequence identity to the mature polypeptide of SEQ ID NO: 8; (b) a polypeptide encoded by a polynucleotide that hybridizes under low stringency conditions with the mature polypeptide coding sequence of SEQ ID NO: 7; or the full-length complement thereof; or (c) a polypeptide encoded by a polynucleotide having at least 60% sequence identity to the mature polypeptide coding sequence of SEQ ID NO: 7.

In another embodiment, the parent cellobiohydrolase may also be (a) a polypeptide having at least 60% sequence identity to the mature polypeptide of SEQ ID NO: 10; (b) a polypeptide encoded by a polynucleotide that hybridizes under low stringency conditions with the mature polypeptide coding sequence of SEQ ID NO: 9 or the full-length complement thereof; or (c) a polypeptide encoded by a polynucleotide having at least 60% sequence identity to the mature polypeptide coding sequence of SEQ ID NO: 9.

In another embodiment, the parent cellobiohydrolase may also be (a) a polypeptide having at least 60% sequence identity to the mature polypeptide of SEQ ID NO: 12; (b) a polypeptide encoded by a polynucleotide that hybridizes under low stringency conditions with the mature polypeptide coding sequence of SEQ ID NO: 11 or the full-length complement thereof; or (c) a polypeptide encoded by a polynucleotide having at least 60% sequence identity to the mature polypeptide coding sequence of SEQ ID NO: 11.

In another embodiment, the parent cellobiohydrolase may also be (a) a polypeptide having at least 60% sequence identity to the mature polypeptide of SEQ ID NO: 14; (b) a polypeptide encoded by a polynucleotide that hybridizes under low stringency conditions with the mature polypeptide coding sequence of SEQ ID NO: 13 or the full-length complement thereof; or (c) a polypeptide encoded by a polynucleotide having at least 60% sequence identity to the mature polypeptide coding sequence of SEQ ID NO: 13.

In another embodiment, the parent cellobiohydrolase may also be (a) a polypeptide having at least 60% sequence identity to the mature polypeptide of SEQ ID NO: 16; (b) a polypeptide encoded by a polynucleotide that hybridizes under low stringency conditions with the mature polypeptide coding sequence of SEQ ID NO: 15 or the full-length complement thereof; or (c) a polypeptide encoded by a polynucleotide having at least 60% sequence identity to the mature polypeptide coding sequence of SEQ ID NO: 15.

In another embodiment, the parent cellobiohydrolase may also be (a) a polypeptide having at least 60% sequence identity to the mature polypeptide of SEQ ID NO: 18; (b) a polypeptide encoded by a polynucleotide that hybridizes under low stringency conditions with the mature polypeptide coding sequence of SEQ ID NO: 17 or the full-length complement thereof; or (c) a polypeptide encoded by a polynucleotide having at least 60% sequence identity to the mature polypeptide coding sequence of SEQ ID NO: 17.

In another embodiment, the parent cellobiohydrolase may also be (a) a polypeptide having at least 60% sequence identity to the mature polypeptide of SEQ ID NO: 20; (b) a polypeptide encoded by a polynucleotide that hybridizes under low stringency conditions with the mature polypeptide coding sequence of SEQ ID NO: 19 or the full-length complement thereof; or (c) a polypeptide encoded by a polynucleotide having at least 60% sequence identity to the mature polypeptide coding sequence of SEQ ID NO: 19.

In another embodiment, the parent cellobiohydrolase may also be (a) a polypeptide having at least 60% sequence identity to the mature polypeptide of SEQ ID NO: 22; (b) a polypeptide encoded by a polynucleotide that hybridizes under low stringency conditions with the mature polypeptide coding sequence of SEQ ID NO: 21 or the full-length complement thereof; or (c) a polypeptide encoded by a polynucleotide having at least 60% sequence identity to the mature polypeptide coding sequence of SEQ ID NO: 21.

In one aspect, the parent has a sequence identity to the mature polypeptide of SEQ ID NO: 2 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from the mature polypeptide of SEQ ID NO: 2.

In another aspect, the parent has a sequence identity to the mature polypeptide of SEQ ID NO: 8 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from the mature polypeptide of SEQ ID NO: 8.

In another aspect, the parent has a sequence identity to the mature polypeptide of SEQ ID NO: 10 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from the mature polypeptide of SEQ ID NO: 10.

In another aspect, the parent has a sequence identity to the mature polypeptide of SEQ ID NO: 12 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from the mature polypeptide of SEQ ID NO: 12.

In another aspect, the parent has a sequence identity to the mature polypeptide of SEQ ID NO: 14 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from the mature polypeptide of SEQ ID NO: 14.

In another aspect, the parent has a sequence identity to the mature polypeptide of SEQ ID NO: 16 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from the mature polypeptide of SEQ ID NO: 16.

In another aspect, the parent has a sequence identity to the mature polypeptide of SEQ ID NO: 18 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from the mature polypeptide of SEQ ID NO: 18.

In another aspect, the parent has a sequence identity to the mature polypeptide of SEQ ID NO: 20 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from the mature polypeptide of SEQ ID NO: 20.

In another aspect, the parent has a sequence identity to the mature polypeptide of SEQ ID NO: 22 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from the mature polypeptide of SEQ ID NO: 22.

In another aspect, the parent comprises or consists of the amino acid sequence of SEQ ID NO: 2. In another aspect, the parent comprises or consists of the mature polypeptide of SEQ ID NO: 2. In another aspect, the parent comprises or consists of amino acids 1 to 497 of SEQ ID NO: 2.

In another aspect, the parent comprises or consists of the amino acid sequence of SEQ ID NO: 8. In another aspect, the parent comprises or consists of the mature polypeptide of SEQ ID NO: 8. In another aspect, the parent comprises or consists of amino acids 1 to 506 of SEQ ID NO: 8.

In another aspect, the parent comprises or consists of the amino acid sequence of SEQ ID NO: 10. In another aspect, the parent comprises or consists of the mature polypeptide of SEQ ID NO: 10. In another aspect, the parent comprises or consists of amino acids 1 to 437 of SEQ ID NO: 10.

In another aspect, the parent comprises or consists of the amino acid sequence of SEQ ID NO: 12. In another aspect, the parent comprises or consists of the mature polypeptide of SEQ ID NO: 12. In another aspect, the parent comprises or consists of amino acids 1 to 437 of SEQ ID NO: 12.

In another aspect, the parent comprises or consists of the amino acid sequence of SEQ ID NO: 14. In another aspect, the parent comprises or consists of the mature polypeptide of SEQ ID NO: 14. In another aspect, the parent comprises or consists of amino acids 1 to 507 of SEQ ID NO: 14.

In another aspect, the parent comprises or consists of the amino acid sequence of SEQ ID NO: 16. In another aspect, the parent comprises or consists of the mature polypeptide of SEQ ID NO: 16. In another aspect, the parent comprises or consists of amino acids 1 to 507 of SEQ ID NO: 16.

In another aspect, the parent comprises or consists of the amino acid sequence of SEQ ID NO: 18. In another aspect, the parent comprises or consists of the mature polypeptide of SEQ ID NO: 18. In another aspect, the parent comprises or consists of amino acids 1 to 437 of SEQ ID NO: 18.

In another aspect, the parent comprises or consists of the amino acid sequence of SEQ ID NO: 20. In another aspect, the parent comprises or consists of the mature polypeptide of SEQ ID NO: 20. In another aspect, the parent comprises or consists of amino acids 1 to 430 of SEQ ID NO: 20.

In another aspect, the parent comprises or consists of the amino acid sequence of SEQ ID NO: 22. In another aspect, the parent comprises or consists of the mature polypeptide of SEQ ID NO: 22. In another aspect, the parent comprises or consists of amino acids 1 to 511 of SEQ ID NO: 22.

In another aspect, the parent is a fragment of the mature polypeptide of SEQ ID NO: 2 containing at least 420 amino acid residues, e.g., at least 445 amino acid residues or at least 470 amino acid residues.

In another aspect, the parent is a fragment of the mature polypeptide of SEQ ID NO: 8 containing at 430 amino acid residues, e.g., at least 455 amino acid residues or at least 480 amino acid residues.

In another aspect, the parent is a fragment of the mature polypeptide of SEQ ID NO: 10 containing at least 380 amino acid residues, e.g., at least 400 amino acid residues or at least 420 amino acid residues.

In another aspect, the parent is a fragment of the mature polypeptide of SEQ ID NO: 12 containing at least 380 amino acid residues, e.g., at least 400 amino acid residues or at least 420 amino acid residues.

In another aspect, the parent is a fragment of the mature polypeptide of SEQ ID NO: 14 containing at least 430 amino acid residues, e.g., at least 455 amino acid residues or at least 480 amino acid residues.

In another aspect, the parent is a fragment of the mature polypeptide of SEQ ID NO: 16 containing at least 430 amino acid residues, e.g., at least 455 amino acid residues or at least 480 amino acid residues.

In another aspect, the parent is a fragment of the mature polypeptide of SEQ ID NO: 18 containing at least 380 amino acid residues, e.g., at least 400 amino acid residues or at least 420 amino acid residues.

In another aspect, the parent is a fragment of the mature polypeptide of SEQ ID NO: 20 containing at least 370 amino acid residues, e.g., at least 390 amino acid residues or at least 410 amino acid residues.

In another aspect, the parent is a fragment of the mature polypeptide of SEQ ID NO: 22 containing at least 435 amino acid residues, e.g., at least 460 amino acid residues or at least 485 amino acid residues.

In another aspect, the parent is encoded by a polynucleotide that hybridizes under very low stringency conditions, low stringency conditions, medium stringency conditions, medium-high stringency conditions, high stringency conditions, or very high stringency conditions with the mature polypeptide coding sequence of SEQ ID NO: 1, SEQ ID NO: 3, or SEQ ID NO: 4; or the full-length complement thereof (Sambrook et al., 1989, *Molecular Cloning, A Laboratory Manual,* 2d edition, Cold Spring Harbor, New York).

In another aspect, the parent is encoded by a polynucleotide that hybridizes under low stringency conditions, medium stringency conditions, medium-high stringency conditions, high stringency conditions, or very high stringency conditions with the mature polypeptide coding sequence of SEQ ID NO: 7; or the full-length complement thereof (Sambrook et al., 1989, supra).

In another aspect, the parent is encoded by a polynucleotide that hybridizes under low stringency conditions, medium stringency conditions, medium-high stringency conditions, high stringency conditions, or very high stringency conditions with the mature polypeptide coding sequence of SEQ ID NO: 9; or the full-length complement thereof (Sambrook et al., 1989, supra).

In another aspect, the parent is encoded by a polynucleotide that hybridizes under low stringency conditions, medium stringency conditions, medium-high stringency conditions, high stringency conditions, or very high stringency conditions with the mature polypeptide coding sequence of SEQ ID NO: 11; or the full-length complement thereof (Sambrook et al., 1989, supra).

In another aspect, the parent is encoded by a polynucleotide that hybridizes under low stringency conditions, medium stringency conditions, medium-high stringency conditions, high stringency conditions, or very high stringency conditions with the mature polypeptide coding sequence of SEQ ID NO: 13; or the full-length complement thereof (Sambrook et al., 1989, supra).

In another aspect, the parent is encoded by a polynucleotide that hybridizes under low stringency conditions, medium stringency conditions, medium-high stringency conditions, high stringency conditions, or very high stringency conditions with the mature polypeptide coding sequence of SEQ ID NO: 15; or the full-length complement thereof (Sambrook et al., 1989, supra).

In another aspect, the parent is encoded by a polynucleotide that hybridizes under low stringency conditions, medium stringency conditions, medium-high stringency conditions, high stringency conditions, or very high stringency conditions with the mature polypeptide coding sequence of SEQ ID NO: 17; or the full-length complement thereof (Sambrook et al., 1989, supra).

In another aspect, the parent is encoded by a polynucleotide that hybridizes under low stringency conditions, medium stringency conditions, medium-high stringency conditions, high stringency conditions, or very high stringency conditions with the mature polypeptide coding sequence of SEQ ID NO: 19; or the full-length complement thereof (Sambrook et al., 1989, supra).

In another aspect, the parent is encoded by a polynucleotide that hybridizes under low stringency conditions, medium stringency conditions, medium-high stringency conditions, high stringency conditions, or very high stringency conditions with the mature polypeptide coding sequence of SEQ ID NO: 21; or the full-length complement thereof (Sambrook et al., 1989, supra).

The polynucleotide of SEQ ID NO: 1, SEQ ID NO: 3, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21, or a subsequence thereof, as well as the polypeptide of SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22, or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21, or a subsequence thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 3, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21; (ii) the mature polypeptide coding sequence of SEQ ID NO: 1, SEQ ID NO: 3, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1, SEQ ID NO: 3, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21. In another aspect, the nucleic acid probe is nucleotides 52 to 1673 of SEQ ID NO: 1, nucleotides 52 to 1542 of SEQ ID NO: 3, nucleotides 52 to 1542 of SEQ ID NO: 4, nucleotides 79 to 1596 of SEQ ID NO: 7, nucleotides 52 to 1371 of SEQ ID NO: 9, nucleotides 55 to 1482 of SEQ ID NO: 11, nucleotides 76 to 1596 of SEQ ID NO: 13, nucleotides 76 to 1596 of SEQ ID NO: 15, nucleotides 55 to 1504 of SEQ ID NO: 17, nucleotides 61 to 1350 of SEQ ID NO: 19, or nucleotides 55 to 1587 of SEQ ID NO: 21. In another aspect, the nucleic acid probe is a polynucleotide that encodes the polypeptide of SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22; the mature polypeptide thereof; or a fragment thereof. In another aspect, the nucleic acid probe is SEQ ID NO: 1, SEQ ID NO: 3, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21.

In another aspect, the parent is encoded by a polynucleotide having a sequence identity to the mature polypeptide coding sequence of SEQ ID NO: 1, SEQ ID NO: 3, or SEQ ID NO: 4 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another aspect, the parent is encoded by a polynucleotide having a sequence identity to the mature polypeptide coding sequence of SEQ ID NO: 7 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another aspect, the parent is encoded by a polynucleotide having a sequence identity to the mature polypeptide coding sequence of SEQ ID NO: 9 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another aspect, the parent is encoded by a polynucleotide having a sequence identity to the mature polypeptide coding sequence of SEQ ID NO: 11 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another aspect, the parent is encoded by a polynucleotide having a sequence identity to the mature polypeptide coding sequence of SEQ ID NO: 13 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another aspect, the parent is encoded by a polynucleotide having a sequence identity to the mature polypeptide coding sequence of SEQ ID NO: 15 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another aspect, the parent is encoded by a polynucleotide having a sequence identity to the mature polypeptide coding sequence of SEQ ID NO: 17 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another aspect, the parent is encoded by a polynucleotide having a sequence identity to the mature polypeptide coding sequence of SEQ ID NO: 19 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another aspect, the parent is encoded by a polynucleotide having a sequence identity to the mature polypeptide coding sequence of SEQ ID NO: 21 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the parent is an allelic variant of the mature polypeptide of SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22.

The parent may also be a hybrid or chimeric polypeptide in which a region of parent is replaced with a region of another polypeptide. In one aspect, the region is a carbohydrate binding domain. The carbohydrate binding domain of a parent may be replaced with another (heterologous) carbohydrate binding domain.

The parent may also be a fusion polypeptide or cleavable fusion polypeptide in which another polypeptide is fused at the N-terminus or the C-terminus of the parent. In one aspect, the other polypeptide is a carbohydrate binding domain. The catalytic domain of a parent without a carbohydrate binding domain may be fused to a carbohydrate binding domain. A fusion polypeptide is produced by fusing a polynucleotide encoding another polypeptide to a polynucleotide encoding a parent. Techniques for producing fusion polypeptides are described supra. A fusion polypeptide can further comprise a cleavage site between the two polypeptides as described supra.

In one embodiment, the parent is a hybrid polypeptide in which the carbohydrate binding domain of the parent is replaced with a different carbohydrate binding domain. In another embodiment, the parent is a fusion protein in which a heterologous carbohydrate binding domain is fused to the parent without a carbohydrate binding domain. In one aspect, the carbohydrate binding domain is fused to the N-terminus of the parent. In another aspect, the carbohydrate binding domain is fused to the C-terminus of the parent. In another aspect, the fusion protein comprises or consists of SEQ ID NO: 73 or the mature polypeptide thereof. The polynucleotide of SEQ ID NO: 72 encodes the polypeptide of SEQ ID NO: 73.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a filamentous fungal cellobiohydrolase. For example, the parent may be a filamentous fungal cellobiohydrolase such as an *Aspergillus, Chaetomium, Chrysosporium, Myceliophthora, Penicillium, Talaromyces, Thermoascus,* or *Trichoderma* cellobiohydrolase.

In one aspect, the parent is an *Aspergillus aculeatus, Aspergillus awamori, Aspergillus foetidus, Aspergillus fumigatus, Aspergillus japonicus, Aspergillus nidulans, Aspergillus niger, Aspergillus oryzae, Chaetomium thermophilum, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Myceliophthora thermophila, Penicillium emersonii, Penicillium funiculosum, Penicillium purpurogenum, Talaromyces byssochlamydoides, Talaromyces emersonii, Talaromyces leycettanus, Trichoderma harzianum, Trichoderma koningii, Trichoderma longibrachiaturn, Trichoderma reesei,* or *Trichoderma viride* cellobiohydrolase.

In another aspect, the parent is a *Trichoderma reesei* cellobiohydrolase, e.g., the cellobiohydrolase of SEQ ID NO: 2 or the mature polypeptide thereof.

In another aspect, the parent is an *Aspergillus fumigatus* cellobiohydrolase, e.g., the cellobiohydrolase of SEQ ID NO: 8 or the mature polypeptide thereof.

In another aspect, the parent is a *Thermoascus aurantiacus* cellobiohydrolase, e.g., the cellobiohydrolase of SEQ ID NO: 10 or the mature polypeptide thereof.

In another aspect, the parent is a *Penicillium emersonii* (*Rasamsonia emersonii*) cellobiohydrolase, e.g., the cellobiohydrolase of SEQ ID NO: 12 or the mature polypeptide thereof.

In another aspect, the parent is a *Talaromyces leycettanus* cellobiohydrolase, e.g., the cellobiohydrolase of SEQ ID NO: 14 or the mature polypeptide thereof.

In another aspect, the parent is another *Talaromyces leycettanus* cellobiohydrolase, e.g., the cellobiohydrolase of SEQ ID NO: 16 or the mature polypeptide thereof. In another aspect, the parent is a *Talaromyces byssochlamydoides* cellobiohydrolase, e.g., the cellobiohydrolase of SEQ ID NO: 18 or the mature polypeptide thereof.

In another aspect, the parent is another *Myceliophthora thermophila* cellobiohydrolase, e.g., the cellobiohydrolase of SEQ ID NO: 20 or the mature polypeptide thereof.

In another aspect, the parent is another *Chaetomium thermophilum* cellobiohydrolase, e.g., the cellobiohydrolase of SEQ ID NO: 22 or the mature polypeptide thereof.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a cellobiohydrolase variant, comprising: (a) introducing into a parent cellobiohydrolase deletions at two or more consecutive positions of the B2-loop, wherein the variant has cellobiohydrolase activity; and optionally (b) recovering the variant.

The present invention also relates to methods for obtaining a cellobiohydrolase variant, comprising: (a) introducing into a parent cellobiohydrolase a deletion at one or more positions corresponding to positions 195, 196, 197, and 198 of SEQ ID NO: 2, wherein the variant has cellobiohydrolase activity; and optionally (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent. Any site-directed mutagenesis procedure can be used in the present invention. There are many commercial kits available that can be used to prepare variants.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Site-saturation mutagenesis systematically replaces a polypeptide coding sequence with sequences encoding all 19 amino acids at one or more (e.g., several) specific positions (Parikh and Matsumura, 2005, *J. Mol. Biol.* 352: 621-628).

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide recognized by a host cell for expression of a polynucleotide encoding a variant of the present invention. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the variant. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active variant by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a variant and the signal peptide sequence is positioned next to the N-terminus of the propeptide sequence.

It may also be desirable to add regulatory sequences that regulate expression of the variant relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked to the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Talaromyces emersonii, Thielavia terrestris, Trametes villosa, Trametes versicolor, Trichoderma harzianum, Trichoderma koningii, Trichoderma longibrachiatum, Trichoderma reesei, or Trichoderma viride cell.

Fungal cells may be transformed by a process involving protoplast formation, transformation of the protoplasts, and regeneration of the cell wall in a manner known per se. Suitable procedures for transformation of Aspergillus and Trichoderma host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming Fusarium species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp. 182-187, Academic Press, Inc., New York; Ito et al., 1983, J. Bacteriol. 153: 163; and Hinnen et al., 1978, Proc. Natl. Acad. Sci. USA 75: 1920.

Methods of Production

The present invention also relates to methods of producing a variant, comprising (a) cultivating a recombinant host cell of the present invention under conditions conducive for production of the variant; and optionally (b) recovering the variant.

The host cells are cultivated in a nutrient medium suitable for production of the variant using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variants may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation. In one aspect, a whole fermentation broth comprising a variant of the present invention is recovered.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

Fermentation Broth Formulations or Cell Compositions

The present invention also relates to a fermentation broth formulation or a cell composition comprising a variant of the present invention. The fermentation broth product further comprises additional ingredients used in the fermentation process, such as, for example, cells (including, the host cells containing the gene encoding the variant of the present invention which are used to produce the variant), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, a catalase, an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Enzyme Compositions

The present invention also relates to compositions comprising a variant of the present invention. Preferably, the compositions are enriched in such a variant. The term "enriched" indicates that the cellobiohydrolase activity of the composition has been increased, e.g., with an enrichment factor of at least 1.1.

The compositions may comprise a variant of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, a GH61 polypeptide having cellulolytic enhancing activity, a catalase, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase. The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The present invention is also directed to the following processes for using the variants having cellobiohydrolase I activity of the present invention, or compositions thereof.

The present invention also relates to processes for degrading a cellulosic material, comprising: treating the cellulosic material with an enzyme composition in the presence of a cellobiohydrolase variant of the present invention. In one aspect, the processes further comprise recovering the degraded cellulosic material. Soluble products of degradation of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition in the presence of a cellobiohydrolase variant of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a cellobiohydrolase variant of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel (ethanol, n-butanol, isobutanol, biodiesel, jet fuel) and/or platform chemicals (e.g., acids, alcohols, ketones, gases, oils, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd et al., 2002, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technol.* 100: 10-18; Mosier et al., 2005, *Bioresource Technol.* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technology* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment.

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber expansion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.* 105-108: 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic material and held at a temperature in the range of preferably 140-200° C., e.g., 165-190° C., for periods from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a cellobiohydrolase variant of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzymes(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 4.5 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a ligninolytic enzyme, an oxidoreductase, a pectinase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another aspect, the oxidoreductase is preferably one or more (e.g., several) enzymes selected from the group consisting of a catalase, a laccase, and a peroxidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a GH61 polypeptide having cellulolytic enhancing activity. In another aspect, the enzyme composition comprises an endoglucanase and a GH61 polypeptide having cellulolytic enhancing activity. In another aspect, the enzyme composition comprises a cellobiohydrolase and a GH61 polypeptide having cellulolytic enhancing activity. In another aspect, the enzyme composition comprises a beta-glucosidase and a GH61 polypeptide having cellulolytic enhancing activity. In another aspect, the enzyme composition comprises an endoglucanase and a cellobiohydrolase. In another aspect, the enzyme composition comprises an endoglucanase and a cellobiohydrolase I, a cellobiohydrolase II, or a combination of a cellobiohydrolase I and a cellobiohydrolase I and a cellobiohydrolase II. In another aspect, the enzyme composition comprises an endoglucanase and a beta-glucosidase. In another aspect, the enzyme composition comprises a beta-glucosidase and a cellobiohydrolase. In another aspect, the enzyme composition comprises a beta-glucosidase and a cellobiohydrolase I, a cellobiohydrolase II, or a combination of a cellobiohydrolase I and a cellobiohydrolase II In another aspect, the enzyme composition comprises an endoglucanase, a GH61 polypeptide having cellulolytic enhancing activity, and a cellobiohydrolase. In another aspect, the enzyme composition comprises an endoglucanase, a GH61 polypeptide having cellulolytic enhancing activity, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and a GH61 polypeptide having cellulolytic enhancing activity. In another aspect, the enzyme composition comprises a beta-glucosidase, a GH61 polypeptide having cellulolytic enhancing activity, and a cellobiohydrolase. In another aspect, the enzyme composition comprises a beta-glucosidase, a GH61 polypeptide having cellulolytic enhancing activity, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and a cellobiohydrolase. In another aspect, the enzyme composition comprises an endoglucanase, a beta-glucosidase, and a cellobiohydrolase I, a cellobiohydrolase II, or a combination of a cellobiohydrolase I and a cellobiohydrolase II. In another aspect, the enzyme composition comprises an endoglucanase, a cellobiohydrolase, a beta-glucosidase, and a GH61 polypeptide having cellulolytic enhancing activity. In another aspect, the enzyme composition comprises an endoglucanase, a beta-glucosidase, a GH61 polypeptide having cellulolytic enhancing activity, and a cellobiohydrolase I, a cellobiohydrolase II, or a combination of a cellobiohydrolase I and a cellobiohydrolase II.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another preferred aspect, the xylanase is a Family 11 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a H$_2$O$_2$-producing enzyme. In another aspect, the enzyme composition comprises a pectinase. In another aspect, the enzyme composition comprises an oxidoreductase. In another preferred aspect, the oxidoreductase is a catalase. In another preferred aspect, the oxidoreductase is a laccase. In another preferred aspect, the oxidoreductase is a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be native proteins, recombinant proteins, or a combination of native proteins and recombinant proteins. For example, one or more (e.g., several) components may be native proteins of a cell, which is used as a host cell to express recombinantly one or more (e.g., several) other components of the enzyme composition. It is understood herein that the recombinant proteins may be heterologous (e.g., foreign) and native to the host cell. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and the cellobiohydrolase variant depend on several factors including, but not limited to, the mixture of component cellulolytic enzymes and/or hemicellulolytic enzymes, the cellulosic material, the concentration of cellulosic material, the pretreatment(s) of the cellulosic material, temperature, time, pH, and inclusion of fermenting organism (e.g., for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a cellobiohydrolase variant to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a cellobiohydrolase variant to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material, e.g., GH61 polypeptides having cellulolytic enhancing activity, (collectively hereinafter "polypeptides having enzyme activity") can be derived or obtained from any suitable origin, including, archaeal, bacterial, fungal, yeast, plant, or animal origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained by, for example, site-directed mutagenesis or shuffling.

A polypeptide having enzyme activity may be a bacterial polypeptide. For example, the polypeptide may be a Gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia,* or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having enzyme activity.

In another aspect, the polypeptide is a *Streptococcus equisimilis, Streptococcus pyogenes, Streptococcus uberis,* or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus,* or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces,* or *Yarrowia* polypeptide having enzyme activity; or more preferably a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus,*

*Thielavia, Tolypocladium, Trichoderma, Trichophaea, Verticillium, Volvariella,* or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminurn, Fusarium heterosporum, Fusarium negundi, Fusarium oxysporum, Fusarium reticulaturn, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianurn, Trichoderma koningii, Trichoderma longibrachiatum, Trichoderma reesei, Trichoderma viride,* or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host can be a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes NS), CELLIC® CTec2 (Novozymes NS), CELLIC® CTec3 (Novozymes NS), CELLUCLAST™ (Novozymes NS), NOVOZYM™ 188 (Novozymes NS), SPEZYME™ CP (Genencor Int.), ACCELLERASE™ TRIO (DuPont), FILTRASE® NL (DSM); METHAPLUS® S/L 100 (DSM), ROHAMENT™ 7069 W (Röhm GmbH), or ALTERNAFUEL® CMAX3™ (Dyadic International, Inc.). The cellulolytic enzyme preparation is added in an amount effective from about 0.001 to about 5.0 wt. % of solids, e.g., about 0.025 to about 4.0 wt. % of solids or about 0.005 to about 2.0 wt. % of solids.

Examples of bacterial endoglucanases that can be used in the processes of the present invention, include, but are not limited to, *Acidothermus cellulolyticus* endoglucanase (WO 91/05039; WO 93/15186; U.S. Pat. No. 5,275,944; WO 96/02551; U.S. Pat. No. 5,536,655; WO 00/70031; WO 05/093050), *Erwinia carotovara* endoglucanase (Saarilahti et al., 1990, *Gene* 90: 9-14), *Thermobifida fusca* endoglucanase III (WO 05/093050), and *Thermobifida fusca* endoglucanase V (WO 05/093050).

Examples of fungal endoglucanases that can be used in the present invention, include, but are not limited to, *Trichoderma reesei* endoglucanase I (Penttila et al., 1986, *Gene* 45: 253-263, *Trichoderma reesei* Cel7B endoglucanase I (GenBank:M15665), *Trichoderma reesei* endoglucanase II (Saloheimo et al., 1988, *Gene* 63:11-22), *Trichoderma reesei* Cel5A endoglucanase II (GenBank: M19373), *Trichoderma reesei* endoglucanase III (Okada et al., 1988, *Appl. Environ. Microbiol.* 64: 555-563, GenBank: AB003694), *Trichoderma reesei* endoglucanase V (Saloheimo et al., 1994, *Molecular Microbiology* 13: 219-228, GenBank:Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Fusarium oxysporum* endoglucanase (GenBank:L29381), *Humicola grisea* var. *thermoidea* endoglucanase (GenBank:AB003107), *Melanocarpus albomyces* endoglucanase (GenBank:MAL515703), *Neurospora crassa* endoglucanase (Gen Bank: XM_324477), *Humicola insolens* endoglucanase V, *Myceliophthora thermophila* CBS 117.65 endoglucanase, *Thermoascus aurantiacus* endoglucanase I (GenBank: AF487830), *Trichoderma reesei* strain No. VTT-D-80133 endoglucanase (GenBank:M15665), and *Penicillium pinophilum* endoglucanase (WO 2012/062220).

Examples of cellobiohydrolases useful in the present invention include, but are not limited to, *Aspergillus aculeatus* cellobiohydrolase II (WO 2011/059740), *Aspergillus fumigatus* cellobiohydrolase I (WO 2013/028928), *Aspergillus fumigatus* cellobiohydrolase II (WO 2013/028928), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Penicillium occitanis* cellobiohydrolase I (GenBank:AY690482), *Talaromyces emersonii* cellobiohydrolase I (GenBank:AF439936), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 02/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Other useful endoglucanases, cellobiohydrolases, and beta-glucosidases are disclosed in numerous Glycosyl Hydrolase families using the classification according to Henrissat, 1991, *Biochem. J.* 280: 309-316, and Henrissat and Bairoch, 1996, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593.

In the processes of the present invention, any GH61 polypeptide having cellulolytic enhancing activity can be used as a component of the enzyme composition.

Examples of GH61 polypeptides useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290 and WO 2012/149344), *Myceliophthora thermophila* (WO 2009/085935, WO 2009/085859, WO 2009/085864, WO 2009/085868, and WO 2009/033071), *Aspergillus fumigatus* (WO 2010/138754), *Penicillium pinophilum* (WO 2011/005867), *Thermoascus* sp. (WO 2011/039319), *Penicillium* sp. (*emersonii*) (WO 2011/041397 and WO 2012/000892), *Thermoascus crustaceous* (WO 2011/041504), *Aspergillus aculeatus* (WO 2012/125925), *Thermomyces lanuginosus* (WO 2012/113340, WO 2012/129699, WO 2012/130964, and WO 2012/129699), *Aurantiporus alborubescens* (WO 2012/122477), *Trichophaea saccata* (WO 2012/122477), *Penicillium thomii* (WO 2012/122477), *Talaromyces stipitatus* (WO 2012/135659), *Humicola insolens* (WO 2012/146171), *Malbranchea cinnamomea* (WO 2012/101206), *Talaromyces leycettanus* (WO 2012/101206), and *Chaetomium thermophilum* (WO 2012/101206), and *Talaromyces thermophilus* (WO 2012/129697 and WO 2012/130950).

In one aspect, the GH61 polypeptide having cellulolytic enhancing activity is used in the presence of a soluble activating divalent metal cation according to WO 2008/151043, e.g., manganese or copper.

In another aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4′-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothienopyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4- benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above is added to cellulosic material at a molar ratio of the compound to glucosyl units of cellulose of about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described in WO 2012/021401, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulolytic enzyme preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes NS), CELLIC® HTec (Novozymes NS), CELLIC® HTec2 (Novozymes NS), CELLIC® HTec3 (Novozymes NS), VISCOZYME® (Novozymes NS), ULTRAFLO® (Novozymes NS), PULPZYME® HC (Novozymes NS), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK), ALTERNA FUEL 100P (Dyadic), and ALTERNA FUEL 200P (Dyadic).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thermomyces lanuginosus* (GeneSeqP: BAA22485), *Talaromyces thermophilus* (GeneSeqP: BAA22834), *Thielavia terrestris* NRRL 8126 (WO 2009/079210), and *Trichophaea saccata* (WO 2011/057083).

Examples of beta-xylosidases useful in the processes of the present invention include, but are not limited to, beta-xylosidases from *Neurospora crassa* (SwissProt:Q7SOW4), *Trichoderma reesei* (UniProtKB/TrEMBL:Q92458), *Talaromyces emersonii* (SwissProt:Q8X212), and *Talaromyces thermophilus* (GeneSeqP:BAA22816).

Examples of acetylxylan esterases useful in the processes of the present invention include, but are not limited to, acetylxylan esterases from *Aspergillus aculeatus* (WO 2010/108918), *Chaetomium globosum* (UniProt:Q2GWX4), *Chaetomium gracile* (GeneSeqP:AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt:q7s259), *Phaeosphaeria nodorum* (UniProt:Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt:A1 D9T4), *Neurospora crassa* (UniProt:Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP: AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt: alcc12), *Aspergillus fumigatus* (SwissProt:Q4WW45), *Aspergillus niger* (UniProt:Q96WX9), *Aspergillus terreus* (SwissProt:Q0CJ P9), *Humicola insolens* (WO 2010/014706), *Penicillium aurantiogriseum* (WO 2009/068565), *Talaromyces emersonii* (UniProt:Q8X211), and *Trichoderma reesei* (UniProt:Q99024).

Examples of oxidoreductases useful in the processes of the present invention include, but are not limited to, *Aspergillus fumigatus* catalase, *Aspergillus lentilus* catalase, *Aspergillus niger* catalase, *Aspergillus oryzae* catalase, *Humicola insolens* catalase, *Neurospora crassa* catalase, *Penicillium emersonii* catalase, *Scytalidium thermophilum* catalase, *Talaromyces stipitatus* catalase, *Thermoascus aurantiacus* catalase, *Coprinus cinereus* laccase, *Myceliophthora thermophila* laccase, *Polyporus pinsitus* laccase, *Pycnoporus cinnabarinus* laccase, *Rhizoctonia solani* laccase, *Streptomyces coelicolor* laccase, *Coprinus cinereus* peroxidase, Soy peroxidase, and Royal palm peroxidase.

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous.

Any suitable hydrolyzed cellulosic material can be used in the fermentation step in practicing the present invention. The material is generally selected based on economics, i.e., costs per equivalent sugar potential, and recalcitrance to enzymatic conversion.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Yeast include strains of *Candida*, *Kluyveromyces*, and *Saccharomyces*, e.g., *Candida sonorensis*, *Kluyveromyces marxianus*, and *Saccharomyces cerevisiae*.

Examples of fermenting organisms that can ferment pentose sugars in their native state include bacterial and fungal organisms, such as some yeast. Xylose fermenting yeast include strains of *Candida*, preferably *C. sheatae* or *C. sonorensis*; and strains of *Pichia*, e.g., *P. stipitis*, such as *P. stipitis* CBS 5773. Pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans*, *Clostridium acetobutylicum*, *Clostridium thermocellum*, *Clostridium phytofermentans*, *Geobacillus* sp., *Thermoanaerobacter saccharolyticum*, and *Zymomonas mobilis* (Philippidis, G. P., 1996, Cellulose bioconversion technology, in *Handbook on Bioethanol: Production and Utilization*, Wyman, C. E., ed., Taylor & Francis, Washington, D.C., 179-212).

Other fermenting organisms include strains of *Bacillus*, such as *Bacillus coagulans*; *Candida*, such as *C. sonorensis*, *C. methanosorbosa*, *C. diddensiae*, *C. parapsilosis*, *C. naedodendra*, *C. blankii*, *C. entomophilia*, *C. brassicae*, *C. pseudotropicalis*, *C. boidinii*, *C. utilis*, and *C. scehatae*; *Clostridium*, such as *C. acetobutylicum*, *C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus*, *K. lactis*, *K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In an aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, *Appl. Biochem. Biotechnol.* 39-40: 135-147; Ho et al., 1998, *Appl. Environ. Microbiol.* 64: 1852-1859; Kotter and Ciriacy, 1993, *Appl. Microbiol. Biotechnol.* 38: 776-783; Walfridsson et al., 1995, *Appl. Environ. Microbiol.* 61: 4184-4190; Kuyper et al., 2004, *FEMS Yeast Research* 4: 655-664; Beall et al., 1991, *Biotech. Bioeng.* 38: 296-303; Ingram et al., 1998, *Biotechnol. Bioeng.* 58: 204-214; Zhang et al., 1995, *Science* 267: 240-243; Deanda et al., 1996, *Appl. Environ. Microbiol.* 62: 4465-4470; WO 03/062430).

In one aspect, the fermenting organism comprises a polynucleotide encoding a variant of the present invention.

In another aspect, the fermenting organism comprises one or more polynucleotides encoding one or more cellulolytic enzymes, hemicellulolytic enzymes, and accessory enzymes described herein.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide.

In one aspect, the fermentation product is an alcohol. The term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603.

In another aspect, the fermentation product is an alkane. The alkane may be an unbranched or a branched alkane. The alkane can be, but is not limited to, pentane, hexane, heptane, octane, nonane, decane, undecane, or dodecane.

In another aspect, the fermentation product is a cycloalkane. The cycloalkane can be, but is not limited to, cyclopentane, cyclohexane, cycloheptane, or cyclooctane.

In another aspect, the fermentation product is an alkene. The alkene may be an unbranched or a branched alkene. The alkene can be, but is not limited to, pentene, hexene, heptene, or octene.

In another aspect, the fermentation product is an amino acid. The organic acid can be, but is not limited to, aspartic acid, glutamic acid, glycine, lysine, serine, or threonine. See, for example, Richard and Margaritis, 2004, *Biotechnology and Bioengineering* 87(4): 501-515.

In another aspect, the fermentation product is a gas. The gas can be, but is not limited to, methane, $H_2$, $CO_2$, or CO. See, for example, Kataoka et al., 1997, *Water Science and Technology* 36(6-7): 41-47; and Gunaseelan, 1997, *Biomass and Bioenergy* 13(1-2): 83-114.

In another aspect, the fermentation product is isoprene.

In another aspect, the fermentation product is a ketone. The term "ketone" encompasses a substance that contains one or more ketone moieties. The ketone can be, but is not limited to, acetone.

In another aspect, the fermentation product is an organic acid. The organic acid can be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Plants

The present invention also relates to isolated plants, e.g., a transgenic plant, plant part, or plant cell, comprising a polynucleotide of the present invention so as to express and produce a cellobiohydrolase variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed (Sticklen, 2008, *Nature Reviews* 9: 433-443). For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and optionally (b) recovering the variant.

The present invention may be further described by the following numbered paragraphs:

[1] A cellobiohydrolase variant, comprising deletions at two or more consecutive positions corresponding to positions of the B2-loop, wherein the variant has cellobiohydrolase activity, and wherein the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the mature polypeptide of a parent cellobiohydrolase.

[2] A cellobiohydrolase variant, comprising a deletion at one or more positions corresponding to positions 195, 196, 197, and 198 of SEQ ID NO: 2, wherein the variant has cellobiohydrolase activity, and wherein the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the mature polypeptide of a parent cellobiohydrolase.

[3] The variant of paragraph 1 or 2, wherein the parent cellobiohydrolase is selected from the group consisting of: (a) a polypeptide having at least 60% sequence identity to the mature polypeptide of SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22; (b) a polypeptide encoded by a polynucleotide that hybridizes under low stringency conditions with the mature polypeptide coding sequence of SEQ ID NO: 1, SEQ ID NO: 3, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21; or the full-length complement thereof; (c) a polypeptide encoded by a polynucleotide having at least 60% identity to the mature polypeptide coding sequence of SEQ ID NO: 1, SEQ ID NO: 3, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21; and (d) a fragment of the mature polypeptide of SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22, which has cellobiohydrolase activity.

[4] The variant of paragraph 3, wherein the parent cellobiohydrolase has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, at least 99%, or 100% sequence identity to the mature polypeptide of SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22.

[5] The variant of paragraph 3 or 4, wherein the parent cellobiohydrolase is encoded by a polynucleotide that hybridizes under low stringency conditions, medium stringency conditions, medium-high stringency conditions, high stringency conditions, or very high stringency conditions with the mature polypeptide coding sequence of SEQ ID NO: 1, SEQ ID NO: 3, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21; or the full-length complement thereof.

[6] The variant of any of paragraphs 3-5, wherein the parent cellobiohydrolase is encoded by a polynucleotide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, at least 99%, or 100% sequence identity to the mature polypeptide coding sequence of SEQ ID NO: 1, SEQ ID NO: 3, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21.

[7] The variant of any of paragraphs 3-6, wherein the parent cellobiohydrolase comprises or consists of the mature polypeptide of SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22.

[8] The variant of any of paragraphs 3-7, wherein the parent cellobiohydrolase is a fragment of the mature polypeptide of SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22, wherein the fragment has cellobiohydrolase activity.

[9] The variant of any of paragraphs 1-8, which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 95% identity, at least 96%, at least 97%, at least 98%, or at least 99%, but less than 100%, sequence identity to the amino acid sequence of the parent cellobiohydrolase or the mature polypeptide thereof.

[10] The variant of any of paragraphs 1-9, wherein the number of alterations is 1-7, e.g., 1, 2, 3, 4, 5, 6, and 7 alterations.

[11] The variant of any of paragraphs 1, or 3-10, which comprises deletions at positions corresponding to positions 195 and 196 of SEQ ID NO: 2 (e.g., S195*+S196*, or S195*+A196*).

[12] The variant of any of paragraphs 1, or 3-10, which comprises deletions at positions corresponding to positions 196 and 197 of SEQ ID NO: 2 (e.g., S196*+N197*, or A196*+N197*)

[13] The variant of any of paragraphs 1, or 3-10, which comprises deletions at positions corresponding to positions 197 and 198 of SEQ ID NO: 2 (e.g., N197*+N198*, N197*+D198*).

[14] The variant of any of paragraphs 1, or 3-10, which comprises deletions at positions corresponding to positions 198 and 199 of SEQ ID NO: 2 (e.g., N198*+A199*, D198*+A199*, or D198*+P199*).

[15] The variant of any of paragraphs 1, or 3-10, which comprises deletions at positions corresponding to positions 199 and 200 of SEQ ID NO: 2 (e.g., A199*+N200*, or P199*+N200*).

[16] The variant of any of paragraphs 1, or 3-10, which comprises deletions at positions corresponding to positions 200 and 201 of SEQ ID NO: 2 (e.g., N200*+T201*, N200*+A201*, or N200*+S201*).

[17] The variant of any of paragraphs 1, or 3-10, which comprises deletions at three or more consecutive positions of the B2-loop (e.g., deletions at positions corresponding to positions 194*+195*+196*, 195*+196*+197*, 196*+197*+198*, 197*+198*+199*, 198*+199*+200*, or 199*+200*+201* of SEQ ID NO: 2).

[18] The variant of any of paragraphs 1, or 3-10, which comprises deletions at four or more consecutive positions of the B2-loop (e.g., deletions at positions corresponding to positions 194*+195*+196*+197*, 195*+196*+197*+198*, 196*+197*+198*+199*, 197*+198*+199*+200*, or 198*+199*+200*+201* of SEQ ID NO: 2).

[19] The variant of any of paragraphs 1, or 3-10, which comprises deletions at five or more consecutive positions of the B2-loop (e.g., deletions at positions corresponding to positions 194*+195*+196*+197*+198*, 195*+196*+197*+198*+199*, 196*+197*+198*+199*+200*, or 197*+198*+199*+200*+201* of SEQ ID NO: 2).

[20] The variant of any of paragraphs 1, or 3-10, which comprises deletions at six or more consecutive positions of the B2-loop. (e.g., deletions at positions corresponding to positions 194*+195*+196*+197*+198*+199*, 195*+196*+197*+198*+199*+200*, or 196*+197*+198*+199*+200*+201* of SEQ ID NO: 2).

[21] The variant of any of paragraphs 1, or 3-10, which comprises deletions at seven or more consecutive positions of the B2-loop (e.g., deletions at positions corresponding to positions 194*+195*+196*+197*+198*+199*+200*, or 195*+196*+197*+198*+199*+200*+201* of SEQ ID NO: 2).

[22] The variant of any of paragraphs 1, or 3-10, which comprises deletions at eight consecutive positions of the B2-loop (e.g., deletions at positions corresponding to positions 194*+195*+196*+197*+198*+199*+200*+201* of SEQ ID NO: 2).

[23] The variant of any of paragraphs 2-10, which comprises a deletion at a position corresponding to position 195 of SEQ ID NO: 2 (e.g., an S195* deletion).

[24] The variant of any of paragraphs 2-11, which comprises a deletion at a position corresponding to position 196 of SEQ ID NO: 2 (e.g., an S196* deletion).

[25] The variant of any of paragraphs 2-12, which comprises a deletion at a position corresponding to position 197 of SEQ ID NO: 2 (e.g., an N197* deletion).

[26] The variant of any of paragraphs 2-13, which comprises a deletion at a position corresponding to position 198 of SEQ ID NO: 2 (e.g., an N198* deletion).

[27] The variant of any of paragraphs 2-10, which comprises a deletion at two positions corresponding to any of positions 195, 196, 197, and 198 of SEQ ID NO: 2 (e.g., 195 and 196, such as S195*+S196*; 195 and 197, such as S195*+N197*; 195 and 198, such as S195*+N198*; 196 and 197, such as S196*+N197*; 196 and 198, such as S196*+N198*; or 197 and 198, such as N197*+N198*

[28] The variant of any of paragraphs 2-10, which comprises a deletion at positions corresponding to positions 196, 197, and 198 of SEQ ID NO: 2 (e.g., S196*+N197*+N198*).

[29] The variant of any of paragraphs 2-10, which comprises a deletion at each position corresponding to positions 195, 196, 197, and 198 of SEQ ID NO: 2 (e.g., S195*+S196*+N197*+N198*).

[30] The variant of any of paragraphs 1-29, wherein the variant further comprises an alteration (e.g., a substitution) at one or more positions corresponding to positions 197, 198, and 199 of SEQ ID NO: 2

[31] The variant of any of paragraphs 1-30, wherein the variant further comprises a deletion at a position corresponding to position 200 of SEQ ID NO: 2.

[32] The variant of paragraph 1 or 2, which comprises or consists of amino acids 1-434 of SEQ ID NO: 78, amino acids 1-495 of SEQ ID NO: 80, amino acids 1-495 of SEQ ID NO: 82, or amino acids 1-503 of SEQ ID NO: 95.

[33] The variant of any of paragraphs 1-31, wherein the parent is a hybrid or chimeric polypeptide in which the carbohydrate binding domain of the parent is replaced with a different carbohydrate binding domain.

[34] The variant of any of paragraphs 1-31, which is a hybrid or chimeric polypeptide in which the carbohydrate binding domain of the variant is replaced with a different carbohydrate binding domain.

[35] The variant of any of paragraphs 1-31, wherein the parent is a fusion protein in which a heterologous carbohydrate binding domain is fused to the parent.

[36] The variant of paragraph 35, wherein the carbohydrate binding domain is fused to the N-terminus or the C-terminus of the parent.

[37] The variant of paragraph 35 or 36, wherein the fusion protein comprises or consists of SEQ ID NO: 78 or the mature polypeptide thereof.

[38] The variant of any of paragraphs 1-31, which is a fusion protein in which a heterologous carbohydrate binding domain is fused to the variant.

[39] The variant of paragraph 38, wherein the carbohydrate binding domain is fused to the N-terminus or the C-terminus of the variant.

[40] The variant of paragraph 38 or 39, which comprises or consists of SEQ ID NO: 78 or the mature polypeptide thereof.

[41] The variant of any of paragraphs 1-40, which has an increased specific performance relative to the parent.

[42] The variant of any of paragraphs 1-41, which is isolated.

[43] An isolated polynucleotide encoding the variant of any of paragraphs 1-42.

[44] A nucleic acid construct or expression vector comprising the polynucleotide of paragraph 43.

[45] A host cell comprising the polynucleotide of paragraph 43.

[46] A method of producing a cellobiohydrolase variant, comprising: cultivating the host cell of paragraph 45 under conditions suitable for expression of the variant.

[47] The method of paragraph 46, further comprising recovering the variant.

[48] A transgenic plant, plant part or plant cell transformed with the polynucleotide of paragraph 43.

[49] A method of producing the variant of any of paragraphs 1-42, comprising: cultivating a transgenic plant or a plant cell comprising a polynucleotide encoding the variant under conditions conducive for production of the variant.

[50] The method of paragraph 49, further comprising recovering the variant

[51] A method for obtaining a cellobiohydrolase variant, comprising introducing into a parent cellobiohydrolase deletions at two or more consecutive positions of the B2-loop, wherein the variant has cellobiohydrolase activity.

[52] A method for obtaining a cellobiohydrolase variant, comprising introducing into a parent cellobiohydrolase a deletion at one or more positions corresponding to positions 195, 196, 197, and 198, of SEQ ID NO: 2, wherein the variant has cellobiohydrolase activity.

[53] The method of paragraph 51 or 52, further comprising recovering the variant.

[54] A composition comprising the variant of any of paragraphs 1-42.

[55] A whole broth formulation or cell culture composition comprising the variant of any of paragraphs 1-42.

[56] A process for degrading a cellulosic material, comprising: treating the cellulosic material with an enzyme composition in the presence of the variant of any of paragraphs 1-42.

[57] The process of paragraph 56, wherein the cellulosic material is pretreated.

[58] The process of paragraph 56 or 57, wherein the enzyme composition comprises one or more enzymes selected from the group consisting of a cellulase, a GH61 polypeptide having cellulolytic enhancing activity, a hemicellulase, a catalase, an esterase, an expansin, a laccase, a ligninolytic enzyme, a pectinase, a peroxidase, a protease, and a swollenin.

[59] The process of paragraph 58, wherein the cellulase is one or more enzymes selected from the group consisting of an endoglucanase, a cellobiohydrolase, and a beta-glucosidase.

[60] The process of paragraph 58, wherein the hemicellulase is one or more enzymes selected from the group consisting of a xylanase, an acetylxylan esterase, a feruloyl esterase, an arabinofuranosidase, a xylosidase, and a glucuronidase.

[61] The process of any of paragraphs 56-60, further comprising recovering the degraded cellulosic material.

[62] The process of paragraph 61, wherein the degraded cellulosic material is a sugar.

[63] The process of paragraph 62, wherein the sugar is selected from the group consisting of glucose, xylose, mannose, galactose, and arabinose.

[64] A process for producing a fermentation product, comprising: (a) saccharifying a cellulosic material with an enzyme composition in the presence of the variant of any of paragraphs 1-42; (b) fermenting the saccharified cellulosic material with one or more fermenting microorganisms to produce the fermentation product; and (c) recovering the fermentation product from the fermentation.

[65] The process of paragraph 64, wherein the cellulosic material is pretreated.

[66] The process of paragraph 64 or 65, wherein the enzyme composition comprises the enzyme composition comprises one or more enzymes selected from the group consisting of a cellulase, a GH61 polypeptide having cellulolytic enhancing activity, a hemicellulase, a catalase, an esterase, an expansin, a laccase, a ligninolytic enzyme, a pectinase, a peroxidase, a protease, and a swollenin.

[67] The process of paragraph 66, wherein the cellulase is one or more enzymes selected from the group consisting of an endoglucanase, a cellobiohydrolase, and a beta-glucosidase.

[68] The process of paragraph 66, wherein the hemicellulase is one or more enzymes selected from the group consisting of a xylanase, an acetylxylan esterase, a feruloyl esterase, an arabinofuranosidase, a xylosidase, and a glucuronidase.

[69] The process of any of paragraphs 64-68, wherein steps (a) and (b) are performed simultaneously in a simultaneous saccharification and fermentation.

[70] The process of any of paragraphs 64-69, wherein the fermentation product is an alcohol, an alkane, a cycloalkane, an alkene, an amino acid, a gas, isoprene, a ketone, an organic acid, or polyketide.

[71] A process of fermenting a cellulosic material, comprising: fermenting the cellulosic material with one or more fermenting microorganisms, wherein the cellulosic material is saccharified with an enzyme composition in the presence of the variant of any of paragraphs 1-42.

[72] The process of paragraph 71, wherein the fermenting of the cellulosic material produces a fermentation product.

[73] The process of paragraph 72, further comprising recovering the fermentation product from the fermentation.

[74] The process of paragraph 72 or 73, wherein the fermentation product is an alcohol, an alkane, a cycloalkane, an alkene, an amino acid, a gas, isoprene, a ketone, an organic acid, or polyketide.

[75] The process of any of paragraphs 71-74, wherein the cellulosic material is pretreated before saccharification.

[76] The process of any of paragraphs 71-75, wherein the enzyme composition comprises one or more enzymes selected from the group consisting of a cellulase, a GH61 polypeptide having cellulolytic enhancing activity, a hemicellulase, a catalase, an esterase, an expansin, a laccase, a ligninolytic enzyme, a pectinase, a peroxidase, a protease, and a swollenin.

[77] The process of paragraph 76, wherein the cellulase is one or more enzymes selected from the group consisting of an endoglucanase, a cellobiohydrolase, and a beta-glucosidase.

[78] The process of paragraph 77, wherein the hemicellulase is one or more enzymes selected from the group consisting of a xylanase, an acetylxylan esterase, a feruloyl esterase, an arabinofuranosidase, a xylosidase, and a glucuronidase.

The present invention is further described by the following examples that should not be construed as limiting the scope of the invention.

EXAMPLES

Strains

*Aspergillus oryzae* strain MT3568 was used as a host for expression of the *Trichoderma reesei* gene encoding cellobiohydrolase I and a variant thereof. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene.

Media and Solutions

COVE sucrose plates or slants were composed of 342 g of sucrose, 20 g of agar powder, 20 ml of COVE salt solution, and deionized water to 1 liter. The medium was sterilized by autoclaving at 15 psi for 15 minutes (Bacteriological Analytical Manual, 8th Edition, Revision A, 1998). The medium was cooled to 60° C. and then acetamide to 10 mM, CsCl to 15 mM, and TRITON® X-100 (50 µl/500 ml) were added.

COVE salt solution was composed of 26 g of $MgSO_4.7H_2O$, 26 g of KCl, 26 g of $KH_2PO_4$, 50 ml of COVE trace metals solution, and deionized water to 1 liter.

COVE trace metals solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionized water to 1 liter.

DAP-4C medium was composed of 20 g of dextrose, 10 g of maltose, 11 g of $MgSO_4.7H_2O$, 1 g of $KH_2PO_4$, 2 g of citric acid, 5.2 g of $K_3PO_4.H_2O$, 0.5 g of yeast extract (Difco), 1 ml of antifoam, 0.5 ml of KU6 trace metals solution, 2.5 g of $CaCO_3$, and deionized water to 1 liter. The medium was sterilized by autoclaving at 15 psi for 15 minutes (Bacteriological Analytical Manual, 8th Edition, Revision A, 1998). Before use, 3.5 ml of sterile 50% $(NH_4)_2HPO_4$ and 5 ml of sterile 20% lactic acid were added per 150 ml.

G2-Gly medium was composed of 18 g of yeast extract, 24 g of glycerol (86-88%), 1 ml of antifoam, and deionized water to 1 liter.

KU6 trace metals solution was composed of 0.13 g of $NiCl_2$, 2.5 g of $CuSO_4.5H_2O$, 13.9 g of $FeSO_4.7H_2O$, 8.45 g of $MnSO_4.H_2O$, 6.8 g of $ZnCl_2$, 3 g of citric acid, and deionized water to 1 liter.

LB medium was composed of 10 g of Bacto-Tryptone, 5 g of yeast extract, 10 g of sodium chloride, and deionized water to 1 liter.

LB plates were composed of 10 g of Bacto-Tryptone, 5 g of yeast extract, 10 g of sodium chloride, 15 g of Bacto-agar, and deionized water to 1 liter.

PDA plates were composed of potato infusion made by boiling 300 g of sliced (washed but unpeeled) potatoes in water for 30 minutes and then decanting or straining the broth through cheesecloth. Distilled water was then added until the total volume of the suspension was 1 liter. Then 20 g of dextrose and 20 g of agar powder were added. The medium was sterilized by autoclaving at 15 psi for 15 minutes (Bacteriological Analytical Manual, 8th Edition, Revision A, 1998).

TAE buffer was composed of 40 mM Tris base, 20 mM sodium acetate, and 1 mM disodium EDTA.

YP+2% glucose medium was composed of 1% yeast extract, 2% peptone, and 2% glucose in deionized water.

YP+2% maltose medium was composed of 10 g of yeast extract, 20 g of peptone, 20 g of maltose, and deionized water to 1 liter.

Example 1: Source of DNA Sequence Information for *Trichoderma reesei* Cellobiohydrolase I The genomic DNA sequence and deduced amino acid sequence of the *Trichoderma reesei* GH7 cellobiohydrolase I gene is shown in SEQ ID NO: 1 and SEQ ID NO: 2, respectively. Genomic sequence information was generated by the U.S. Department of Energy Joint Genome Institute (JGI) and published by Martinez et al., 2008, *Nature Biotechnology* 26 (5): 553-560. The amino acid sequence of the full-length cellobiohydrolase I is publicly available from the National Center for Biotechnology Information (NCBI) and annotated as GenBank: EGR44817.1 (SEQ ID NO: 2). The cDNA sequence and deduced amino acid sequence of the *Trichoderma reesei* cellobiohydrolase I gene is shown in SEQ ID NO: 3 and SEQ ID NO: 2, respectively.

Based on the publicly available amino acid sequence, a codon-optimized synthetic gene encoding the full-length cellobiohydrolase I was generated for *Aspergillus oryzae* expression based on the algorithm developed by Gustafsson et al., 2004, *Trends in Biotechnology* 22 (7): 346-353. The codon-optimized coding sequence (SEQ ID NO: 4) was synthesized by the GENEART® Gene Synthesis service (Life Technologies Corp., San Diego. Calif., USA) with a 5' Bam HI restriction site, a 3' Hind III restriction site, and a Kozac consensus sequence (CACC) situated between the start codon and the Bam HI restriction site.

Example 2: Site-Directed Mutagenesis of the *Trichoderma reesei* Cellobiohydrolase I The codon-optimized synthetic gene encoding the *T. reesei* cellobiohydrolase I was provided in a non-specified kanamycin-resistant *E. coli* cloning vector. To generate the *T. reesei* cellobiohydrolase I M6 variant (SEQ ID NO: 5 for the mutant DNA sequence and SEQ ID NO: 6 for the variant), an AAC codon (N197) was replaced with a GCC codon (197A) and an AAC codon (N200) was replaced with a GCC codon (200A). Two synthetic primers for site-directed mutagenesis were designed as shown below using the QUIKCHANGE® Primer Design (Agilent Technologies, Inc., Wilmington, Del., USA) online tool to introduce the site-directed mutations changing an AAC codon (N197) to a GCC codon (197A) and an AAC codon (N200) to a GCC codon (200A).

Site-directed mutagenesis of the synthetic gene encoding the wild-type *T. reesei* cellobiohydrolase was facilitated by two PCR amplifications of the kanamycin-resistant *E. coli* cloning vector provided by GENEART® Gene Synthesis using the primers and procedure described below:

```
Primer F-N197A:
                           (SEQ ID NO: 23)
5'-GGGAACCCTCGTCGGCCAACGCCAACACCG-3'

Primer R-N197A:
                           (SEQ ID NO: 24)
5'-CGGTGTTGGCGTTGGCCGACGAGGGTTCCC-3'

Primer F-N200A:
                           (SEQ ID NO: 25)
5'-TCGTCGGCCAACGCCGCCACCGGCATTGGAGG-3'

Primer R-N200A:
                           (SEQ ID NO: 26)
5'-CCTCCAATGCCGGTGGCGGCGTTGGCCGACGA-3'
```

The two mutations were introduced consecutively by PCR using a PHUSION® High-Fidelity PCR Kit (Finnzymes Oy, Espoo, Finland). The PCR solution was composed of 10 µl of 5× HF buffer (Finnzymes Oy, Espoo, Finland), 1 µl of dNTPs (10 mM), 0.5 µl of PHUSION® DNA polymerase (0.2 units/µl) (Finnzymes Oy, Espoo, Finland), 2.5 µl of primer F-N197A (10 µM), 2.5 µl of primer R-N197A (10 µM), 1 µl of template DNA (GENEART® vector, 10 ng/µl), and 32.5 µl of deionized water in a total volume of 50 µl. The PCR was performed using a PTC-200 DNA Engine (MJ Research Inc., Waltham, Mass., USA) programmed for 1 cycle at 98° C. for 30 seconds; and 16 cycles each at 98° C. for 30 seconds, 55° C. for 1 minute, and 72° C. for 4 minutes. The PCR solution was then held at 15° C. until removed from the PCR machine.

Following PCR, 10 units of Dpn I were added directly to the PCR solution and incubated at 37° C. for 1 hour. Then 1 µl of the Dpn I treated PCR solution was transformed into ONE SHOT® TOP10F' Chemically Competent *E. coli* cells (Invitrogen, Carlsbad, Calif., USA) according to the manufacturer's protocol and spread onto LB plates supplemented with 0.05 mg of kanamycin per ml. After incubation at 37° C. overnight, transformants were observed growing under selection on the LB kanamycin plates. Two transformants were cultivated in LB medium supplemented with 0.05 mg of kanamycin per ml and plasmids were isolated using a QIAPREP® Spin Miniprep Kit (QIAGEN Inc., Valencia, Calif., USA).

The isolated plasmids were sequenced using an Applied Biosystems 3730xl DNA Analyzer (Applied Biosystems, Foster City, Calif., USA) with vector primers and a *T. reesei* cellobiohydrolase I gene specific primer (R-Central), shown below, in order to determine a representative plasmid that was free of PCR errors and contained the AAC to GCC mutation.

```
Primer F-vector:
                                        (SEQ ID NO: 27)
5'-CGTTGTAAAACGACGGCC-3'

Primer R-vector:
                                        (SEQ ID NO: 28)
5'-TGTTAATGCAGCTGGCAC-3'

Primer R-Central:
                                        (SEQ ID NO: 29)
5'-CTTGTCGGAGAACGACGA-3'
```

One plasmid clone free of PCR errors and containing the AAC (N197) to GCC (197A) mutation was chosen and designated plasmid pN197A.

A second round of PCR was performed to introduce the N200A mutation by PCR using a PHUSION® High-Fidelity PCR Kit. The PCR solution was composed of 10 µl of 5× HF buffer, 1 µl of dNTPs (10 mM), 0.5 µl of PHUSION® DNA polymerase (0.2 units/µl), 2.5 µl of primer F-N200A (10 µM), 2.5 µl of primer R-N200A (10 µM), 1 µl of template DNA (pN197A, 10 ng/µl), and 32.5 µl of deionized water in a total volume of 50 µl. The PCR was performed using a PTC-200 DNA Engine programmed for 1 cycle at 98° C. for 30 seconds; and 16 cycles each at 98° C. for 30 seconds, 55° C. for 1 minute, and 72° C. for 4 minutes. The PCR solution was then held at 15° C. until removed from the PCR machine.

Following PCR, 10 units of Dpn I were added directly to the PCR solution and incubated at 37° C. for 1 hour. Then 1 µl of the Dpn I treated PCR solution was transformed into ONE SHOT® TOP10F' Chemically Competent *E. coli* cells according to the manufacturer's protocol and spread onto LB plates supplemented with 0.05 mg of kanamycin per ml. After incubation at 37° C. overnight, transformants were observed growing under selection on the LB kanamycin plates. Two transformants were cultivated in LB medium supplemented with 0.05 mg of kanamycin per ml and plasmids were isolated using a QIAPREP® Spin Miniprep Kit.

The isolated plasmids were sequenced using an Applied Biosystems 3730xl DNA Analyzer with primers F-vector, R-vector, and R-Central shown above in order to determine a representative plasmid that was free of PCR errors and contained the AAC to GCC mutation.

One plasmid clone free of PCR errors and containing the AAC (N197) to GCC (197A) and ACC (N200) to GCC (200A) mutations was chosen and designated plasmid pM6. The variant is designated herein as "M6 variant".

Example 3: Construction of an *Aspergillus oryzae* Expression Vector Containing a *Trichoderma reesei* cDNA Sequence Encoding Cellobiohydrolase I The kanamycin-resistant *E. coli* cloning vector provided by GENEART® Gene Synthesis encoding the *T. reesei* cellobiohydrolase I (SEQ ID NO: 4) was digested with Fast Digest Bam HI and Hind III (Fermentas Inc., Glen Burnie, Md., USA) according to manufacturer's instructions. The reaction products were isolated by 1.0% agarose gel electrophoresis using TAE buffer where a 1552 bp product band was excised from the gel and purified using an ILLUSTRA™ GFX™ DNA Purification Kit (GE Healthcare Life Sciences, Brondby, Denmark).

The 1552 bp fragment was then cloned into pDau109 (WO 2005/042735) digested with Bam HI and Hind III using T4 DNA ligase (New England Biolabs, Ipswich, Mass., USA). The Bam HI-Hind III digested pDau109 and the Bam HI/Hind III fragment containing the *T. reesei* cellobiohydrolase I coding sequence were mixed in a molar ratio of 1:3 (i.e., mass ratio approximately 2.5:1 or 20 ng:50 ng) and ligated with 50 units of T4 DNA ligase in 1× T4 DNA ligase buffer (New England Biolabs, Ipswich, Mass., USA) with 1 mM ATP at 16° C. over-night in accordance with the manufacturer's instructions. Cloning of the *T. reesei* cellobiohydrolase I gene into the Bam HI-Hind III digested pDau109 resulted in transcription of the *T. reesei* cellobiohydrolase I gene under the control of a NA2-tpi double promoter. The NA2-tpi promoter is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The ligation mixture was transformed into ONE SHOT® TOP10F' Chemically Competent *E. coli* cells according to the manufacturer's protocol and spread onto LB plates supplemented with 0.1 mg of ampicillin per ml. After incubation at 37° C. overnight, colonies were observed growing under selection on the LB ampicillin plates Insertion of the *T. reesei* cellobiohydrolase I gene into pDau109 was verified by PCR on colonies as described below using the following primers.

```
Primer F-pDau109
                                        (SEQ ID NO: 30)
5'-CCCTTGTCGATGCGATGTATC-3'

Primer R-pDau109
                                        (SEQ ID NO: 31)
5'-ATCCTCAATTCCGTCGGTCGA-3'
```

A 1.1× REDDYMIX® Master Mix (Thermo Fisher Scientific, Roskilde, Denmark) was used for the PCR. The PCR solution was composed of 10 µl of 1.1× REDDYMIX® Master Mix, 0.5 µl of primer F-pDau109 (10 µM), and 0.5 µl of primer R-pDau109 (10 µM). A toothpick was used to transfer a small amount of cells to the PCR solution. The PCR was performed using a PTC-200 DNA Engine programmed for 1 cycle at 94° C. for 3 minutes; 30 cycles each at 94° C. for 30 seconds, 50° C. for 1 minute, and 72° C. for 2 minutes; and 1 cycle at 72° C. for 1 minute. The PCR solution was then held at 15° C. until removed from the PCR machine.

The PCR products were analyzed by 1.0% agarose gel electrophoresis using TAE buffer where a 1860 bp PCR product band was observed confirming insertion of the *T. reesei* cellobiohydrolase I coding sequence into pDau109.

An *E. coli* transformant containing the *T. reesei* cellobiohydrolase I plasmid construct was cultivated in LB medium supplemented with 0.1 mg of ampicillin per ml and plasmid DNA was isolated using a QIAPREP® Spin Miniprep Kit. The plasmid was designated pKHJN0036.

Example 4: Construction of an *Aspergillus oryzae* Expression Vector Containing *Trichoderma reesei* cDNA Sequence Encoding the Cellobiohydrolase I M6 Variant Plasmid pM6 encoding the *T. reesei* cellobiohydrolase I M6 variant was digested with Fast Digest Bam HI and Hind III according to manufacturer's instructions. The reaction products were isolated by 1.0% agarose gel electrophoresis using TAE buffer where a 1552 bp product band was excised from the gel and purified using an ILLUSTRA™ GFX™ DNA Purification Kit.

The 1552 bp fragment was then cloned into pDau109 digested with Bam HI and Hind III using T4 DNA ligase. The Bam HI-Hind III digested pDau109 and the Bam HI/Hind III fragment containing the *T. reesei* cellobiohydrolase I M6 variant coding sequence were mixed in a molar ratio of 1:3 (i.e., mass ratio approximately 2.5:1 or 20 ng:50 ng) and ligated with 50 units of T4 DNA ligase in 1× T4 DNA ligase buffer with 1 mM ATP at 16° C. overnight. Cloning of the *T. reesei* cellobiohydrolase I M6 variant gene into the Bam HI-Hind III digested pDau109 resulted in transcription of the *T. reesei* cellobiohydrolase I M6 variant gene under the control of a NA2-tpi double promoter described above.

The ligation mixture was transformed into ONE SHOT® TOP10F' Chemically Competent *E. coli* cells according to the manufacturer's protocol and spread onto LB plates supplemented with 0.1 mg of ampicillin per ml. After incubation at 37° C. overnight, colonies were observed growing under selection on the LB ampicillin plates Insertion of the *T. reesei* cellobiohydrolase I M6 variant gene into pDau109 was verified by PCR on colonies as described below using primers F-pDau109 and R-pDau109 (Example 3) shown below.

```
Primer F-pDau109
                                  (SEQ ID NO: 30)
5'-CCCTTGTCGATGCGATGTATC-3'

Primer R-pDau109
                                  (SEQ ID NO: 31)
5'-ATCCTCAATTCCGTCGGTCGA-3'
```

A 1.1× REDDYMIX® Master Mix was used for the PCR. The PCR solution was composed of 10 µl of 1.1× REDDYMIX® Master Mix, 0.5 µl of primer F-pDau109 (10 µM), and 0.5 µl of primer R-pDau109 (10 µM). A toothpick was used to transfer a small amount of cells to the PCR solution. The PCR was performed using a PTC-200 DNA Engine programmed for 1 cycle at 94° C. for 3 minutes; 30 cycles each at 94° C. for 30 seconds, 50° C. for 1 minute, and 72° C. for 2 minutes; and 1 cycle at 72° C. for 1 minute. The PCR solution was then held at 15° C. until removed from the PCR machine.

The PCR reaction products were analyzed by 1.0% agarose gel electrophoresis using TAE buffer where a 1860 bp PCR product band was observed confirming insertion of the *T. reesei* cellobiohydrolase I M6 variant coding sequence into pDau109.

An *E. coli* transformant containing the *T. reesei* cellobiohydrolase I M6 variant plasmid construct was cultivated in LB medium supplemented with 0.1 mg of ampicillin per ml and plasmid was isolated using a QIAPREP® Spin Miniprep Kit. The plasmid was designated pKHJN0059.

Example 5: Expression of the Wild-Type *Trichoderma reesei* Cellobiohydrolase I

The expression plasmid pKHJN0036 was transformed into *Aspergillus oryzae* MT3568 protoplasts according to Christensen et al., 1988, *Biotechnology* 6, 1419-1422 and WO 2004/032648. *A. oryzae* MT3568 protoplasts were prepared according to the method of EP 0238023 B1, pages 14-15.

Transformants were purified on COVE sucrose plates through single conidia prior to sporulating them on PDA plates. Spores of the transformants were inoculated into 96 deep well plates containing 0.75 ml of YP+2% glucose medium and incubated stationary at 30° C. for 4 days. Production of the *T. reesei* cellobiohydrolase I by the transformants was analyzed from culture supernatants of the 96 deep well cultivations. Expression was verified by SDS-PAGE analysis using an E-Page 8% SDS-PAGE 48 well gel (Invitrogen, Carlsbad, Calif., USA) and Coomassie blue staining. Based on the level of expression by SDS-PAGE, one transformant was selected and designated *Aspergillus oryzae* CBH I.

For larger scale production, *A. oryzae* CBH I spores were spread onto COVE sucrose slants and incubated for five days at 37° C. The confluent spore slants were washed twice with 5 ml of 0.01% TWEEN® 20 to maximize the number of spores collected. The spore suspensions were then used to inoculate seven 500 ml flasks containing 150 ml of DAP-4C medium. The cultures were incubated at 30° C. with constant shaking at 100 rpm. At day four post-inoculation, the culture broths were collected by filtration through a bottle top MF75 Supor MachV 0.2 µm PES filter (Thermo Fisher Scientific, Roskilde, Denmark). Expression was verified by SDS-PAGE analysis using an E-Page 8% SDS-PAGE 48 well gel and Coomassie staining. The culture broths from *A. oryzae* CBH I produced a band at approximately 80 kDa for the *T. reesei* cellobiohydrolase I.

Example 6: Expression of the *Trichoderma reesei* Cellobiohydrolase I M6 Variant The expression plasmid pKHJN0059 was transformed into *Aspergillus oryzae* MT3568 protoplasts according to Christensen et al., 1988, supra and WO 2004/032648. *A.*

*oryzae* MT3568 protoplasts were prepared according to the method of European Patent, EP0238023, pages 14-15.

Transformants were purified on COVE sucrose plates through single conidia prior to sporulating them on PDA plates. Spores of the transformants were inoculated into 96 deep well plates containing 0.75 ml of YP+2% glucose medium and incubated stationary at 30° C. for 4 days. Production of the *T. reesei* cellobiohydrolase I M6 variant by the transformants was analyzed from culture supernatants of the 96 deep well cultivations. Expression was verified by SDS-PAGE analysis using an E-Page 8% SDS-PAGE 48 well gel and Coomassie staining. Based on the level of expression by SDS-PAGE, one transformant was selected for further work and designated *Aspergillus oryzae* M6.

For larger scale production, *A. oryzae* M6 spores were spread onto COVE sucrose slants and incubated for five days at 37° C. The confluent spore slants were washed twice with 5 ml of 0.01% TWEEN® 20 to maximize the number of spores collected. The spore suspensions were then used to inoculate seven 500 ml flasks containing 150 ml of DAP-4C medium. The cultures were incubated at 30° C. with constant shaking at 100 rpm. At day four post-inoculation, the culture broths were collected by filtration through a bottle top MF75 Supor MachV 0.2 µm PES filter. Expression was verified by SDS-PAGE analysis using an E-Page 8% SDS-PAGE 48 well gel and Coomassie staining. The culture broths from *A. oryzae* M6 produced a band at approximately 80 kDa for the *T. reesei* cellobiohydrolase I M6 variant.

Example 7: Purification of the *Trichoderma reesei* Wild-Type Cellobiohydrolase I and Cellobiohydrolase I M6 Variant The filtered broths of *A. oryzae* CBH I (Example 5) and *A. oryzae* M6 (Example 6) were adjusted to pH 7.0 and filtered using a 0.22 µm PES filter (Nalge Nunc International Corp., Rochester, N.Y., USA). Then ammonium sulphate was added to each filtrate to a concentration of 1.8 M.

Each filtrate was purified according to the following procedure. The filtrate was loaded onto a Phenyl SEPHAROSE® 6 Fast Flow column (high sub) (GE Healthcare, United Kingdom) equilibrated with 1.8 M ammonium sulphate, 25 mM HEPES pH 7.0. After a wash with 0.54 M ammonium sulphate, the bound proteins were batch eluted with 25 mM HEPES pH 7.0. Fractions were collected and analyzed by SDS-PAGE using 12-well NUPAGE® 4-12% Bis-Tris gel (GE Healthcare, Piscataway, N.J., USA). The fractions were pooled based on SDS-PAGE as above and applied to a SEPHADEX™ G-25 (medium) column (GE Healthcare, United Kingdom) equilibrated with 25 mM MES pH 6.0. Fractions were collected, analyzed by SDS-PAGE as above, and pooled. The pooled fractions were applied to a 6 ml RESOURCE™ 15Q column (GE Healthcare, United Kingdom) equilibrated with 25 mM MES pH 6.0 and bound proteins were eluted with a linear 0-300 mM sodium chloride gradient (12 column volumes) for the wild-type cellobiohydrolase or a linear 0-350 mM sodium chloride gradient (14 column volumes) for the variant. Fractions were collected and analyzed by SDS-PAGE, $A_{280}$, and activity measurements using 4-nitrophenyl-beta-D-glucopyranoside (Sigma Chemical Co., St. Louis, Mo., USA) and 4-nitrophenyl-beta-D-lactopyranoside (Sigma Chemical Co., St. Louis, Mo., USA) as substrates. The assays were performed in 96-well Nunc microtiter plates (Thermo Scientific, Sunnyvale, Calif., USA). The assay buffer was 50 mM Britton-Robinson buffer (50 mM $H_3PO_4$, 50 mM $CH_3COOH$, 50 mM $H_3BO_3$) with 50 mM KCl, 1 mM $CaCl_2$, 0.01% TRITON® X-100, pH adjusted to 6.0 with NaOH. A 20 µl sample of protein solution was pipetted into each well and 120 µl of 1 mM substrate in the assay buffer were added. The substrate 4-nitrophenyl-beta-D-glucopyranoside was used to determine beta-glucosidase activity and 4-nitrophenyl-beta-D-lactopyranoside for cellobiohydrolase I and cellobiohydrolase variant activity. A standard curve was made by replacing the protein solution with 20 µl of 4-nitrophenolate standard (0, 0.05, 0.075, 0.1, 0.2, 0.3, 0.4, 0.5 mM). If necessary, samples were diluted in the assay buffer to yield absorptions within the range of the standard curve. The plate was sealed and incubated in a thermomixer at 37° C. for 15 minutes with 750 rpm shaking. Immediately after incubation the reaction was stopped by adding 100 µl of 0.5 M glycine-2 mM EDTA pH 10 and the absorption was measured at 405 nm. The absorption of a "blank", in which the protein was added after the stop solution, was recorded for each sample and subtracted from the result to obtain the absorption of released 4-nitrophenolate.

Based on SDS-PAGE, $A_{280}$, and the activity measurements, the fractions were pooled to the final product.

The *T. reesei* wild-type cellobiohydrolase I and cellobiohydrolase I M6 variant were purified to a concentration of 57 µM and 38 µM, respectively, as determined by $A_{280}$ using the calculated molar extinction coefficient 84810 $M^{-1} \cdot cm^{-1}$ and 84810 $M^{-1} \cdot cm^{-1}$, respectively.

Example 8: Activity Measurement on Microcrystalline Cellulose of the *Trichoderma Reesei* Cellobiohydrolase M6 Variant The activity of the purified cellobiohydrolase I M6 variant (Example 7) was compared to the purified *T. reesei* wild-type cellobiohydrolase I (Example 7) using microcrystalline cellulose (AVICEL® PH101; Sigma-Aldrich, St. Louis, Mo., USA) as a substrate. The microcrystalline cellulose was suspended at 60 g per liter of 2 mM $CaCl_2$-50 mM sodium acetate pH 5 as assay buffer.

Activity of the *T. reesei* wild-type cellobiohydrolase I and cellobiohydrolase I M6 variant was measured in a water-jacketed glass cell connected to a Julabo F12 water bath (Buch & Holm A/S, Herlev, Denmark). Each reaction chamber was filled with 5 ml of the microcrystalline cellulose suspension and magnetically stirred at 600 rpm. The enzyme was injected into the cell using 250 µl glass syringes (Hamilton Co., Boston, Mass., USA) with a Fusion 100 syringe pump (Chemyx Inc., Stafford, Tex., USA) to a final concentration of 100 nM (5 µg/ml) with an injection time of 1 second (wild-type: 8.8 µl, 528 µl/minute; M6 variant: 13.16 µl, 789 µl/minute). The reactions were allowed to proceed for 5 hours at 25° C. before being quenched with 80 µl of 1 M NaOH.

From each reaction 2 samples of 2 ml were removed and filtered with a 0.2 µM hydrophilic MINISART® NML syringe filter (Sartorius Stedim Biotech S.A., Goettingen, Germany). The filtrates were diluted 1:10 with milliQ water (control was measured undiluted) and the glucose, cellobiose, and cellotriose contents were analyzed using a Dionex ICS-5000 DC High-Performance Liquid Chromatography (HPLC) System (Thermo Scientific, Sunnyvale, Calif., USA) equipped with a 4 mm×25 cm CARBOPAC™ PA10 column (Thermo Scientific, Sunnyvale, Calif., USA), a Dionex GP40 gradient pump (Thermo Scientific, Sunnyvale, Calif., USA), and a Dionex ED40 electrochemical detector (Thermo Scientific, Sunnyvale, Calif., USA) with a gold working electrode (standard carbohydrate settings). Oligosaccharides were separated on the CARBOPAC™ PA10 column using the following gradient program at a flow rate of 1 ml per minute: 0-4 minutes isocratic elution with 50 mM sodium hydroxide; 4-28 minutes linear gradient to 100 mM sodium acetate in 90 mM sodium hydroxide; 28-29 minutes linear gradient to 450 mM sodium acetate in 200 mM sodium hydroxide; 29-30 minutes linear gradient to 100 mM sodium hydroxide; 30-31 minutes linear gradient to 50 mM sodium hydroxide; and 31-35 minutes reequilibration under the initial conditions. Combined external standards were ([glucose]/[cellobiose]/[cellotriose]): 1 µM/2 µM/0.5 µM, 2 µM/4 µM/1 µM, 3 µM/6 µM/1.5 µM, 4 µM/8 µM/2 µM, and 5 µM/10 µM/2.5 µM. Chromatogram peak integration, standard curve, and concentration determination were performed using a CHROMELEON® 7 Chromatography Data System (Thermo Fisher Scientific, Roskilde, Denmark).

The results as shown in FIG. 1 and Table 1 demonstrated that the cellobiohydrolase I M6 variant had an approximately 65% increase in activity toward microcrystalline cellulose compared to the wild-type cellobiohydrolase.

TABLE 1

Saccharide production from microcrystalline cellulose by the T. reesei wild-type cellobiohydrolase I and the cellobiohydrolase I M6 variant thereof after 5 hours at pH 5 and 25° C.

|  | [glucose] (µM) | [cellobiose] (µM) | [cellotriose] (µM) |
| --- | --- | --- | --- |
| Control | 15.9 | 1.6 | 2.5 |
| Wild-type | 22.9 ± 0.3 | 121.4 ± 4.3 | $5.4 ± 4 \times 10^{-3}$ |
| M6 Variant | $29.1 ± 10^{-3}$ | 201.7 ± 0.5 | 8.1 ± 0.04 |

Example 9: Pretreated Corn Stover Hydrolysis Assay

Corn stover was pretreated at the U.S. Department of Energy National Renewable Energy Laboratory (NREL) using 1.4 wt % sulfuric acid at 165° C. and 107 psi for 8 minutes. The water-insoluble solids in the pretreated corn stover (PCS) contained 56.5% cellulose, 4.6% hemicellulose, and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

Unmilled, unwashed PCS (whole slurry PCS) was prepared by adjusting the pH of the PCS to 5.0 by addition of 10 M NaOH with extensive mixing, and then autoclaving for 20 minutes at 120° C. The dry weight of the whole slurry PCS was 29%. Milled unwashed PCS (dry weight 32.35%) was prepared by milling whole slurry PCS in a Cosmos ICMG 40 wet multi-utility grinder (EssEmm Corporation, Tamil Nadu, India).

The hydrolysis of PCS was conducted using 2.2 ml deep-well plates (Axygen, Union City, Calif., USA) in a total reaction volume of 1.0 ml. The hydrolysis was performed with 50 mg of insoluble PCS solids per ml of 50 mM sodium acetate pH 5.0 buffer containing 1 mM manganese sulfate and various protein loadings of various enzyme compositions (expressed as mg protein per gram of cellulose). Enzyme compositions were prepared and then added simultaneously to all wells in a volume ranging from 50 µl to 200 µl, for a final volume of 1 ml in each reaction. The plate was then sealed using an ALPS-300™ plate heat sealer (Abgene, Epsom, United Kingdom), mixed thoroughly, and incubated at a specific temperature for 72 hours. All experiments reported were performed in triplicate.

Following hydrolysis, samples were filtered using a 0.45 µm MULTISCREEN® 96-well filter plate (Millipore, Bedford, Mass., USA) and filtrates analyzed for sugar content as described below. When not used immediately, filtered aliquots were frozen at −20° C. The sugar concentrations of samples diluted in 0.005 M $H_2SO_4$ were measured using a 4.6×250 mm AMINEX® HPX-87H column (Bio-Rad Laboratories, Inc., Hercules, Calif., USA) by elution with 0.05% w/w benzoic acid-0.005 M $H_2SO_4$ at 65° C. at a flow rate of 0.6 ml per minute, and quantitation by integration of the glucose, cellobiose, and xylose signals from refractive index detection (CHEMSTATION®, AGILENT® 1100 HPLC, Agilent Technologies, Santa Clara, Calif., USA) calibrated by pure sugar samples. The resultant glucose and cellobiose equivalents were used to calculate the percentage of cellulose conversion for each reaction.

Glucose and cellobiose were measured individually. Measured sugar concentrations were adjusted for the appropriate dilution factor. The net concentrations of enzymatically-produced sugars from unwashed PCS were determined by adjusting the measured sugar concentrations for corresponding background sugar concentrations in unwashed PCS at zero time point. All HPLC data processing was performed using MICROSOFT EXCEL™ software (Microsoft, Richland, Wash., USA).

The degree of cellulose conversion to glucose was calculated using the following equation: % cellulose conversion=[glucose concentration+(1.053× cellobiose concentration)]/[(glucose concentration+(1.053× cellobiose concentration) in a limit digest]×100. In order to calculate % cellulose conversion, a 100% conversion point was set based on a cellulase control (100 mg of T. reesei cellulase per gram cellulose. Triplicate data points were averaged and standard deviation was calculated.

Example 10: Preparation of an Enzyme Composition without Cellobiohydrolase I

The Aspergillus fumigatus GH6A cellobiohydrolase II (SEQ ID NO: 32 [DNA sequence] and SEQ ID NO: 33 [deduced amino acid sequence]) was prepared recombinantly in Aspergillus oryzae as described in WO 2011/057140. The filtered broth of the A. fumigatus cellobiohydrolase II was buffer exchanged into 50 mM sodium acetate pH 5.0 using a 400 ml SEPHADEX™ G-25 column. The fractions were pooled.

The T. reesei GH5 endoglucanase II (SEQ ID NO: 34 [DNA sequence] and SEQ ID NO: 35 [deduced amino acid sequence]) was prepared recombinantly according to WO 2011/057140 using Aspergillus oryzae as a host. The filtered broth of the T. reesei endoglucanase II was desalted and buffer-exchanged into 20 mM Tris pH 8.0 using tangential flow (10K membrane, Pall Corporation).

The Penicillium sp. (emersonii) GH61A polypeptide (SEQ ID NO: 36 [DNA sequence] and SEQ ID NO: 37 [deduced amino acid sequence]) was prepared recombinantly according to WO 2011/041397 using T. reesei as a host. To purify P. emersonii GH61A polypeptide, a fermentation culture medium was desalted using a tangential flow concentrator (Pall Filtron, Northborough, Mass., USA) equipped with a 5 kDa polyethersulfone membrane (Pall Filtron, Northborough, Mass., USA) into 20 mM Tris-HCl pH 8.5. The buffer-exchanged sample was loaded onto a Q SEPHAROSE® Fast Flow column (GE Healthcare, Piscataway, N.J., USA) preequilibrated with 20 mM Tris-HCl, pH 8.0, eluted with 20 mM Tris-HCl pH 8.0 and 1 M NaCl. Selected fractions were pooled, made in 0.85 M ammonium sulfate, and loaded onto a Phenyl SEPHAROSE® Fast Flow column preequilibrated with 20 mM Tris-HCl, pH 7.5 and 0.85 M ammonium sulfate, eluted with 20 mM Tris-HCl, pH 7.5. The fractions were pooled and desalted using a tangential flow concentrator (Pall Filtron, Northborough, Mass., USA) equipped with a 5 kDa polyethersulfone membrane into 50 mM sodium acetate pH 5.0.

The *Aspergillus fumigatus* GH10 xylanase (xyn3) (SEQ ID NO: 38 [DNA sequence] and SEQ ID NO: 39 [deduced amino acid sequence]) was prepared recombinantly according to WO 2006/078256 using *Aspergillus oryzae* BECh2 (WO 2000/39322) as a host. The filtered broth of the *A. fumigatus* xylanase was desalted and buffer-exchanged into 50 mM sodium acetate pH 5.0 using a HIPREP® 26/10 Desalting Column (GE Healthcare, Piscataway, N.J., USA).

The *Aspergillus fumigatus* Cel3A beta-glucosidase 4M mutant (SEQ ID NO: 40 [DNA sequence] and SEQ ID NO: 41 [deduced amino acid sequence]) was recombinantly prepared according to WO 2012/044915. The filtered broth of *Aspergillus fumigatus* Cel3A beta-glucosidase 4M was concentrated and buffer exchanged using a tangential flow concentrator (Pall Filtron, Northborough, Mass., USA) equipped with a 10 kDa polyethersulfone membrane (Pall Filtron, Northborough, Mass., USA) with 50 mM sodium acetate pH 5.0 containing 100 mM sodium chloride.

The *Talaromyces emersonii* CBS 393.64 beta-xylosidase (SEQ ID NO: 42 [DNA sequence] and SEQ ID NO: 43 [deduced amino acid sequence]) was prepared recombinantly according to Rasmussen et al., 2006, *Biotechnology and Bioengineering* 94: 869-876 using *Aspergillus oryzae* JaL355 as a host (WO 2003/070956). The filtered broth was concentrated and desalted with 50 mM sodium acetate pH 5.0 using a tangential flow concentrator equipped with a 10 kDa polyethersulfone membrane.

The protein concentration for each of the monocomponents described above was determined using a Microplate BCA™ Protein Assay Kit (Thermo Fischer Scientific, Waltham, Mass., USA) in which bovine serum albumin was used as a protein standard. An enzyme composition was prepared composed of each monocomponent as follows: 39.7% *Aspergillus fumigatus* Cel6A cellobiohydrolase II, 15.9% *T. reesei* GH5 endoglucanase II, 23.8% *Penicillium* sp. (*emersonii*) GH61A polypeptide, 7.9% *Aspergillus fumigatus* GH10 xylanase, 7.9% *Aspergillus fumigatus* beta-glucosidase, and 4.8% *Talaromyces emersonii* beta-xylosidase. The enzyme composition is designated herein as "cellulolytic enzyme composition without cellobiohydrolase I".

Example 11: Comparison of the Effect of the *Trichoderma reesei* Cellobiohydrolase I M6 Variant and *Trichoderma reesei* Wild-Type Cellobiohydrolase I in the Hydrolysis of Milled Unwashed PCS by a Cellulase Enzyme Composition The *T. reesei* cellobiohydrolase I M6 variant and *T. reesei* wild-type cellobiohydrolase I were added to the cellulolytic enzyme composition without cellobiohydrolase I (Example 10) at 40° C. using milled unwashed PCS as a substrate. Each cellobiohydrolase I was added individually at 0.8633, 1.295, and 1.9425 mg enzyme protein per g cellulose to 2.205 mg enzyme protein of the cellulase enzyme composition without cellobiohydrolase I per g cellulose.

The assay was performed as described in Example 9. The 1 ml reactions with milled unwashed PCS (5% insoluble solids) were conducted for 24, 48, and 72 hours in 50 mM sodium acetate pH 5.0 buffer containing 1 mM manganese sulfate. All reactions were performed in triplicate and involved single mixing at the beginning of hydrolysis.

Figure 2:
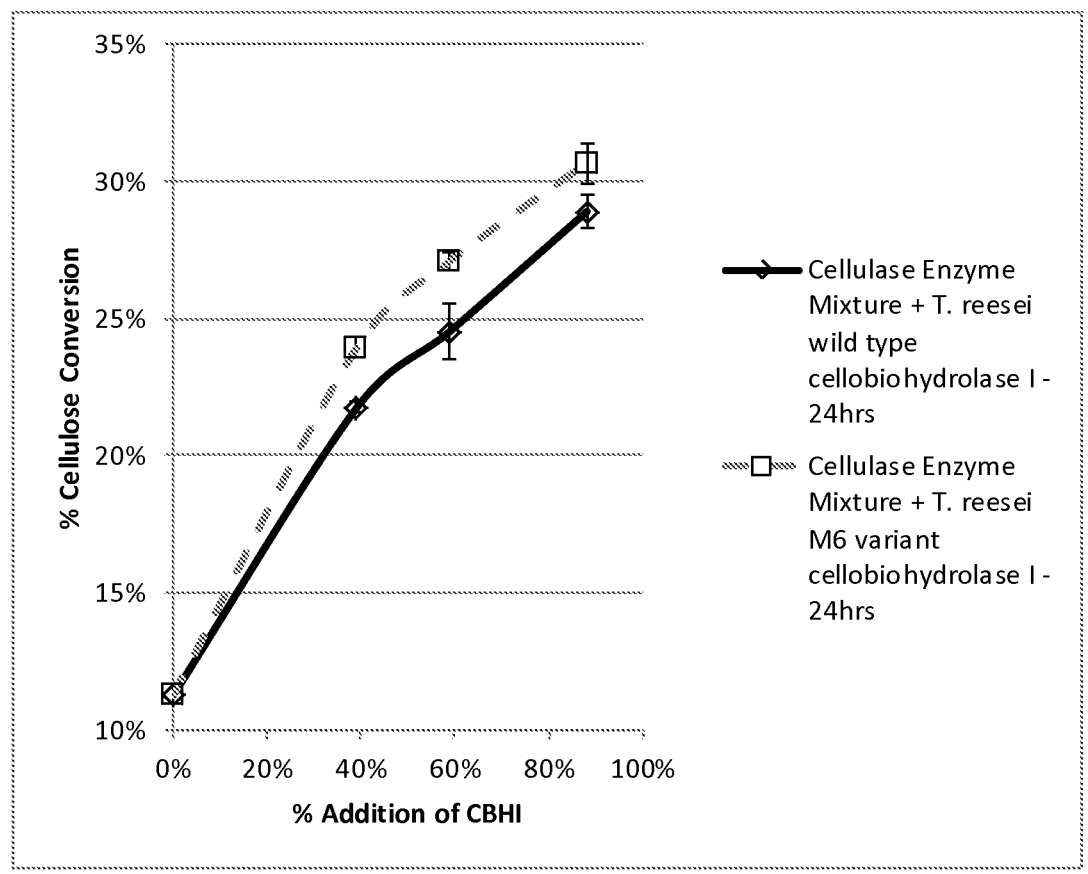
FIG. 2 shows the effect of *T. reesei* cellobiohydrolase I M6 variant and *T. reesei* wild-type cellobiohydrolase I on hydrolysis of milled unwashed PCS by a cellulolytic enzyme composition at 24 hours.
Figure 3:
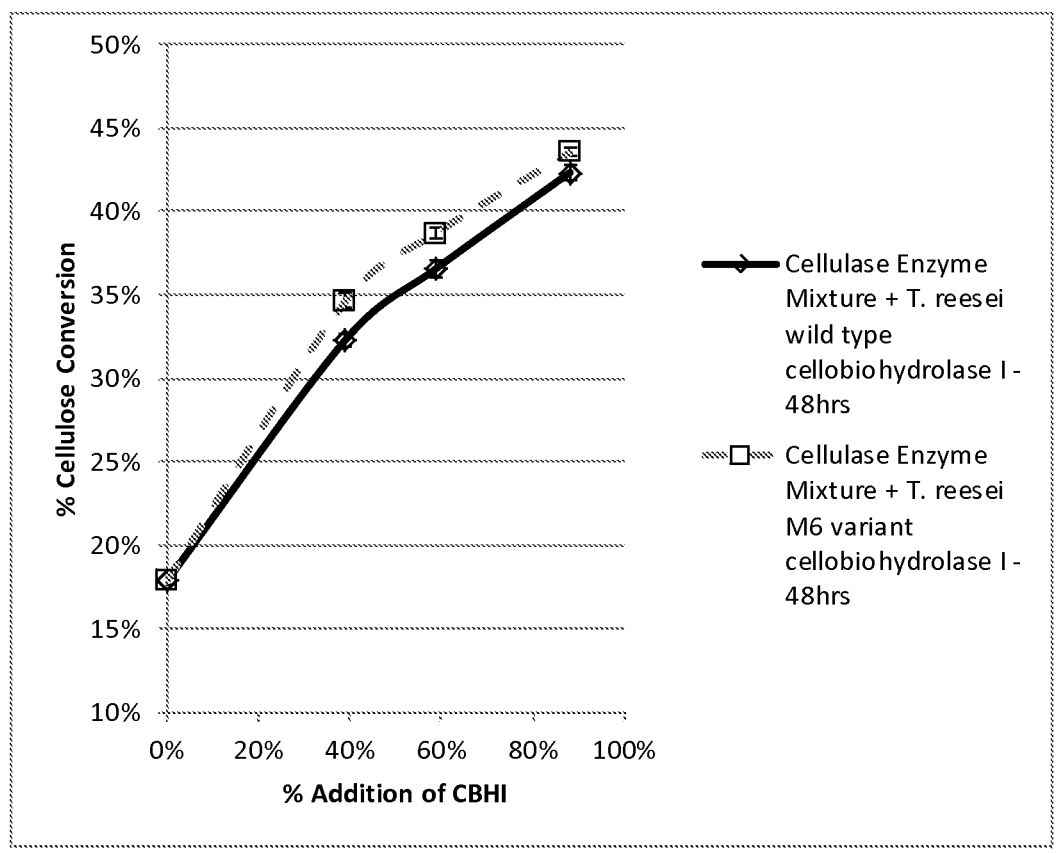
FIG. 3 shows the effect of *Trichoderma reesei* cellobiohydrolase I M6 variant and *Trichoderma reesei* wild-type cellobiohydrolase I on hydrolysis of milled unwashed pretreated corn stover (PCS) by a cellulolytic enzyme composition at 48 hours.
Figure 4:
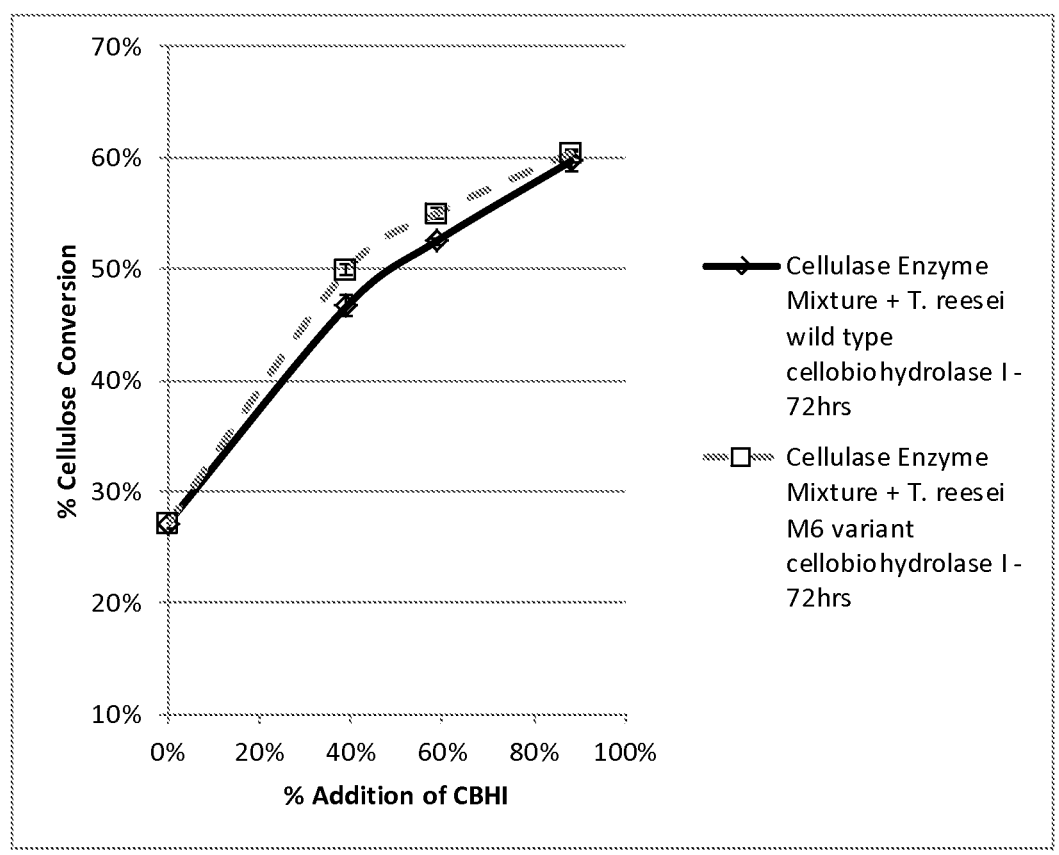
FIG. 4 shows the effect of *T. reesei* cellobiohydrolase I M6 variant and *T. reesei* wild-type cellobiohydrolase I on hydrolysis of milled unwashed PCS by a cellulolytic enzyme composition at 72 hours.

The results shown in FIGS. 2, 3, and 4 demonstrated that at 24, 48, and 72 hours, the cellulase enzyme composition that included the *T. reesei* cellobiohydrolase I M6 variant had significantly higher cellulose conversion than the cellulase enzyme composition that included *T. reesei* wild-type cellobiohydrolase I.

Example 12: Determination of Td by Differential Scanning Calorimetry of the *Trichoderma reesei* Cellobiohydrolase I M6 Variant and *Trichoderma reesei* Wild-Type Cellobiohydrolase I The thermostability of the *T. reesei* wild-type cellobiohydrolase I and cellobiohydrolase I M6 variant was determined by Differential Scanning calorimetry (DSC) using a VP-Capillary Differential Scanning calorimeter (MicroCal Inc., Piscataway, N.J., USA). The thermal denaturation temperature, Td (° C.), was taken as the top of denaturation peak (major endothermic peak) in thermograms (Cp vs. T) obtained after heating enzyme solutions (approx. 1 mg/ml) in 50 mM sodium acetate pH 5.0 at a constant programmed heating rate of 200 K/hour.

Sample- and reference-solutions (approx. 0.2 ml) were loaded into the calorimeter (reference: buffer without enzyme) from storage conditions at 10° C. and thermally pre-equilibrated for 20 minutes at 20° C. prior to DSC scan from 20° C. to 100° C. Denaturation temperatures were determined at an accuracy of approximately +/−1° C.

The results demonstrated that the *T. reesei* wild-type cellobiohydrolase I has a Td of 69° C. compared to 68° C. for the cellobiohydrolase I M6 variant thereof.

Example 13: Site-Directed Mutagenesis of the Wild-Type *Trichoderma reesei* Cellobiohydrolase I The codon-optimized synthetic gene encoding the wild-type *T. reesei* cellobiohydrolase I (Example 1) was used to generate the *T. reesei* cellobiohydrolase I TC1-111 variant (SEQ ID NO: 44 for the mutant DNA sequence and SEQ ID NO: 45 for the variant), an AAC codon (N198) was replaced with a GCA codon (198A).

To generate the *T. reesei* cellobiohydrolase I TC1-116 variant (SEQ ID NO: 46 for the mutant DNA sequence and SEQ ID NO: 47 for the variant), a GCC codon (A199) was deleted (A199*).

To generate the *T. reesei* cellobiohydrolase I TC1-61 variant (SEQ ID NO: 48 for the mutant DNA sequence and SEQ ID NO: 49 for the variant), an AAC codon (N200) was replaced with a TGG codon (200W).

To generate the *T. reesei* cellobiohydrolase I TC1-103 variant (SEQ ID NO: 50 for the mutant DNA sequence and SEQ ID NO: 51 for the variant), an AAC codon (N200) was replaced with a GGA codon (200G).

Two synthetic primers for each site-directed mutagenesis were designed as shown below using an SOE primer design tool. The introduced site-directed mutation changed an AAC codon (N198) to a GCA codon (198A), an AAC codon (N200) to a TGG codon (200W), and an AAC codon (N200) to a GGA codon (200G), and a GCC codon (A199) was deleted.

```
Primer F-N198A:
                                        (SEQ ID NO: 52)
5'-GCTGGGAACCCTCGTCGAACGCAGCCAACACCGGCATTGGA-3'

Primer R-N198A:
                                        (SEQ ID NO: 53)
5'-GTTCGACGAGGGTTCCCAGCCTTCGACGTTTG-3'

Primer F-ΔA199:
                                        (SEQ ID NO: 54)
5'-TGGGAACCCTCGTCGAACAACAACACCGGCATTGGAGGCCAT-3'

Primer R-ΔA199:
                                        (SEQ ID NO: 55)
5'-GTTGTTCGACGAGGGTTCCCAGCCTTCGACG-3'

Primer F-N200W:
                                        (SEQ ID NO: 56)
5'-GAACCCTCGTCGAACAACGCCTGGACCGGCATTGGAGGCCATGG-3'

Primer R-N200W:
                                        (SEQ ID NO: 57)
5'-GGCGTTGTTCGACGAGGGTTCCCAGCCTTCG-3'

Primer F-N200G:
                                        (SEQ ID NO: 58)
5'-GAACCCTCGTCGAACAACGCCGGAACCGGCATTGGAGGCCAT-3'

Primer R-N200G:
                                        (SEQ ID NO: 59)
5'-GGCGTTGTTCGACGAGGGTTCCCAGCCTTCG-3'
```

Site-directed mutagenesis of the synthetic gene encoding the wild-type *T. reesei* cellobiohydrolase was facilitated by PCR amplifications of the pDau109 vector containing the *T. reesei* cellobiohydrolase I gene: The *T. reesei* cellobiohydrolase I gene was previously cloned into Bam HI-Hind III digested pDau109 resulting in transcription of the *T. reesei* cellobiohydrolase I gene under the control of a NA2-tpi double promoter.

The mutations were introduced by PCR using a PHUSION® High-Fidelity PCR Kit. The PCR solution was composed of 10 μl of 5× HF buffer, 1 μl of dNTPs (10 mM), 0.5 μl of PHUSION® DNA polymerase (0.2 units/μl), 2.5 μl of primer F-N198A (10 μM), 2.5 μl of primer R-N198A (10 μM), 10 μl of template DNA (pDAu222-*T. reesei* cellobiohydrolase I, 1 ng/μl), and 23.5 μl of deionized water in a total volume of 50 μl. For the GCC deletion (A199* variant) 2.5 μl of primer F-ΔA199 (10 μM), 2.5 μl of primer R-ΔA199 (10 μM) were used. For the ACC to TGG mutation (N200W variant) 2.5 μl primer-F-N200W (10 μM) and 2.5 μl primer R-N200W (10 μM) were used. For the ACC to GGA mutation (N200G variant) 2.5 μl primer-F-N200G (10 μM) and 2.5 μl primer R-N200G (10 μM) were used.

The PCR was performed using a GeneAmp® PCR System 9700 (Applied Biosystems, Foster City, Calif., USA) programmed for 1 cycle at 98° C. for 30 seconds; and 19 cycles each at 98° C. for 30 seconds, 55° C. for 1 minute, and 72° C. for 4 minutes. The PCR solution was then held at 15° C. until removed from the PCR machine.

Following PCR, 10 units of Dpn I were added directly to the PCR solution and incubated at 37° C. for 1 hour. Then 1 μl of the Dpn I treated PCR solution was transformed into ONE SHOT® TOP10F' Chemically Competent *E. coli* cells according to the manufacturer's protocol and spread onto LB plates supplemented with 0.15 mg of ampicillin per ml. After incubation at 37° C. overnight, transformants were observed growing under selection on the LB ampicillin plates. Two transformants were cultivated in LB medium supplemented with 0.15 mg of ampicillin per ml and plasmids were isolated using a QIAPREP® Spin Miniprep Kit.

The isolated plasmids were sequenced using an Applied Biosystems 3730xl DNA Analyzer with vector primers and *T. reesei* cellobiohydrolase 1 gene specific primers, shown below, in order to determine a representative plasmid that was free of PCR errors and contained the desired mutations.

```
Primer F-pDau109
                                        (SEQ ID NO: 30)
5'-CCCTTGTCGATGCGATGTATC-3'

Primer F-Central1
                                        (SEQ ID NO: 60)
5'-CATGTATCGTAAGCTCGCAGTCATCTCC-3'

Primer F-Central2
                                        (SEQ ID NO: 61)
5'-CTTCGTGTCGATGGACGCGG-3'

Primer R-Central3
                                        (SEQ ID NO: 62)
5'-GAACACGAGCCCCTCACTGC-3'

Primer R-pDau109
                                        (SEQ ID NO: 31)
5'-ATCCTCAATTCCGTCGGTCGA-3'
```

One plasmid clone free of PCR errors and containing the AAC (N198) to GCA (198A) mutation was chosen and designated plasmid pN198A.

One plasmid clone free of PCR errors and containing the deletion of the GCC codon (A199) to (A199*) mutation was chosen and designated plasmid pΔA199.

One plasmid clone free of PCR errors and containing the AAC (N200) to TGG (200W) mutation was chosen and designated plasmid pN200W.

One plasmid clone free of PCR errors and containing the AAC (N200) to GGA (200G) mutation was chosen and designated plasmid pN200G.

pN198A was sequenced using primers F-Central1, F-Central2, R-Central3 and R-pDau109. pΔA199 was sequenced using primers F-pDau109 F-Central1, F-Central2, R-Central3 and R-pDau109. pN200W was sequenced using primers F-Central1, F-Central2 and R-pDau109. pN200G was sequenced using primers F-Central1, F-Central2 and R-pDau109

Example 14: Expression of the *Trichoderma reesei* Cellobiohydrolase I TC1-111, TC1-116, TC1-61, and TC1-103 Variants Expression of plasmids pN198A, pΔA199, pN200W, and pN200G in *Aspergillus oryzae* MT3568 was performed according to the protocol described in Example 6.

Expression was verified by SDS-PAGE analysis using an E-Page 8% SDS-PAGE 48 well gel and Coomassie staining. Based on the level of expression by SDS-PAGE, one transformant was selected for each of plasmids pN198A, pΔA199, pN200W, and pN200G and designated *Aspergillus oryzae* ΔA199, N200G, N197A, and N200W, respectively.

For larger scale production, spores for each *A. oryzae* strain were spread onto COVE sucrose slants and incubated for five days at 37° C. Each confluent spore slant was washed twice with 5 ml of 0.01% TWEEN® 20 to maximize the number of spores collected. Each spore suspensions were then used to inoculate seven 500 ml flasks containing 150 ml of DAP-4C medium. The cultures were incubated at 30° C. with constant shaking at 100 rpm. At day four post-inoculation, the culture broths were collected by filtration through a bottle top MF75 Supor MachV 0.2 µm PES filter. Expression was verified by SDS-PAGE analysis using an E-Page 8% SDS-PAGE 48 well gel and Coomassie staining. The culture broths from each *A. oryzae* strain produced a band at approximately 80 kDa for the *T. reesei* A199*, N200G, N197A, and N200W cellobiohydrolase variant.

Example 15: Purification of the *Trichoderma reesei* Cellobiohydrolase I TC1-111, TC1-116, TC1-61, and TC1-103 Variants The fermentation broths were filtered through PES Bottle top filter with a 0.22 µm cut-off (Thermo Fisher Scientific, Roskilde, Denmark). Ammonium sulphate was added to the filtered fermentation broths to make a 1.8 M solution.

The fermentation broths were purified by HIC/affinity chromatography followed by IEX/affinity chromatography.

In the HIC/affinity chromatographic step, the fermentation broths were applied to a 200 ml Phenyl SEPHAROSE® 6 Fast Flow column (high sub) equilibrated with 1.8 M ammonium sulphate, 25 mM HEPES pH 7.0. After applying the sample, the column was washed with 2 column volumes of 1.8 M ammonium sulphate followed by 1 column volume of 0.54 M ammonium sulphate. The bound proteins were batch eluted with 25 mM HEPES pH 7.0.

The elution of the protein was monitored at 280 nm. Fractions with high 280 nm absorbance were analyzed by SDS-PAGE using 12-well NUPAGE® 4-12% Bis-Tris gel for their cellobiohydrolase content. Fractions with high content of this protein were pooled and collected for further purification. The pooled fractions were desalted on a SEPHADEX™ G-25 (medium) column equilibrated with 25 mM MES pH 6.0. The elution of the protein was monitored at 280 nm and fractions with high absorbance at 280 nm were chosen for the second chromatographic step.

The pooled fractions were applied to the 60 ml RESOURCE™ 15Q column (equilibrated with 25 mM MES pH 6.0 and bound proteins were eluted with a linear 50-300 mM sodium chloride gradient for 3 column volumes. The elution of the protein was monitored at 280 nm and fractions with high absorbance at 280 nm were analysed on SDS-PAGE.

Fractions with high content of cellobiohydrolase I were pooled.

Example 16: Activity Measurement on Microcrystalline Cellulose of the *Trichoderma Reesei* Cellobiohydrolase I TC1-111, TC1-116, TC1-61, and TC1-103 Variants The activity of the purified *Trichoderma reesei* cellobiohydrolase I TC1-111, TC1-116, TC1-61, and TC1-103 (variants were compared to the purified *T. reesei* wild-type cellobiohydrolase I using washed microcrystalline cellulose (AVICEL® PH101; Sigma-Aldrich, St. Louis, Mo., USA) as a substrate.

The washed microcrystalline cellulose was prepared by applying and mixing (by hand) 180 g of microcrystalline cellulose and approximately 400 ml of 0.22 µm filtered water to a centrifuge bottle (1 L). The centrifuge bottle was centrifuged at 4000 rpm for 5 minutes at 18° C. (Sorvall Hereaus Thermoscientific Sorvall Evolution RC superspeed centrifuge). The supernatant was removed and 400 ml of MQ water were added again. This was repeated 4 times. At the 4$^{th}$ repeat the pellet and 0.22 µm filtered water were mixed on a "Rocker" o/n (IKA KS 130 basic) before centrifuging. The supernatant was removed and pellet was re-suspended with 50 mM sodium acetate, 2 mM $CaCl_2$ pH 5 buffer to a final concentration of 90 g/L.

The purified cellobiohydrolase variants were diluted in 50 mM sodium acetate, 2 mM $CaCl_2$ pH 5 to a concentration of 9 µM. Then 100 µl of the diluted cellobiohydrolase I variants were added to each well of a microtiter plate followed by 200 µl of washed microcrystalline cellulose at 90 g/liter to each well. The microtiter plate was quickly transferred to a thermomixer and incubated for 1 hour at 1100 rpm and 25° C. The reaction was stopped by centrifugation at 3500 rpm for 3 minutes at 5° C. using a HERAEUS® MULTIFUGE® 3 s-r centrifuge (Thermo Fisher Scientific, Roskilde, Denmark). Fifty µl of supernatant were transferred to PCR sample tubes (0.2 ml non-skirted 96-well PCR plate; Thermo Fisher Scientific, Roskilde, Denmark). PAHBAH (4-hydroxy-benzhydrazide) was dissolved in buffer (0.18 M K—Na-tartrate and 0.5 M NaOH) to make a 15 mg/ml solution. Seventy-five µl of the PAHBAH solution were added to the supernatants in the PCR samples tubes.

The PCR sample tubes were placed in a Peltier Thermal Cycler and incubated at 95° C. for 10 minutes and 20° C. for 5 minutes. After incubation 100 µl were transferred to a 96 well microtiter plate and the absorbance was measured at 410 nm. For each run a standard was included. The standard used was cellobiose diluted in 50 mM sodium acetate, 2 mM $CaCl_2$ pH 5 to a concentration of 0.008, 0.016, 0.0312, 0.0625, 0.125, 0.25, 0.5, and 1 mM. In addition to the standard, a blank (without cellobiohydrolase) for each run was included. For all the measurements, the blank measurement was subtracted. The absorbance data were normalized to cellobiose concentration using the standards.

Figure 5:
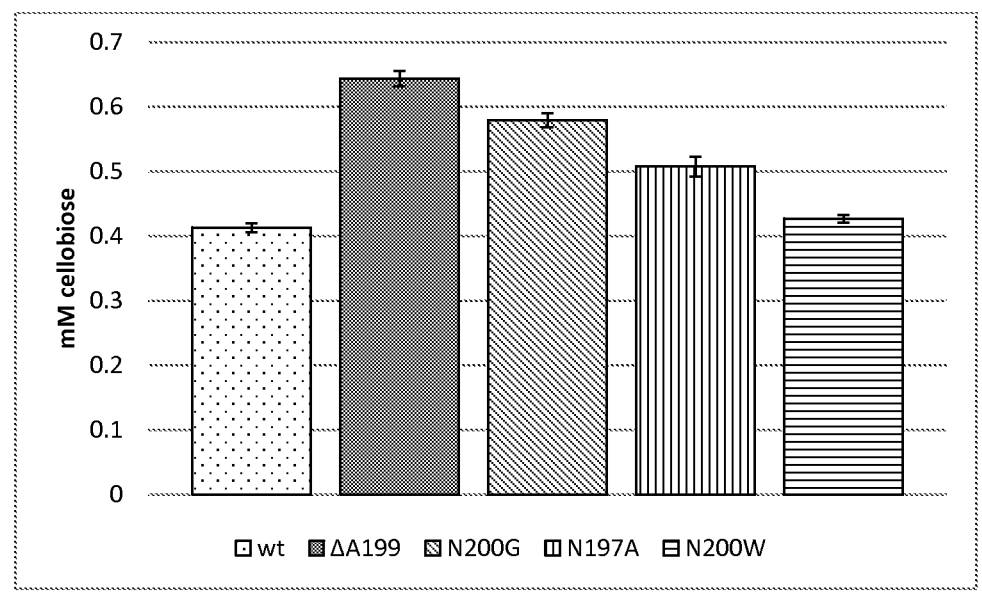
FIG. 5 shows hydrolysis of microcrystalline cellulose by the *T. reesei* wild-type cellobiohydrolase I and the *T. reesei* cellobiohydrolase I A199*, N198A, N200G, and N200W variants. Values are shown in mM released cellobiose after 1 hour at pH 5, at 25° C. and at 1100 rpm.

The results as shown in FIG. 5 demonstrated that the cellobiohydrolase A199* variant had an approximately 56% increase in activity toward microcrystalline cellulose compared to the wild-type cellobiohydrolase I. N200G variant had 40%, N198A had 23% and N200W had 3% increase in activity compared with wild-type cellobiohydrolase I.

Example 17: Pretreated Corn Stover Hydrolysis Assay

Corn stover was pretreated at the U.S. Department of Energy National Renewable Energy Laboratory (NREL) as described in Example 9.

Unmilled, unwashed PCS (whole slurry PCS) was prepared by adjusting the pH of the PCS to 5.0 by addition of 10 M NaOH with extensive mixing, and then autoclaving for 20 minutes at 120° C. The dry weight of the whole slurry PCS was 29%.

A 96-well plate was generated by machining a teflon plate of depth ¼ inch with 96, cone-shaped wells, diameter ¼ inch at the upper surface and diameter ⅛ inch at the lower surface. The center of each well was at an equivalent position to the center of a corresponding well in a standard 96-well microtiter plate, approximately 23/64 inch on center. The resulting volume of each well was approximately 135 µl. This 96-well aluminum plate is hereinafter referred to as the "fill plate". The pH-adjusted unmilled, unwashed PCS was used to fill the holes in the fill plate by applying a suitable volume of the PCS to the upper surface of the plate, then using a spatula to spread the material over the surface and into the holes. Holes were deemed sufficiently full when the PCS was extruded through the hole in the bottom surface, forming noodle-like tubes. A MULTISCREEN® Column Loader Scraper (Millipore, Billerica, Mass., USA)

held perpendicular to the fill plate surface was used to scrape excess PCS from the top and bottom surfaces of the fill plate, leaving the surfaces of the PCS in each well flush with the surfaces of the fill plate. The fill plate was then placed on the top of a 2.2 ml deep well plate (Axygen, Union City, Calif., USA) with the top surface adjacent to the open end of the well plate (e.g., the top of the well plate), and the wells aligned with the PCS-filled holes in the fill plate. The fill plate was secured in this position, and the assembly centrifuged at 2500 rpm (1350× g) for 5 minutes in a Sorvall Legend RT+(Thermo Scientific, Waltham, Mass., USA). Following centrifugation, the PCS had been transferred to the deep well plate. A 3 mm glass bead (Fisher Scientific, Waltham, Mass., USA) was placed in each well for mixing.

The hydrolysis of PCS was conducted in a total reaction volume of 0.2 ml. The hydrolysis was performed with 50 mg of insoluble PCS solids containing 50 mM sodium acetate pH 5.0 buffer containing 1 mM manganese sulfate and various protein loadings of various enzyme compositions (expressed as mg protein per gram of cellulose). Enzyme compositions were prepared and then added simultaneously to all wells in a volume ranging from 20 µl to 50 µl, for a final volume of 0.2-0.50 ml in each reaction. The plate was then sealed using an ALPS-300™ plate heat sealer, mixed thoroughly, and incubated at a specific temperature for 72 hours. All experiments reported were performed in triplicate.

Following hydrolysis, samples were filtered using a 0.45 µm MULTISCREEN® 96-well filter plate and filtrates analyzed for sugar content as described in Example 9.

Glucose was measured. The measured glucose concentration was adjusted for the appropriate dilution factor. The net concentration of enzymatically-produced glucose from unwashed PCS was determined by adjusting the measured glucose concentration for corresponding background glucose concentration in the unmilled, unwashed PCS at zero time point. All HPLC data processing was performed using MICROSOFT EXCEL™ software.

The degree of glucose conversion to glucose was calculated using the following equation: % glucose conversion= (glucose concentration)/(glucose concentration in a limit digest)×100. In order to calculate % glucose conversion, a 100% conversion point was set based on a cellulase control (100 mg of *T. reesei* cellulase per gram cellulose. Triplicate data points were averaged and standard deviation was calculated.

Example 18: Preparation of an Enzyme Composition #2 without Cellobiohydrolase I

An *Aspergillus fumigatus* GH6A cellobiohydrolase II variant (GENESEQP:AZN71803) was prepared recombinantly in *Aspergillus oryzae* as described in WO 2011/123450. The filtered broth of the *A. fumigatus* cellobiohydrolase II was desalted and buffer-exchanged into 50 mM sodium acetate pH 5.0 containing 100 mM sodium chloride using a tangential flow (10K membrane, Pall Corporation).

The *Thermoascus aurantiacus* GH5 endoglucanase II (GENESEQP:AZI04862) was prepared recombinantly according to WO 2011/057140 using *Aspergillus oryzae* as a host. The filtered broth of the *T. aurantiacus* endoglucanase II was concentrated using tangential flow (5K membrane, Pall Corporation). The concentrated protein was desalted using a 400 ml SEPHADEX™ G-25 column into 20 mM Tris pH 8.0.

The *Penicillium* sp. (*emersonii*) GH61A polypeptide was prepared as disclosed in Example 10.

The *Aspergillus fumigatus* GH10 xylanase (xyn3) was prepared as disclosed in Example 10.

The *Aspergillus fumigatus* Cel3A beta-glucosidase 4M mutant was prepared as described in Example 10. The protein concentration was determined using a Microplate BCA™ Protein Assay Kit (Thermo Fischer Scientific, Waltham, Mass., USA) in which bovine serum albumin was used as a protein standard.

The *Talaromyces emersonii* CBS 393.64 beta-xylosidase was prepared as described in Example 10.

The protein concentration for each of the monocomponents described above was determined using a Microplate BCA™ Protein Assay Kit in which bovine serum albumin was used as a protein standard, except the *Penicillium* sp. (*emersonii*) GH61A polypeptide, which was determined at $A_{280}$ using the theoretical molar extinction coefficient 41730 $M^{-1} \cdot cm^{-1}$. An enzyme composition was prepared composed of each monocomponent as follows: 39.7% *Aspergillus fumigatus* Cel6A variant cellobiohydrolase II, 15.9% *T. reesei* GH5 endoglucanase II, 23.8% *Penicillium* sp. (*emersonii*) GH61A polypeptide, 7.9% *Aspergillus fumigatus* GH10 xylanase, 7.9% *Aspergillus fumigatus* beta-glucosidase, and 4.8% *Talaromyces emersonii* beta-xylosidase. The enzyme composition is designated herein as "cellulolytic enzyme composition #2 without cellobiohydrolase I".

Example 19: Source of DNA Sequence Information for *Rasamsonia emersonii* Cellobiohydrolase I The genomic DNA sequence and deduced amino acid sequence of the wild-type *Rasamsonia emersonii* GH7 cellobiohydrolase I gene is shown in SEQ ID NO: 11 and SEQ ID NO: 12, respectively. The gene sequence is 99% identical to Genbank entry AF439935.4. The cDNA sequence and deduced amino acid sequence of the *Rasamsonia emersonii* cellobiohydrolase I gene is shown in SEQ ID NO: 63 and SEQ ID NO: 12, respectively.

Based on the cDNA sequence for *Rasamsonia emersonii* cellobiohydrolase I, a codon-optimized synthetic gene encoding the full-length cellobiohydrolase I was generated for *Aspergillus oryzae* expression based on the algorithm developed by Gustafsson et al., 2004, *Trends in Biotechnology* 22 (7): 346-353. The codon-optimized coding sequence (SEQ ID NO: 64) was synthesized by the GENEART® Gene Synthesis service (Life Technologies Corp., San Diego, Calif., USA) with a 5' Bam HI restriction site, a 3' Hind III restriction site, and a Kozac consensus sequence (CACC) situated between the start codon and the Bam HI restriction site.

Example 20: Site-Directed Mutagenesis of the Wild-Type *Rasamsonia emersonii* Cellobiohydrolase I The codon-optimized synthetic gene encoding the wild-type *Rasamsonia emersonii* cellobiohydrolase I was provided in a non-specified kanamycin-resistant *E. coli* cloning vector.

To generate the *R. emersonii* cellobiohydrolase I PC1-146 variant (SEQ ID NO: 65 for the mutant DNA sequence and SEQ ID NO: 66 for the variant), an AAC codon (N194) was replaced with a GCA codon (194A) and an AAC codon (N197) was replaced with a GCA codon (197A).

Two synthetic primers for site-directed mutagenesis were designed as shown below using a SOE primer design tool. The introduced site-directed mutation changed an AAC codon (N194) to a GCA codon (194A) and an AAC codon (N197) to a GCA codon (197A).

```
Primer F-N194A N197A:
                                    (SEQ ID NO: 67)
5'-AAGGATGGCAGCCCTCGTCCGCAAACGCGGCAACTGGCATCGGTGAT

CAC-3'

Primer R-N194A N197A:
                                    (SEQ ID NO: 68)
5'-GGACGAGGGCTGCCATCCTTCCACGTTCGC-3'
```

Site-directed mutagenesis of the synthetic gene encoding the wild-type *R. emersonii* cellobiohydrolase I was facilitated by PCR amplification of the pDau109 vector containing the *R. emersonii* cellobiohydrolase 1 gene designated pDau222-*R. emersonii* cellobiohydrolase I. The *R. emersonii* cellobiohydrolase 1 gene was previously cloned into Bam HI-Hind III digested pDau109 resulting in transcription of the *R. emersonii* cellobiohydrolase 1 gene under the control of a NA2-tpi double promoter.

The mutations were introduced by PCR using a PHUSION® High-Fidelity PCR Kit. The PCR solution was composed of 10 μl of 5× HF buffer, 1 μl of dNTPs (10 mM), 0.5 μl of PHUSION® DNA polymerase (0.2 units/μl), 0.25 μl of primer F-N194A N197A (100 μM), 0.25 μl of primer R-N194A N197A (100 μM), 10 μl of template DNA (pDau222-*R. emersonii* cellobiohydrolase I, 1 ng/μl), and 28 μl of deionized water in a total volume of 50 μl. The PCR was performed using a GeneAmp® PCR System 9700 (Applied Biosystems, Foster City, Calif., USA) programmed for 1 cycle at 98° C. for 30 seconds; and 19 cycles each at 98° C. for 30 seconds, 55° C. for 1 minute, and 72° C. for 4 minutes. The PCR solution was then held at 8° C. until removed from the PCR machine.

Following PCR, 10 units of Dpn I were added directly to the PCR solution and incubated at 37° C. for 1 hour. Then 1 μl of the Dpn I treated PCR solution was transformed into ONE SHOT® TOP10F' Chemically Competent *E. coli* cells according to the manufacturer's protocol and spread onto LB plates supplemented with 0.15 mg of ampicillin per ml. After incubation at 37° C. overnight, transformants were observed growing under selection on the LB ampicillin plates. Four transformants were cultivated in LB medium supplemented with 0.15 mg of ampicillin per ml and plasmids were isolated using a QIAPREP® Spin Miniprep Kit.

The isolated plasmids were sequenced using an Applied Biosystems 3730xl DNA Analyzer with vector primers and *R. emersonii* cellobiohydrolase 1 gene specific primers, shown below, in order to determine a representative plasmid that was free of PCR errors and contained the desired mutations.

```
             Primer F-pDau109
                                    (SEQ ID NO: 69)
             5'-CCACACTTCTCTTCCTTCCTCAATCCTC-3'

Primer F-Central1
                                    (SEQ ID NO: 70)
             5'-GTGAGGCGAACGTGGAAGGATG-3'

Primer R-Central2
                                    (SEQ ID NO: 71)
             5'-gtacctgtgtccgtgccgtcatctg-3'

Primer R-pDau109
                                    (SEQ ID NO: 31)
             5'-ATCCTCAATTCCGTCGGTCGA-3'
```

One plasmid clone free of PCR errors and containing the AAC (N194) to GCA (194A) mutation and the AAC (N197) to GCA (197A) mutation was chosen and designated plasmid pE146. The variant is designated herein as PC1-146.

Example 21: Construction of an *Aspergillus oryzae* Expression Vector Containing a *Rasamsonia emersonii* DNA Sequence Encoding Cellobiohydrolase I The kanamycin-resistant *E. coli* cloning vector provided by GENEART® Gene Synthesis encoding the *Rasamsonia emersonii* cellobiohydrolase I was digested with Fast Digest Bam HI and Hind III (Fermentas Inc., Glen Burnie, Md., USA) according to manufacturer's instructions. The reaction products were isolated by 1.0% agarose gel electrophoresis using TAE buffer where a 1375 bp product band was excised from the gel and purified using an ILLUSTRA™ GFX™ DNA Purification Kit.

The 1375 bp fragment was then cloned into pDau109 digested with Bam HI and Hind III using T4 DNA ligase. The Bam HI-Hind III digested pDau109 and the Bam HI/Hind III digested pDau109 fragment containing the *T. reesei* cellobiohydrolase I coding sequence were mixed in a molar ratio of 1:3 (i.e., mass ratio approximately 2.5:1 or 20 ng:50 ng) and ligated with 50 units of T4 DNA ligase in 1× T4 DNA ligase buffer with 1 mM ATP at 16° C. over-night in accordance with the manufacturer's instructions. Cloning of the *Rasamsonia emersonii* cellobiohydrolase I gene into Bam HI-Hind III digested pDau109 resulted in the transcription of the *Rasamsonia emersonii* cellobiohydrolase I gene under the control of a NA2-tpi double promoter.

The ligation mixture was transformed into ONE SHOT® TOP10F' Chemically Competent *E. coli* cells according to the manufacturer's protocol and spread onto LB plates supplemented with 0.1 mg of ampicillin per ml. After incubation at 37° C. overnight, transformants were observed growing under selection on the LB ampicillin plates. Insertion of the *Rasamsonia emersonii* cellobiohydrolase I gene into pDau109 was verified by PCR on the transformants as described below using primers F-pDau109 and R-pDau109.

A 1.1× REDDYMIX® Master Mix (Thermo Fisher Scientific, Roskilde, Denmark) was used for the PCR. The PCR solution was composed of 10 μl of 1.1× REDDYMIX® Master Mix, 0.5 μl of primer F-pDau109 (10 μM), and 0.5 μl of primer R-pDau109 (10 μM). A toothpick was used to transfer a small amount of cells to the PCR solution. The PCR was performed using a PTC-200 DNA Engine programmed for 1 cycle at 94° C. for 3 minutes; 30 cycles each at 94° C. for 30 seconds, 50° C. for 1 minute, and 72° C. for 2 minutes; and 1 cycle at 72° C. for 1 minute. The PCR solution was then held at 15° C. until removed from the PCR machine.

The PCR products were analyzed by 1.0% agarose gel electrophoresis using TAE buffer where a 1600 bp PCR product band was observed confirming insertion of the *Rasamsonia emersonii* cellobiohydrolase I coding sequence into pDau109.

An *E. coli* transformant containing the *Rasamsonia emersonii* cellobiohydrolase I plasmid construct was cultivated in LB medium supplemented with 0.1 mg of ampicillin per ml and plasmid DNA was isolated using a QIAPREP® Spin Miniprep Kit. The plasmid was designated pKHJN0135.

Example 22: Expression of the Wild-Type *Rasamsonia emersonii* Cellobiohydrolase I The expression plasmid pKHJN0135 was transformed into *Aspergillus oryzae* MT3568 protoplasts according to Christensen et al., 1988, supra and WO 2004/032648. *A. oryzae* MT3568 protoplasts were prepared according to the method of EP 0238023 B1, pages 14-15.

Transformants were purified on COVE sucrose plates through single conidia prior to sporulating them on PDA plates. Spores of the transformants were inoculated into 96 deep well plates containing 0.75 ml of YP+2% glucose medium and incubated stationary at 30° C. for 4 days. Production of the *Rasamsonia emersonii* cellobiohydrolase I by the transformants was analyzed from culture supernatants of the 96 deep well cultivations. Expression was verified by SDS-PAGE analysis using an E-Page 8% SDS-PAGE 48 well gel and Coomassie blue staining. Based on the level of expression by SDS-PAGE, one transformant was selected for further work and designated *Aspergillus oryzae* ReCBH I.

For larger scale production, *A. oryzae* ReCBH I spores were spread onto COVE sucrose slants and incubated for five days at 37° C. The confluent spore slants were washed twice with 5 ml of 0.01% TWEEN® 20 to maximize the number of spores collected. The spore suspensions were then used to inoculate seven 500 ml flasks containing 150 ml of DAP-4C medium. The cultures were incubated at 30° C. with constant shaking at 100 rpm. At day four post-inoculation, the culture broths were collected by filtration through a bottle top MF75 Supor MachV 0.2 µm PES filter. Expression was verified by SDS-PAGE analysis using an E-Page 8% SDS-PAGE 48 well gel and Coomassie staining. The culture broths from *A. oryzae* ReCBH I produced a band at approximately 60 kDa for the *Rasamsonia emersonii* cellobiohydrolase I.

For larger scale production, *A. oryzae* ReCBH I spores were spread onto COVE sucrose slants and incubated for five days at 37° C. The confluent spore slants were washed twice with 5 ml G2-Gly medium. The spore suspensions were then used to inoculate 500 ml flasks containing 150 ml of G2-Gly medium. These pre-cultures were incubated at 30° C. with constant shaking at 150 rpm. After one day, each of the pre-cultures was used to inoculate four 500 ml flasks containing 150 ml DAP4C-1 medium. At day four post-inoculation, the culture broths were collected by filtration through a bottle top MF75 Supor MachV 0.2 µm PES filter.

Example 23: Expression of the *Rasamsonia emersonii* Cellobiohydrolase I PC1-146 Variant The expression plasmid pE146 was transformed into *Aspergillus oryzae* MT3568 protoplasts according to Christensen et al., 1988, supra and WO 2004/032648. *A. oryzae* MT3568 protoplasts were prepared according to the method of EP 0238023 B1, pages 14-15.

Transformants were purified on COVE sucrose plates without CsCl through single conidia. Spores of the transformants were inoculated into 96 deep well plates containing 0.50 ml of YP+2% maltose medium and incubated stationary at 34° C. for 6 days. Production of the *R. emersonii* cellobiohydrolase I PC1-146 variant by the transformants was analyzed from culture supernatants of the 96 deep well cultivations. Expression was verified by measuring released reducing sugars from hydrolysis of microcrystalline cellulose. The hydrolysis was performed in 96 well microtiter plates (NUNC Thermo Fisher Scientific, Roskilde, Denmark) at 25° C. and 1100 rpm. Each hydrolysis reaction mixture contained 167 µl of microcrystalline cellulose at 90 g/liter in 50 mM sodium acetate pH 5.0, 0.01% TRITON® X-100, 20 µl of culture supernatant, and 63 µl of 50 mM sodium acetate pH 5.0, 0.01% TRITON® X-100. The plates were sealed with tape. The hydrolysis reaction was stopped by spinning the plate at 3500 rpm for 3 minutes. Then 50 µl of the reaction supernatant were added to 75 µl of stop solution in a 96 well PCR plate (Thermo Fisher Scientific, Roskilde, Denmark). The stop solution was composed of 15 mg/ml 4-hydroxybenzhydrazide (Sigma Chemical Co., Inc., St. Louis, Mo., USA), 50 mg/ml K—Na-tartrate (Sigma Chemical Co., Inc., St. Louis, Mo., USA) in 2% (w/v) NaOH. The plate was sealed with a lid and the mixture was incubated at 95° C. for 10 minutes and 5 minutes at 20° C. Then 100 µl was transferred to a microtiter plate and absorbance at 410 nm was measured using a SPECTRAMAX® Plus 384 (Molecular Devices, Sunnyvale, Calif., USA). The concentration of reducing sugar was proportional to the absorbance at 410 nm of the oxidized 4-hydroxybenzhydrazide. The reducing sugar content in the culture supernatants was measured by adding 4 µl of culture supernatant to a mixture of 75 µl of stop solution and 46 µl of milliQ water in a 96 well PCR plate. The plate was sealed with a lid and the mixture was incubated at 95° C. for 10 minutes and 5 minutes at 20° C. Then 100 µl was transferred to a microtiter plate and the absorbance at 410 nm was measured. The absorbance at 410 nm from the cell culture supernatant was subtracted from the absorbance at 410 nm of the hydrolysis reaction, to measure the amount of reducing sugar released by the enzymes.

Based on the level of hydrolysis of the microcrystalline cellulose one transformant was selected and designated *A. oryzae* PC1-146.

For larger scale production, *A. oryzae* PC1-146 spores were spread onto COVE sucrose slants and incubated for five days at 37° C. The confluent spore slants were washed twice with 5 ml of G2-Gly medium. The spore suspensions were then used to inoculate 500 ml flasks containing 150 ml of G2-Gly medium. These pre-cultures were incubated at 30° C. with constant shaking at 150 rpm. After one day, each of the pre-cultures was used to inoculate four 500 ml flasks containing 150 ml of DAP-4C medium. At day four post-inoculation, the culture broths were collected by filtration through a bottle top MF75 Supor MachV 0.2 µm PES filter.

Example 24: Purification of the *Rasamsonia emersonii* Wild-Type Cellobiohydrolase I and *R. emersonii* Cellobiohydrolase I PC1-146 Variant The fermentation broths were filtered through a PES Bottle top filter with a 0.22 µm cut-off. Ammonium sulphate was added to the filtered fermentation broths to a concentration of 1.8 M. The fermentation broths were purified by HIC/affinity chromatography followed by IEX/affinity chromatography.

In the HIC/affinity chromatographic step, the fermentation broths were applied to a 200 ml Phenyl SEPHAROSE® 6 Fast Flow column (high sub) equilibrated with 1.8 M ammonium sulphate, 25 mM HEPES pH 7.0. After applying the sample, the column was washed with 2 column volumes of 1.8 M ammonium sulphate followed by 1 column volume of 0.54 M ammonium sulphate. The bound proteins were batch eluted with 25 mM HEPES pH 7.0.

The elution of the protein was monitored at 280 nm. Fractions with high 280 nm absorbance were analyzed by SDS-PAGE using 12-well NUPAGE® 4-12% Bis-Tris gel for their cellobiohydrolase content. Fractions with high content of the protein were pooled and collected for further purification. The pooled fractions were desalted on a SEPHADEX™ G-25 (medium) column equilibrated with 25 mM MES pH 6.0. The elution of the protein was monitored at 280 nm and fractions with high absorbance at 280 nm were chosen for the second chromatographic step.

The pooled fractions were applied to a 60 ml RESOURCE™ 15Q column equilibrated with 25 mM MES pH 6.0 and bound proteins were eluted with a linear 100-200 mM sodium chloride gradient for 1.5 column volumes followed by 1.5 column volumes of 300 mM sodium chloride, and followed by 1.5 column volumes of 1 M sodium chloride. The elution of the protein was monitored at 280 nm and fractions with high absorbance at 280 nm were analyzed on SDS-PAGE. Fractions with high content of cellobiohydrolase I were pooled.

Example 25: Activity Measurement on Microcrystalline Cellulose of the *Rasamsonia Emersonii* Cellobiohydrolase I PC1-146 Variant The activity of the purified *R. emersonii* cellobiohydrolase I PC1-146 variant was compared to the purified *T. reesei* wild-type cellobiohydrolase I using washed microcrystalline cellulose (AVICEL® PH101; Sigma-Aldrich, St. Louis, Mo., USA) as a substrate.

The purified cellobiohydrolase variant was diluted in 50 mM sodium acetate, 2 mM CaCl$_2$ pH 5 to a concentration of 0.4 µM. Then 50 µl of the diluted cellobiohydrolase I variant were added to each well of a microtiter plate followed by 200 µl of washed microcrystalline cellulose at 90 g/liter to each well. The microtiter plate was quickly transferred to a thermomixer and incubated for 1 hour at 1100 rpm and 50° C. The reaction was stopped by centrifugation at 3500 rpm for 3 minutes at 5° C. using a HERAEUS® MULTIFUGE® 3 s-r centrifuge. Fifty µl of supernatant were transferred to PCR sample tubes (0.2 ml non-skirtet 96-well PCR plate). PAHBAH (4-hydroxy-benzhydrazide) was dissolved in buffer (0.18 M K—Na-tartrate and 0.5 M NaOH) to make a 15 mg/ml solution. Seventy-five µl of the PAHBAH solution were added to the supernatants in the PCR samples tubes.

The PCR sample tubes were placed in a Peltier Thermal Cycler and incubated at 95° C. for 10 minutes and 20° C. for 5 minutes. After incubation 100 µl were transferred to a 96 well microtiter plate and the absorbance was measured at 410 nm. For each run a standard was included. The standard used was cellobiose diluted in 50 mM sodium acetate, 2 mM CaCl$_2$ pH 5 to a concentration of 0.008, 0.016, 0.0312, 0.0625, 0.125, 0.25, 0.5, and 1 mM. In addition to the standard, a blank (without cellobiohydrolase) for each run was included. For all the measurements, the blank measurement was subtracted. The absorbance data were normalized to cellobiose concentration using the standards.

Figure 6:
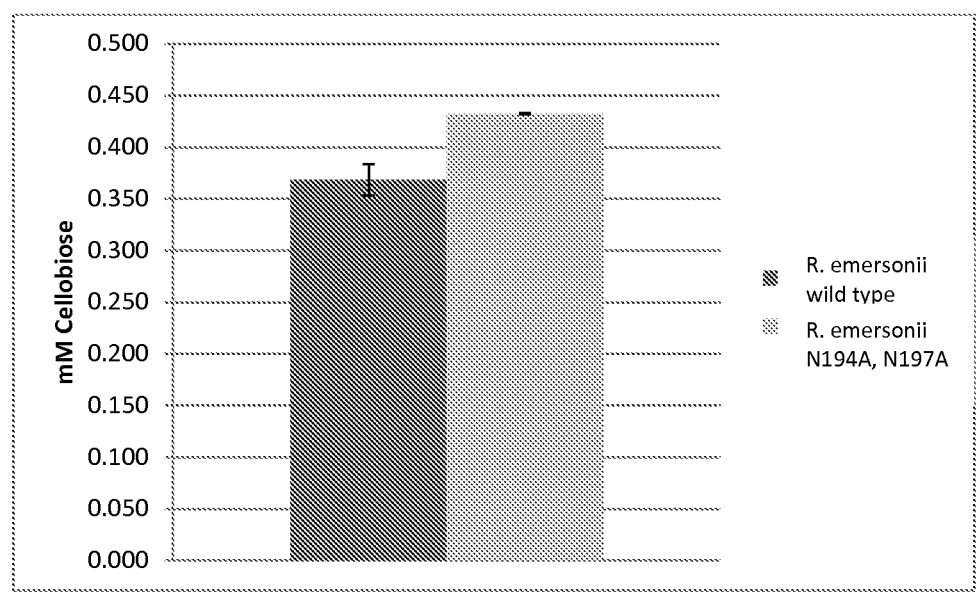
FIG. 6 shows hydrolysis of microcrystalline cellulose by the *Rasamsonia emersonii* wild-type cellobiohydrolase I and *R. emersonii* cellobiohydrolase I PC1-146 variant. Values are shown in mM released cellobiose after 1 hour at pH 5, at 50° C. and at 1100 rpm.

The results as shown in FIG. 6 demonstrated that the *R. emersonii* cellobiohydrolase I PC1-146 variant had an approximately 17% increase in activity toward microcrystalline cellulose compared to the *R. emersonii* wild-type cellobiohydrolase I.

Example 26: Determination of Td of the *Rasamsonia emersonii* Cellobiohydrolase I PC1-146 Variant by Differential Scanning Calorimetry The thermostability of the *R. emersonii* cellobiohydrolase I PC1-146 variant was determined by Differential Scanning calorimetry (DSC) using a VP-Capillary Differential Scanning calorimeter as described in Example 12.

The results demonstrated that the *R. emersonii* wild-type cellobiohydrolase I has a Td of 78° C. compared to 78° C. for the *R. emersonii* cellobiohydrolase I PC1-146 variant thereof.

Example 27: Comparison of the Effect of *Rasamsonia emersonii* Cellobiohydrolase I PC1-146 Variant and *Rasamsonia emersonii* Wild-Type Cellobiohydrolase I on the Hydrolysis of Unwashed PCS by a Cellulase Enzyme Composition The *R. emersonii* cellobiohydrolase I PC1-146 variant and *R. emersonii* wild-type cellobiohydrolase I were added to cellulolytic enzyme composition #2 without cellobiohydrolase I (Example 18) at 25° C. using unmilled, unwashed PCS as a substrate. For hydrolysis at 8% total solids, each cellobiohydrolase I was added individually at 2.22 mg enzyme protein per g cellulose to 3.78 mg enzyme protein of the cellulase enzyme composition #2 without cellobiohydrolase I per g cellulose. For hydrolysis as 20% total solids, each cellobiohydrolase I was added individually at 4.44 mg enzyme protein per g cellulose to 7.56 mg enzyme protein of the cellulase enzyme composition #2 without cellobiohydrolase I per g cellulose.

The assay was performed as described in Example 17. The reactions with unmilled, unwashed PCS (8% and 20% total solids) were conducted for 24, 48, and 72 hours in 50 mM sodium acetate pH 5.0 buffer containing 1 mM manganese sulfate. All reactions were performed in quadruplicate and shaking at 200 rpm throughout the hydrolysis.

Figure 7:
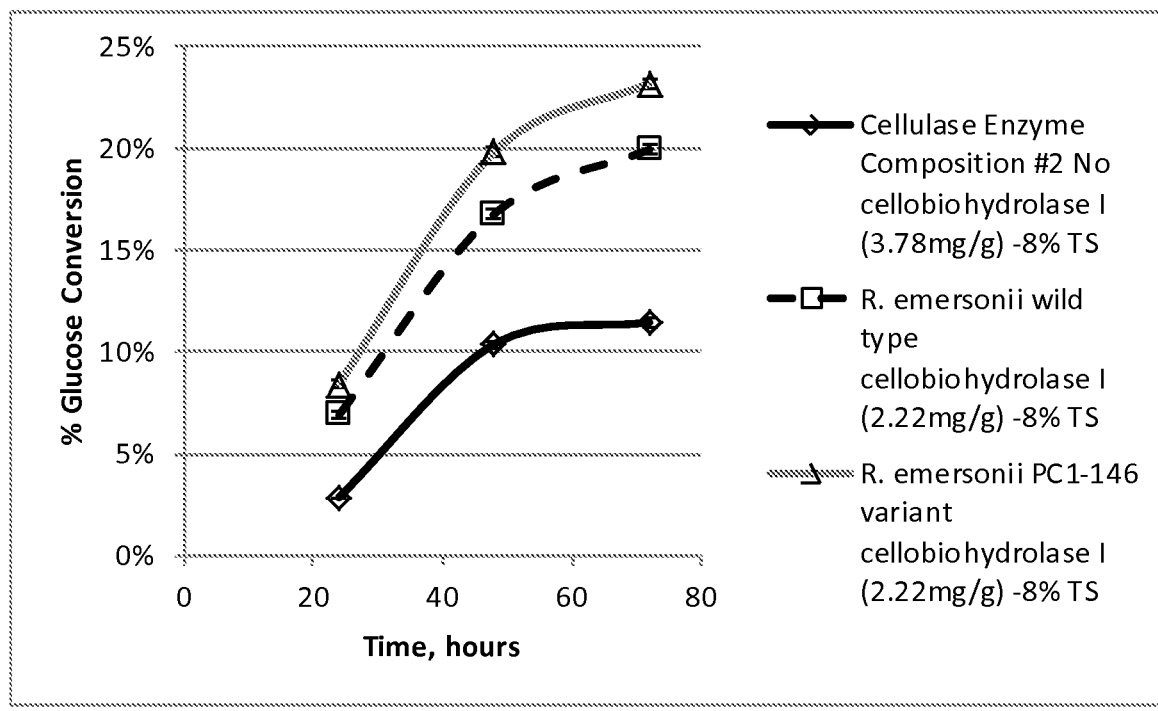
FIG. 7 shows a comparison of the effect of the *R. emersonii* cellobiohydrolase I variant and *R. emersonii* wild-type cellobiohydrolase I on the hydrolysis of unwashed PCS (8% total solids) by a cellulase enzyme composition.
Figure 8:
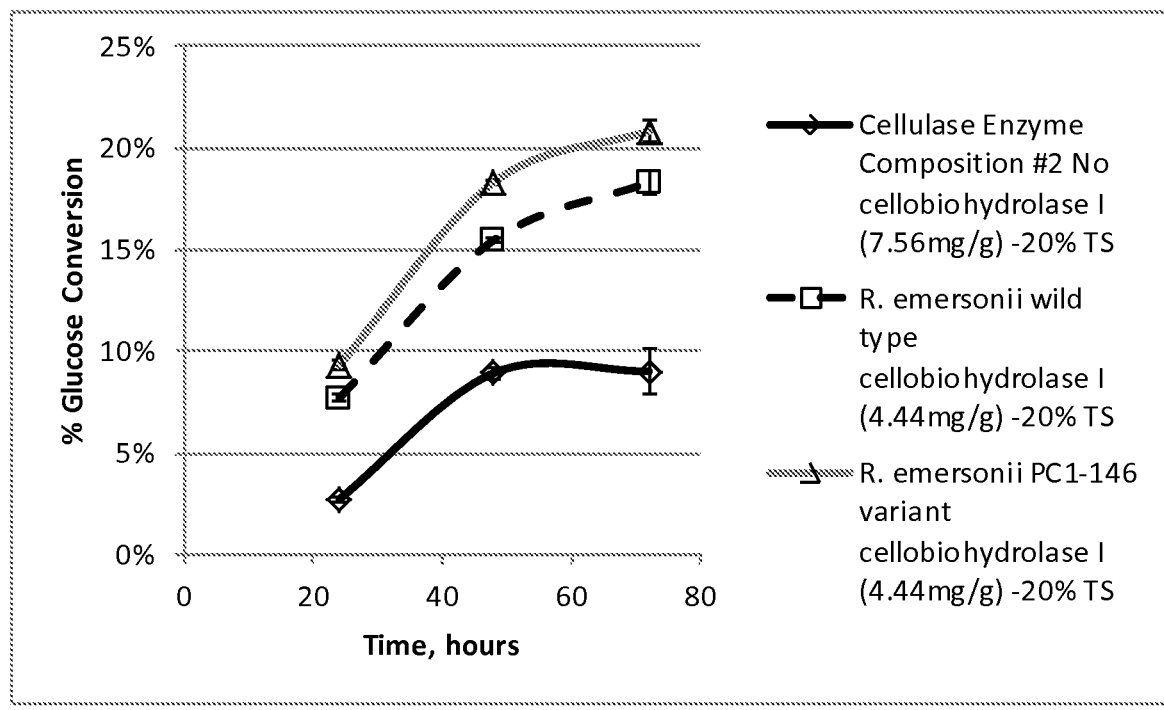
FIG. 8 shows a comparison of the effect of the *R. emersonii* cellobiohydrolase I PC1-146 variant and *R. emersonii* wild-type cellobiohydrolase I on the hydrolysis of unwashed PCS (20% total solids) by a cellulase enzyme composition.

The results shown in FIG. 7 (8% total solids) and FIG. 8 (20% total solids) demonstrated that at 24, 48, and 72 hours, the cellulase enzyme composition that included the *R. emersonii* cellobiohydrolase I PC1-146 variant had significantly higher cellulose conversion than the cellulase enzyme composition that included *R. emersonii* wild-type cellobiohydrolase I.

Example 28: Comparison of *Rasamsonia emersonii* Cellobiohydrolase I PC1-146 Variant with *Rasamsonia emersonii* Wild-Type Cellobiohydrolase I During Hydrolysis Evaluation of the *R. emersonii* cellobiohydrolase I PC1-146 variant and the *R. emersonii* wild-type cellobiohydrolase I was performed on unmilled, unwashed PCS at 20% TS. The enzyme matrix design is shown below in Table 1. CELLIC® HTec3 was obtained from Novozymes A/S, Bagsvaerd, Denmark. Enzymatic hydrolysis was conducted at 32° C. for 3 and 5 days. The sugar released was analyzed by HPLC (1200 Series LC System, Agilent Technologies Inc., Palo Alto, Calif., USA) equipped with a Rezex ROA-Organic acid H$^+$ column (8%) (7.8×300 mm) (Phenomenex Inc., Torrance, Calif., USA), 0.2 mm in line filter, an automated sampler, a gradient pump and a refractive index detector. The mobile phase used was 5 mM sulfuric acid at a flow rate of 0.9 ml/min. Glucose at different concentrations was used as standards.

Figure 9:
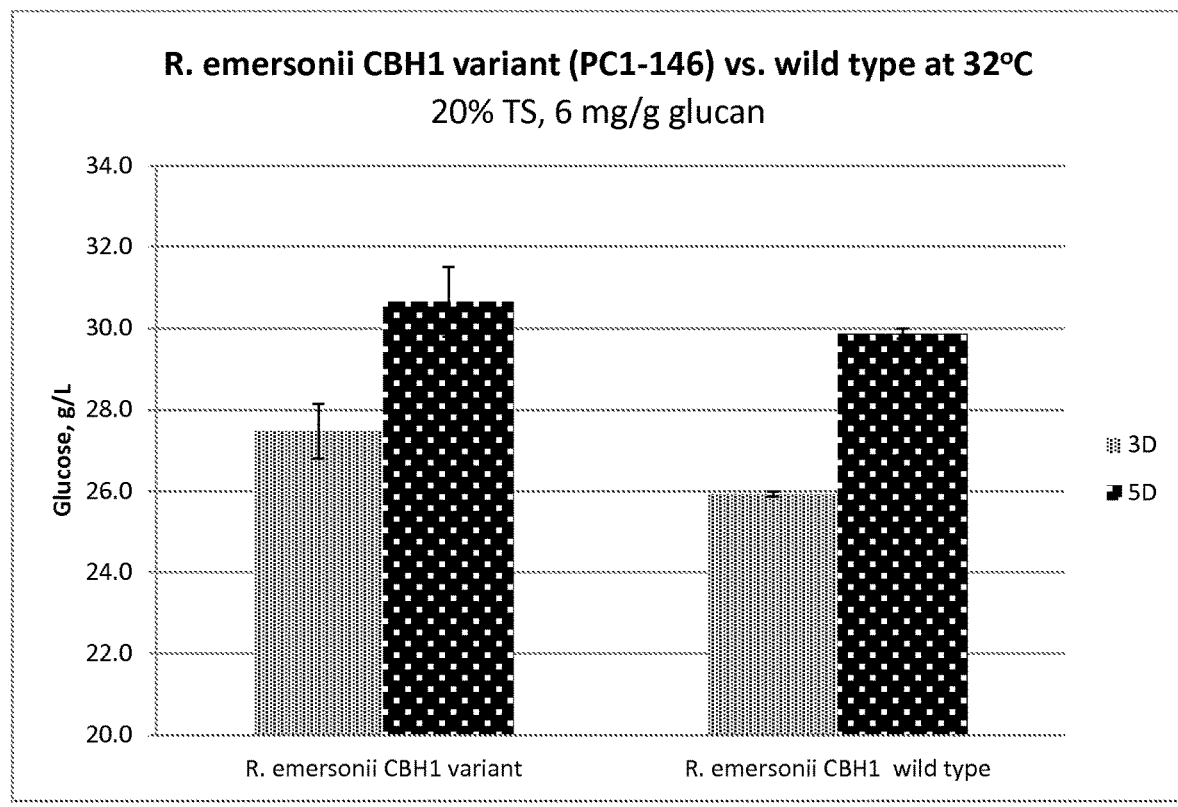
FIG. 9 shows a comparison of the *R. emersonii* cellobiohydrolase I PC1-146 variant with the *R. emersonii* wild-type cellobiohydrolase I during hydrolysis.

The results as shown in FIG. 9 demonstrated that the *R. emersonii* cellobiohydrolase I PC1-146 variant performed better than the wild-type *R. emersonii* cellobiohydrolase I.

TABLE 1

| Tube | enzyme dose mg/g glucan | *R. emersonii* CBH I Variant | *R. emersonii* CBH I Wild-type | Af CBH II | Ta EG | Aa BG | CELLIC® Htec3 |
|---|---|---|---|---|---|---|---|
| 1 | 6 | 37.5% |  | 37.5% | 10% | 5% | 10% |
| 2 | 6 |  | 37.5% | 37.5% | 10% | 5% | 10% |

Example 29: Comparison of *Rasamsonia emersonii* Cellobiohydrolase I PC1-146 Variant with *Rasamsonia emersonii* Wild-Type Cellobiohydrolase I During Simultaneous Saccharification and Fermentation (SSF)

The experimental design was the same as shown in Example 28, except that RED STAR® yeast at 1 g per liter and urea at 2 g per liter were added together with the enzyme during the beginning of the hydrolysis. Ethanol release was analyzed by HPLC using the system described in Example 28. Ethanol at different concentrations was used as standards.

Figure 10:
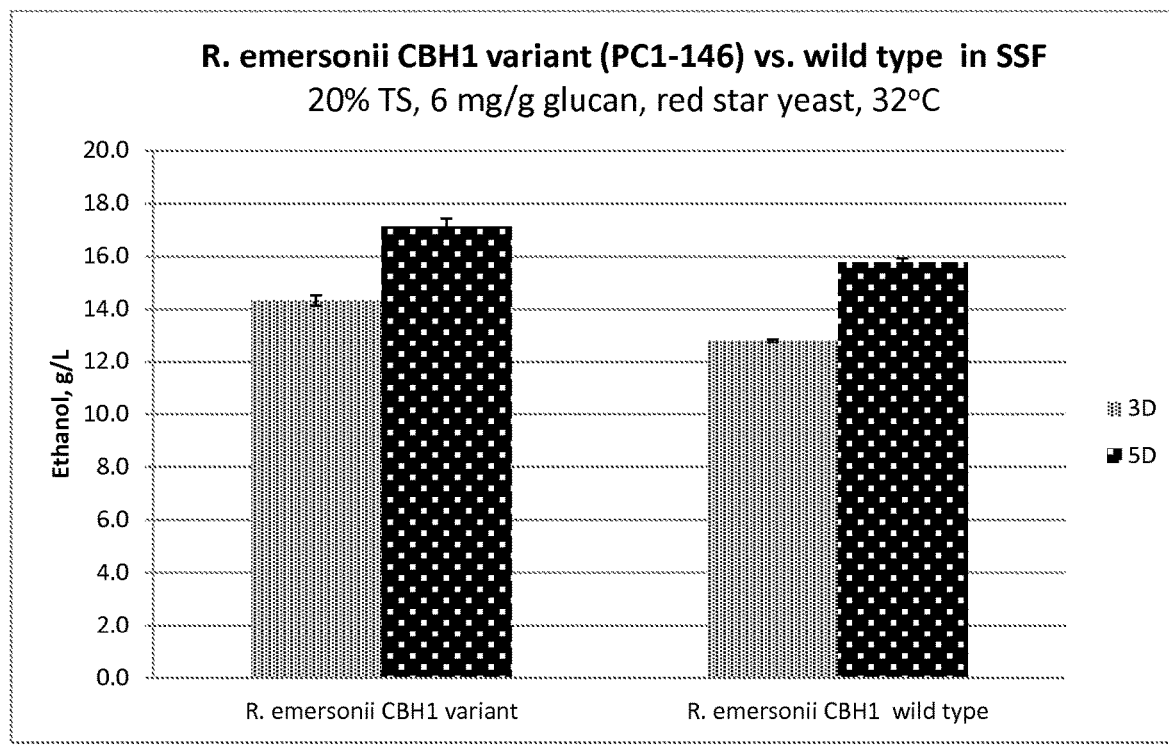
FIG. 10 shows a comparison of the *R. emersonii* cellobiohydrolase I PC1-146 variant with the *Rasamsonia emersonii* wild-type cellobiohydrolase I during simultaneous saccharification and fermentation (SSF).

The results as shown in FIG. 10 demonstrate that the *R. emersonii* cellobiohydrolase I PC1-146 variant performed better than the wild-type *R. emersonii* cellobiohydrolase I during SSF.

Example 30: Construction of a *Rasamsonia emersonii* Fusion Cellobiohydrolase I with Linker and Carbohydrate Binding Module from *Trichoderma reesei* Cellobiohydrolase I The codon-optimized synthetic gene encoding the *T. reesei* (*H. jecorina*) cellobiohydrolase I is described in Example 1.

The codon-optimized synthetic gene encoding the *R. emersonii* cellobiohydrolase I is described in Example 19.

To generate a gene encoding a *R. emersonii* fusion cellobiohydrolase I with linker and carbohydrate binding module (CBM) from *T. reesei* cellobiohydrolase I (SEQ ID NO: 72 for the fusion protein DNA sequence and SEQ ID NO: 73 for the fusion protein), a DNA fragment encoding *T. reesei* cellobiohydrolase I linker and CBM was assembled to the 3'-end of the gene encoding the *R. emersonii* cellobiohydrolase I using splicing overlap extension (SOE) PCR.

The DNA fragment encoding the *T. reesei* cellobiohydrolase I linker and CBM was amplified using primer F-SOE and primer R-pDau109 shown below.

```
Primer F-SOE
                                       (SEQ ID NO: 74)
5'-GGTCCCATCAACTCGACATTCACAGCCTCGGGTGGAAACCCTCCTGG
CGGAAACCCTC-3'

Primer R-pDau109
                                       (SEQ ID NO: 31)
5'-ATCCTCAATTCCGTCGGTCGA-3'

Primer F-pDau109
                                       (SEQ ID NO: 69)
5'-CCACACTTCTCTTCCTTCCTCAATCCTC-3'
```

The amplification of the DNA fragment encoding the *T. reesei* cellobiohydrolase 1 linker and CBM was performed using a PHUSION® High-Fidelity PCR Kit. The PCR solution was composed of 10 μl of 5× HF buffer, 1 μl of dNTPs (10 mM), 0.5 μl of PHUSION® DNA polymerase (0.2 units/μl), 0.25 μl of primer F-SOE (100 μM), 0.25 μl of primer R-pDau109 (100 μM), 10 μl of template DNA (pDAu222-*T. reesei* cellobiohydrolase I, 1 ng/μl), and 28 μl of deionized water in a total volume of 50 μl. The PCR was performed using a GeneAmp® PCR System 9700 programmed for 1 cycle at 98° C. for 30 seconds; and 30 cycles each at 98° C. for 10 seconds, 55° C. for 30 seconds, and 72° C. for 1 minute. The PCR solution was then held at 8° C. until removed from the PCR machine.

The PCR solution was submitted to 1% agarose gel electrophoresis using TAE buffer where a 405 bp PCR fragment encoding the *T. reesei* a linker and CBM was excised from the gel and purified using a MinElute Gel Extraction Kit (QIAGEN Inc., Valencia, Calif., USA).

A DNA fragment encoding the *R. emersonii* cellobiohydrolase I was amplified using primer F-pDau109 and primer R-pDau109 above.

The amplification of the DNA fragment encoding the *R. emersonii* wild-type cellobiohydrolase I was performed using a PHUSION® High-Fidelity PCR Kit. The PCR solution was composed of 10 μl of 5× HF buffer, 1 μl of dNTPs (10 mM), 0.5 μl of PHUSION® DNA polymerase (0.2 units/μl), 0.25 μl of primer F-pDAu109 (100 μM), 0.25 μl of primer R-pDau109 (100 μM), 10 μl of template DNA (pDAu222-*R. emersonii* cellobiohydrolase I, 1 ng/μl), and 28 μl of deionized water in a total volume of 50 μl. The PCR was performed using a GeneAmp® PCR System 9700 programmed for 1 cycle at 98° C. for 30 seconds; and 30 cycles each at 98° C. for 10 seconds, 55° C. for 30 seconds, and 72° C. for 1 minute. The PCR solution was then held at 8° C. until removed from the PCR machine.

The PCR solution was submitted to 1% agarose gel electrophoresis using TAE buffer where a 1600 bp fragment encoding the *R. emersonii* wild-type cellobiohydrolase I was excised from the gel and purified using a MinElute Gel Extraction Kit.

The two purified DNA fragments were assembled using SOE PCR and a PHUSION® High-Fidelity PCR Kit. The PCR solution was composed of 10 μl of 5× HF buffer, 1 μl of dNTPs (10 mM), 0.5 μl of PHUSION® DNA polymerase (0.2 units/μl), 0.25 μl of primer F-pDAu109 (100 μM), 10 μl of gel purified fragment encoding *T. reesei* cellobiohydrolase 1 linker and CBM, 2 μl of DNA fragment encoding *R. emersonii* cellobiohydrolase I, and 26 μl of deionized water in a total volume of 50 μl. The PCR was performed using a GeneAmp® PCR System 9700 programmed for 1 cycle at 98° C. for 30 seconds; and 30 cycles each at 98° C. for 20 seconds, 55° C. for 30 seconds, and 72° C. for 1 minute. The PCR solution was then held at 8° C. until removed from the PCR machine.

The PCR generated DNA fragment was then digested with Bam HI (New England Biolabs, Ipswich, Mass., USA) and Hind III (New England Biolabs, Ipswich, Mass., USA) as follows. Forty μl of PCR product were mixed with 5 μl buffer 2 (New England Biolabs, Ipswich, Mass., USA), 1 μl of Bam HI, and 1 μl of Hind III and incubated for 4 hours at 37° C. The resulting DNA product was submitted to 1% agarose gel electrophoresis using TAE buffer. A band of approximately 1567 bp was excised from the gel and purified using a MinElute Gel Extraction Kit.

The purified 1567 bp fragment encoding the *R. emersonii* cellobiohydrolase I with linker and carbohydrate binding module (CBM) from *T. reesei* cellobiohydrolase I was cloned into pDAu109 digested with Bam HI and Hind III using T4 DNA ligase. The Bam HI-Hind III digested pDau109 and the Bam HI/Hind III fragment containing the *R. emersonii* cellobiohydrolase I with linker and carbohydrate binding module (CBM) from *T. reesei* cellobiohydrolase I coding sequence were mixed in a molar ratio of 1:3 (i.e., equal volumes of gel purified products) and ligated with 50 units of T4 DNA ligase in 1× T4 DNA ligase buffer with 1 mM ATP and incubated at 22° C. for 10 minutes.

The ligation mixture was transformed into ONE SHOT® TOP10F' Chemically Competent *E. coli* cells according to the manufacturer's protocol and spread onto LB plates supplemented with 0.1 mg of ampicillin per ml. After incubation at 37° C. overnight, transformants were observed growing under selection on the LB ampicillin plates. Two transformants were cultivated in LB medium supplemented with 0.15 mg of ampicillin per ml and plasmids were isolated using a QIAPREP® Spin Miniprep Kit.

The insertion of the DNA fragment encoding the *R. emersonii* cellobiohydrolase I with linker and carbohydrate binding module (CBM) from *T. reesei* cellobiohydrolase I into pDAu109 was verified by sequencing. The isolated plasmids were sequenced using an Applied Biosystems 3730xl DNA Analyzer with vector primers F-pDau109 and R-pDau109 in order to determine a representative plasmid that was free of PCR errors and contained the correct insertion.

One plasmid clone free of PCR errors and containing the DNA fragment encoding the *R. emersonii* cellobiohydrolase I with linker and carbohydrate binding module (CBM) from *T. reesei* cellobiohydrolase I was chosen and designated plasmid pE147. The fusion cellobiohydrolase I is designated herein as PC1-147.

Example 31: Site-Directed Mutagenesis of the *Rasamsonia emersonii* PC1-147 Fusion Cellobiohydrolase I The fusion protein gene encoding the *R. emersonii* PC1-147 fusion cellobiohydrolase I was provided in pE147.

To generate a variant of the *R. emersonii* PC1-147 fusion cellobiohydrolase I (SEQ ID NO: 75 for the mutant DNA sequence and SEQ ID NO: 76 for the variant), an AAC codon (N194) was replaced with a GCA codon (194A) and an AAC codon (N197) was replaced with a GCA codon (197A) in the gene encoding the *R. emersonii* PC1-147 fusion cellobiohydrolase I.

Two synthetic primers for site-directed mutagenesis were designed as shown below using a SOE primer design tool. The introduced site-directed mutation changed an AAC codon (N194) to a GCA codon (194A) and an AAC codon (N197) to a GCA codon (197A).

```
Primer F-N194A N197A:
                                 (SEQ ID NO: 67)
5'-AAGGATGGCAGCCCTCGTCCGCAAACGCGGCAACTGGCATCGGTG

ATCAC-3'

Primer R-N194A N197A:
                                 (SEQ ID NO: 68)
5'-GGACGAGGGCTGCCATCCTTCCACGTTCGC-3'
```

Site-directed mutagenesis of the *R. emersonii* PC1-147 fusion cellobiohydrolase I gene was facilitated by PCR amplifications of the pDau109 vector containing the *R. emersonii* PC1-147 fusion cellobiohydrolase I gene. The *R. emersonii* PC1-147 fusion cellobiohydrolase I gene was previously cloned into Bam HI-Hind III digested pDau109 resulting in transcription of the *R. emersonii* PC1-147 fusion cellobiohydrolase I gene under the control of a NA2-tpi double promoter.

The mutations were introduced by PCR using a PHUSION® High-Fidelity PCR Kit. The PCR solution was composed of 10 µl of 5× HF buffer, 1 µl of dNTPs (10 mM), 0.5 µl of PHUSION® DNA polymerase (0.2 units/µl), 0.25 µl of primer F-N194A N197A (100 µM), 0.25 µl of primer R-N194A N197A (100 µM), 10 µl of plasmid pE147 DNA (1 ng/µl), and 28 µl of deionized water in a total volume of 50 µl. The PCR was performed using a GeneAmp® PCR System 9700 programmed for 1 cycle at 98° C. for 30 seconds; and 19 cycles each at 98° C. for 30 seconds, 55° C. for 1 minute, and 72° C. for 4 minutes. The PCR solution was then held at 8° C. until removed from the PCR machine.

Following the PCR, 10 units of Dpn I were added directly to the PCR solution and incubated at 37° C. for 1 hour. Then 1 µl of the Dpn I treated PCR solution was transformed into ONE SHOT® TOP10F' Chemically Competent *E. coli* cells according to the manufacturer's protocol and spread onto LB plates supplemented with 0.15 mg of ampicillin per ml. After incubation at 37° C. overnight, transformants were observed growing under selection on the LB ampicillin plates. Four transformants were cultivated in LB medium supplemented with 0.15 mg of ampicillin per ml and plasmids were isolated using a QIAPREP® Spin Miniprep Kit.

The isolated plasmids were sequenced using an Applied Biosystems 3730xl DNA Analyzer with primers F-pDau109, F-Central1, R-Central2 and R-pDau109, in order to determine a representative plasmid that was free of PCR errors and contained the desired mutations.

```
Primer F-pDau109
                                 (SEQ ID NO: 69)
5'-CCACACTTCTCTTCCTTCCTCAATCCTC-3'

Primer F-Central1
                                 (SEQ ID NO: 70)
5'-GTGAGGCGAACGTGGAAGGATG-3'

Primer R-Central2
                                 (SEQ ID NO: 71)
5'-gtacctgtgtccgtgccgtcatctg-3'

Primer R-pDau109
                                 (SEQ ID NO: 31)
5'-ATCCTCAATTCCGTCGGTCGA-3'
```

One plasmid clone free of PCR errors and containing the AAC (N194) to GCA (194A) mutation and the AAC (N197) to GCA (197A) mutation was chosen and designated plasmid pE378. The variant is designated herein as PC1-378.

Example 32: Expression of the *Rasamsonia emersonii* PC1-147 Fusion Cellobiohydrolase I and *R. emersonii* Cellobiohydrolase I PC1-378 Variant The expression plasmids pE147 and pE378 were transformed into *Aspergillus oryzae* MT3568 protoplasts according to Christensen et al., 1988, supra and WO 2004/032648. *A. oryzae* MT3568 protoplasts were prepared according to the method of EP 0238023 B1, pages 14-15.

Transformants were purified on COVE sucrose plates without CsCl through single conidia. Spores of the transformants were inoculated into 96 deep well plates containing 0.50 ml of YP+2% maltose+0.5% glucose medium and incubated stationary at 34° C. for 6 days. Production of the *R. emersonii* PC1-147 fusion cellobiohydrolase I and the *R. emersonii* cellobiohydrolase I PC1-378 variant by the transformants were analyzed from culture supernatants of the 96 deep well cultivations. Expression was verified by measuring the released reducing sugars from hydrolysis of microcrystalline cellulose according to the procedure described in Example 23.

Based on the level of hydrolysis of the microcrystalline cellulose one transformant for the *R. emersonii* PC1-147 fusion cellobiohydrolase I and the *R. emersonii* cellobiohydrolase I PC1-378 variant were selected and designated *A. oryzae* PC1-147 and *A. oryzae* PC1-378, respectively.

For larger scale production, *A. oryzae* PC1-147 or *A. oryzae* PC1-378 spores were spread onto COVE sucrose slants and incubated for five days at 37° C. The confluent spore slants were washed twice with 5 ml of G2-Gly medium. The spore suspensions were then used to inoculate 500 ml flasks containing 150 ml of G2-Gly medium. These pre-cultures were incubated at 30° C. with constant shaking at 150 rpm. After one day, each of the pre-cultures was used to inoculate four 500 ml flasks containing 150 ml of DAP-4C medium. At day four post-inoculation, the culture broths were collected by filtration through a bottle top MF75 Supor MachV 0.2 µm PES filter.

Example 33: Purification of the *Rasamsonia emersonii* PC1-147 Fusion Cellobiohydrolase I and *R. emersonii* Cellobiohydrolase I PC1-378 Variant The fermentation broths were filtered through a PES Bottle top filter with a 0.22 µm cut-off. Ammonium sulphate was added to the filtered fermentation broths to a concentration of 1.8 M.

The fermentation broths were purified by HIC/affinity chromatography followed by IEX/affinity chromatography.

In the HIC/affinity chromatographic step, the fermentation broths were applied to a 200 ml Phenyl SEPHAROSE® 6 Fast Flow column (high sub) which had been pre-equilibrated with 1.8 M ammonium sulphate, 25 mM HEPES pH 7.0. After applying the sample, the column was washed with 2 column volumes of 1.8 M ammonium sulphate followed by 1 column volume of 0.54 M ammonium sulphate. The bound proteins were batch eluted with 25 mM HEPES pH 7.0.

The elution of the protein was monitored at 280 nm. Fractions with high 280 nm absorbance were analysed on SDS-PAGE using 12-well NUPAGE® 4-12% Bis-Tris gel for their cellobiohydrolase I content. Fractions with high content of this protein were pooled and collected for further purification. The pooled fractions were desalted on a SEPHADEX™ G-25 (medium) column equilibrated with 25 mM MES pH 6.0. The elution of the protein was monitored at 280 nm and fractions with high absorbance at 280 nm were chosen for the second chromatographic step.

The pooled fractions were applied to the 60 ml RESOURCE™ 15Q column equilibrated with 25 mM MES pH 6.0 and bound proteins were eluted with a linear 100-200 mM sodium chloride gradient for 1.5 column volumes followed by 1.5 column volumes of 300 mM sodium chloride, followed by 1.5 column volumes of 1 M sodium chloride. The elution of the protein was monitored at 280 nm and fractions with high absorbance at 280 nm were analysed on SDS-PAGE.

Fractions with high content of cellobiohydrolase I were pooled.

Example 34: Activity Measurement on Microcrystalline Cellulose of the *Rasamsonia Emersonii* PC1-147 Fusion Cellobiohydrolase I and the *R. emersonii* Cellobiohydrolase I PC1-378 Variant The activity of the purified *R. emersonii* PC1-147 fusion cellobiohydrolase I and the *R. emersonii* cellobiohydrolase I PC1-378 variant (Example 33) were compared to the purified wild-type *R. emersonii* cellobiohydrolase I (Example 24) using washed microcrystalline cellulose as a substrate according to Example 25. Values are shown in relative activity where 100% was set as the activity of *R. emersonii* wild-type cellobiohydrolase I. The assay conditions were 24 hours incubation at pH 5, 50° C. and 1100 rpm.

Figure 11:
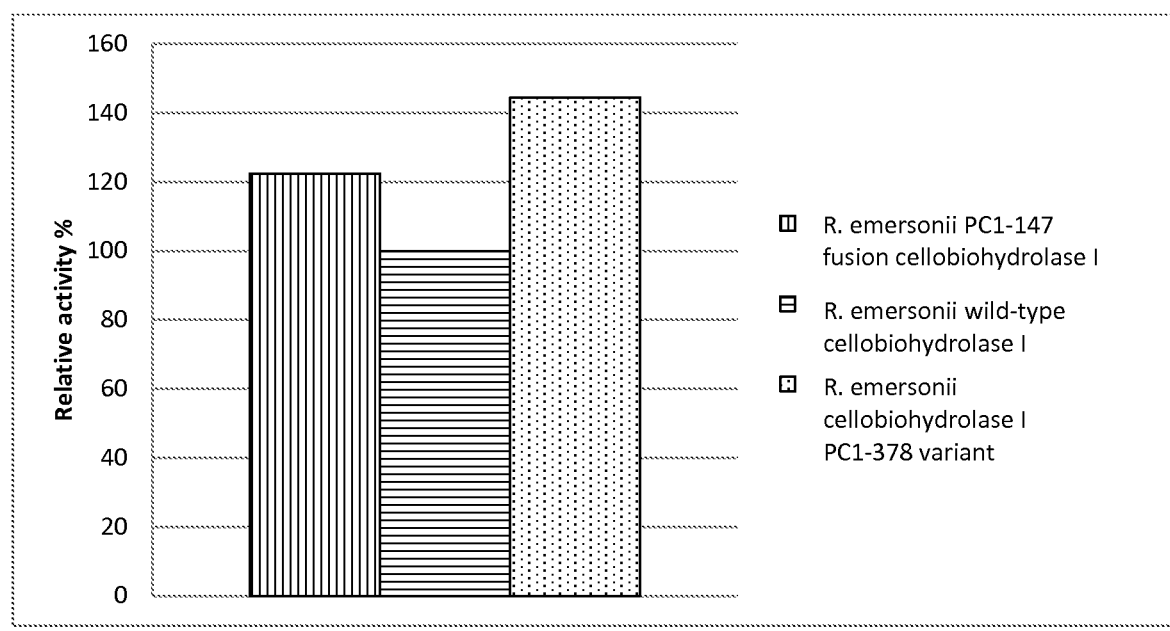
FIG. 11 shows a comparison of the hydrolysis of microcrystalline cellulose by the *R. emersonii* wild-type cellobiohydrolase I, *R. emersonii* PC1-147 fusion cellobiohydrolase I, and *R. emersonii* cellobiohydrolase I PC1-378 variant.

The results as shown in FIG. 11 demonstrated that the *R. emersonii* PC1-147 fusion cellobiohydrolase I and the *R. emersonii* cellobiohydrolase I PC1-378 variant had an approximately 22% and 44% increase in activity toward microcrystalline cellulose, respectively, compared to the *R. emersonii* wild-type cellobiohydrolase I.

Example 35: Preparation, Expression, and Purification of the *R. emersonii* Cellobiohydrolase I PC1-496 Variant The *R. emersonii* cellobiohydrolase I variant PC1-496 of the *R. emersonii* PC1-147 fusion cellobiohydrolase I (supra) was designed with deletions at positions S193*, N194*, and N195* (corresponding to deletions at positions 196, 197, and 198 of SEQ ID NO: 2), and then constructed and expressed using procedures similar to those described above. The variant PC1-496 coding sequence and corresponding amino acid sequence are shown in SEQ ID NOs: 77 and 78, respectively.

The fermentation broths were filtered through PES Bottle top filter with a 0.22 µm cut-off. Ammonium sulphate was added to the filtered fermentation broths to make a 1.8 M solution.

The cellobiohydrolases I were purified by HIC/affinity chromatography followed by IEX/affinity chromatography.

In the HIC/affinity chromatographic step, the fermentation broths were applied to a 200 ml Phenyl SEPHAROSE® 6 Fast Flow column (high sub) (GE Healthcare, Piscataway, N.J., USA) which had been pre-equilibrated with 1.8 M ammonium sulphate, 25 mM HEPES pH 7.0. After applying the sample, the column was washed with 2 CV 1.8 M ammonium sulphate followed by 1 CV 0.54 M ammonium sulphate. The bound proteins were batch eluted with 25 mM HEPES pH 7.0.

The elution of the protein was monitored at 280 nm. Fractions with high 280 nm absorbance were analyzed on SDS-PAGE using 12-well NUPAGE® 4-12% Bis-Tris gel (GE Healthcare, Piscataway, N.J., USA) for their cellobiohydrolase I content. Fractions with high content of this protein were pooled and collected for further purification. The pooled fractions were desalted on a SEPHADEX™ G-25 (medium) column (GE Healthcare, Piscataway, N.J., USA) equilibrated with 25 mM MES pH 6.0. The elution of the protein was monitored at 280 nm and fractions with high absorbance at 280 nm were chosen for the second chromatographic step.

The pooled fractions were applied to the 60 ml RESOURCE™ 15Q column (GE Healthcare, Piscataway, N.J., USA) equilibrated with 25 mM MES pH 6.0 and bound proteins were eluted with a linear 100-200 mM sodium chloride gradient for 1.5 CV followed by 1.5 CV 300 mM sodium chloride, followed by 1.5 CV 1 M sodium chloride. The elution of the protein was monitored at 280 nm and fractions with high absorbance at 280 nm were analyzed on SDS-PAGE.

Fractions with high content of cellobiohydrolase I were pooled.

Example 36: Activity Measurement on Microcrystalline Cellulose on Microcrystalline Cellulose of the *Rasamsonia emersonii* PC1-147 Fusion Cellobiohydrolase I and the *R. emersonii* Cellobiohydrolase I PC1-496 Variant The activity of the purified *R. emersonii* cellobiohydrolase I PC1-496 variant (Example 35) was compared to purified *R. emersonii* PC1-147 fusion cellobiohydrolase I using washed microcrystalline cellulose (AVICEL® PH101; Sigma-Aldrich, St. Louis, Mo., USA) as a substrate.

The purified cellobiohydrolase variants were diluted in 50 mM sodium acetate, 2 mM $CaCl_2$ pH 5. The diluted cellobiohydrolase I variants were added to each well (microwell plate 96F 26960 Thermo scientific). Following washed AVICEL was added to each well and the microtiter plate was quickly transferred to a thermomixer (eppendorf) and incubated for 30 min at 1100 rpm and 25° C. The final concentration of cellobiohydrolase I variants in the reaction was 2.4 µM and the concentration of AVICEL was 24.5 g/l. The reaction was stopped by centrifugation at 3500 rpm for 3 min at 5° C. (Hereaus multifuge 3 S—R). 50 µl supernatants were transferred to PCR sample tubes (Thermoscientific 0.2 ml non-skirtet 96-well PCR plate AB0600). PAHBAH (4-hydroxy-benzhydrazid) (Sigma, H 9882) was dissolved in buffer (0.18 M K—Na-tartrate (Merck, 1.08087) and 0.5 M NaOH) to make a 15 mg/ml solution. 75 µl of the PAHBAH solution was added to the supernatants in the PCR sample tubes.

The PCR sample tubes were placed in a Peltier Thermal Cycler and incubated at 95° C. for 10 min and 20° C. for 5 min. After incubation 100 µl were transferred to a 96 well microtiter plate (microwell plate 96F 26960 Thermo scientific) and the absorbance was measured at 410 nm. For each run a standard was included. The standard used was cellobiose diluted in 50 mM sodium acetate, 2 mM $CaCl_2$ pH 5 to a concentration of 0.008, 0.016, 0.0312, 0.0625, 0.125, 0.25, 0.5 mM. In addition to the standard, a blank (without cellobiohydrolases) was included. For all the measurement, the blank measurement was subtracted. The absorbance data were normalized to cellobiose concentration using the standards.

Figure 12:
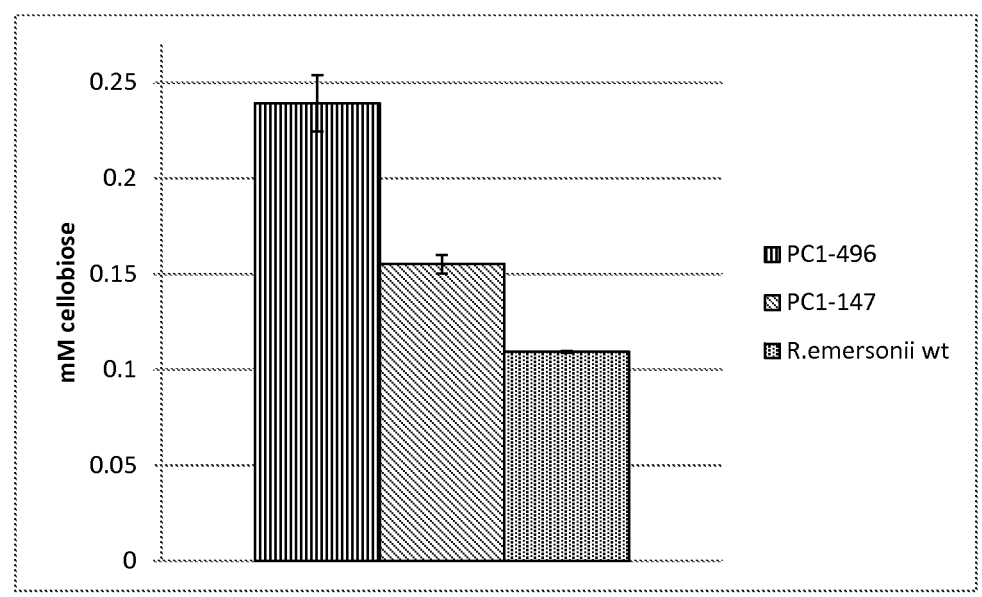
FIG. 12 shows a comparison of the hydrolysis of microcrystalline cellulose by the *R. emersonii* wild-type cellobiohydrolase I, *R. emersonii* PC1-147 fusion cellobiohydrolase I, and *R. emersonii* cellobiohydrolase I PC1-496 variant after 30 min at pH 5 and 25° C.

The results as shown in FIG. 12 demonstrated that the cellobiohydrolase variant PC1-496 (comprising deletions at positions corresponding to 196, 197, and 198 of SEQ ID NO: 2) had an approximately 119% increase in activity toward microcrystalline cellulose compared to the wild-type cellobiohydrolase I at 25° C. and an increase of 54% compared with the *R. emersonii* PC1-147 fusion cellobiohydrolase I.

Example 37: Pretreated Corn Stover Hydrolysis Assay

Corn stover was pretreated at the U.S. Department of Energy National Renewable Energy Laboratory (NREL) using 1.4 wt % sulfuric acid at 165° C. and 107 psi for 8 minutes. The water-insoluble solids in the pretreated corn stover (PCS) contained 56.5% cellulose, 4.6% hemicellulose, and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

Unmilled, unwashed PCS (whole slurry PCS) was prepared by adjusting the pH of the PCS to 5.0 by addition of 10 M NaOH with extensive mixing, and then autoclaving for 20 minutes at 120° C. The dry weight of the whole slurry PCS was 29%.

A 96-well plate was generated by machining a teflon plate of depth ¼ inch with 96, cone-shaped wells, diameter ¼ inch at the upper surface and diameter ⅛ inch at the lower surface. The center of each well was at an equivalent position to the center of a corresponding well in a standard 96-well microtiter plate, approximately ²³⁄₆₄ inch on center. The resulting volume of each well was approximately 135 µl. This 96-well aluminum plate is hereinafter referred to as the "fill plate". The pH-adjusted corn stover was used to fill the holes in the fill plate by applying a suitable volume of the corn stover to the upper surface of the plate, then using a spatula to spread the material over the surface and into the holes. Holes were deemed sufficiently full when corn stover was extruded through the hole in the bottom surface, forming noodle-like tubes. A MULTISCREEN® Column Loader Scraper (Millipore) held perpendicular to the fill plate surface was used to scrape excess corn stover from the top and bottom surfaces of the fill plate, leaving the surfaces of the corn stover in each well flush with the surfaces of the fill plate. The fill plate was then placed on the top of a 2.2 ml deep well plate (Axygen, Union City, Calif., USA) with the top surface adjacent to the open end of the well plate (e.g. the top of the well plate), and the wells aligned with the corn stover-filled holes in the fill plate. The fill plate was secured in this position, and the assembly centrifuged at 2500 rpm (1350× g) for 5 minutes in a Sorvall Legend RT+(Thermo Scientific, Waltham, Mass., USA). Following centrifugation, the corn stover had been transferred to the deep well plate. A 3 mm glass bead (Fisher Scientific, Waltham, Mass., USA) was placed in each well for mixing.

The hydrolysis of PCS was conducted in a total reaction volume of 0.2 ml. The hydrolysis was performed with 50 mg of insoluble PCS solids containing 50 mM sodium acetate pH 5.0 buffer containing 1 mM manganese sulfate and various protein loadings of various enzyme compositions (expressed as mg protein per gram of cellulose). Enzyme compositions were prepared and then added simultaneously to all wells in a volume ranging from 20 µl to 50 µl, for a final volume of 0.2-0.50 ml in each reaction. The plate was then sealed using an ALPS-300™ plate heat sealer (Abgene, Epsom, United Kingdom), mixed thoroughly, and incubated at a specific temperature for 72 hours.

Following hydrolysis, samples were filtered using a 0.45 µm MULTISCREEN® 96-well filter plate (Millipore, Bedford, Mass., USA) and filtrates analyzed for sugar content as described below. When not used immediately, filtered aliquots were frozen at −20° C. The sugar concentrations of samples diluted in 0.005 M $H_2SO_4$ were measured using a 4.6×250 mm AMINEX® HPX-87H column (Bio-Rad Laboratories, Inc., Hercules, Calif., USA) by elution with 0.05% w/w benzoic acid-0.005 M $H_2SO_4$ at 65° C. at a flow rate of 0.6 ml per minute, and quantitation by integration of the glucose, cellobiose, and xylose signals from refractive index detection (CHEMSTATION®, AGILENT® 1100 HPLC, Agilent Technologies, Santa Clara, Calif., USA) calibrated by pure sugar samples. The resultant glucose and cellobiose equivalents were used to calculate the percentage of cellulose conversion for each reaction.

Glucose and cellobiose were measured individually. Measured sugar concentrations were adjusted for the appropriate dilution factor. The net concentrations of enzymatically-produced sugars from unwashed PCS were determined by adjusting the measured sugar concentrations for corresponding background sugar concentrations in unwashed PCS at zero time point. All HPLC data processing was performed using MICROSOFT EXCEL™ software (Microsoft, Richland, Wash., USA).

The degree of glucose conversion to glucose was calculated using the following equation: % cellulose conversion= (glucose concentration)/(glucose concentration in a limit digest)×100. In order to calculate % glucose conversion, a 100% conversion point was set based on a cellulase control (100 mg of *T. reesei* cellulase supplemented with *Thermoascus aurantiacus* GH61A polypeptide, *Aspergillus fumigatus* GH10 xylanase (xyn3), and *Talaromyces emersonii* beta-xylosidase per gram cellulose). Quadruplicate data points were averaged and standard deviation was calculated.

Example 38: Preparation of an Enzyme Composition #3 without Cellobiohydrolase I

The *Talaromyces leycettanus* GH6 cellobiohydrolase II (GENESEQP:AZY49446) was prepared recombinantly in *Aspergillus oryzae* as described in WO 2012/103288. The filtered broth of the *Talaromyces leycettanus* GH6 cellobiohydrolase II was concentrated and buffer exchanged into 20 mM Tris pH 8.0 using a 400 ml SEPHADEX™ G-25 column (GE Healthcare, United Kingdom). The fractions were pooled, and 3 M ammonia sulfate, 20 mM Tris pH 8.0 was added to the desalted protein to a final concentration of 1.2 M ammonia sulfate, 20 mM Tris pH 8.0. The protein was loaded onto a Phenyl Sepharose™ 6 Fast Flow column (high sub) (GE Healthcare, Piscataway, N.J., USA) equilibrated in 20 mM Tris pH 8.0 with 1.2 M ammonium sulfate, and bound proteins were eluted with 20 mM Tris pH 8.0 with no ammonium sulfate. Fractions were analyzed by 8-16% Tris-HCl SDS-PAGE gels (Bio-Rad, Hercules, Calif., USA), and pooled. The pooled protein was buffer exchanged into 20 mM MES pH 6.0 using a Vivaflow 200 with 10 kDa molecular weight cut-off tangential flow membrane (Sartorius, Bohemia, N.Y., USA).

The *Trichoderma reesei* GH5 endoglucanase II (GENESEQP:AZI04858) was prepared recombinantly according to WO 2011/057140 using *Aspergillus oryzae* as a host. The filtered broth of the *T. reesei* endoglucanase II was desalted and buffer-exchanged into 20 mM Tris pH 8.0 using a tangential flow concentrator (Pall Filtron, Northborough, Mass., USA) equipped with a 10 kDa polyethersulfone membrane (Pall Filtron, Northborough, Mass., USA).

*Thermoascus aurantiacus* CGMCC 0583 GH61A polypeptide having cellulolytic enhancing activity (GENESEQP: AEC05922) was recombinantly prepared according to WO 2005/074656 using *Aspergillus oryzae* JaL250 as a host. The broth was filtered using a 0.22 µm EXPRESS™ Plus Membrane (Millipore, Bedford, Mass., USA).

The *Aspergillus fumigatus* GH10 xylanase (xyn3) (GENESEQP:AZI04884) was prepared recombinantly according to WO 2006/078256 using *Aspergillus oryzae* BECh2 (WO 2000/39322) as a host. The filtered broth of the *A. fumigatus* xylanase was desalted and buffer-exchanged into 50 mM sodium acetate pH 5.0 using a HIPREP® 26/10 Desalting Column (GE Healthcare, Piscataway, N.J., USA).

The *Aspergillus fumigatus* Cel3A beta-glucosidase 4M mutant (GENESEQP:AZU67153) was recombinantly prepared according to WO 2012/044915. The filtered broth of *Aspergillus fumigatus* Cel3A beta-glucosidase 4M was concentrated and buffer exchanged using a tangential flow concentrator (Pall Filtron, Northborough, Mass., USA) equipped with a 10 kDa polyethersulfone membrane (Pall Filtron, Northborough, Mass., USA) with 50 mM sodium acetate pH 5.0 containing 100 mM sodium chloride.

The *Talaromyces emersonii* CBS 393.64 beta-xylosidase (GENESEQP:AZI04896) was prepared recombinantly according to Rasmussen et al., 2006, *Biotechnology and Bioengineering* 94: 869-876 using *Aspergillus oryzae* JaL355 as a host (WO 2003/070956). The filtered broth was concentrated and desalted with 50 mM sodium acetate pH 5.0 using a tangential flow concentrator equipped with a 10 kDa polyethersulfone membrane (Pall Filtron, Northborough, Mass., USA).

The protein concentration for each of the monocomponents described above was determined using a Microplate BCA™ Protein Assay Kit (Thermo Fischer Scientific, Waltham, Mass., USA) in which bovine serum albumin was used as a protein standard. An enzyme composition was prepared composed of each monocomponent as follows: 39.7% *Talaromyces leycettanus* GH6 cellobiohydrolase II, 15.9% *Trichoderma reesei* GH5 endoglucanase II, 23.8% *Thermoascus aurantiacus* GH61A polypeptide, 7.9% *Aspergillus fumigatus* GH10 xylanase, 7.9% *Aspergillus fumigatus* beta-glucosidase, and 4.8% *Talaromyces emersonii* beta-xylosidase. The enzyme composition is designated herein as "cellulolytic enzyme composition #3 without cellobiohydrolase I".

Example 39: Comparison of the Effect of the *Rasamsonia emersonii* PC1-147 Fusion Cellobiohydrolase I and the *R. emersonii* Cellobiohydrolase I PC1-496 Variant on the Hydrolysis of Unwashed PCS by a Cellulase Enzyme Composition The *R. emersonii* cellobiohydrolase I PC1-496 variant (Example 35) was added to the cellulolytic enzyme composition #3 without cellobiohydrolase I (Example 39) at 35° C., 50° C., and 60° C. using unwashed PCS as a substrate, and compared against the *R. emersonii* PC1-147 fusion cellobiohydrolase I added to the cellulolytic enzyme composition #3 without cellobiohydrolase I. Each cellobiohydrolase I was added individually at 3.33 mg enzyme protein per g cellulose to 5.67 mg enzyme protein of the cellulase enzyme composition #3 without cellobiohydrolase I per g cellulose.

The assay was performed as described supra. The reactions with unwashed PCS (20% total solids) were conducted for 72 hours at 35° C., 50° C., and 60° C. in 50 mM sodium acetate pH 5.0 buffer containing 1 mM manganese sulfate. All reactions were performed in quadruplicate and shaking at 200 rpm throughout the hydrolysis.

Figure 13:
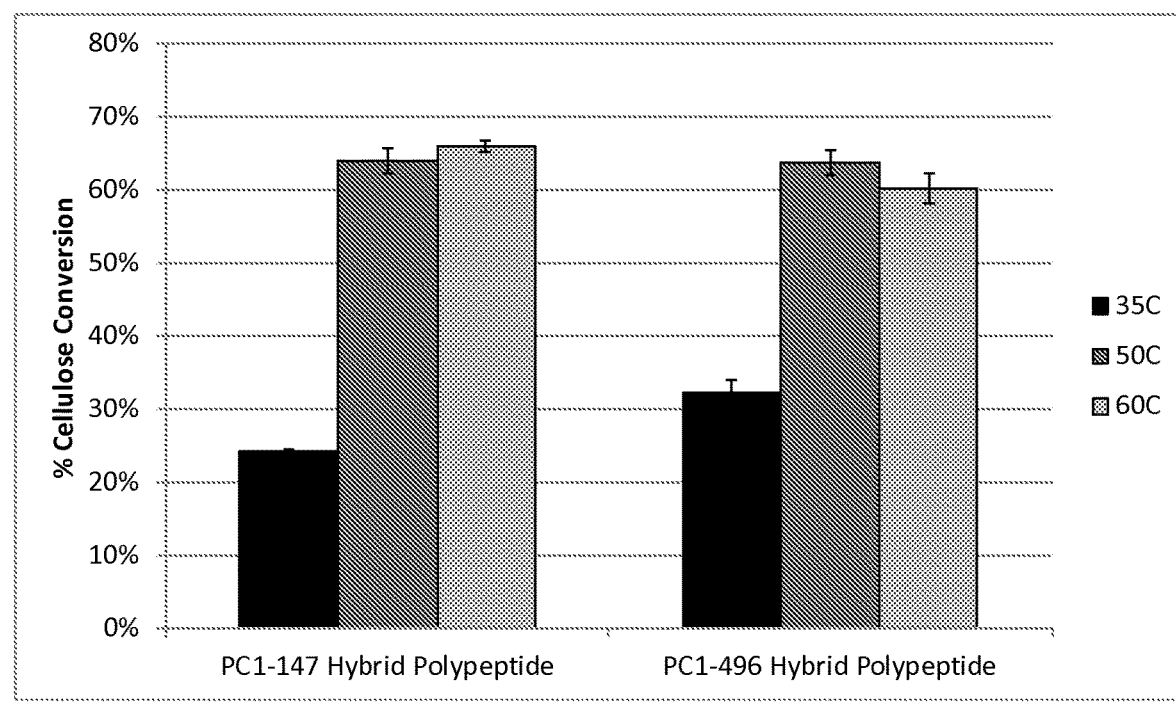
FIG. 13 shows a comparison of percent cellulose conversion of pretreated corn stover at 35° C., 50° C., and 60° C. by enzyme compositions comprising the *R. emersonii* PC1-147 fusion cellobiohydrolase I and the *R. emersonii* cellobiohydrolase I PC1-496 variant.

The results shown in FIG. 13 demonstrated that the cellulase enzyme composition containing the *R. emersonii* cellobiohydrolase I PC1-496 variant had significantly higher cellulose conversion than the cellulase enzyme composition that included *R. emersonii* PC1-147 fusion cellobiohydrolase I at 35° C.

Example 40: Preparation, Expression, and Purification of the *Trichoderma reesei* Cellobiohydrolase I Variants TC1-213 and TC1-216

The *Trichoderma reesei* cellobiohydrolase I variant TC1-213 of the *Trichoderma reesei* wild-type GH7 cellobiohydrolase I of SEQ ID NO: 2 was designed with deletions at positions N197* and N198*, and then constructed and expressed using procedures similar to those described above. The variant TC1-213 coding sequence and corresponding amino acid sequence are shown in SEQ ID NOs: 79 and 80 respectively.

The *Trichoderma reesei* cellobiohydrolase I variant TC1-216 of the *Trichoderma reesei* wild-type GH7 cellobiohydrolase I of SEQ ID NO: 2 was designed with deletions at positions S195* and S196*, and then constructed and expressed using procedures similar to those described above. The variant TC1-216 coding sequence and corresponding amino acid sequence are shown in SEQ ID NOs: 81 and 82, respectively.

Two synthetic primers for each site-directed mutagenesis were designed as below using the SOE primer design tool. Primers F-N197* N198* and R-N197* N198* were used to generate the deletions of variant TC1-213. Primers F-S195* S196* and R-S195* S196* were used to generate the deletions of variant TC1-216.

```
Primer F-N197* N198*:
                                        (SEQ ID NO: 83)
5'-AAGGC TGGGA ACCCT CGTCG GCCAA CACCG GCATT

GGAGG-3'

Primer R-N197* N198*:
                                        (SEQ ID NO: 84)
5'-CGACG AGGGT TCCCA GCCTT CGACG TTTGC C-3'

Primer F-S195* S196*:
                                        (SEQ ID NO: 85)
5'-ACGTC GAAGG CTGGG AACCC AACAA CGCCA ACACC

GGCAT TG-3'

Primer R-S195* S196*:
                                        (SEQ ID NO: 86)
5'-GGGTT CCCAG CCTTC GACGT TGCC TGGCC-3'
```

The variants were constructed using the plasmid pKHJN0036 (Example 3) which contains the codon optimized gene encoding the *Trichoderma reesei* cellobiohydrolase I, and then expressed and purified using procedures as described above in Examples 2, 5 and 7.

Example 41: Comparison of the Effect of *Trichoderma reesei* Cellobiohydrolase I TC1-213 Variant Polypeptides (TC1-213 and TC1-216) Against *Trichoderma reesei* Cellobiohydrolase I Wild-Type on the Hydrolysis of Unwashed PCS by a Cellulase Enzyme Composition The *Trichoderma reesei* variant polypeptides TC1-213 and TC1-216 from Example 40 (corresponding to a deletion of N197+N198 and S195+S196 respectively) were added to the cellulolytic enzyme composition without cellobiohydrolase I (Example 38) at 35° C. using unwashed PCS as a substrate, and compared against the *Trichoderma reesei* cellobiohydrolase I wild-type polypeptide. Each cellobiohydrolase I was added individually at 2, 3, and 4 mg enzyme protein per g cellulose to 5.108 mg enzyme protein of the cellulase enzyme composition without cellobiohydrolase I per g cellulose.

The assay was performed as described in Example 37. The reactions with unwashed PCS (20% total solids) were conducted for 72 hours at 35° C. in 80 mM sodium acetate pH 5.0 buffer containing 1 mM manganese sulfate. All reactions were performed in quadruplicate and shaking at 200 rpm throughout the hydrolysis.

Figure 14:
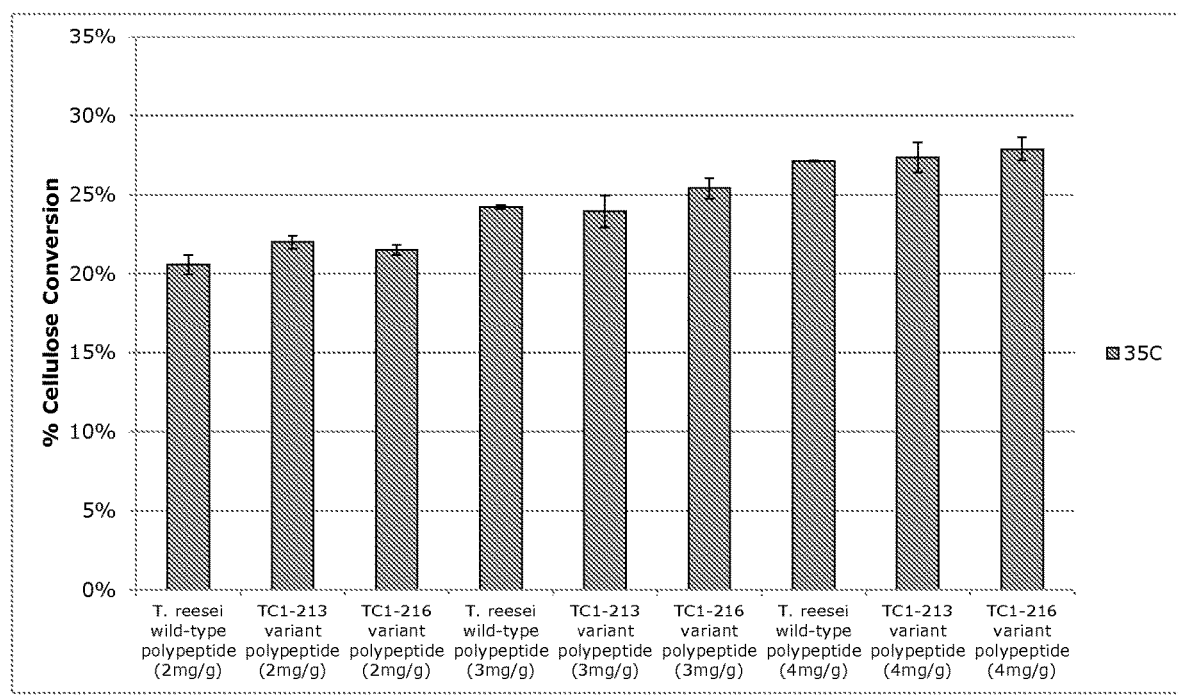
FIG. 14 shows a comparison of percent cellulose conversion of pretreated corn stover at 35° C. by enzyme compositions comprising the *T. reesei* cellobiohydrolase I variants TC1-213 and TC1-216 to those comprising the wild-type *T. reesei* cellobiohydrolase I.

The results shown in FIG. 14 demonstrated that the cellulase enzyme composition containing the variant polypeptide TC1-213 had significantly higher cellulose conversion at 35° C. compared to the cellulase enzyme composition that included the *Trichoderma reesei* cellobiohydrolase I wild-type at 2 mg enzyme protein per g cellulose only. In addition, the cellulase enzyme composition containing the variant polypeptide TC1-216 had significantly higher cellulose conversion at 35° C. compared to the cellulase enzyme composition that included the *Trichoderma reesei* cellobiohydrolase I wild-type at all protein loadings.

Example 42: Source of DNA Sequence Information for *Aspergillus fumigatus* Cellobiohydrolase I The genomic DNA sequence and deduced amino acid sequence of the *Aspergillus fumigatus* Af293 GH7 cellobiohydrolase I gene is shown in SEQ ID NO: 87 and SEQ ID NO: 8, respectively. Genomic sequence information was generated by The Institute for Genomic Research, Rockville, Md. 20850, USA and published by Nierman, W. C. et al., 2005, *Nature* 438 (7071): 1151-1156. The amino acid sequence of the full-length cellobiohydrolase I is publicly available from the National Center for Biotechnology Information (NCBI) and annotated as GenBank: EAL89006.1 The cDNA sequence and deduced amino acid sequence of the *Aspergillus fumigatus* cellobiohydrolase I gene is shown in SEQ ID NO: 88 and SEQ ID NO: 8, respectively.

Based on the publicly available amino acid sequence, a codon-optimized synthetic gene encoding the full-length cellobiohydrolase I was generated for *Aspergillus oryzae* expression based on the algorithm developed by Gustafsson et al., 2004, *Trends in Biotechnology* 22 (7): 346-353. The codon-optimized coding sequence (SEQ ID NO: 89) was synthesized by the GENEART® Gene Synthesis service (Life Technologies Corp., San Diego. Calif., USA) with a 5' Bam HI restriction site, a 3' Hind III restriction site, and a Kozac consensus sequence (CACC) situated between the start codon and the Bam HI restriction site.

Example 43: Construction of an *Aspergillus oryzae* Expression Vector Containing an *Aspergillus fumigatus* DNA Sequence Encoding Cellobiohydrolase I The ampicillin-resistant *E. coli* cloning vector provided by GENEART® Gene Synthesis encoding the *A. fumigatus* cellobiohydrolase I (Example 14) was digested with Barn HI and Hind III (New England Biolabs, MA, USA) according to manufacturer's instructions. The reaction products were isolated by 1.0% agarose gel electrophoresis using TAE buffer where a 1606 bp product band was excised from the gel and purified using a MinElute Gel Extraction Kit (QIAGEN Inc., Valencia, Calif., USA).

The purified 1606 bp fragment encoding the *A. fumigatus* cellobiohydrolase I was cloned into pDau109 (WO 2005/042735) digested with Bam HI and Hind III using T4 DNA ligase (New England Biolabs, MA, USA). The Bam HI-Hind III digested pDau109 and the Barn HI/Hind III fragment containing the *A. fumigatus* cellobiohydrolase I were mixed in a molar ratio of 1:3 (i.e., equal volumes of gel purified products) and ligated with 50 units of T4 DNA ligase in 1× T4 DNA ligase buffer with 1 mM ATP and incubated at 22° C. for 10 minutes.

Cloning of the *A. fumigatus* cellobiohydrolase I gene into the Bam HI-Hind III digested pDau109 will result in transcription of the *A. fumigatus* cellobiohydrolase I gene under the control of a NA2-tpi double promoter. The NA2-tpi promoter is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The ligation mixture was transformed into ONE SHOT® TOP10F' Chemically Competent *E. coli* cells according to the manufacturer's protocol and spread onto LB plates supplemented with 0.1 mg of ampicillin per ml. After incubation at 37° C. overnight, colonies were observed growing under selection on the LB ampicillin plates.

Insertion of the *A. fumigatus* cellobiohydrolase I gene into pDau109 was verified by DNA sequencing. The isolated plasmids were sequenced using an Applied Biosystems 3730xl DNA Analyzer with vector primers and *A. fumigatus* cellobiohydrolase I gene specific primers, shown below, in order to determine a representative plasmid that was free of PCR errors and contained the desired insert.

```
Primer F-pDau109
                                    (SEQ ID NO: 90)
5'-CCCTT GTCGA TGCGA TGTAT C-3'

Primer R-pDau109
                                    (SEQ ID NO: 91)
5'-ATCCT CAATT CCGTC GGTCG A-3'

Primer F-pE596
                                    (SEQ ID NO: 92)
5'-GTGAT ACACC CGGAC AGGTG ATGTG-3'

Primer R-pE596
                                    (SEQ ID NO: 93)
5'-CCATA TCGAT CCGAC GAGTA GGTTC-3'
```

An *E. coli* transformant containing the *A. fumigatus* cellobiohydrolase I plasmid construct was cultivated in LB medium supplemented with 0.1 mg of ampicillin per ml and plasmid DNA was isolated using a QIAPREP® Spin Miniprep Kit. The plasmid was designated pE596 and the corresponding polypeptide was designated as AC1-596.

Example 44: Site-Directed Mutagenesis of the *Aspergillus fumigatus* Cellobiohydrolase I (AC1-865)

Plasmid pE596 (Example 43) was used to generate the *A. fumigatus* cellobiohydrolase I AC1-865 variant (SEQ ID NO: 94 for the mutant DNA sequence and SEQ ID NO: 95 for the variant), where three codons TCG AAC GAT were deleted (S196 N197 D198) to give S196* N197* D198* (corresponding to deletions at positions 196, 197, and 198 of SEQ ID NO: 2).

Two synthetic primers for site-directed mutagenesis were designed using a SOE primer design tool. Site-directed mutagenesis of the synthetic gene encoding the wild-type *A. fumigatus* cellobiohydrolase I was facilitated by PCR amplifications of pE596 using the primers and procedure described below:

```
Primer F-S196* N197* D198*:
                                    (SEQ ID NO: 96)
5'-TCGAG GGTTG GCAGC CTTCG GCCAA CGCAG GTACC GGCAA
C-3'

Primer R-S196* N197* D198*:
                                    (SEQ ID NO: 97)
5'-CGAAG GCTGC CAACC CTCGA CGTTG GCCTG-3'
```

The mutations were introduced by PCR using a PHUSION® High-Fidelity PCR Kit (New England Biolabs, MA, USA). The PCR solution was composed of 10 μl of 5× HF buffer (New England Biolabs, MA, USA), 4 μl of dNTPs (2.5 mM), 0.5 μl of PHUSION® DNA polymerase (0.2 units/μl) (New England Biolabs, MA, USA), 0.25 μl of primer F-S196* N197* D198* (100 μM), 0.25 μl of primer R-S196* N197* D198* (100 μM), 5 μl of template DNA (pE596, 1 ng/μl), and 30 μl of deionized water in a total volume of 50 μl. The PCR was performed using an Applied Biosystems® Veriti® 96 well thermal cycler programmed for 1 cycle at 98° C. for 30 seconds; and 19 cycles each at 98° C. for 30 seconds, 55° C. for 1 minute, and 72° C. for 7 minutes. The PCR solution was then held at 8° C. until removed from the PCR machine.

Following the PCR, 10 units of Dpn I were added directly to the PCR solution and incubated at 37° C. for 1 hour. Then 1 μl of the Dpn I treated PCR solution was transformed into ONE SHOT® TOP10F' Chemically Competent *E. coli* cells according to the manufacturer's protocol and spread onto LB plates supplemented with 0.15 mg of ampicillin per ml. After incubation at 37° C. overnight, transformants were observed growing under selection on the LB ampicillin plates. Four transformants were cultivated in LB medium supplemented with 0.10 mg of ampicillin per ml and plasmids were isolated using a QIAPREP® Spin Miniprep Kit (QIAGEN Inc., Valencia, Calif., USA).

The isolated plasmids were sequenced using an Applied Biosystems 3730xl DNA Analyzer (Applied Biosystems, Foster City, Calif., USA) with primers F-pDau109 (SEQ ID NO: 30), R-pDau109 (SEQ ID NO: 310), F-pE596 (SEQ ID NO: 92) and R-pE596 (SEQ ID NO: 93), in order to determine a representative plasmid that was free of PCR errors and contained the desired mutations.

```
Primer F-pDau109:
                                    (SEQ ID NO: 30)
5'-CCCTT GTCGA TGCGA TGTAT C-3'

Primer R-pDau109:
                                    (SEQ ID NO: 31)
5'-ATCCT CAATT CCGTC GGTCG A-3'

Primer F-pE596:
                                    (SEQ ID NO: 92)
5'-GTGAT ACACC CGGAC AGGTG ATGTG-3'

Primer R-pE596:
                                    (SEQ ID NO: 93)
5'-CCATA TCGAT CCGAC GAGTA GGTTC-3'
```

One plasmid clone free of PCR errors and containing the deletion of codons TCG AAC GAT (S196* N197* D198*) was chosen and designated plasmid pE865 and the corresponding polypeptide was designated as AC1-865.

Generating the *Aspergillus oryzae* strain expressing the AC1-865 variant and the AC1-596 wild type were done using the same method as described in Example 5. Based on the level of hydrolysis of the microcrystalline cellulose one transformant expressing the *A. fumigatus* cellobiohydrolase I variant AC1-865 was selected and designated *A. oryzae* AC1-865 and one transformant expressing the wild type *A. fumigatus* cellobiohydrolase I was selected and designated *A. oryzae* AC1-596.

Purification of the wild-type *Aspergillus fumigatus* cellobiohydrolase I AC1-596 and the variant AC1-865 were done essentially as described in Example 7.

Example 45: Activity Measurement on Microcrystalline Cellulose of the Variant AC1-865 and the Wild-Type *Aspergillus fumigatus* Cellobiohydrolase I The activity of the purified variant polypeptide AC1-865 was compared to the purified wild-type *A. fumigatus* cellobiohydrolase I AC1-596 using washed microcrystalline cellulose (AVICEL® PH101; Sigma-Aldrich, St. Louis, Mo., USA) as a substrate (see PCT/US2014/022068).

The purified cellobiohydrolases were diluted in 50 mM sodium acetate, 2 mM $CaCl_2$ pH 5. The diluted cellobiohydrolases and β-glucosidase were added to each well (microwell plate 96F 26960 Thermo scientific). Washed AVICEL then was added to each well and the microtiter plate was quickly transferred to a thermomixer (eppendorf) and incubated for 24 hours at 1100 rpm and 35° C. or 55° C. The final concentration of the cellobiohydrolases in the reaction was 3 μM and the concentration of AVICEL was 80 g/l. The reaction was stopped by centrifugation at 3500 rpm for 3 min at 5° C. (Hereaus multifuge 3 S-R). The supernatants are diluted 40 times and 50 μL of diluted supernatants were transferred to PCR sample tubes (Thermoscientific 0.2 ml non-skirted 96-well PCR plate AB0600). PAHBAH (4-hydroxy-benzhydrazid) (Sigma, H 9882) was dissolved in buffer (0.18 M K—Na-tartrate (Merck, 1.08087) and 0.5 M NaOH) to make a 15 mg/ml solution. Seventy-five μL of the PAHBAH solution was added to the supernatants in the PCR samples tubes.

The PCR sample tubes were placed in a Peltier Thermal Cycler and incubated at 95° C. for 10 min and 20° C. for 5 min. After incubation 100 μl were transferred to a 96 well microtiter plate (microwell plate 96F 26960 Thermo scientific) and the absorbance was measured at 410 nm. For each run a standard was included. The standard used was glucose diluted in 50 mM sodium acetate, 2 mM CaCl2 pH 5 to a concentration of 0.008, 0.016, 0.0312, 0.0625, 0.125, 0.25 and 0.5 mM. In addition to the standard, a blank (without cellobiohydrolase) for each run was included. For all the measurement, the blank measurement was subtracted. The absorbance data were normalized to glucose concentration using the standards.

Figure 15:
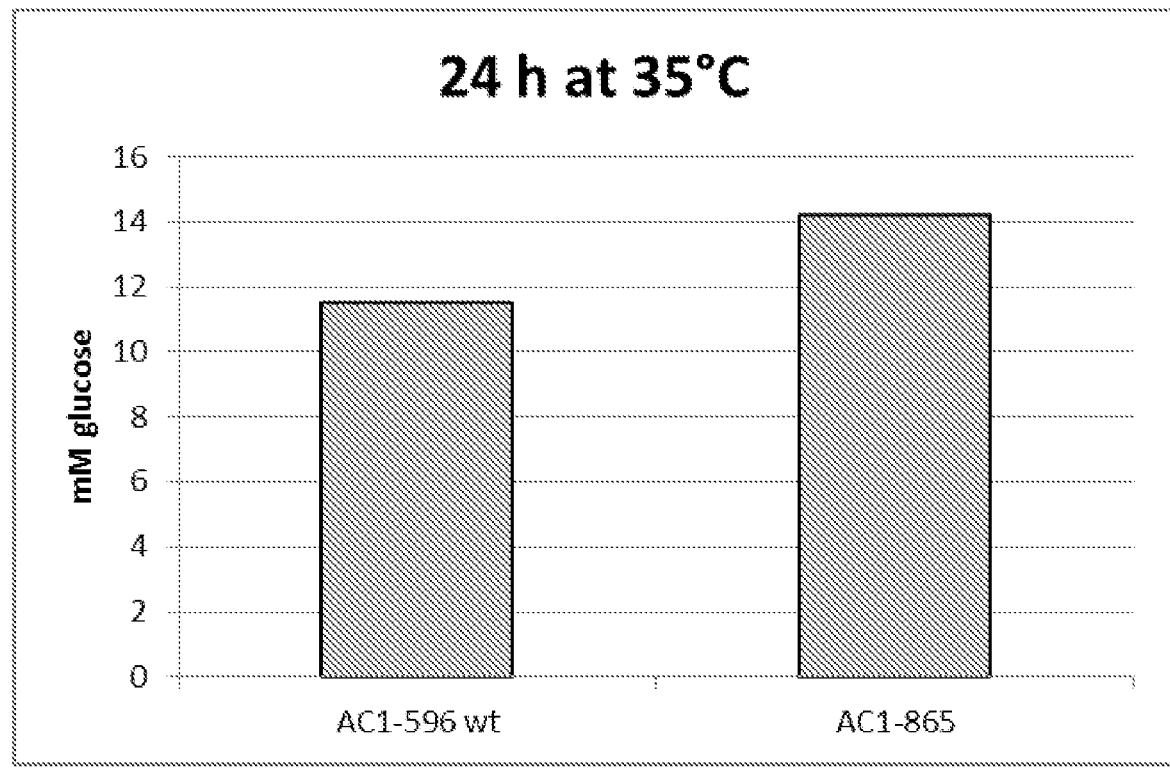
FIG. 15 shows a comparison of the hydrolysis of microcrystalline cellulose by the *Aspergillus fumigatus* wild-type cellobiohydrolase I, and the *Aspergillus fumigatus* cellobiohydrolase I AC1-865 variant after 24 hours at 35° C.

The results as shown in FIG. 15 demonstrated that at 35° C., the variant AC1-865 (with a deletion of S196 N197 and D198) had an approximately 23% increase toward microcrystalline cellulose compared to the wild-type cellobiohydrolase I.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A variant of a parent cellobiohydrolase, comprising deletions at two or more consecutive positions corresponding to positions of the B2-loop, wherein the corresponding positions of the B2-loop are positions 194, 195, 196, 197, 198, 199, 200, and 201 of SEQ ID NO: 2, wherein the variant has cellobiohydrolase activity, and wherein the variant has at least 95%, but less than 100%, sequence identity to the mature polypeptide of the parent cellobiohydrolase.

2. The variant of claim 1, wherein the parent cellobiohydrolase is selected from the group consisting of: (a) a polypeptide having at least 95% sequence identity to the mature polypeptide of SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22; (b) a polypeptide encoded by a polynucleotide that hybridizes under high stringency conditions with the full-length complement of the mature polypeptide coding sequence of SEQ ID NO: 1, SEQ ID NO: 3, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21, wherein the high stringency conditions are defined as prehybridization and hybridization at 42° C. in 5×SSPE, 0.3% SDS, 200 micrograms/ml sheared and denatured salmon sperm DNA, and 50% formamide for 12 to 24 hours, and washing three times each for 15 minutes using 0.2×SSC, 0.2% SDS at 65° C.; (c) a polypeptide encoded by a polynucleotide having at least 95% identity to the mature polypeptide coding sequence of SEQ ID NO: 1, SEQ ID NO: 3, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 19, or SEQ ID NO: 21; and (d) a fragment of the mature polypeptide of SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22, which has cellobiohydrolase activity.

3. The variant of claim 1, which comprises amino acids 1-434 of SEQ ID NO: 78, amino acids 1-495 of SEQ ID NO: 80, amino acids 1-495 of SEQ ID NO: 82, or amino acids 1-503 of SEQ ID NO: 95.

4. The variant of claim 1, which is a fusion protein in which a heterologous carbohydrate binding domain is fused to the variant.

5. The variant of claim 1, which has an increased specific performance relative to the parent.

6. A composition, a whole broth formulation, or a cell culture composition comprising the variant of claim 1.

7. An isolated polynucleotide encoding the variant of claim 1.

8. A nucleic acid construct or expression vector comprising the polynucleotide of claim 7.

9. A recombinant host cell comprising the polynucleotide of claim 7.

10. A method of producing a cellobiohydrolase variant, comprising cultivating the recombinant host cell of claim 9 under conditions suitable for expression of the cellobiohydrolase variant.

11. A transgenic plant, plant part or plant cell transformed with the polynucleotide of claim 7.

12. A method of producing a cellobiohydrolase variant, comprising: cultivating the transgenic plant, plant part or plant cell of claim 11 under conditions conducive for production of the cellobiohydrolase variant.

13. A process for degrading or converting a cellulosic material, said method comprising: treating the cellulosic material with an enzyme composition, wherein the composition comprises the variant of claim 1.

14. A process for producing a fermentation product, said method comprising: (a) saccharifying a cellulosic material with an enzyme composition, wherein the composition comprises the variant of claim 1; and (b) fermenting the saccharified cellulosic material with one or more fermenting microorganisms to produce the fermentation product.

15. The variant of claim 2, wherein the parent cellobiohydrolase has at least 96% sequence identity to the mature polypeptide of SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22.

16. The variant of claim 2, wherein the parent cellobiohydrolase has at least 97% sequence identity to the mature polypeptide of SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22.

17. The variant of claim 2, wherein the parent cellobiohydrolase has at least 98% sequence identity to the mature polypeptide of SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22.

18. The variant of claim 2, wherein the parent cellobiohydrolase has at least 99% sequence identity to the mature polypeptide of SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22.

19. The variant of claim 2, wherein the parent cellobiohydrolase comprises the mature polypeptide of SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, or SEQ ID NO: 22.

20. The method of claim 10, further comprising recovering the variant.

21. The method of claim 12, further comprising recovering the variant.

22. The process of claim 13, wherein the cellulosic material is pretreated.

23. The process of claim 13, wherein the enzyme composition further comprises one or more enzymes selected from the group consisting of a cellulase, a GH61 polypeptide having cellulolytic enhancing activity, a hemicellulase, a catalase, an esterase, an expansin, a laccase, a ligninolytic enzyme, a pectinase, a peroxidase, a protease, and a swollenin.

24. The process of claim 13, further comprising recovering the degraded or converted cellulosic material.

25. The process of claim 24, wherein the degraded or converted cellulosic material is a sugar selected from the group consisting of glucose, xylose, mannose, galactose, and arabinose.

26. The process of claim 14, wherein the cellulosic material is pretreated.

27. The process of claim 14, wherein the enzyme composition further comprises one or more enzymes selected from the group consisting of a cellulase, a GH61 polypeptide having cellulolytic enhancing activity, a hemicellulase, a catalase, an esterase, an expansin, a laccase, a ligninolytic enzyme, a pectinase, a peroxidase, a protease, and a swollenin.

28. The process of claim 14, wherein steps (a) and (b) are performed simultaneously in a simultaneous saccharification and fermentation.

29. The process of claim 14, wherein the fermentation product is an alcohol, an alkane, a cycloalkane, an alkene, an amino acid, a gas, isoprene, a ketone, an organic acid, or polyketide.

\* \* \* \* \*

SEQUENCE LISTING

```
<160> NUMBER OF SEQ ID NOS: 97

<210> SEQ ID NO 1
<211> LENGTH: 1676
<212> TYPE: DNA
<213> ORGANISM: Trichoderma reesei
<220> FEATURE:
<221> NAME/KEY: exon
<222> LOCATION: (1)..(461)
<220> FEATURE:
<221> NAME/KEY: sig_peptide
<222> LOCATION: (1)..(17)
<220> FEATURE:
<221> NAME/KEY: CDS
<222> LOCATION: (1)..(461)
<220> FEATURE:
<221> NAME/KEY: mat_peptide
<222> LOCATION: (52)..(1673)
<220> FEATURE:
<221> NAME/KEY: Intron
<222> LOCATION: (462)..(529)
<220> FEATURE:
<221> NAME/KEY: exon
<222> LOCATION: (530)..(1226)
<220> FEATURE:
<221> NAME/KEY: CDS
<222> LOCATION: (530)..(1226)
<220> FEATURE:
<221> NAME/KEY: Intron
<222> LOCATION: (1227)..(1289)
<220> FEATURE:
<221> NAME/KEY: exon
<222> LOCATION: (1290)..(1673)
<220> FEATURE:
<221> NAME/KEY: CDS
<222> LOCATION: (1290)..(1673)

<400> SEQUENCE: 1 atg tat cgg aag ttg gcc gtc atc tcg gcc ttc ttg gcc aca gct cgt         48
Met Tyr Arg Lys Leu Ala Val Ile Ser Ala Phe Leu Ala Thr Ala Arg
        -15                 -10                  -5 gct cag tcg gcc tgc act ctc caa tcg gag act cac ccg cct ctg aca         96
Ala Gln Ser Ala Cys Thr Leu Gln Ser Glu Thr His Pro Pro Leu Thr
 -1   1               5                  10                  15
```

-continued

| | |
|---|---|
| tgg cag aaa tgc tcg tct ggt ggc acg tgc act caa cag aca ggc tcc<br>Trp Gln Lys Cys Ser Ser Gly Gly Thr Cys Thr Gln Gln Thr Gly Ser<br>20                   25                   30 | 144 |
| gtg gtc atc gac gcc aac tgg cgc tgg act cac gct acg aac agc agc<br>Val Val Ile Asp Ala Asn Trp Arg Trp Thr His Ala Thr Asn Ser Ser<br>35                     40                   45 | 192 |
| acg aac tgc tac gat ggc aac act tgg agc tcg acc cta tgt cct gac<br>Thr Asn Cys Tyr Asp Gly Asn Thr Trp Ser Ser Thr Leu Cys Pro Asp<br>     50                   55                   60 | 240 |
| aac gag acc tgc gcg aag aac tgc tgt ctg gac ggt gcc gcc tac gcg<br>Asn Glu Thr Cys Ala Lys Asn Cys Cys Leu Asp Gly Ala Ala Tyr Ala<br>65                   70                   75 | 288 |
| tcc acg tac gga gtt acc acg agc ggt aac agc ctc tcc att ggc ttt<br>Ser Thr Tyr Gly Val Thr Thr Ser Gly Asn Ser Leu Ser Ile Gly Phe<br>80                   85                   90                   95 | 336 |
| gtc acc cag tct gcg cag aag aac gtt ggc gct cgc ctt tac ctt atg<br>Val Thr Gln Ser Ala Gln Lys Asn Val Gly Ala Arg Leu Tyr Leu Met<br>                     100                 105                 110 | 384 |
| gcg agc gac acg acc tac cag gaa ttc acc ctg ctt ggc aac gag ttc<br>Ala Ser Asp Thr Thr Tyr Gln Glu Phe Thr Leu Leu Gly Asn Glu Phe<br>               115                 120                 125 | 432 |
| tct ttc gat gtt gat gtt tcg cag ctg cc   gtaagtgact taccatgaac<br>Ser Phe Asp Val Asp Val Ser Gln Leu Pro<br>           130                 135 | 481 |
| ccctgacgct atcttcttgt tggctcccag ctgactggcc aattcaag g tgc ggc<br>                                                                                                             Cys Gly | 536 |
| ttg aac gga gct ctc tac ttc gtg tcc atg gac gcg gat ggt ggc gtg<br>Leu Asn Gly Ala Leu Tyr Phe Val Ser Met Asp Ala Asp Gly Gly Val<br>140                     145                   150                   155 | 584 |
| agc aag tat ccc acc aac acc gct ggc gcc aag tac ggc acg ggg tac<br>Ser Lys Tyr Pro Thr Asn Thr Ala Gly Ala Lys Tyr Gly Thr Gly Tyr<br>                     160                 165                 170 | 632 |
| tgt gac agc cag tgt ccc cgc gat ctg aag ttc atc aat ggc cag gcc<br>Cys Asp Ser Gln Cys Pro Arg Asp Leu Lys Phe Ile Asn Gly Gln Ala<br>               175                 180                 185 | 680 |
| aac gtt gag ggc tgg gag ccg tca tcc aac aac gcg aac acg ggc att<br>Asn Val Glu Gly Trp Glu Pro Ser Ser Asn Asn Ala Asn Thr Gly Ile<br>          190                   195                   200 | 728 |
| gga gga cac gga agc tgc tgc tct gag atg gat atc tgg gag gcc aac<br>Gly Gly His Gly Ser Cys Cys Ser Glu Met Asp Ile Trp Glu Ala Asn<br>205                     210                   215 | 776 |
| tcc atc tcc gag gct ctt acc ccc cac cct tgc acg act gtc ggc cag<br>Ser Ile Ser Glu Ala Leu Thr Pro His Pro Cys Thr Thr Val Gly Gln<br>220                     225                   230                 235 | 824 |
| gag atc tgc gag ggt gat ggg tgc ggc gga act tac tcc gat aac aga<br>Glu Ile Cys Glu Gly Asp Gly Cys Gly Gly Thr Tyr Ser Asp Asn Arg<br>               240                 245                 250 | 872 |
| tat ggc ggc act tgc gat ccc gat ggc tgc gac tgg aac cca tac cgc<br>Tyr Gly Gly Thr Cys Asp Pro Asp Gly Cys Asp Trp Asn Pro Tyr Arg<br>                     255                 260                 265 | 920 |
| ctg ggc aac acc agc ttc tac ggc cct ggc tca agc ttt acc ctc gat<br>Leu Gly Asn Thr Ser Phe Tyr Gly Pro Gly Ser Ser Phe Thr Leu Asp<br>           270                   275                   280 | 968 |
| acc acc aag aaa ttg acc gtt gtc acc cag ttc gag acg tcg ggt gcc<br>Thr Thr Lys Lys Leu Thr Val Val Thr Gln Phe Glu Thr Ser Gly Ala<br>285                     290                   295 | 1016 |
| atc aac cga tac tat gtc cag aat ggc gtc act ttc cag cag ccc aac<br>Ile Asn Arg Tyr Tyr Val Gln Asn Gly Val Thr Phe Gln Gln Pro Asn<br>300                     305                   310                 315 | 1064 |

| | | |
|---|---|---|
| gcc gag ctt ggt agt tac tct ggc aac gag ctc aac gat gat tac tgc | 1112 | |
| Ala Glu Leu Gly Ser Tyr Ser Gly Asn Glu Leu Asn Asp Asp Tyr Cys | | |
| 320 325 330 | | | aca gct gag gag gca gaa ttc ggc gga tcc tct ttc tca gac aag ggc    1160
Thr Ala Glu Glu Ala Glu Phe Gly Gly Ser Ser Phe Ser Asp Lys Gly
            335                 340                 345 ggc ctg act cag ttc aag aag gct acc tct ggc ggc atg gtt ctg gtc    1208
Gly Leu Thr Gln Phe Lys Lys Ala Thr Ser Gly Gly Met Val Leu Val
    350                 355                 360 atg agt ctg tgg gat gat gtgagtttga tggacaaaca tgcgcgttga           1256
Met Ser Leu Trp Asp Asp
    365 caaagagtca agcagctgac tgagatgtta cag tac tac gcc aac atg ctg tgg   1310
                                    Tyr Tyr Ala Asn Met Leu Trp
                                            370             375 ctg gac tcc acc tac ccg aca aac gag acc tcc tcc aca ccc ggt gcc    1358
Leu Asp Ser Thr Tyr Pro Thr Asn Glu Thr Ser Ser Thr Pro Gly Ala
            380                 385                 390 gtg cgc gga agc tgc tcc acc agc tcc ggt gtc cct gct cag gtc gaa    1406
Val Arg Gly Ser Cys Ser Thr Ser Ser Gly Val Pro Ala Gln Val Glu
        395                 400                 405 tct cag tct ccc aac gcc aag gtc acc ttc tcc aac atc aag ttc gga    1454
Ser Gln Ser Pro Asn Ala Lys Val Thr Phe Ser Asn Ile Lys Phe Gly
    410                 415                 420 ccc att ggc agc acc ggc aac cct agc ggc ggc aac cct ccc ggc gga    1502
Pro Ile Gly Ser Thr Gly Asn Pro Ser Gly Gly Asn Pro Pro Gly Gly
425                 430                 435                 440 aac ccg cct ggc acc acc acc acc cgc cgc cca gcc act acc act gga    1550
Asn Pro Pro Gly Thr Thr Thr Thr Arg Arg Pro Ala Thr Thr Thr Gly
            445                 450                 455 agc tct ccc gga cct acc cag tct cac tac ggc cag tgc ggc ggt att    1598
Ser Ser Pro Gly Pro Thr Gln Ser His Tyr Gly Gln Cys Gly Gly Ile
        460                 465                 470 ggc tac agc ggc ccc acg gtc tgc gcc agc ggc aca act tgc cag gtc    1646
Gly Tyr Ser Gly Pro Thr Val Cys Ala Ser Gly Thr Thr Cys Gln Val
    475                 480                 485 ctg aac cct tac tac tct cag tgc ctg taa                             1676
Leu Asn Pro Tyr Tyr Ser Gln Cys Leu
    490                 495

<210> SEQ ID NO 2
<211> LENGTH: 514
<212> TYPE: PRT
<213> ORGANISM: Trichoderma reesei

<400> SEQUENCE: 2

Met Tyr Arg Lys Leu Ala Val Ile Ser Ala Phe Leu Ala Thr Ala Arg
        -15                 -10                 -5

Ala Gln Ser Ala Cys Thr Leu Gln Ser Glu Thr His Pro Pro Leu Thr
-1   1               5                  10                  15

Trp Gln Lys Cys Ser Ser Gly Gly Thr Cys Thr Gln Thr Gly Ser
                20                  25                  30

Val Val Ile Asp Ala Asn Trp Arg Trp Thr His Ala Thr Asn Ser Ser
            35                  40                  45

Thr Asn Cys Tyr Asp Gly Asn Thr Trp Ser Ser Thr Leu Cys Pro Asp
        50                  55                  60

Asn Glu Thr Cys Ala Lys Asn Cys Cys Leu Asp Gly Ala Ala Tyr Ala
    65                  70                  75

```
Ser Thr Tyr Gly Val Thr Thr Ser Gly Asn Ser Leu Ser Ile Gly Phe
 80              85                  90                  95

Val Thr Gln Ser Ala Gln Lys Asn Val Gly Ala Arg Leu Tyr Leu Met
            100                 105                 110

Ala Ser Asp Thr Thr Tyr Gln Glu Phe Thr Leu Leu Gly Asn Glu Phe
            115                 120                 125

Ser Phe Asp Val Asp Val Ser Gln Leu Pro Cys Gly Leu Asn Gly Ala
            130                 135                 140

Leu Tyr Phe Val Ser Met Asp Ala Asp Gly Gly Val Ser Lys Tyr Pro
            145                 150                 155

Thr Asn Thr Ala Gly Ala Lys Tyr Gly Thr Gly Tyr Cys Asp Ser Gln
160                 165                 170                 175

Cys Pro Arg Asp Leu Lys Phe Ile Asn Gly Gln Ala Asn Val Glu Gly
            180                 185                 190

Trp Glu Pro Ser Ser Asn Asn Ala Asn Thr Gly Ile Gly Gly His Gly
            195                 200                 205

Ser Cys Cys Ser Glu Met Asp Ile Trp Glu Ala Asn Ser Ile Ser Glu
            210                 215                 220

Ala Leu Thr Pro His Pro Cys Thr Thr Val Gly Gln Glu Ile Cys Glu
225                 230                 235

Gly Asp Gly Cys Gly Gly Thr Tyr Ser Asp Asn Arg Tyr Gly Gly Thr
240                 245                 250                 255

Cys Asp Pro Asp Gly Cys Asp Trp Asn Pro Tyr Arg Leu Gly Asn Thr
            260                 265                 270

Ser Phe Tyr Gly Pro Gly Ser Ser Phe Thr Leu Asp Thr Thr Lys Lys
            275                 280                 285

Leu Thr Val Val Thr Gln Phe Glu Thr Ser Gly Ala Ile Asn Arg Tyr
            290                 295                 300

Tyr Val Gln Asn Gly Val Thr Phe Gln Gln Pro Asn Ala Glu Leu Gly
            305                 310                 315

Ser Tyr Ser Gly Asn Glu Leu Asn Asp Asp Tyr Cys Thr Ala Glu Glu
320                 325                 330                 335

Ala Glu Phe Gly Gly Ser Ser Phe Ser Asp Lys Gly Gly Leu Thr Gln
            340                 345                 350

Phe Lys Lys Ala Thr Ser Gly Gly Met Val Leu Val Met Ser Leu Trp
            355                 360                 365

Asp Asp Tyr Tyr Ala Asn Met Leu Trp Leu Asp Ser Thr Tyr Pro Thr
            370                 375                 380

Asn Glu Thr Ser Ser Thr Pro Gly Ala Val Arg Gly Ser Cys Ser Thr
385                 390                 395

Ser Ser Gly Val Pro Ala Gln Val Glu Ser Gln Ser Pro Asn Ala Lys
400                 405                 410                 415

Val Thr Phe Ser Asn Ile Lys Phe Gly Pro Ile Gly Ser Thr Gly Asn
            420                 425                 430

Pro Ser Gly Gly Asn Pro Pro Gly Gly Asn Pro Pro Gly Thr Thr Thr
            435                 440                 445

Thr Arg Arg Pro Ala Thr Thr Thr Gly Ser Ser Pro Gly Pro Thr Gln
            450                 455                 460

Ser His Tyr Gly Gln Cys Gly Gly Ile Gly Tyr Ser Gly Pro Thr Val
            465                 470                 475

Cys Ala Ser Gly Thr Thr Cys Gln Val Leu Asn Pro Tyr Tyr Ser Gln
480                 485                 490                 495

Cys Leu
```

<210> SEQ ID NO 3
<211> LENGTH: 1545
<212> TYPE: DNA
<213> ORGANISM: Trichoderma reesei

<400> SEQUENCE: 3

| | | |
|---|---|---|
| atgtatcgga agttggccgt catctcggcc ttcttggcca cagctcgtgc tcagtcggcc | 60 |
| tgcactctcc aatcggagac tcacccgcct ctgacatggc agaaatgctc gtctggtggc | 120 |
| acgtgcactc aacagacagg ctccgtggtc atcgacgcca actggcgctg gactcacgct | 180 |
| acgaacagca gcacgaactg ctacgatggc aacacttgga gctcgaccct atgtcctgac | 240 |
| aacgagacct gcgcgaagaa ctgctgtctg acggtgccg cctacgcgtc cacgtacgga | 300 |
| gttaccacga gcgtaacag cctctccatt ggctttgtca cccagtctgc gcagaagaac | 360 |
| gttggcgctc gcctttacct tatggcgagc gacacgacct accaggaatt caccctgctt | 420 |
| ggcaacgagt tctctttcga tgttgatgtt tcgcagctgc cgtgcggctt gaacggagct | 480 |
| ctctacttcg tgtccatgga cgcggatggt ggcgtgagca agtatcccac caacaccgct | 540 |
| ggcgccaagt acggcacggg gtactgtgac agccagtgtc cccgcgatct gaagttcatc | 600 |
| aatggccagg ccaacgttga gggctgggag ccgtcatcca caacgcgaa cacgggcatt | 660 |
| ggaggacacg gaagctgctg ctctgagatg gatatctggg aggccaactc catctccgag | 720 |
| gctcttaccc cccacccttg cacgactgtc ggccaggaga tctgcgaggg tgatgggtgc | 780 |
| ggcggaactt actccgataa cagatatggc ggcacttgcg atcccgatgg ctgcgactgg | 840 |
| aacccatacc gcctgggcaa caccagcttc tacggccctg gctcaagctt taccctcgat | 900 |
| accaccaaga aattgaccgt tgtcacccag ttcgagacgt cgggtgccat caaccgatac | 960 |
| tatgtccaga atggcgtcac tttccagcag cccaacgccg agcttggtag ttactctggc | 1020 |
| aacgagctca cgatgatta ctgcacagct gaggaggcag aattcggcgg atcctctttc | 1080 |
| tcagacaagg gcggcctgac tcagttcaag aaggctacct ctggcggcat ggttctggtc | 1140 |
| atgagtctgt gggatgatta ctacgccaac atgctgtggc tggactccac ctacccgaca | 1200 |
| aacgagacct cctccacacc cggtgccgtg cgcggaagct gctccaccag ctccggtgtc | 1260 |
| cctgctcagg tcgaatctca gtctcccaac gccaaggtca ccttctccaa catcaagttc | 1320 |
| ggacccattg gcagcaccgg caaccctagc ggcggcaacc ctcccggcgg aaacccgcct | 1380 |
| ggcaccacca ccacccgccg cccagccact accactggaa gctctcccgg acctacccag | 1440 |
| tctcactacg gccagtgcgg cggtattggc tacagcggcc ccacggtctg cgccagcggc | 1500 |
| acaacttgcc aggtcctgaa cccttactac tctcagtgcc tgtaa | 1545 |

<210> SEQ ID NO 4
<211> LENGTH: 1545
<212> TYPE: DNA
<213> ORGANISM: Trichoderma reesei

<400> SEQUENCE: 4

| | | |
|---|---|---|
| atgtatcgta agctcgcagt catctccgcg ttcctcgcaa cagcacgagc gcagtccgcc | 60 |
| tgtaccttgc agtcggaaac acatcctccc ctcacttggc agaaatgttc gtccggagga | 120 |
| acgtgtacgc agcagactgg ctcggtggtc atcgacgcca actggaggtg gacgcatgca | 180 |
| accaactcct ccaccaactg ttacgatggc aacacttggt cctccacctt gtgtcccgat | 240 |
| aacgaaacct gtgccaagaa ctgttgtttg gatggtgcag cctacgcctc gacatacgga | 300 |

-continued

```
gtcactactt ccggcaactc gctctcgatc ggcttcgtga ctcagtccgc acagaaaaac    360
gtcggagcgc gactctactt gatggcatcc gatacaacct accaggaatt cactctcttg    420
ggcaacgagt tctccttcga cgtcgacgtc tcccagctcc cttgtggcct caacggagca    480
ctctacttcg tgtcgatgga cgcggatgga ggtgtctcca agtacccgac caacacagca    540
ggagcgaaat acggcacggg ttactgtgac tcgcagtgtc ctcgcgatct caagttcatc    600
aacggccagg caaacgtcga aggctgggaa ccctcgtcga caacgccaa caccggcatt    660 ggaggccatg gctcctgttg ttcggaaatg gatatctggg aggccaactc gatctccgag    720
gcactcacac cccacccctg tacaaccgtc ggccaggaga tttgtgaagg agacggctgt    780
ggcggaactt actccgataa ccgttacggt ggtacctgtg atcccgatgg ctgtgactgg    840 aaccccctacc gcctcggtaa cacatcgttc tacggtccgg ttcctccttc caccctcgac    900
actaccaaaa agttgacggt ggtcacgcag ttcgagactt ccggagccat caaccggtac    960
tacgtgcaga acgagtcac attccagcag cccaacgcag aactcggctc gtactcggga    1020
aacgagctca cgatgatta ctgtacagcg gaagaggcag aattcggagg atcgtcgttc    1080
tccgacaagg gtggtttgac ccagttcaag aaggccacat cgggaggaat ggtgttggtc    1140
atgtccttgt gggacgacta ctatgccaac atgctctggc tcgactccac ctaccccacc    1200
aacgagacct cctcgacacc tggcgcagtg aggggctcgt gttccacttc gtcgggagtg    1260
cctgcacagg tggagtccca gtcgccgaac gccaaggtca cttctccaa cattaagttc    1320 ggacccatcg gttcgaccgg caaccccctcc ggtggaaacc ctcctggcgg aaaccctcct    1380
ggcacaacta caaacgacg gcctgcgact acaacgggtt cgtcccctgg accgacccag    1440
tcccactacg gacagtgtgg aggcatcggt tattccggtc cgaccgtctg tgcgtccggc    1500
acaacctgtc aggtcttgaa cccttactat tcgcagtgtc tctaa                   1545
```

<210> SEQ ID NO 5  
<211> LENGTH: 1545  
<212> TYPE: DNA  
<213> ORGANISM: Trichoderma reesei  
<220> FEATURE:  
<221> NAME/KEY: sig_peptide  
<222> LOCATION: (1)..(51)  
<220> FEATURE:  
<221> NAME/KEY: CDS  
<222> LOCATION: (1)..(1542)  
<220> FEATURE:  
<221> NAME/KEY: mat_peptide  
<222> LOCATION: (52)..(1542)

<400> SEQUENCE: 5

```
atg tat cgt aag ctc gca gtc atc tcc gcg ttc ctc gca aca gca cga     48
Met Tyr Arg Lys Leu Ala Val Ile Ser Ala Phe Leu Ala Thr Ala Arg
        -15                 -10                 -5 gcg cag tcc gcc tgt acc ttg cag tcg gaa aca cat cct ccc ctc act     96
Ala Gln Ser Ala Cys Thr Leu Gln Ser Glu Thr His Pro Pro Leu Thr
 -1   1               5                  10                  15 tgg cag aaa tgt tcg tcc gga gga acg tgt acg cag cag act ggc tcg    144
Trp Gln Lys Cys Ser Ser Gly Gly Thr Cys Thr Gln Gln Thr Gly Ser
                 20                  25                  30 gtg gtc atc gac gcc aac tgg agg tgg acg cat gca acc aac tcc tcc    192
Val Val Ile Asp Ala Asn Trp Arg Trp Thr His Ala Thr Asn Ser Ser
             35                  40                  45 acc aac tgt tac gat ggc aac act tgg tcc tcc acc ttg tgt ccc gat    240
Thr Asn Cys Tyr Asp Gly Asn Thr Trp Ser Ser Thr Leu Cys Pro Asp
         50                  55                  60
```

-continued

| | | |
|---|---|---|
| aac gaa acc tgt gcc aag aac tgt tgt ttg gat ggt gca gcc tac gcc<br>Asn Glu Thr Cys Ala Lys Asn Cys Cys Leu Asp Gly Ala Ala Tyr Ala<br>65                     70                    75 | 288 |
| tcg aca tac gga gtc act act tcc ggc aac tcg ctc tcg atc ggc ttc<br>Ser Thr Tyr Gly Val Thr Thr Ser Gly Asn Ser Leu Ser Ile Gly Phe<br>80                     85                    90               95 | 336 |
| gtg act cag tcc gca cag aaa aac gtc gga gcg cga ctc tac ttg atg<br>Val Thr Gln Ser Ala Gln Lys Asn Val Gly Ala Arg Leu Tyr Leu Met<br>100                 105                  110 | 384 |
| gca tcc gat aca acc tac cag gaa ttc act ctc ttg ggc aac gag ttc<br>Ala Ser Asp Thr Thr Tyr Gln Glu Phe Thr Leu Leu Gly Asn Glu Phe<br>115                 120                  125 | 432 |
| tcc ttc gac gtc gac gtc tcc cag ctc cct tgt ggc ctc aac gga gca<br>Ser Phe Asp Val Asp Val Ser Gln Leu Pro Cys Gly Leu Asn Gly Ala<br>130                 135                  140 | 480 |
| ctc tac ttc gtg tcg atg gac gcg gat gga ggt gtc tcc aag tac ccg<br>Leu Tyr Phe Val Ser Met Asp Ala Asp Gly Gly Val Ser Lys Tyr Pro<br>145                 150                  155 | 528 |
| acc aac aca gca gga gcg aaa tac ggc acg ggt tac tgt gac tcg cag<br>Thr Asn Thr Ala Gly Ala Lys Tyr Gly Thr Gly Tyr Cys Asp Ser Gln<br>160                 165                  170               175 | 576 |
| tgt cct cgc gat ctc aag ttc atc aac ggc cag gca aac gtc gaa ggc<br>Cys Pro Arg Asp Leu Lys Phe Ile Asn Gly Gln Ala Asn Val Glu Gly<br>180                 185                  190 | 624 |
| tgg gaa ccc tcg tcg gcc aac gcc gcc acc ggc att gga ggc cat ggc<br>Trp Glu Pro Ser Ser Ala Asn Ala Ala Thr Gly Ile Gly Gly His Gly<br>195                 200                  205 | 672 |
| tcc tgt tgt tcg gaa atg gat atc tgg gag gcc aac tcg atc tcc gag<br>Ser Cys Cys Ser Glu Met Asp Ile Trp Glu Ala Asn Ser Ile Ser Glu<br>210                 215                  220 | 720 |
| gca ctc aca ccc cac ccc tgt aca acc gtc ggc cag gag att tgt gaa<br>Ala Leu Thr Pro His Pro Cys Thr Thr Val Gly Gln Glu Ile Cys Glu<br>225                 230                  235 | 768 |
| gga gac ggc tgt ggc gga act tac tcc gat aac cgt tac ggt ggt acc<br>Gly Asp Gly Cys Gly Gly Thr Tyr Ser Asp Asn Arg Tyr Gly Gly Thr<br>240                 245                  250               255 | 816 |
| tgt gat ccc gat ggc tgt gac tgg aac ccc tac cgc ctc ggt aac aca<br>Cys Asp Pro Asp Gly Cys Asp Trp Asn Pro Tyr Arg Leu Gly Asn Thr<br>260                 265                  270 | 864 |
| tcg ttc tac ggt ccg ggt tcc tcc ttc acc ctc gac act acc aaa aag<br>Ser Phe Tyr Gly Pro Gly Ser Ser Phe Thr Leu Asp Thr Thr Lys Lys<br>275                 280                  285 | 912 |
| ttg acg gtg gtc acg cag ttc gag act tcc gga gcc atc aac cgg tac<br>Leu Thr Val Val Thr Gln Phe Glu Thr Ser Gly Ala Ile Asn Arg Tyr<br>290                 295                  300 | 960 |
| tac gtg cag aac gga gtc aca ttc cag cag ccc aac gca gaa ctc ggc<br>Tyr Val Gln Asn Gly Val Thr Phe Gln Gln Pro Asn Ala Glu Leu Gly<br>305                 310                  315 | 1008 |
| tcg tac tcg gga aac gag ctc aac gat gat tac tgt aca gcg gaa gag<br>Ser Tyr Ser Gly Asn Glu Leu Asn Asp Asp Tyr Cys Thr Ala Glu Glu<br>320                 325                  330               335 | 1056 |
| gca gaa ttc gga gga tcg tcg ttc tcc gac aag ggt ggt ttg acc cag<br>Ala Glu Phe Gly Gly Ser Ser Phe Ser Asp Lys Gly Gly Leu Thr Gln<br>340                 345                  350 | 1104 |
| ttc aag aag gcc aca tcg gga gga atg gtg ttg gtc atg tcc ttg tgg<br>Phe Lys Lys Ala Thr Ser Gly Gly Met Val Leu Val Met Ser Leu Trp<br>355                 360                  365 | 1152 |
| gac gac tac tat gcc aac atg ctc tgg ctc gac tcc acc tac ccc acc<br>Asp Asp Tyr Tyr Ala Asn Met Leu Trp Leu Asp Ser Thr Tyr Pro Thr<br>370                 375                  380 | 1200 |

```
aac gag acc tcc tcg aca cct ggc gca gtg agg ggc tcg tgt tcc act     1248
Asn Glu Thr Ser Ser Thr Pro Gly Ala Val Arg Gly Ser Cys Ser Thr
    385                 390                 395 tcg tcg gga gtg cct gca cag gtg gag tcc cag tcg ccg aac gcc aag     1296
Ser Ser Gly Val Pro Ala Gln Val Glu Ser Gln Ser Pro Asn Ala Lys
400                 405                 410                 415 gtc act ttc tcc aac att aag ttc gga ccc atc ggt tcg acc ggc aac     1344
Val Thr Phe Ser Asn Ile Lys Phe Gly Pro Ile Gly Ser Thr Gly Asn
                420                 425                 430 ccc tcc ggt gga aac cct cct ggc gga aac cct cct ggc aca act aca     1392
Pro Ser Gly Gly Asn Pro Pro Gly Gly Asn Pro Pro Gly Thr Thr Thr
                435                 440                 445 aca cga cgg cct gcg act aca acg ggt tcg tcc cct gga ccg acc cag     1440
Thr Arg Arg Pro Ala Thr Thr Thr Gly Ser Ser Pro Gly Pro Thr Gln
    450                 455                 460 tcc cac tac gga cag tgt gga ggc atc ggt tat tcc ggt ccg acc gtc     1488
Ser His Tyr Gly Gln Cys Gly Gly Ile Gly Tyr Ser Gly Pro Thr Val
    465                 470                 475 tgt gcg tcc ggc aca acc tgt cag gtc ttg aac cct tac tat tcg cag     1536
Cys Ala Ser Gly Thr Thr Cys Gln Val Leu Asn Pro Tyr Tyr Ser Gln
480                 485                 490                 495 tgt ctc taa                                                         1545
Cys Leu <210> SEQ ID NO 6
<211> LENGTH: 514
<212> TYPE: PRT
<213> ORGANISM: Trichoderma reesei

<400> SEQUENCE: 6

Met Tyr Arg Lys Leu Ala Val Ile Ser Ala Phe Leu Ala Thr Ala Arg
        -15                 -10                  -5

Ala Gln Ser Ala Cys Thr Leu Gln Ser Glu Thr His Pro Pro Leu Thr
 -1  1               5                  10                  15

Trp Gln Lys Cys Ser Ser Gly Gly Thr Cys Thr Gln Gln Thr Gly Ser
                20                  25                  30

Val Val Ile Asp Ala Asn Trp Arg Trp Thr His Ala Thr Asn Ser Ser
                35                  40                  45

Thr Asn Cys Tyr Asp Gly Asn Thr Trp Ser Ser Thr Leu Cys Pro Asp
            50                  55                  60

Asn Glu Thr Cys Ala Lys Asn Cys Cys Leu Asp Gly Ala Ala Tyr Ala
 65                  70                  75

Ser Thr Tyr Gly Val Thr Thr Ser Gly Asn Ser Leu Ser Ile Gly Phe
 80                  85                  90                  95

Val Thr Gln Ser Ala Gln Lys Asn Val Gly Ala Arg Leu Tyr Leu Met
                100                 105                 110

Ala Ser Asp Thr Thr Tyr Gln Glu Phe Thr Leu Leu Gly Asn Glu Phe
            115                 120                 125

Ser Phe Asp Val Asp Val Ser Gln Leu Pro Cys Gly Leu Asn Gly Ala
            130                 135                 140

Leu Tyr Phe Val Ser Met Asp Ala Asp Gly Gly Val Ser Lys Tyr Pro
    145                 150                 155

Thr Asn Thr Ala Gly Ala Lys Tyr Gly Thr Gly Tyr Cys Asp Ser Gln
160                 165                 170                 175

Cys Pro Arg Asp Leu Lys Phe Ile Asn Gly Gln Ala Asn Val Glu Gly
                180                 185                 190
```

```
Trp Glu Pro Ser Ser Ala Asn Ala Ala Thr Gly Ile Gly Gly His Gly
            195                 200                 205

Ser Cys Cys Ser Glu Met Asp Ile Trp Glu Ala Asn Ser Ile Ser Glu
        210                 215                 220

Ala Leu Thr Pro His Pro Cys Thr Thr Val Gly Gln Glu Ile Cys Glu
    225                 230                 235

Gly Asp Gly Cys Gly Gly Thr Tyr Ser Asp Asn Arg Tyr Gly Gly Thr
240                 245                 250                 255

Cys Asp Pro Asp Gly Cys Asp Trp Asn Pro Tyr Arg Leu Gly Asn Thr
                260                 265                 270

Ser Phe Tyr Gly Pro Gly Ser Ser Phe Thr Leu Asp Thr Thr Lys Lys
            275                 280                 285

Leu Thr Val Val Thr Gln Phe Glu Thr Ser Gly Ala Ile Asn Arg Tyr
        290                 295                 300

Tyr Val Gln Asn Gly Val Thr Phe Gln Gln Pro Asn Ala Glu Leu Gly
    305                 310                 315

Ser Tyr Ser Gly Asn Glu Leu Asn Asp Asp Tyr Cys Thr Ala Glu Glu
320                 325                 330                 335

Ala Glu Phe Gly Gly Ser Ser Phe Ser Asp Lys Gly Gly Leu Thr Gln
                340                 345                 350

Phe Lys Lys Ala Thr Ser Gly Gly Met Val Leu Val Met Ser Leu Trp
            355                 360                 365

Asp Asp Tyr Tyr Ala Asn Met Leu Trp Leu Asp Ser Thr Tyr Pro Thr
        370                 375                 380

Asn Glu Thr Ser Ser Thr Pro Gly Ala Val Arg Gly Ser Cys Ser Thr
    385                 390                 395

Ser Ser Gly Val Pro Ala Gln Val Glu Ser Gln Ser Pro Asn Ala Lys
400                 405                 410                 415

Val Thr Phe Ser Asn Ile Lys Phe Gly Pro Ile Gly Ser Thr Gly Asn
                420                 425                 430

Pro Ser Gly Gly Asn Pro Pro Gly Gly Asn Pro Pro Gly Thr Thr Thr
            435                 440                 445

Thr Arg Arg Pro Ala Thr Thr Thr Gly Ser Ser Pro Gly Pro Thr Gln
        450                 455                 460

Ser His Tyr Gly Gln Cys Gly Gly Ile Gly Tyr Ser Gly Pro Thr Val
    465                 470                 475

Cys Ala Ser Gly Thr Thr Cys Gln Val Leu Asn Pro Tyr Tyr Ser Gln
480                 485                 490                 495

Cys Leu

<210> SEQ ID NO 7
<211> LENGTH: 1599
<212> TYPE: DNA
<213> ORGANISM: Aspergillus fumigatus
<220> FEATURE:
<221> NAME/KEY: sig_peptide
<222> LOCATION: (1)..(26)
<220> FEATURE:
<221> NAME/KEY: CDS
<222> LOCATION: (1)..(1596)
<220> FEATURE:
<221> NAME/KEY: mat_peptide
<222> LOCATION: (79)..(1596)

<400> SEQUENCE: 7 atg ctg gcc tcc acc ttc tcc tac cgc atg tac aag acc gcg ctc atc    48
Met Leu Ala Ser Thr Phe Ser Tyr Arg Met Tyr Lys Thr Ala Leu Ile
    -25                 -20                 -15
```

```
ctg gcc gcc ctt ctg ggc tct ggc cag gct cag cag gtc ggt act tcc        96
Leu Ala Ala Leu Leu Gly Ser Gly Gln Ala Gln Gln Val Gly Thr Ser
-10              -5                  -1  1               5 cag gcg gaa gtg cat ccg tcc atg acc tgg cag agc tgc acg gct ggc       144
Gln Ala Glu Val His Pro Ser Met Thr Trp Gln Ser Cys Thr Ala Gly
             10                  15                  20 ggc agc tgc acc acc aac aac ggc aag gtg gtc atc gac gcg aac tgg       192
Gly Ser Cys Thr Thr Asn Asn Gly Lys Val Val Ile Asp Ala Asn Trp
         25                  30                  35 cgt tgg gtg cac aaa gtc ggc gac tac acc aac tgc tac acc ggc aac       240
Arg Trp Val His Lys Val Gly Asp Tyr Thr Asn Cys Tyr Thr Gly Asn
     40                  45                  50 acc tgg gac acg act atc tgc cct gac gat gcg acc tgc gca tcc aac       288
Thr Trp Asp Thr Thr Ile Cys Pro Asp Asp Ala Thr Cys Ala Ser Asn
55                  60                  65                  70 tgc gcc ctt gag ggt gcc aac tac gaa tcc acc tat ggt gtg acc gcc       336
Cys Ala Leu Glu Gly Ala Asn Tyr Glu Ser Thr Tyr Gly Val Thr Ala
                 75                  80                  85 agc ggc aat tcc ctc cgc ctc aac ttc gtc acc acc agc cag cag aag       384
Ser Gly Asn Ser Leu Arg Leu Asn Phe Val Thr Thr Ser Gln Gln Lys
             90                  95                 100 aac att ggc tcg cgt ctg tac atg atg aag gac gac tcg acc tac gag       432
Asn Ile Gly Ser Arg Leu Tyr Met Met Lys Asp Asp Ser Thr Tyr Glu
         105                 110                 115 atg ttt aag ctg ctg aac cag gag ttc acc ttc gat gtc gat gtc tcc       480
Met Phe Lys Leu Leu Asn Gln Glu Phe Thr Phe Asp Val Asp Val Ser
     120                 125                 130 aac ctc ccc tgc ggt ctc aac ggt gct ctg tac ttt gtc gcc atg gac       528
Asn Leu Pro Cys Gly Leu Asn Gly Ala Leu Tyr Phe Val Ala Met Asp
135                 140                 145                 150 gcc gac ggt ggc atg tcc aag tac cca acc aac aag gcc ggt gcc aag       576
Ala Asp Gly Gly Met Ser Lys Tyr Pro Thr Asn Lys Ala Gly Ala Lys
                 155                 160                 165 tac ggt act gga tac tgt gac tcg cag tgc cct cgc gac ctc aag ttc       624
Tyr Gly Thr Gly Tyr Cys Asp Ser Gln Cys Pro Arg Asp Leu Lys Phe
             170                 175                 180 atc aac ggt cag gcc aac gtc gaa ggg tgg cag ccc tcc tcc aac gat       672
Ile Asn Gly Gln Ala Asn Val Glu Gly Trp Gln Pro Ser Ser Asn Asp
         185                 190                 195 gcc aat gcg ggt acc ggc aac cac ggg tcc tgc tgc gcg gag atg gat       720
Ala Asn Ala Gly Thr Gly Asn His Gly Ser Cys Cys Ala Glu Met Asp
     200                 205                 210 atc tgg gag gcc aac agc atc tcc acg gcc ttc acc ccc cat ccg tgc       768
Ile Trp Glu Ala Asn Ser Ile Ser Thr Ala Phe Thr Pro His Pro Cys
215                 220                 225                 230 gac acg ccc ggc cag gtg atg tgc acc ggt gat gcc tgc ggt ggc acc       816
Asp Thr Pro Gly Gln Val Met Cys Thr Gly Asp Ala Cys Gly Gly Thr
                 235                 240                 245 tac agc tcc gac cgc tac ggc ggc acc tgc gac ccc gac gga tgt gat       864
Tyr Ser Ser Asp Arg Tyr Gly Gly Thr Cys Asp Pro Asp Gly Cys Asp
             250                 255                 260 ttc aac tcc ttc cgc cag ggc aac aag acc ttc tac ggc cct ggc atg       912
Phe Asn Ser Phe Arg Gln Gly Asn Lys Thr Phe Tyr Gly Pro Gly Met
         265                 270                 275 acc gtc gac acc aag agc aag ttt acc gtc gtc acc cag ttc atc acc       960
Thr Val Asp Thr Lys Ser Lys Phe Thr Val Val Thr Gln Phe Ile Thr
     280                 285                 290 gac gac ggc acc tcc agc ggc acc ctc aag gag atc aag cgc ttc tac      1008
Asp Asp Gly Thr Ser Ser Gly Thr Leu Lys Glu Ile Lys Arg Phe Tyr
```

```
                  295                 300                 305                 310
gtg cag aac ggc aag gtg atc ccc aac tcg gag tcg acc tgg acc ggc       1056
Val Gln Asn Gly Lys Val Ile Pro Asn Ser Glu Ser Thr Trp Thr Gly
                        315                 320                 325 gtc agc ggc aac tcc atc acc acc gag tac tgc acc gcc cag aag agc       1104
Val Ser Gly Asn Ser Ile Thr Thr Glu Tyr Cys Thr Ala Gln Lys Ser
            330                 335                 340 ctg ttc cag gac cag aac gtc ttc gaa aag cac ggc ggc ctc gag ggc       1152
Leu Phe Gln Asp Gln Asn Val Phe Glu Lys His Gly Gly Leu Glu Gly
        345                 350                 355 atg ggt gct gcc ctc gcc cag ggt atg gtt ctc gtc atg tcc ctg tgg       1200
Met Gly Ala Ala Leu Ala Gln Gly Met Val Leu Val Met Ser Leu Trp
    360                 365                 370 gat gat cac tcg gcc aac atg ctc tgg ctc gac agc aac tac ccg acc       1248
Asp Asp His Ser Ala Asn Met Leu Trp Leu Asp Ser Asn Tyr Pro Thr
375                 380                 385                 390 act gcc tct tcc acc act ccc ggc gtc gcc cgt ggt acc tgc gac atc       1296
Thr Ala Ser Ser Thr Thr Pro Gly Val Ala Arg Gly Thr Cys Asp Ile
                395                 400                 405 tcc tcc ggc gtc cct gcg gat gtc gag gcg aac cac ccc gac gcc tac       1344
Ser Ser Gly Val Pro Ala Asp Val Glu Ala Asn His Pro Asp Ala Tyr
            410                 415                 420 gtc gtc tac tcc aac atc aag gtc ggc ccc atc ggc tcg acc ttc aac       1392
Val Val Tyr Ser Asn Ile Lys Val Gly Pro Ile Gly Ser Thr Phe Asn
        425                 430                 435 agc ggt ggc tcg aac ccc ggt ggc gga acc acc acg aca act acc acc       1440
Ser Gly Gly Ser Asn Pro Gly Gly Gly Thr Thr Thr Thr Thr Thr Thr
    440                 445                 450 cag cct act acc acc acg acc acg gct gga aac cct ggc ggc acc gga       1488
Gln Pro Thr Thr Thr Thr Thr Thr Ala Gly Asn Pro Gly Gly Thr Gly
455                 460                 465                 470 gtc gca cag cac tat ggc cag tgt ggt gga atc gga tgg acc gga ccc       1536
Val Ala Gln His Tyr Gly Gln Cys Gly Gly Ile Gly Trp Thr Gly Pro
                475                 480                 485 aca acc tgt gcc agc cct tat acc tgc cag aag ctg aat gat tat tac       1584
Thr Thr Cys Ala Ser Pro Tyr Thr Cys Gln Lys Leu Asn Asp Tyr Tyr
            490                 495                 500 tct cag tgc ctg tag                                                   1599
Ser Gln Cys Leu
        505

<210> SEQ ID NO 8
<211> LENGTH: 532
<212> TYPE: PRT
<213> ORGANISM: Aspergillus fumigatus

<400> SEQUENCE: 8

Met Leu Ala Ser Thr Phe Ser Tyr Arg Met Tyr Lys Thr Ala Leu Ile
    -25                 -20                 -15

Leu Ala Ala Leu Leu Gly Ser Gly Gln Ala Gln Gln Val Gly Thr Ser
-10                  -5                 -1   1               5

Gln Ala Glu Val His Pro Ser Met Thr Trp Gln Ser Cys Thr Ala Gly
                10                  15                  20

Gly Ser Cys Thr Thr Asn Asn Gly Lys Val Val Ile Asp Ala Asn Trp
            25                  30                  35

Arg Trp Val His Lys Val Gly Asp Tyr Thr Asn Cys Tyr Thr Gly Asn
        40                  45                  50

Thr Trp Asp Thr Thr Ile Cys Pro Asp Asp Ala Thr Cys Ala Ser Asn
55                  60                  65                  70
```

```
Cys Ala Leu Glu Gly Ala Asn Tyr Glu Ser Thr Tyr Gly Val Thr Ala
                75                  80                  85

Ser Gly Asn Ser Leu Arg Leu Asn Phe Val Thr Thr Ser Gln Gln Lys
            90                  95                  100

Asn Ile Gly Ser Arg Leu Tyr Met Met Lys Asp Asp Ser Thr Tyr Glu
            105                 110                 115

Met Phe Lys Leu Leu Asn Gln Glu Phe Thr Phe Asp Val Asp Val Ser
    120                 125                 130

Asn Leu Pro Cys Gly Leu Asn Gly Ala Leu Tyr Phe Val Ala Met Asp
135                 140                 145                 150

Ala Asp Gly Gly Met Ser Lys Tyr Pro Thr Asn Lys Ala Gly Ala Lys
                155                 160                 165

Tyr Gly Thr Gly Tyr Cys Asp Ser Gln Cys Pro Arg Asp Leu Lys Phe
            170                 175                 180

Ile Asn Gly Gln Ala Asn Val Glu Gly Trp Gln Pro Ser Ser Asn Asp
            185                 190                 195

Ala Asn Ala Gly Thr Gly Asn His Gly Ser Cys Cys Ala Glu Met Asp
    200                 205                 210

Ile Trp Glu Ala Asn Ser Ile Ser Thr Ala Phe Thr Pro His Pro Cys
215                 220                 225                 230

Asp Thr Pro Gly Gln Val Met Cys Thr Gly Asp Ala Cys Gly Gly Thr
            235                 240                 245

Tyr Ser Ser Asp Arg Tyr Gly Gly Thr Cys Asp Pro Asp Gly Cys Asp
            250                 255                 260

Phe Asn Ser Phe Arg Gln Gly Asn Lys Thr Phe Tyr Gly Pro Gly Met
            265                 270                 275

Thr Val Asp Thr Lys Ser Lys Phe Thr Val Thr Gln Phe Ile Thr
    280                 285                 290

Asp Asp Gly Thr Ser Ser Gly Thr Leu Lys Glu Ile Lys Arg Phe Tyr
295                 300                 305                 310

Val Gln Asn Gly Lys Val Ile Pro Asn Ser Glu Ser Thr Trp Thr Gly
            315                 320                 325

Val Ser Gly Asn Ser Ile Thr Thr Glu Tyr Cys Thr Ala Gln Lys Ser
            330                 335                 340

Leu Phe Gln Asp Gln Asn Val Phe Glu Lys His Gly Gly Leu Glu Gly
            345                 350                 355

Met Gly Ala Ala Leu Ala Gln Gly Met Val Leu Val Met Ser Leu Trp
    360                 365                 370

Asp Asp His Ser Ala Asn Met Leu Trp Leu Asp Ser Asn Tyr Pro Thr
375                 380                 385                 390

Thr Ala Ser Ser Thr Thr Pro Gly Val Ala Arg Gly Thr Cys Asp Ile
            395                 400                 405

Ser Ser Gly Val Pro Ala Asp Val Glu Ala Asn His Pro Asp Ala Tyr
            410                 415                 420

Val Val Tyr Ser Asn Ile Lys Val Gly Pro Ile Gly Ser Thr Phe Asn
    425                 430                 435

Ser Gly Gly Ser Asn Pro Gly Gly Thr Thr Thr Thr Thr Thr
440                 445                 450

Gln Pro Thr Thr Thr Thr Thr Ala Gly Asn Pro Gly Gly Thr Gly
455                 460                 465                 470

Val Ala Gln His Tyr Gly Gln Cys Gly Gly Ile Gly Trp Thr Gly Pro
            475                 480                 485
```

```
Thr Thr Cys Ala Ser Pro Tyr Thr Cys Gln Lys Leu Asn Asp Tyr Tyr
            490                 495                 500
Ser Gln Cys Leu
        505

<210> SEQ ID NO 9
<211> LENGTH: 1374
<212> TYPE: DNA
<213> ORGANISM: Thermoascus aurantiacus
<220> FEATURE:
<221> NAME/KEY: sig_peptide
<222> LOCATION: (1)..(17)
<220> FEATURE:
<221> NAME/KEY: CDS
<222> LOCATION: (1)..(1371)
<220> FEATURE:
<221> NAME/KEY: mat_peptide
<222> LOCATION: (52)..(1371)

<400> SEQUENCE: 9 atg tat cag cgc gct ctt ctc ttc tct ttc ttc ctc tcc gcc gcc cgc      48
Met Tyr Gln Arg Ala Leu Leu Phe Ser Phe Phe Leu Ser Ala Ala Arg
        -15                 -10                  -5 gcg cag cag gcc ggt acc cta acc gca gag aat cac cct tcc ctg acc      96
Ala Gln Gln Ala Gly Thr Leu Thr Ala Glu Asn His Pro Ser Leu Thr
 -1   1               5                  10                  15 tgg cag caa tgc tcc agc ggc ggt agt tgt acc acg cag aat gga aaa     144
Trp Gln Gln Cys Ser Ser Gly Gly Ser Cys Thr Thr Gln Asn Gly Lys
                20                  25                  30 gtc gtt atc gat gcg aac tgg cgt tgg gtc cat acc acc tct gga tac     192
Val Val Ile Asp Ala Asn Trp Arg Trp Val His Thr Thr Ser Gly Tyr
            35                  40                  45 acc aac tgc tac acg ggc aat acg tgg gac acc agt atc tgt ccc gac     240
Thr Asn Cys Tyr Thr Gly Asn Thr Trp Asp Thr Ser Ile Cys Pro Asp
        50                  55                  60 gac gtg acc tgc gct cag aat tgt gcc ttg gat gga gcg gat tac agt     288
Asp Val Thr Cys Ala Gln Asn Cys Ala Leu Asp Gly Ala Asp Tyr Ser
 65                  70                  75 ggc acc tat ggt gtt acg acc agt ggc aac gcc ctg aga ctg aac ttt     336
Gly Thr Tyr Gly Val Thr Thr Ser Gly Asn Ala Leu Arg Leu Asn Phe
 80                  85                  90                  95 gtc acc caa agc tca ggg aag aac att ggc tcg cgc ctg tac ctg ctg     384
Val Thr Gln Ser Ser Gly Lys Asn Ile Gly Ser Arg Leu Tyr Leu Leu
                100                 105                 110 cag gac gac acc act tat cag atc ttc aag ctg ctg ggt cag gag ttt     432
Gln Asp Asp Thr Thr Tyr Gln Ile Phe Lys Leu Leu Gly Gln Glu Phe
            115                 120                 125 acc ttc gat gtc gac gtc tcc aat ctc cct tgc ggg ctg aac ggc gcc     480
Thr Phe Asp Val Asp Val Ser Asn Leu Pro Cys Gly Leu Asn Gly Ala
        130                 135                 140 ctc tac ttt gtg gcc atg gac gcc gac ggc gga ttg tcc aaa tac cct     528
Leu Tyr Phe Val Ala Met Asp Ala Asp Gly Gly Leu Ser Lys Tyr Pro
145                 150                 155 ggc aac aag gca ggc gct aag tat ggc act ggt tac tgc gac tct cag     576
Gly Asn Lys Ala Gly Ala Lys Tyr Gly Thr Gly Tyr Cys Asp Ser Gln
160                 165                 170                 175 tgc cct cgg gat ctc aag ttc atc aac ggt cag gcc aac gtt gaa ggc     624
Cys Pro Arg Asp Leu Lys Phe Ile Asn Gly Gln Ala Asn Val Glu Gly
                180                 185                 190 tgg cag ccg tct gcc aac gac cca aat gcc ggc gtt ggt aac cac ggt     672
Trp Gln Pro Ser Ala Asn Asp Pro Asn Ala Gly Val Gly Asn His Gly
            195                 200                 205
```

```
tcc tgc tgc gct gag atg gat gtc tgg gaa gcc aac agc atc tct act    720
Ser Cys Cys Ala Glu Met Asp Val Trp Glu Ala Asn Ser Ile Ser Thr
        210                 215                 220 gcg gtg acg cct cac cca tgc gac acc ccc ggc cag acc atg tgc cag    768
Ala Val Thr Pro His Pro Cys Asp Thr Pro Gly Gln Thr Met Cys Gln
    225                 230                 235 gga gac gac tgt ggt gga acc tac tcc tcc act cga tat gct ggt acc    816
Gly Asp Asp Cys Gly Gly Thr Tyr Ser Ser Thr Arg Tyr Ala Gly Thr
240                 245                 250                 255 tgc gac cct gat ggc tgc gac ttc aat cct tac cgc cag ggc aac cac    864
Cys Asp Pro Asp Gly Cys Asp Phe Asn Pro Tyr Arg Gln Gly Asn His
                260                 265                 270 tcg ttc tac ggc ccc ggg aag atc gtc gac act agc tcc aaa ttc acc    912
Ser Phe Tyr Gly Pro Gly Lys Ile Val Asp Thr Ser Ser Lys Phe Thr
            275                 280                 285 gtc gtc acc cag ttc atc acc gac gac ggg acc ccc tcc ggc acc ctg    960
Val Val Thr Gln Phe Ile Thr Asp Asp Gly Thr Pro Ser Gly Thr Leu
        290                 295                 300 acg gag atc aaa cgc ttc tac gtc cag aac ggc aag gtg atc ccc cag   1008
Thr Glu Ile Lys Arg Phe Tyr Val Gln Asn Gly Lys Val Ile Pro Gln
    305                 310                 315 tcg gag tcg acg atc agc ggc gtc acc ggc aac tca atc acc acc gag   1056
Ser Glu Ser Thr Ile Ser Gly Val Thr Gly Asn Ser Ile Thr Thr Glu
320                 325                 330                 335 tat tgc acg gcc cag aag gcc gcc ttc ggc gac aac acc ggc ttc ttc   1104
Tyr Cys Thr Ala Gln Lys Ala Ala Phe Gly Asp Asn Thr Gly Phe Phe
                340                 345                 350 acg cac ggc ggg ctt cag aag atc agt cag gct ctg gct cag ggc atg   1152
Thr His Gly Gly Leu Gln Lys Ile Ser Gln Ala Leu Ala Gln Gly Met
            355                 360                 365 gtc ctc gtc atg agc ctg tgg gac gat cac gcc gcc aac atg ctc tgg   1200
Val Leu Val Met Ser Leu Trp Asp Asp His Ala Ala Asn Met Leu Trp
        370                 375                 380 ctg gac agc acc tac ccg act gat gcg gac ccg gac acc cct ggc gtc   1248
Leu Asp Ser Thr Tyr Pro Thr Asp Ala Asp Pro Asp Thr Pro Gly Val
    385                 390                 395 gcg cgc ggt acc tgc ccc acg acc tcc ggc gtc ccg gcc gac gtt gag   1296
Ala Arg Gly Thr Cys Pro Thr Thr Ser Gly Val Pro Ala Asp Val Glu
400                 405                 410                 415 tcg cag aac ccc aat tca tat gtt atc tac tcc aac atc aag gtc gga   1344
Ser Gln Asn Pro Asn Ser Tyr Val Ile Tyr Ser Asn Ile Lys Val Gly
                420                 425                 430 ccc atc aac tcg acc ttc acc gcc aac taa                            1374
Pro Ile Asn Ser Thr Phe Thr Ala Asn
            435                 440

<210> SEQ ID NO 10
<211> LENGTH: 457
<212> TYPE: PRT
<213> ORGANISM: Thermoascus aurantiacus

<400> SEQUENCE: 10

Met Tyr Gln Arg Ala Leu Leu Phe Ser Phe Phe Leu Ser Ala Ala Arg
    -15                 -10                 -5

Ala Gln Gln Ala Gly Thr Leu Thr Ala Glu Asn His Pro Ser Leu Thr
-1   1               5                  10                  15

Trp Gln Gln Cys Ser Ser Gly Gly Ser Cys Thr Thr Gln Asn Gly Lys
                20                  25                  30

Val Val Ile Asp Ala Asn Trp Arg Trp Val His Thr Thr Ser Gly Tyr
            35                  40                  45
```

Thr Asn Cys Tyr Thr Gly Asn Thr Trp Asp Thr Ser Ile Cys Pro Asp
                50                  55                  60

Asp Val Thr Cys Ala Gln Asn Cys Ala Leu Asp Gly Ala Asp Tyr Ser
65                  70                  75

Gly Thr Tyr Gly Val Thr Thr Ser Gly Asn Ala Leu Arg Leu Asn Phe
80                  85                  90                  95

Val Thr Gln Ser Ser Gly Lys Asn Ile Gly Ser Arg Leu Tyr Leu Leu
                100                 105                 110

Gln Asp Asp Thr Thr Tyr Gln Ile Phe Lys Leu Leu Gly Gln Glu Phe
                115                 120                 125

Thr Phe Asp Val Asp Val Ser Asn Leu Pro Cys Gly Leu Asn Gly Ala
                130                 135                 140

Leu Tyr Phe Val Ala Met Asp Ala Asp Gly Gly Leu Ser Lys Tyr Pro
                145                 150                 155

Gly Asn Lys Ala Gly Ala Lys Tyr Gly Thr Gly Tyr Cys Asp Ser Gln
160                 165                 170                 175

Cys Pro Arg Asp Leu Lys Phe Ile Asn Gly Gln Ala Asn Val Glu Gly
                180                 185                 190

Trp Gln Pro Ser Ala Asn Asp Pro Asn Ala Gly Val Gly Asn His Gly
                195                 200                 205

Ser Cys Cys Ala Glu Met Asp Val Trp Glu Ala Asn Ser Ile Ser Thr
                210                 215                 220

Ala Val Thr Pro His Pro Cys Asp Thr Pro Gly Gln Thr Met Cys Gln
                225                 230                 235

Gly Asp Asp Cys Gly Gly Thr Tyr Ser Ser Thr Arg Tyr Ala Gly Thr
240                 245                 250                 255

Cys Asp Pro Asp Gly Cys Asp Phe Asn Pro Tyr Arg Gln Gly Asn His
                260                 265                 270

Ser Phe Tyr Gly Pro Gly Lys Ile Val Asp Thr Ser Ser Lys Phe Thr
                275                 280                 285

Val Val Thr Gln Phe Ile Thr Asp Asp Gly Thr Pro Ser Gly Thr Leu
                290                 295                 300

Thr Glu Ile Lys Arg Phe Tyr Val Gln Asn Gly Lys Val Ile Pro Gln
305                 310                 315

Ser Glu Ser Thr Ile Ser Gly Val Thr Gly Asn Ser Ile Thr Thr Glu
320                 325                 330                 335

Tyr Cys Thr Ala Gln Lys Ala Ala Phe Gly Asp Asn Thr Gly Phe Phe
                340                 345                 350

Thr His Gly Gly Leu Gln Lys Ile Ser Gln Ala Leu Ala Gln Gly Met
                355                 360                 365

Val Leu Val Met Ser Leu Trp Asp Asp His Ala Ala Asn Met Leu Trp
                370                 375                 380

Leu Asp Ser Thr Tyr Pro Thr Asp Ala Asp Pro Asp Thr Pro Gly Val
                385                 390                 395

Ala Arg Gly Thr Cys Pro Thr Thr Ser Gly Val Pro Ala Asp Val Glu
400                 405                 410                 415

Ser Gln Asn Pro Asn Ser Tyr Val Ile Tyr Ser Asn Ile Lys Val Gly
                420                 425                 430

Pro Ile Asn Ser Thr Phe Thr Ala Asn
                435                 440

<210> SEQ ID NO 11
<211> LENGTH: 1428

```
<212> TYPE: DNA
<213> ORGANISM: Rasamsonia emersonii
<220> FEATURE:
<221> NAME/KEY: exon
<222> LOCATION: (1)..(603)
<220> FEATURE:
<221> NAME/KEY: CDS
<222> LOCATION: (1)..(603)
<220> FEATURE:
<221> NAME/KEY: sig_peptide
<222> LOCATION: (1)..(18)
<220> FEATURE:
<221> NAME/KEY: mat_peptide
<222> LOCATION: (55)..(1425)
<220> FEATURE:
<221> NAME/KEY: Intron
<222> LOCATION: (604)..(663)
<220> FEATURE:
<221> NAME/KEY: exon
<222> LOCATION: (664)..(1425)
<220> FEATURE:
<221> NAME/KEY: CDS
<222> LOCATION: (664)..(1425)

<400> SEQUENCE: 11
```

| | | | | | | | | | | | | | | | | |
|---|---|---|---|---|---|---|---|---|---|---|---|---|---|---|---|---|
| atg | ctt | cga | cgg | gct | ctt | ctt | cta | tcc | tct | tcc | gcc | atc | ctt | gct | gtc | 48 |
| Met | Leu | Arg | Arg | Ala | Leu | Leu | Leu | Ser | Ser | Ser | Ala | Ile | Leu | Ala | Val | |
| | | -15 | | | | | -10 | | | | | -5 | | | | |

| aag | gca | cag | cag | gcc | ggc | acg | gcg | acg | gca | gag | aac | cac | ccg | ccc | ctg | 96 |
|---|---|---|---|---|---|---|---|---|---|---|---|---|---|---|---|---|
| Lys | Ala | Gln | Gln | Ala | Gly | Thr | Ala | Thr | Ala | Glu | Asn | His | Pro | Pro | Leu | |
| -1 | 1 | | | | 5 | | | | | 10 | | | | | | |

| aca | tgg | cag | gaa | tgc | acc | gcc | cct | ggg | agc | tgc | acc | acc | cag | aac | ggg | 144 |
|---|---|---|---|---|---|---|---|---|---|---|---|---|---|---|---|---|
| Thr | Trp | Gln | Glu | Cys | Thr | Ala | Pro | Gly | Ser | Cys | Thr | Thr | Gln | Asn | Gly | |
| 15 | | | | 20 | | | | | 25 | | | | | 30 | | |

| gcg | gtc | gtt | ctt | gat | gcg | aac | tgg | cgt | tgg | gtg | cac | gat | gtg | aac | gga | 192 |
|---|---|---|---|---|---|---|---|---|---|---|---|---|---|---|---|---|
| Ala | Val | Val | Leu | Asp | Ala | Asn | Trp | Arg | Trp | Val | His | Asp | Val | Asn | Gly | |
| | | | 35 | | | | | 40 | | | | | 45 | | | |

| tac | acc | aac | tgc | tac | acg | ggc | aat | acc | tgg | aac | ccc | acg | tac | tgc | cct | 240 |
|---|---|---|---|---|---|---|---|---|---|---|---|---|---|---|---|---|
| Tyr | Thr | Asn | Cys | Tyr | Thr | Gly | Asn | Thr | Trp | Asn | Pro | Thr | Tyr | Cys | Pro | |
| | | 50 | | | | | 55 | | | | | 60 | | | | |

| gac | gac | gaa | acc | tgc | gcc | cag | aac | tgt | gcg | ctg | gac | ggc | gcg | gat | tac | 288 |
|---|---|---|---|---|---|---|---|---|---|---|---|---|---|---|---|---|
| Asp | Asp | Glu | Thr | Cys | Ala | Gln | Asn | Cys | Ala | Leu | Asp | Gly | Ala | Asp | Tyr | |
| 65 | | | | | 70 | | | | | 75 | | | | | | |

| gag | ggc | acc | tac | ggc | gtg | act | tcg | tcg | ggc | agc | tcc | ttg | aag | ctc | aat | 336 |
|---|---|---|---|---|---|---|---|---|---|---|---|---|---|---|---|---|
| Glu | Gly | Thr | Tyr | Gly | Val | Thr | Ser | Ser | Gly | Ser | Ser | Leu | Lys | Leu | Asn | |
| | 80 | | | | | 85 | | | | | 90 | | | | | |

| ttc | gtc | acc | ggg | tcg | aac | gtc | gga | tcc | cgt | ctc | tac | ctg | ctg | cag | gac | 384 |
|---|---|---|---|---|---|---|---|---|---|---|---|---|---|---|---|---|
| Phe | Val | Thr | Gly | Ser | Asn | Val | Gly | Ser | Arg | Leu | Tyr | Leu | Leu | Gln | Asp | |
| 95 | | | | | 100 | | | | | 105 | | | | | 110 | |

| gac | tcg | acc | tat | cag | atc | ttc | aag | ctt | ctg | aac | cgc | gag | ttt | acc | ttt | 432 |
|---|---|---|---|---|---|---|---|---|---|---|---|---|---|---|---|---|
| Asp | Ser | Thr | Tyr | Gln | Ile | Phe | Lys | Leu | Leu | Asn | Arg | Glu | Phe | Thr | Phe | |
| | | | | 115 | | | | | 120 | | | | | 125 | | |

| gac | gtc | gat | gtc | tcc | aat | ctt | ccg | tgc | gga | ttg | aac | ggc | gct | ctg | tac | 480 |
|---|---|---|---|---|---|---|---|---|---|---|---|---|---|---|---|---|
| Asp | Val | Asp | Val | Ser | Asn | Leu | Pro | Cys | Gly | Leu | Asn | Gly | Ala | Leu | Tyr | |
| | | 130 | | | | | 135 | | | | | 140 | | | | |

| ttt | gtc | gcc | atg | gac | gcc | gac | ggc | ggc | gtg | tcc | aag | tac | ccg | aac | aac | 528 |
|---|---|---|---|---|---|---|---|---|---|---|---|---|---|---|---|---|
| Phe | Val | Ala | Met | Asp | Ala | Asp | Gly | Gly | Val | Ser | Lys | Tyr | Pro | Asn | Asn | |
| | 145 | | | | | 150 | | | | | 155 | | | | | |

| aag | gct | ggt | gcc | aag | tac | gga | acc | ggg | tat | tgc | gac | tcc | caa | tgc | cca | 576 |
|---|---|---|---|---|---|---|---|---|---|---|---|---|---|---|---|---|
| Lys | Ala | Gly | Ala | Lys | Tyr | Gly | Thr | Gly | Tyr | Cys | Asp | Ser | Gln | Cys | Pro | |
| 160 | | | | | 165 | | | | | 170 | | | | | | |

| cgg | gac | ctc | aag | ttc | atc | gac | ggc | gag | gtatgtccag tggtaaaatc | 623 |
|---|---|---|---|---|---|---|---|---|---|---|
| Arg | Asp | Leu | Lys | Phe | Ile | Asp | Gly | Glu | | |
| 175 | | | | | 180 | | | | | |

| gatcgtctcg tgaacttctg ctgacaggtt cgatctacag gcc aac gtc gag ggc | 678 |
|---|---|

|  |  |  |  |  |  |  |  |  |  |  |  | Ala | Asn | Val | Glu | Gly |  |
|---|---|---|---|---|---|---|---|---|---|---|---|---|---|---|---|---|---|
|  |  |  |  |  |  |  |  |  |  |  |  |  |  | 185 |  |  |  |

```
tgg cag ccg tct tcg aac aac gcc aac acc gga att ggc gac cat ggc      726
Trp Gln Pro Ser Ser Asn Asn Ala Asn Thr Gly Ile Gly Asp His Gly
    190                 195                 200 tcc tgc tgt gcg gag atg gat gtc tgg gaa gcc aac agc atc tcc aat      774
Ser Cys Cys Ala Glu Met Asp Val Trp Glu Ala Asn Ser Ile Ser Asn
205                 210                 215                 220 gcg gtc act ccg cac ccg tgc gac acg cca ggc cag acg atg tgc tct      822
Ala Val Thr Pro His Pro Cys Asp Thr Pro Gly Gln Thr Met Cys Ser
                225                 230                 235 ggc gat gac tgc ggt ggc aca tac tct aac gat cgc tac gcg gga acc      870
Gly Asp Asp Cys Gly Gly Thr Tyr Ser Asn Asp Arg Tyr Ala Gly Thr
        240                 245                 250 tgc gat cct gac ggc tgt gac ttc aac cct tac cgc atg ggc aac act      918
Cys Asp Pro Asp Gly Cys Asp Phe Asn Pro Tyr Arg Met Gly Asn Thr
            255                 260                 265 tct ttc tac ggg cct ggc aag atc atc gat acc acc aag cct ttc act      966
Ser Phe Tyr Gly Pro Gly Lys Ile Ile Asp Thr Thr Lys Pro Phe Thr
270                 275                 280 gtc gtg acg cag ttc ctc act gat gat ggt acg gat act gga act ctc     1014
Val Val Thr Gln Phe Leu Thr Asp Asp Gly Thr Asp Thr Gly Thr Leu
285                 290                 295                 300 agc gag atc aag cgc ttc tac gtc cag aac ggc aac gtc att ccg cag     1062
Ser Glu Ile Lys Arg Phe Tyr Val Gln Asn Gly Asn Val Ile Pro Gln
                305                 310                 315 ccc aac tcg gac atc agt ggc gtg acc ggc aac tcg atc acg acg gag     1110
Pro Asn Ser Asp Ile Ser Gly Val Thr Gly Asn Ser Ile Thr Thr Glu
        320                 325                 330 ttc tgt act gct cag aag cag gcc ttt ggc gac acg gac gac ttc tct     1158
Phe Cys Thr Ala Gln Lys Gln Ala Phe Gly Asp Thr Asp Asp Phe Ser
            335                 340                 345 cag cac ggt ggc ctg gcc aag atg gga gcg gcc atg cag cag ggt atg     1206
Gln His Gly Gly Leu Ala Lys Met Gly Ala Ala Met Gln Gln Gly Met
350                 355                 360 gtc ctg gtg atg agt ttg tgg gac gac tac gcc gcg cag atg ctg tgg     1254
Val Leu Val Met Ser Leu Trp Asp Asp Tyr Ala Ala Gln Met Leu Trp
365                 370                 375                 380 ctg gat tcc gac tac ccg acg gat gcg gac ccc acg acc cct ggt att     1302
Leu Asp Ser Asp Tyr Pro Thr Asp Ala Asp Pro Thr Thr Pro Gly Ile
                385                 390                 395 gcc cgt gga acg tgt ccg acg gac tcg ggc gtc cca tcg gat gtc gag     1350
Ala Arg Gly Thr Cys Pro Thr Asp Ser Gly Val Pro Ser Asp Val Glu
        400                 405                 410 tcg cag agc ccc aac tcc tac gtg acc tac tcg aac atc aag ttt ggt     1398
Ser Gln Ser Pro Asn Ser Tyr Val Thr Tyr Ser Asn Ile Lys Phe Gly
            415                 420                 425 ccg atc aac tcg acc ttc acc gct tcg tga                             1428
Pro Ile Asn Ser Thr Phe Thr Ala Ser
430                 435
```

<210> SEQ ID NO 12
<211> LENGTH: 455
<212> TYPE: PRT
<213> ORGANISM: Rasamsonia emersonii

<400> SEQUENCE: 12

```
Met Leu Arg Arg Ala Leu Leu Leu Ser Ser Ala Ile Leu Ala Val
            -15                 -10                  -5

Lys Ala Gln Gln Ala Gly Thr Ala Thr Ala Glu Asn His Pro Pro Leu
```

-continued

```
      -1   1               5                          10
     Thr  Trp  Gln  Glu  Cys  Thr  Ala  Pro  Gly  Ser  Cys  Thr  Thr  Gln  Asn  Gly
     15                  20                       25                            30

Ala  Val  Val  Leu  Asp  Ala  Asn  Trp  Arg  Trp  Val  His  Asp  Val  Asn  Gly
                              35                       40                       45

Tyr  Thr  Asn  Cys  Tyr  Thr  Gly  Asn  Thr  Trp  Asn  Pro  Thr  Tyr  Cys  Pro
                         50                       55                       60

Asp  Asp  Glu  Thr  Cys  Ala  Gln  Asn  Cys  Ala  Leu  Asp  Gly  Ala  Asp  Tyr
                    65                       70                       75

Glu  Gly  Thr  Tyr  Gly  Val  Thr  Ser  Ser  Gly  Ser  Ser  Leu  Lys  Leu  Asn
               80                       85                       90

Phe  Val  Thr  Gly  Ser  Asn  Val  Gly  Ser  Arg  Leu  Tyr  Leu  Leu  Gln  Asp
     95                  100                      105                           110

Asp  Ser  Thr  Tyr  Gln  Ile  Phe  Lys  Leu  Leu  Asn  Arg  Glu  Phe  Thr  Phe
                         115                      120                      125

Asp  Val  Asp  Val  Ser  Asn  Leu  Pro  Cys  Gly  Leu  Asn  Gly  Ala  Leu  Tyr
                    130                      135                      140

Phe  Val  Ala  Met  Asp  Ala  Asp  Gly  Gly  Val  Ser  Lys  Tyr  Pro  Asn  Asn
               145                      150                      155

Lys  Ala  Gly  Ala  Lys  Tyr  Gly  Thr  Gly  Tyr  Cys  Asp  Ser  Gln  Cys  Pro
     160                      165                      170

Arg  Asp  Leu  Lys  Phe  Ile  Asp  Gly  Glu  Ala  Asn  Val  Glu  Gly  Trp  Gln
     175                      180                      185                      190

Pro  Ser  Ser  Asn  Asn  Ala  Asn  Thr  Gly  Ile  Gly  Asp  His  Gly  Ser  Cys
                         195                      200                      205

Cys  Ala  Glu  Met  Asp  Val  Trp  Glu  Ala  Asn  Ser  Ile  Ser  Asn  Ala  Val
                    210                      215                      220

Thr  Pro  His  Pro  Cys  Asp  Thr  Pro  Gly  Gln  Thr  Met  Cys  Ser  Gly  Asp
               225                      230                      235

Asp  Cys  Gly  Gly  Thr  Tyr  Ser  Asn  Asp  Arg  Tyr  Ala  Gly  Thr  Cys  Asp
     240                      245                      250

Pro  Asp  Gly  Cys  Asp  Phe  Asn  Pro  Tyr  Arg  Met  Gly  Asn  Thr  Ser  Phe
     255                      260                      265                      270

Tyr  Gly  Pro  Gly  Lys  Ile  Ile  Asp  Thr  Thr  Lys  Pro  Phe  Thr  Val  Val
                         275                      280                      285

Thr  Gln  Phe  Leu  Thr  Asp  Asp  Gly  Thr  Asp  Thr  Gly  Thr  Leu  Ser  Glu
                    290                      295                      300

Ile  Lys  Arg  Phe  Tyr  Val  Gln  Asn  Gly  Asn  Val  Ile  Pro  Gln  Pro  Asn
               305                      310                      315

Ser  Asp  Ile  Ser  Gly  Val  Thr  Gly  Asn  Ser  Ile  Thr  Thr  Glu  Phe  Cys
     320                      325                      330

Thr  Ala  Gln  Lys  Gln  Ala  Phe  Gly  Asp  Thr  Asp  Asp  Phe  Ser  Gln  His
     335                      340                      345                      350

Gly  Gly  Leu  Ala  Lys  Met  Gly  Ala  Ala  Met  Gln  Gln  Gly  Met  Val  Leu
                         355                      360                      365

Val  Met  Ser  Leu  Trp  Asp  Asp  Tyr  Ala  Ala  Gln  Met  Leu  Trp  Leu  Asp
                    370                      375                      380

Ser  Asp  Tyr  Pro  Thr  Asp  Ala  Asp  Pro  Thr  Thr  Pro  Gly  Ile  Ala  Arg
               385                      390                      395

Gly  Thr  Cys  Pro  Thr  Asp  Ser  Gly  Val  Pro  Ser  Asp  Val  Glu  Ser  Gln
     400                      405                      410

Ser  Pro  Asn  Ser  Tyr  Val  Thr  Tyr  Ser  Asn  Ile  Lys  Phe  Gly  Pro  Ile
     415                      420                      425                      430
```

```
Asn Ser Thr Phe Thr Ala Ser
                435

<210> SEQ ID NO 13
<211> LENGTH: 1599
<212> TYPE: DNA
<213> ORGANISM: Talaromyces leycettanus
<220> FEATURE:
<221> NAME/KEY: sig_peptide
<222> LOCATION: (1)..(25)
<220> FEATURE:
<221> NAME/KEY: CDS
<222> LOCATION: (1)..(1596)
<220> FEATURE:
<221> NAME/KEY: mat_peptide
<222> LOCATION: (76)..(1596)

<400> SEQUENCE: 13 atg gcc agc ctc ttc tct ttc aag atg tac aag gcc gct ctg gtc ctc     48
Met Ala Ser Leu Phe Ser Phe Lys Met Tyr Lys Ala Ala Leu Val Leu
-25                 -20                 -15                 -10 tcc tct ctc ctt gcg gcc acc cag gcc cag cag gcc ggc acc ctg acc     96
Ser Ser Leu Leu Ala Ala Thr Gln Ala Gln Gln Ala Gly Thr Leu Thr
            -5                  -1  1                   5 acc gaa acc cat cct tct ctg acc tgg cag caa tgc tct gcc ggc ggc    144
Thr Glu Thr His Pro Ser Leu Thr Trp Gln Gln Cys Ser Ala Gly Gly
        10                  15                  20 agc tgc acc act cag aac ggc aag gtc gtc atc gac gcc aac tgg cgc    192
Ser Cys Thr Thr Gln Asn Gly Lys Val Val Ile Asp Ala Asn Trp Arg
    25                  30                  35 tgg gtt cac agc acc agc ggc tcg aac aac tgc tac act ggc aac act    240
Trp Val His Ser Thr Ser Gly Ser Asn Asn Cys Tyr Thr Gly Asn Thr
40                  45                  50                  55 tgg gat gct act ctc tgc cct gac gac gtg act tgc gct gcc aac tgc    288
Trp Asp Ala Thr Leu Cys Pro Asp Asp Val Thr Cys Ala Ala Asn Cys
                60                  65                  70 gcc ctg gac ggc gct gac tac tcg ggc acc tac ggt gtc acc acc agc    336
Ala Leu Asp Gly Ala Asp Tyr Ser Gly Thr Tyr Gly Val Thr Thr Ser
            75                  80                  85 ggc aac tct ctg cgc ctg aac ttc gtc acc cag gcg tcg cag aag aac    384
Gly Asn Ser Leu Arg Leu Asn Phe Val Thr Gln Ala Ser Gln Lys Asn
        90                  95                  100 gtc ggc tct cgt ctc tat ctg atg gag aat gac aca acc tac cag atc    432
Val Gly Ser Arg Leu Tyr Leu Met Glu Asn Asp Thr Thr Tyr Gln Ile
    105                 110                 115 ttc aag ttg ctg aac cag gag ttc acc ttt gac gtt gat gtc tcc aac    480
Phe Lys Leu Leu Asn Gln Glu Phe Thr Phe Asp Val Asp Val Ser Asn
120                 125                 130                 135 ctt ccc tgc ggt ctc aac ggt gct ctc tac ctg gtt gcc atg gat gcc    528
Leu Pro Cys Gly Leu Asn Gly Ala Leu Tyr Leu Val Ala Met Asp Ala
                140                 145                 150 gac ggc ggc atg gcc aag tac cca acc aac aag gct ggt gcg aag tac    576
Asp Gly Gly Met Ala Lys Tyr Pro Thr Asn Lys Ala Gly Ala Lys Tyr
            155                 160                 165 gga acc ggt tac tgc gac tcc cag tgc cct cgc gac ctg aag ttc atc    624
Gly Thr Gly Tyr Cys Asp Ser Gln Cys Pro Arg Asp Leu Lys Phe Ile
        170                 175                 180 aac ggt gag gcc aat gtt gag gga tgg cag cct tct tcc aat gac ccc    672
Asn Gly Glu Ala Asn Val Glu Gly Trp Gln Pro Ser Ser Asn Asp Pro
    185                 190                 195 aac tct ggc att ggc aac cac ggc tct tgc tgt gct gag atg gac atc    720
Asn Ser Gly Ile Gly Asn His Gly Ser Cys Cys Ala Glu Met Asp Ile
```

-continued

| | | | | | |
|---|---|---|---|---|---|
| | 200 | 205 | 210 | 215 | |
| tgg gag gcc aac agc atc tcc aat gca gtc act cct cac cct tgc gac<br>Trp Glu Ala Asn Ser Ile Ser Asn Ala Val Thr Pro His Pro Cys Asp<br>                      220                      225                      230 | | | | | 768 |
| acc ccg gga cag gtc atg tgc acc ggc aac aac tgt ggt ggc act tac<br>Thr Pro Gly Gln Val Met Cys Thr Gly Asn Asn Cys Gly Gly Thr Tyr<br>             235                      240                        245 | | | | | 816 |
| agc act act cgc tat gct ggc act tgc gat cct gat ggc tgc gac ttc<br>Ser Thr Thr Arg Tyr Ala Gly Thr Cys Asp Pro Asp Gly Cys Asp Phe<br>        250                      255                      260 | | | | | 864 |
| aac ccc tac cgc atg ggc aac cac tcc ttc tac ggc ccc aaa cag atc<br>Asn Pro Tyr Arg Met Gly Asn His Ser Phe Tyr Gly Pro Lys Gln Ile<br>265                        270                      275 | | | | | 912 |
| gtc gac acc agc tcc aag ttc act gtt gtt act cag ttc ctc acc gat<br>Val Asp Thr Ser Ser Lys Phe Thr Val Val Thr Gln Phe Leu Thr Asp<br>280                        285                      290                      295 | | | | | 960 |
| gat ggc acc tcc acc ggc acc ctc agc gag atc agg cgc ttc tac gtt<br>Asp Gly Thr Ser Thr Gly Thr Leu Ser Glu Ile Arg Arg Phe Tyr Val<br>                      300                      305                      310 | | | | | 1008 |
| cag aac ggc cag gtc atc ccc aac tcc gtg tcc acg atc agc ggc gtc<br>Gln Asn Gly Gln Val Ile Pro Asn Ser Val Ser Thr Ile Ser Gly Val<br>             315                      320                        325 | | | | | 1056 |
| tcc ggc aac tcc atc acc acc gag ttc tgc acg gcc cag aag cag gct<br>Ser Gly Asn Ser Ile Thr Thr Glu Phe Cys Thr Ala Gln Lys Gln Ala<br>        330                      335                      340 | | | | | 1104 |
| ttc ggc gac act gat gac ttc agc aag cac ggc ggt ctg tct ggc atg<br>Phe Gly Asp Thr Asp Asp Phe Ser Lys His Gly Gly Leu Ser Gly Met<br>345                        350                      355 | | | | | 1152 |
| tcc gcc gcc ctc tcc cag ggt atg gtt ctc gtc atg agc ttg tgg gac<br>Ser Ala Ala Leu Ser Gln Gly Met Val Leu Val Met Ser Leu Trp Asp<br>360                        365                      370                      375 | | | | | 1200 |
| gac cac gcc gcc aac atg ctc tgg ctt gac agc acc tac ccg acc aac<br>Asp His Ala Ala Asn Met Leu Trp Leu Asp Ser Thr Tyr Pro Thr Asn<br>                      380                      385                      390 | | | | | 1248 |
| gcc acc tct tcc acc ccc ggt gcc gcc cgt ggt act tgc gac atc tcc<br>Ala Thr Ser Ser Thr Pro Gly Ala Ala Arg Gly Thr Cys Asp Ile Ser<br>             395                      400                      405 | | | | | 1296 |
| tcc ggt gtc ccc gcc gat gtt gag tcc aac gac ccc aac gcc tac gtc<br>Ser Gly Val Pro Ala Asp Val Glu Ser Asn Asp Pro Asn Ala Tyr Val<br>        410                      415                      420 | | | | | 1344 |
| gtc tac tcc aac atc aag gtc ggc ccg atc ggc tct acc ttc agc agc<br>Val Tyr Ser Asn Ile Lys Val Gly Pro Ile Gly Ser Thr Phe Ser Ser<br>425                        430                      435 | | | | | 1392 |
| tct ggc tct ggc tct agc tcc agc tcc agc acc acc acc acc acc<br>Ser Gly Ser Gly Ser Ser Ser Ser Ser Thr Thr Thr Thr Thr<br>440                        445                      450                      455 | | | | | 1440 |
| gct tcc cca acc acg acc acc tcc agc gct tcc agc acc ggc act ggc<br>Ala Ser Pro Thr Thr Thr Thr Ser Ser Ala Ser Ser Thr Gly Thr Gly<br>             460                      465                      470 | | | | | 1488 |
| gtt gct cag cac tgg ggt cag tgc ggt ggc cag gga tgg acc ggt ccg<br>Val Ala Gln His Trp Gly Gln Cys Gly Gly Gln Gly Trp Thr Gly Pro<br>        475                      480                      485 | | | | | 1536 |
| acc acc tgc gtt agc ccc tac acc tgc cag gag ctg aac ccc tac tac<br>Thr Thr Cys Val Ser Pro Tyr Thr Cys Gln Glu Leu Asn Pro Tyr Tyr<br>             490                      495                      500 | | | | | 1584 |
| tac cag tgc ctg taa<br>Tyr Gln Cys Leu<br>        505 | | | | | 1599 |

-continued

<210> SEQ ID NO 14
<211> LENGTH: 532
<212> TYPE: PRT
<213> ORGANISM: Talaromyces leycettanus

<400> SEQUENCE: 14

Met Ala Ser Leu Phe Ser Phe Lys Met Tyr Lys Ala Ala Leu Val Leu
-25                 -20                 -15                 -10

Ser Ser Leu Leu Ala Ala Thr Gln Ala Gln Gln Ala Gly Thr Leu Thr
            -5                  -1   1               5

Thr Glu Thr His Pro Ser Leu Thr Trp Gln Gln Cys Ser Ala Gly Gly
                10                  15                  20

Ser Cys Thr Thr Gln Asn Gly Lys Val Val Ile Asp Ala Asn Trp Arg
    25                  30                  35

Trp Val His Ser Thr Ser Gly Ser Asn Asn Cys Tyr Thr Gly Asn Thr
40                  45                  50                  55

Trp Asp Ala Thr Leu Cys Pro Asp Asp Val Thr Cys Ala Ala Asn Cys
                60                  65                  70

Ala Leu Asp Gly Ala Asp Tyr Ser Gly Thr Tyr Gly Val Thr Thr Ser
                75                  80                  85

Gly Asn Ser Leu Arg Leu Asn Phe Val Thr Gln Ala Ser Gln Lys Asn
    90                  95                  100

Val Gly Ser Arg Leu Tyr Leu Met Glu Asn Asp Thr Thr Tyr Gln Ile
    105                 110                 115

Phe Lys Leu Leu Asn Gln Glu Phe Thr Phe Asp Val Asp Val Ser Asn
120                 125                 130                 135

Leu Pro Cys Gly Leu Asn Gly Ala Leu Tyr Leu Val Ala Met Asp Ala
                140                 145                 150

Asp Gly Gly Met Ala Lys Tyr Pro Thr Asn Lys Ala Gly Ala Lys Tyr
                155                 160                 165

Gly Thr Gly Tyr Cys Asp Ser Gln Cys Pro Arg Asp Leu Lys Phe Ile
                170                 175                 180

Asn Gly Glu Ala Asn Val Glu Gly Trp Gln Pro Ser Ser Asn Asp Pro
                185                 190                 195

Asn Ser Gly Ile Gly Asn His Gly Ser Cys Cys Ala Glu Met Asp Ile
200                 205                 210                 215

Trp Glu Ala Asn Ser Ile Ser Asn Ala Val Thr Pro His Pro Cys Asp
                220                 225                 230

Thr Pro Gly Gln Val Met Cys Thr Gly Asn Asn Cys Gly Gly Thr Tyr
                235                 240                 245

Ser Thr Thr Arg Tyr Ala Gly Thr Cys Asp Pro Asp Gly Cys Asp Phe
                250                 255                 260

Asn Pro Tyr Arg Met Gly Asn His Ser Phe Tyr Gly Pro Lys Gln Ile
                265                 270                 275

Val Asp Thr Ser Ser Lys Phe Thr Val Val Thr Gln Phe Leu Thr Asp
280                 285                 290                 295

Asp Gly Thr Ser Thr Gly Thr Leu Ser Glu Ile Arg Arg Phe Tyr Val
                300                 305                 310

Gln Asn Gly Gln Val Ile Pro Asn Ser Val Ser Thr Ile Ser Gly Val
                315                 320                 325

Ser Gly Asn Ser Ile Thr Thr Glu Phe Cys Thr Ala Gln Lys Gln Ala
                330                 335                 340

Phe Gly Asp Thr Asp Asp Phe Ser Lys His Gly Gly Leu Ser Gly Met
                345                 350                 355

-continued

```
Ser Ala Ala Leu Ser Gln Gly Met Val Leu Val Met Ser Leu Trp Asp
360             365                 370                 375

Asp His Ala Ala Asn Met Leu Trp Leu Asp Ser Thr Tyr Pro Thr Asn
            380                 385                 390

Ala Thr Ser Ser Thr Pro Gly Ala Ala Arg Gly Thr Cys Asp Ile Ser
        395                 400                 405

Ser Gly Val Pro Ala Asp Val Glu Ser Asn Asp Pro Asn Ala Tyr Val
    410                 415                 420

Val Tyr Ser Asn Ile Lys Val Gly Pro Ile Gly Ser Thr Phe Ser Ser
    425                 430                 435

Ser Gly Ser Gly Ser Ser Ser Ser Ser Thr Thr Thr Thr Thr Thr Thr
440             445                 450                 455

Ala Ser Pro Thr Thr Thr Thr Ser Ser Ala Ser Ser Thr Gly Thr Gly
            460                 465                 470

Val Ala Gln His Trp Gly Gln Cys Gly Gly Gln Gly Trp Thr Gly Pro
            475                 480                 485

Thr Thr Cys Val Ser Pro Tyr Thr Cys Gln Glu Leu Asn Pro Tyr Tyr
        490                 495                 500

Tyr Gln Cys Leu
    505

<210> SEQ ID NO 15
<211> LENGTH: 1599
<212> TYPE: DNA
<213> ORGANISM: Talaromyces leycettanus
<220> FEATURE:
<221> NAME/KEY: sig_peptide
<222> LOCATION: (1)..(25)
<220> FEATURE:
<221> NAME/KEY: CDS
<222> LOCATION: (1)..(1596)
<220> FEATURE:
<221> NAME/KEY: mat_peptide
<222> LOCATION: (76)..(1596)

<400> SEQUENCE: 15 atg gcg tcc tct ctc tct tac agg atc tac aag aat gct ctc atc ttc    48
Met Ala Ser Ser Leu Ser Tyr Arg Ile Tyr Lys Asn Ala Leu Ile Phe
-25                 -20                 -15                 -10 tct tct ctc ctg gcc gct gcc cag ggt cag cag att ggt acc tac cag    96
Ser Ser Leu Leu Ala Ala Ala Gln Gly Gln Gln Ile Gly Thr Tyr Gln
        -5                  -1  1               5 acg gag acc cat ccg cct ctg acc tgg cag aca tgc acc agc ggc ggc   144
Thr Glu Thr His Pro Pro Leu Thr Trp Gln Thr Cys Thr Ser Gly Gly
        10                  15                  20 agt tgc acg acc aac caa ggc tcc atc gtc ctc gat gcc aac tgg cgc   192
Ser Cys Thr Thr Asn Gln Gly Ser Ile Val Leu Asp Ala Asn Trp Arg
    25                  30                  35 tgg gtg cac gag gtc ggc agc acc acc aac tgc tac acc ggc aat acc   240
Trp Val His Glu Val Gly Ser Thr Thr Asn Cys Tyr Thr Gly Asn Thr
40                  45                  50                  55 tgg gac acc tcc atc tgc agc acg gat acg acc tgc gct cag caa tgt   288
Trp Asp Thr Ser Ile Cys Ser Thr Asp Thr Thr Cys Ala Gln Gln Cys
                60                  65                  70 gcc gtc gat ggt gcc gac tac gag ggc acc tat ggt atc acg acc agc   336
Ala Val Asp Gly Ala Asp Tyr Glu Gly Thr Tyr Gly Ile Thr Thr Ser
            75                  80                  85 ggc agc cag gtc cgc atc aac ttc gtc acc aac aac tcg aac gga aag   384
Gly Ser Gln Val Arg Ile Asn Phe Val Thr Asn Asn Ser Asn Gly Lys
        90                  95                  100
```

```
aac gtc ggc gcg cgt gtc tac atg atg gcg gac aac acc cac tac caa      432
Asn Val Gly Ala Arg Val Tyr Met Met Ala Asp Asn Thr His Tyr Gln
        105                 110                 115 att tac cag ctg ctg aac cag gag ttc acc ttt gat gtc gac gtg tcc      480
Ile Tyr Gln Leu Leu Asn Gln Glu Phe Thr Phe Asp Val Asp Val Ser
120                 125                 130                 135 aac ctg cct tgc ggc ctc aac ggt gcc ctc tac ttt gtg gtc atg gac      528
Asn Leu Pro Cys Gly Leu Asn Gly Ala Leu Tyr Phe Val Val Met Asp
                140                 145                 150 gcc gat ggt ggt gtc tcc aag tat ccc aac aac aag gct ggt gcc cag      576
Ala Asp Gly Gly Val Ser Lys Tyr Pro Asn Asn Lys Ala Gly Ala Gln
                    155                 160                 165 tac ggt gtc ggt tac tgc gac tcc cag tgt ccc aga gac ctc aaa ttc      624
Tyr Gly Val Gly Tyr Cys Asp Ser Gln Cys Pro Arg Asp Leu Lys Phe
                170                 175                 180 atc cag gga cag gcc aac gtc gag ggc tgg caa ccg tcg tcc aac aac      672
Ile Gln Gly Gln Ala Asn Val Glu Gly Trp Gln Pro Ser Ser Asn Asn
185                 190                 195 gcc aat acc ggc ctg ggc aac cac ggc tcc tgc tgt gct gaa ctg gac      720
Ala Asn Thr Gly Leu Gly Asn His Gly Ser Cys Cys Ala Glu Leu Asp
200                 205                 210                 215 gtc tgg gag tcg aac agc atc tcc cag gcc ctc act ccc cac ccc tgc      768
Val Trp Glu Ser Asn Ser Ile Ser Gln Ala Leu Thr Pro His Pro Cys
                220                 225                 230 gac act ccc acc aat acc ctg tgc acc ggt gat agc tgc ggt ggc aca      816
Asp Thr Pro Thr Asn Thr Leu Cys Thr Gly Asp Ser Cys Gly Gly Thr
                235                 240                 245 tac agc agc aac cgt tat gcg ggc act tgc gat cct gac ggc tgc gat      864
Tyr Ser Ser Asn Arg Tyr Ala Gly Thr Cys Asp Pro Asp Gly Cys Asp
                250                 255                 260 ttc aac ccc tac cgc ttg ggc aac acc acc ttc tac ggt cct ggc aag      912
Phe Asn Pro Tyr Arg Leu Gly Asn Thr Thr Phe Tyr Gly Pro Gly Lys
265                 270                 275 act att gac acc acc aaa ccc ttc acg gtt gtg acg cag ttc atc acg      960
Thr Ile Asp Thr Thr Lys Pro Phe Thr Val Val Thr Gln Phe Ile Thr
280                 285                 290                 295 gat gac ggc act tcc agc ggc acc ctg tcc gaa att agg cgt ttc tat     1008
Asp Asp Gly Thr Ser Ser Gly Thr Leu Ser Glu Ile Arg Arg Phe Tyr
                300                 305                 310 gtc cag aac ggt gtt acg tac gcc cag ccc aac tct gac gtc agc ggt     1056
Val Gln Asn Gly Val Thr Tyr Ala Gln Pro Asn Ser Asp Val Ser Gly
            315                 320                 325 atc agc ggc aat gcc atc aac agt gct tac tgc act gcg gag aac acc     1104
Ile Ser Gly Asn Ala Ile Asn Ser Ala Tyr Cys Thr Ala Glu Asn Thr
                330                 335                 340 gtc ttc aac ggt gcc ggc acc ttc gcg cag cac ggc ggc ctg gct ggc     1152
Val Phe Asn Gly Ala Gly Thr Phe Ala Gln His Gly Gly Leu Ala Gly
            345                 350                 355 atg agc cag gcc atg tcc acc ggt atg gtc ttg gtg atg agc ctg tgg     1200
Met Ser Gln Ala Met Ser Thr Gly Met Val Leu Val Met Ser Leu Trp
360                 365                 370                 375 gat gat tac tat gcc gac atg ctc tgg ctc gac agc acc tac cca acc     1248
Asp Asp Tyr Tyr Ala Asp Met Leu Trp Leu Asp Ser Thr Tyr Pro Thr
                380                 385                 390 aac gac acc gca agc acg ccc ggt gcg gtc cgt gga acc tgc tct acg     1296
Asn Asp Thr Ala Ser Thr Pro Gly Ala Val Arg Gly Thr Cys Ser Thr
                395                 400                 405 tcg tcc ggt gtc ccc agc cag gtc gaa tcc gcc agc ccg aac gcc tac     1344
Ser Ser Gly Val Pro Ser Gln Val Glu Ser Ala Ser Pro Asn Ala Tyr
            410                 415                 420
```

```
gtg acc tac tcg aac atc aag gtt ggt ccc att ggc tcg act ttc aac    1392
Val Thr Tyr Ser Asn Ile Lys Val Gly Pro Ile Gly Ser Thr Phe Asn
    425             430             435 tct ggc ggc tct ggc tct ggc agc agc tcc agc act acc acg acc act    1440
Ser Gly Gly Ser Gly Ser Gly Ser Ser Ser Ser Thr Thr Thr Thr Thr
440             445             450             455 cac gcc agc acc acg acg acg tcc tcc gcc tcg tct acg gga act ggc    1488
His Ala Ser Thr Thr Thr Thr Ser Ser Ala Ser Ser Thr Gly Thr Gly
            460             465             470 gtg gcc caa cac tgg ggc cag tgt ggt gga cag ggc tgg acc ggc cca    1536
Val Ala Gln His Trp Gly Gln Cys Gly Gly Gln Gly Trp Thr Gly Pro
        475             480             485 aca acc tgc gtt tcc ccg tac act tgc cag gag ctg aac ccg tac tac    1584
Thr Thr Cys Val Ser Pro Tyr Thr Cys Gln Glu Leu Asn Pro Tyr Tyr
    490             495             500 tac cag tgt ctg tag                                                1599
Tyr Gln Cys Leu
    505
```

```
<210> SEQ ID NO 16
<211> LENGTH: 532
<212> TYPE: PRT
<213> ORGANISM: Talaromyces leycettanus

<400> SEQUENCE: 16

Met Ala Ser Ser Leu Ser Tyr Arg Ile Tyr Lys Asn Ala Leu Ile Phe
-25             -20             -15             -10

Ser Ser Leu Leu Ala Ala Ala Gln Gly Gln Gln Ile Gly Thr Tyr Gln
            -5              -1  1               5

Thr Glu Thr His Pro Pro Leu Thr Trp Gln Thr Cys Thr Ser Gly Gly
        10              15              20

Ser Cys Thr Thr Asn Gln Gly Ser Ile Val Leu Asp Ala Asn Trp Arg
    25              30              35

Trp Val His Glu Val Gly Ser Thr Thr Asn Cys Tyr Thr Gly Asn Thr
40              45              50              55

Trp Asp Thr Ser Ile Cys Ser Thr Asp Thr Thr Cys Ala Gln Gln Cys
            60              65              70

Ala Val Asp Gly Ala Asp Tyr Glu Gly Thr Tyr Gly Ile Thr Thr Ser
        75              80              85

Gly Ser Gln Val Arg Ile Asn Phe Val Thr Asn Asn Ser Asn Gly Lys
    90              95              100

Asn Val Gly Ala Arg Val Tyr Met Met Ala Asp Asn Thr His Tyr Gln
105             110             115

Ile Tyr Gln Leu Leu Asn Gln Glu Phe Thr Phe Asp Val Asp Val Ser
120             125             130             135

Asn Leu Pro Cys Gly Leu Asn Gly Ala Leu Tyr Phe Val Val Met Asp
            140             145             150

Ala Asp Gly Gly Val Ser Lys Tyr Pro Asn Asn Lys Ala Gly Ala Gln
        155             160             165

Tyr Gly Val Gly Tyr Cys Asp Ser Gln Cys Pro Arg Asp Leu Lys Phe
    170             175             180

Ile Gln Gly Gln Ala Asn Val Glu Gly Trp Gln Pro Ser Ser Asn Asn
185             190             195

Ala Asn Thr Gly Leu Gly Asn His Gly Ser Cys Cys Ala Glu Leu Asp
200             205             210             215

Val Trp Glu Ser Asn Ser Ile Ser Gln Ala Leu Thr Pro His Pro Cys
```

```
                220                 225                 230
Asp Thr Pro Thr Asn Thr Leu Cys Thr Gly Asp Ser Cys Gly Gly Thr
            235                 240                 245

Tyr Ser Ser Asn Arg Tyr Ala Gly Thr Cys Asp Pro Asp Gly Cys Asp
        250                 255                 260

Phe Asn Pro Tyr Arg Leu Gly Asn Thr Thr Phe Tyr Gly Pro Gly Lys
265                 270                 275

Thr Ile Asp Thr Thr Lys Pro Phe Thr Val Val Thr Gln Phe Ile Thr
280                 285                 290                 295

Asp Asp Gly Thr Ser Gly Thr Leu Ser Glu Ile Arg Arg Phe Tyr
                300                 305                 310

Val Gln Asn Gly Val Thr Tyr Ala Gln Pro Asn Ser Asp Val Ser Gly
            315                 320                 325

Ile Ser Gly Asn Ala Ile Asn Ser Ala Tyr Cys Thr Ala Glu Asn Thr
        330                 335                 340

Val Phe Asn Gly Ala Gly Thr Phe Ala Gln His Gly Gly Leu Ala Gly
    345                 350                 355

Met Ser Gln Ala Met Ser Thr Gly Met Val Leu Val Met Ser Leu Trp
360                 365                 370                 375

Asp Asp Tyr Tyr Ala Asp Met Leu Trp Leu Asp Ser Thr Tyr Pro Thr
                380                 385                 390

Asn Asp Thr Ala Ser Thr Pro Gly Ala Val Arg Gly Thr Cys Ser Thr
            395                 400                 405

Ser Ser Gly Val Pro Ser Gln Val Glu Ser Ala Ser Pro Asn Ala Tyr
        410                 415                 420

Val Thr Tyr Ser Asn Ile Lys Val Gly Pro Ile Gly Ser Thr Phe Asn
    425                 430                 435

Ser Gly Gly Ser Gly Ser Gly Ser Ser Ser Thr Thr Thr Thr Thr
440                 445                 450                 455

His Ala Ser Thr Thr Thr Ser Ser Ala Ser Ser Thr Gly Thr Gly
                460                 465                 470

Val Ala Gln His Trp Gly Gln Cys Gly Gly Gln Gly Trp Thr Gly Pro
            475                 480                 485

Thr Thr Cys Val Ser Pro Tyr Thr Cys Gln Glu Leu Asn Pro Tyr Tyr
        490                 495                 500

Tyr Gln Cys Leu
    505

<210> SEQ ID NO 17
<211> LENGTH: 1507
<212> TYPE: DNA
<213> ORGANISM: Talaromyces byssochlamydoides
<220> FEATURE:
<221> NAME/KEY: exon
<222> LOCATION: (1)..(603)
<220> FEATURE:
<221> NAME/KEY: CDS
<222> LOCATION: (1)..(603)
<220> FEATURE:
<221> NAME/KEY: sig_peptide
<222> LOCATION: (1)..(18)
<220> FEATURE:
<221> NAME/KEY: mat_peptide
<222> LOCATION: (55)..(1504)
<220> FEATURE:
<221> NAME/KEY: Intron
<222> LOCATION: (604)..(667)
<220> FEATURE:
<221> NAME/KEY: exon
<222> LOCATION: (668)..(1235)
```

```
<220> FEATURE:
<221> NAME/KEY: CDS
<222> LOCATION: (668)..(1235)
<220> FEATURE:
<221> NAME/KEY: Intron
<222> LOCATION: (1236)..(1310)
<220> FEATURE:
<221> NAME/KEY: exon
<222> LOCATION: (1311)..(1504)
<220> FEATURE:
<221> NAME/KEY: CDS
<222> LOCATION: (1311)..(1504)

<400> SEQUENCE: 17
```

| | | | | | | | | | | | | | | | | |
|---|---|---|---|---|---|---|---|---|---|---|---|---|---|---|---|---|
| atg | ttt | cga | cgg | gct | ctt | ttc | ctg | tcc | tct | tcc | gcc | ttc | ctt | gct | gtc | 48 |
| Met | Phe | Arg | Arg | Ala | Leu | Phe | Leu | Ser | Ser | Ser | Ala | Phe | Leu | Ala | Val | |
| | | | -15 | | | | -10 | | | | -5 | | | | | |
| aaa | gcc | cag | cag | atc | ggc | acg | gtc | agt | ccg | gag | aac | cat | ccg | ccc | ctg | 96 |
| Lys | Ala | Gln | Gln | Ile | Gly | Thr | Val | Ser | Pro | Glu | Asn | His | Pro | Pro | Leu | |
| | -1 | 1 | | | | 5 | | | | | 10 | | | | | |
| gca | tgg | gag | cag | tgc | act | gcc | cct | ggg | agt | tgc | acg | act | gtg | aat | ggt | 144 |
| Ala | Trp | Glu | Gln | Cys | Thr | Ala | Pro | Gly | Ser | Cys | Thr | Thr | Val | Asn | Gly | |
| 15 | | | | | 20 | | | | | 25 | | | | | 30 | |
| gcg | gtc | gtc | ctt | gat | gcg | aac | tgg | cgt | tgg | gtc | cac | aat | gtt | ggg | gga | 192 |
| Ala | Val | Val | Leu | Asp | Ala | Asn | Trp | Arg | Trp | Val | His | Asn | Val | Gly | Gly | |
| | | | | 35 | | | | | 40 | | | | | 45 | | |
| tac | acc | aac | tgc | tac | act | ggc | aat | acc | tgg | gac | acc | acg | tac | tgc | cct | 240 |
| Tyr | Thr | Asn | Cys | Tyr | Thr | Gly | Asn | Thr | Trp | Asp | Thr | Thr | Tyr | Cys | Pro | |
| | | 50 | | | | | 55 | | | | | 60 | | | | |
| gac | gac | gtg | acc | tgc | gca | gag | aat | tgt | gcg | ctg | gat | ggc | gca | gat | tac | 288 |
| Asp | Asp | Val | Thr | Cys | Ala | Glu | Asn | Cys | Ala | Leu | Asp | Gly | Ala | Asp | Tyr | |
| 65 | | | | | 70 | | | | | 75 | | | | | | |
| gag | ggc | acc | tac | ggc | gtg | acc | acc | tcg | ggc | agc | tcc | ctg | aag | ctc | gat | 336 |
| Glu | Gly | Thr | Tyr | Gly | Val | Thr | Thr | Ser | Gly | Ser | Ser | Leu | Lys | Leu | Asp | |
| | 80 | | | | | 85 | | | | | 90 | | | | | |
| ttc | gtc | acc | ggg | tct | aac | gtc | gga | tct | cgt | ctc | tac | ctg | ttg | gag | aat | 384 |
| Phe | Val | Thr | Gly | Ser | Asn | Val | Gly | Ser | Arg | Leu | Tyr | Leu | Leu | Glu | Asn | |
| 95 | | | | | 100 | | | | | 105 | | | | | 110 | |
| gat | tcg | acc | tat | cag | atc | ttc | aag | ctt | ctg | aac | cag | gaa | ttc | acc | ttt | 432 |
| Asp | Ser | Thr | Tyr | Gln | Ile | Phe | Lys | Leu | Leu | Asn | Gln | Glu | Phe | Thr | Phe | |
| | | | | 115 | | | | | 120 | | | | | 125 | | |
| gac | gtc | gac | gtt | tcc | aat | ctt | ccg | tgc | gga | tta | aac | ggc | gct | ctg | tac | 480 |
| Asp | Val | Asp | Val | Ser | Asn | Leu | Pro | Cys | Gly | Leu | Asn | Gly | Ala | Leu | Tyr | |
| | | | 130 | | | | | 135 | | | | | 140 | | | |
| ctt | gtt | acc | atg | gct | gct | gac | ggc | ggg | gtg | tct | cag | tac | ccg | aat | aac | 528 |
| Leu | Val | Thr | Met | Ala | Ala | Asp | Gly | Gly | Val | Ser | Gln | Tyr | Pro | Asn | Asn | |
| | | 145 | | | | | 150 | | | | | 155 | | | | |
| aag | gcc | ggc | gca | gcg | tat | gga | acc | ggt | tat | tgc | gat | tcc | cag | tgt | cca | 576 |
| Lys | Ala | Gly | Ala | Ala | Tyr | Gly | Thr | Gly | Tyr | Cys | Asp | Ser | Gln | Cys | Pro | |
| 160 | | | | | 165 | | | | | 170 | | | | | | |
| agg | gac | ttg | aag | ttt | atc | gat | ggc | cag | gtatgtagag ctgtaatcac | | | | | | | 623 |
| Arg | Asp | Leu | Lys | Phe | Ile | Asp | Gly | Gln | | | | | | | | |
| 175 | | | | | 180 | | | | | | | | | | | |

```
ccatgttgtg aaatcactct cctactgaca tggtcgattt atag gcc aac gtt gag      679
                                                  Ala Asn Val Glu
                                                             185
```

| | | | | | | | | | | | | | | | |
|---|---|---|---|---|---|---|---|---|---|---|---|---|---|---|---|
| ggc | tgg | cag | ccg | tct | tcg | aac | aac | gcc | aat | aca | ggt | att | ggc | aac | cat | 727 |
| Gly | Trp | Gln | Pro | Ser | Ser | Asn | Asn | Ala | Asn | Thr | Gly | Ile | Gly | Asn | His | |
| | 190 | | | | | 195 | | | | | 200 | | | | | |
| ggc | tcc | tgc | tgt | gcg | gag | atg | gat | atc | tgg | gaa | gcc | aac | agc | atc | tcc | 775 |
| Gly | Ser | Cys | Cys | Ala | Glu | Met | Asp | Ile | Trp | Glu | Ala | Asn | Ser | Ile | Ser | |
| 205 | | | | | 210 | | | | | 215 | | | | | | |

```
aat gcg gtg act ccg cac cca tgc gac aca ccc ggc cag aca atg tgc      823
Asn Ala Val Thr Pro His Pro Cys Asp Thr Pro Gly Gln Thr Met Cys
220             225                 230                 235 gag ggg aac gac tgt ggt ggc acg tat tcc acc aat cgc tat gca ggc      871
Glu Gly Asn Asp Cys Gly Gly Thr Tyr Ser Thr Asn Arg Tyr Ala Gly
            240                 245                 250 acc tgc gat cct gac ggc tgc gac ttc aac ccc tac cgc atg ggc aac      919
Thr Cys Asp Pro Asp Gly Cys Asp Phe Asn Pro Tyr Arg Met Gly Asn
                255                 260                 265 cat tct ttc tac ggc cct ggg gag att gtc gat act acc cag ccc ttc      967
His Ser Phe Tyr Gly Pro Gly Glu Ile Val Asp Thr Thr Gln Pro Phe
            270                 275                 280 act gtc gtg aca cag ttc ctt acc gat gat ggc acg gat act ggc act     1015
Thr Val Val Thr Gln Phe Leu Thr Asp Asp Gly Thr Asp Thr Gly Thr
285                 290                 295 ctc agc gag atc aaa cgc ttc tac gtc caa aac ggg aaa gtc att cct     1063
Leu Ser Glu Ile Lys Arg Phe Tyr Val Gln Asn Gly Lys Val Ile Pro
300                 305                 310                 315 cag ccg aac tcc gac att gcc ggc gtg act ggc aac tcg atc acc agc     1111
Gln Pro Asn Ser Asp Ile Ala Gly Val Thr Gly Asn Ser Ile Thr Ser
                320                 325                 330 gag ttt tgc gat gcc cag aag acg gct ttc ggc gac att aac aac ttt     1159
Glu Phe Cys Asp Ala Gln Lys Thr Ala Phe Gly Asp Ile Asn Asn Phe
            335                 340                 345 gat aca cac ggc ggt ctg gcc agt atg gga gct gcg ctg cag cag ggt     1207
Asp Thr His Gly Gly Leu Ala Ser Met Gly Ala Ala Leu Gln Gln Gly
        350                 355                 360 atg gtt ctg gtg atg agt ctg tgg gac g gtaggtcctt gggagacacc         1255
Met Val Leu Val Met Ser Leu Trp Asp
365                 370 cggacgttct atatcaacca gaactgccag aactgacgaa ttaaaacact tttag at     1312
                                                              Asp tac gcg gca aac atg ctg tgg ttg gac agc att tat cca aca aat gca     1360
Tyr Ala Ala Asn Met Leu Trp Leu Asp Ser Ile Tyr Pro Thr Asn Ala
    375                 380                 385 tct gct agc act cct ggt gct gct cgt gga acc tgt tcg acg agc tcc     1408
Ser Ala Ser Thr Pro Gly Ala Ala Arg Gly Thr Cys Ser Thr Ser Ser
390                 395                 400                 405 ggt gtc cca tcg caa gtc gag tcg cag agc ccc aac gcc tac gtg acg     1456
Gly Val Pro Ser Gln Val Glu Ser Gln Ser Pro Asn Ala Tyr Val Thr
                410                 415                 420 tac tcc aac att aaa gtt gga cca atc aac tcg acc ttc acc act tcg     1504
Tyr Ser Asn Ile Lys Val Gly Pro Ile Asn Ser Thr Phe Thr Thr Ser
            425                 430                 435 taa                                                                 1507

<210> SEQ ID NO 18
<211> LENGTH: 455
<212> TYPE: PRT
<213> ORGANISM: Talaromyces byssochlamydoides

<400> SEQUENCE: 18

Met Phe Arg Arg Ala Leu Phe Leu Ser Ser Ala Phe Leu Ala Val
            -15                 -10                 -5

Lys Ala Gln Gln Ile Gly Thr Val Ser Pro Glu Asn His Pro Leu
    -1   1              5                  10

Ala Trp Glu Gln Cys Thr Ala Pro Gly Ser Cys Thr Thr Val Asn Gly
15                  20                  25                  30

Ala Val Val Leu Asp Ala Asn Trp Arg Trp Val His Asn Val Gly Gly
```

```
                 35                  40                  45
Tyr Thr Asn Cys Tyr Thr Gly Asn Thr Trp Asp Thr Thr Tyr Cys Pro
             50                  55                  60

Asp Asp Val Thr Cys Ala Glu Asn Cys Ala Leu Asp Gly Ala Asp Tyr
             65                  70                  75

Glu Gly Thr Tyr Gly Val Thr Thr Ser Gly Ser Ser Leu Lys Leu Asp
             80                  85                  90

Phe Val Thr Gly Ser Asn Val Gly Ser Arg Leu Tyr Leu Leu Glu Asn
 95                 100                 105                 110

Asp Ser Thr Tyr Gln Ile Phe Lys Leu Leu Asn Gln Glu Phe Thr Phe
                115                 120                 125

Asp Val Asp Val Ser Asn Leu Pro Cys Gly Leu Asn Gly Ala Leu Tyr
                130                 135                 140

Leu Val Thr Met Ala Ala Asp Gly Gly Val Ser Gln Tyr Pro Asn Asn
                145                 150                 155

Lys Ala Gly Ala Ala Tyr Gly Thr Gly Tyr Cys Asp Ser Gln Cys Pro
            160                 165                 170

Arg Asp Leu Lys Phe Ile Asp Gly Gln Ala Asn Val Glu Gly Trp Gln
175                 180                 185                 190

Pro Ser Ser Asn Asn Ala Asn Thr Gly Ile Gly Asn His Gly Ser Cys
                195                 200                 205

Cys Ala Glu Met Asp Ile Trp Glu Ala Asn Ser Ile Ser Asn Ala Val
                210                 215                 220

Thr Pro His Pro Cys Asp Thr Pro Gly Gln Thr Met Cys Glu Gly Asn
                225                 230                 235

Asp Cys Gly Gly Thr Tyr Ser Thr Asn Arg Tyr Ala Gly Thr Cys Asp
            240                 245                 250

Pro Asp Gly Cys Asp Phe Asn Pro Tyr Arg Met Gly Asn His Ser Phe
255                 260                 265                 270

Tyr Gly Pro Gly Glu Ile Val Asp Thr Thr Gln Pro Phe Thr Val Val
                275                 280                 285

Thr Gln Phe Leu Thr Asp Asp Gly Thr Asp Thr Gly Thr Leu Ser Glu
                290                 295                 300

Ile Lys Arg Phe Tyr Val Gln Asn Gly Lys Val Ile Pro Gln Pro Asn
                305                 310                 315

Ser Asp Ile Ala Gly Val Thr Gly Asn Ser Ile Thr Ser Glu Phe Cys
            320                 325                 330

Asp Ala Gln Lys Thr Ala Phe Gly Asp Ile Asn Asn Phe Asp Thr His
335                 340                 345                 350

Gly Gly Leu Ala Ser Met Gly Ala Ala Leu Gln Gln Gly Met Val Leu
                355                 360                 365

Val Met Ser Leu Trp Asp Asp Tyr Ala Ala Asn Met Leu Trp Leu Asp
                370                 375                 380

Ser Ile Tyr Pro Thr Asn Ala Ser Ala Ser Thr Pro Gly Ala Ala Arg
            385                 390                 395

Gly Thr Cys Ser Thr Ser Ser Gly Val Pro Ser Gln Val Glu Ser Gln
        400                 405                 410

Ser Pro Asn Ala Tyr Val Thr Tyr Ser Asn Ile Lys Val Gly Pro Ile
415                 420                 425                 430

Asn Ser Thr Phe Thr Thr Ser
                435

<210> SEQ ID NO 19
```

```
<211> LENGTH: 1353
<212> TYPE: DNA
<213> ORGANISM: Myceliophthora thermophila
<220> FEATURE:
<221> NAME/KEY: sig_peptide
<222> LOCATION: (1)..(20)
<220> FEATURE:
<221> NAME/KEY: CDS
<222> LOCATION: (1)..(1350)
<220> FEATURE:
<221> NAME/KEY: mat_peptide
<222> LOCATION: (61)..(1350)

<400> SEQUENCE: 19 atg aag cag tac ctc cag tac ctc gcg gcg acc ctg ccc ctg gtg ggc      48
Met Lys Gln Tyr Leu Gln Tyr Leu Ala Ala Thr Leu Pro Leu Val Gly
-20             -15                 -10                 -5 ctg gcc acg gcc cag cag gcg ggt aac ctg cag acc gag act cac ccc      96
Leu Ala Thr Ala Gln Gln Ala Gly Asn Leu Gln Thr Glu Thr His Pro
        -1  1               5                   10 agg ctc act tgg tcc aag tgc acg gcc ccg gga tcc tgc caa cag gtc     144
Arg Leu Thr Trp Ser Lys Cys Thr Ala Pro Gly Ser Cys Gln Gln Val
    15                  20                  25 aac ggc gag gtc gtc atc gac tcc aac tgg cgc tgg gtg cac gac gag     192
Asn Gly Glu Val Val Ile Asp Ser Asn Trp Arg Trp Val His Asp Glu
30                  35                  40 aac gcg cag aac tgc tac gac ggc aac cag tgg acc aac gct tgc agc     240
Asn Ala Gln Asn Cys Tyr Asp Gly Asn Gln Trp Thr Asn Ala Cys Ser
45                  50                  55                  60 tct gcc acc gac tgc gcc gag aat tgc gcg ctc gag ggt gcc gac tac     288
Ser Ala Thr Asp Cys Ala Glu Asn Cys Ala Leu Glu Gly Ala Asp Tyr
                65                  70                  75 cag ggc acc tat ggc gcc tcg acc agc ggc aat gcc ctg acg ctc acc     336
Gln Gly Thr Tyr Gly Ala Ser Thr Ser Gly Asn Ala Leu Thr Leu Thr
            80                  85                  90 ttc gtc act aag cac gag tac ggc acc aac att ggc tcg cgc ctc tac     384
Phe Val Thr Lys His Glu Tyr Gly Thr Asn Ile Gly Ser Arg Leu Tyr
        95                  100                 105 ctc atg aac ggc gcg aac aag tac cag atg ttc acc ctc aag ggc aac     432
Leu Met Asn Gly Ala Asn Lys Tyr Gln Met Phe Thr Leu Lys Gly Asn
110                 115                 120 gag ctg gcc ttc gac gtc gac ctc tcg gcc gtc gag tgc ggc ctc aac     480
Glu Leu Ala Phe Asp Val Asp Leu Ser Ala Val Glu Cys Gly Leu Asn
125                 130                 135                 140 agc gcc ctc tac ttc gtg gcc atg gag gag gat ggc ggt gtg tcg agc     528
Ser Ala Leu Tyr Phe Val Ala Met Glu Glu Asp Gly Gly Val Ser Ser
                145                 150                 155 tac ccg acc aac acg gcc ggt gct aag ttc ggc act ggg tac tgc gac     576
Tyr Pro Thr Asn Thr Ala Gly Ala Lys Phe Gly Thr Gly Tyr Cys Asp
            160                 165                 170 gcc caa tgc gca cgc gac ctc aag ttc gtc ggc ggc aag ggc aac atc     624
Ala Gln Cys Ala Arg Asp Leu Lys Phe Val Gly Gly Lys Gly Asn Ile
        175                 180                 185 gag ggc tgg aag ccg tcc acc aac gat gcc aat gcc ggt gtc ggt cct     672
Glu Gly Trp Lys Pro Ser Thr Asn Asp Ala Asn Ala Gly Val Gly Pro
190                 195                 200 tat ggc ggg tgc tgc gct gag atc gac gtc tgg gag tcg aac aag tat     720
Tyr Gly Gly Cys Cys Ala Glu Ile Asp Val Trp Glu Ser Asn Lys Tyr
205                 210                 215                 220 gct ttc gct ttc acc ccg cac ggt tgc gag aac cct aaa tac cac gtc     768
Ala Phe Ala Phe Thr Pro His Gly Cys Glu Asn Pro Lys Tyr His Val
                225                 230                 235
```

| | | |
|---|---|---|
| tgc gag acc acc aac tgc ggt ggc acc tac tcc gag gac cgc ttc gct<br>Cys Glu Thr Thr Asn Cys Gly Gly Thr Tyr Ser Glu Asp Arg Phe Ala<br>240 245 250 | 816 | |
| ggt gac tgc gat gcc aac ggc tgc gac tac aac ccc tac cgc atg ggc<br>Gly Asp Cys Asp Ala Asn Gly Cys Asp Tyr Asn Pro Tyr Arg Met Gly<br>255 260 265 | 864 | |
| aac cag gac ttc tac ggt ccc ggc ttg acg gtc gat acc agc aag aag<br>Asn Gln Asp Phe Tyr Gly Pro Gly Leu Thr Val Asp Thr Ser Lys Lys<br>270 275 280 | 912 | |
| ttc acc gtc gtc agc cag ttc gag gag aac aag ctc acc cag ttc ttc<br>Phe Thr Val Val Ser Gln Phe Glu Glu Asn Lys Leu Thr Gln Phe Phe<br>285 290 295 300 | 960 | |
| gtc cag gac ggc aag aag att gag atc ccc ggc ccc aag gtc gag ggc<br>Val Gln Asp Gly Lys Lys Ile Glu Ile Pro Gly Pro Lys Val Glu Gly<br>305 310 315 | 1008 | |
| atc gat gcg gac agc gcc gct atc acc cct gag ctg tgc agt gcc ctg<br>Ile Asp Ala Asp Ser Ala Ala Ile Thr Pro Glu Leu Cys Ser Ala Leu<br>320 325 330 | 1056 | |
| ttc aag gcc ttc gat gac cgt gac cgc ttc tcg gag gtt ggc ggc ttc<br>Phe Lys Ala Phe Asp Asp Arg Asp Arg Phe Ser Glu Val Gly Gly Phe<br>335 340 345 | 1104 | |
| gat gcc atc aac acg gcc ctc agc act ccc atg gtc ctc gtc atg tcc<br>Asp Ala Ile Asn Thr Ala Leu Ser Thr Pro Met Val Leu Val Met Ser<br>350 355 360 | 1152 | |
| atc tgg gat gat cac tac gcc aat atg ctc tgg ctc gac tcg agc tac<br>Ile Trp Asp Asp His Tyr Ala Asn Met Leu Trp Leu Asp Ser Ser Tyr<br>365 370 375 380 | 1200 | |
| ccc cct gag aag gct ggc cag cct ggc ggt gac cgt ggc ccg tgt cct<br>Pro Pro Glu Lys Ala Gly Gln Pro Gly Gly Asp Arg Gly Pro Cys Pro<br>385 390 395 | 1248 | |
| cag gac tct ggc gtc ccg gcc gac gtt gag gct cag tac cct aat gcc<br>Gln Asp Ser Gly Val Pro Ala Asp Val Glu Ala Gln Tyr Pro Asn Ala<br>400 405 410 | 1296 | |
| aag gtc atc tgg tcc aac atc cgc ttc ggc ccc atc ggc tcg act gtc<br>Lys Val Ile Trp Ser Asn Ile Arg Phe Gly Pro Ile Gly Ser Thr Val<br>415 420 425 | 1344 | |
| aac gtc taa<br>Asn Val<br>430 | 1353 | |

```
<210> SEQ ID NO 20
<211> LENGTH: 450
<212> TYPE: PRT
<213> ORGANISM: Myceliophthora thermophila

<400> SEQUENCE: 20
```

Met Lys Gln Tyr Leu Gln Tyr Leu Ala Ala Thr Leu Pro Leu Val Gly
-20                 -15                 -10                  -5

Leu Ala Thr Ala Gln Gln Ala Gly Asn Leu Gln Thr Glu Thr His Pro
          -1  1                   5                  10

Arg Leu Thr Trp Ser Lys Cys Thr Ala Pro Gly Ser Cys Gln Gln Val
         15                  20                  25

Asn Gly Glu Val Val Ile Asp Ser Asn Trp Arg Trp Val His Asp Glu
 30                  35                  40

Asn Ala Gln Asn Cys Tyr Asp Gly Asn Gln Trp Thr Asn Ala Cys Ser
 45                  50                  55                  60

Ser Ala Thr Asp Cys Ala Glu Asn Cys Ala Leu Glu Gly Ala Asp Tyr
                 65                  70                  75

Gln Gly Thr Tyr Gly Ala Ser Thr Ser Gly Asn Ala Leu Thr Leu Thr 80                  85                  90
Phe Val Thr Lys His Glu Tyr Gly Thr Asn Ile Gly Ser Arg Leu Tyr
                 95                 100                 105

Leu Met Asn Gly Ala Asn Lys Tyr Gln Met Phe Thr Leu Lys Gly Asn
            110                 115                 120

Glu Leu Ala Phe Asp Val Asp Leu Ser Ala Val Glu Cys Gly Leu Asn
125                 130                 135                 140

Ser Ala Leu Tyr Phe Val Ala Met Glu Glu Asp Gly Gly Val Ser Ser
                145                 150                 155

Tyr Pro Thr Asn Thr Ala Gly Ala Lys Phe Gly Thr Gly Tyr Cys Asp
            160                 165                 170

Ala Gln Cys Ala Arg Asp Leu Lys Phe Val Gly Gly Lys Gly Asn Ile
            175                 180                 185

Glu Gly Trp Lys Pro Ser Thr Asn Asp Ala Asn Ala Gly Val Gly Pro
            190                 195                 200

Tyr Gly Gly Cys Cys Ala Glu Ile Asp Val Trp Glu Ser Asn Lys Tyr
205                 210                 215                 220

Ala Phe Ala Phe Thr Pro His Gly Cys Glu Asn Pro Lys Tyr His Val
                225                 230                 235

Cys Glu Thr Thr Asn Cys Gly Gly Thr Tyr Ser Glu Asp Arg Phe Ala
            240                 245                 250

Gly Asp Cys Asp Ala Asn Gly Cys Asp Tyr Asn Pro Tyr Arg Met Gly
            255                 260                 265

Asn Gln Asp Phe Tyr Gly Pro Gly Leu Thr Val Asp Thr Ser Lys Lys
            270                 275                 280

Phe Thr Val Val Ser Gln Phe Glu Glu Asn Lys Leu Thr Gln Phe Phe
285                 290                 295                 300

Val Gln Asp Gly Lys Lys Ile Glu Ile Pro Gly Pro Lys Val Glu Gly
                305                 310                 315

Ile Asp Ala Asp Ser Ala Ala Ile Thr Pro Glu Leu Cys Ser Ala Leu
            320                 325                 330

Phe Lys Ala Phe Asp Asp Arg Asp Arg Phe Ser Glu Val Gly Gly Phe
            335                 340                 345

Asp Ala Ile Asn Thr Ala Leu Ser Thr Pro Met Val Leu Val Met Ser
350                 355                 360

Ile Trp Asp Asp His Tyr Ala Asn Met Leu Trp Leu Asp Ser Ser Tyr
365                 370                 375                 380

Pro Pro Glu Lys Ala Gly Gln Pro Gly Gly Asp Arg Gly Pro Cys Pro
                385                 390                 395

Gln Asp Ser Gly Val Pro Ala Asp Val Glu Ala Gln Tyr Pro Asn Ala
            400                 405                 410

Lys Val Ile Trp Ser Asn Ile Arg Phe Gly Pro Ile Gly Ser Thr Val
            415                 420                 425

Asn Val
    430

<210> SEQ ID NO 21
<211> LENGTH: 1590
<212> TYPE: DNA
<213> ORGANISM: Chaetomium thermophilum
<220> FEATURE:
<221> NAME/KEY: sig_peptide
<222> LOCATION: (1)..(18)
<220> FEATURE:
<221> NAME/KEY: CDS
<222> LOCATION: (1)..(1587)

<220> FEATURE:
<221> NAME/KEY: mat_peptide
<222> LOCATION: (55)..(1587)

<400> SEQUENCE: 21

| | | | | | | | | | | | | | | | | |
|---|---|---|---|---|---|---|---|---|---|---|---|---|---|---|---|---|
| atg | atg | tac | aag | aag | ttc | gcc | gct | ctc | gcc | gcc | ctc | gtg | gct | ggc | gcc | 48 |
| Met | Met | Tyr | Lys | Lys | Phe | Ala | Ala | Leu | Ala | Ala | Leu | Val | Ala | Gly | Ala | |
| | | | -15 | | | | -10 | | | | | -5 | | | | |
| gcc | gcc | cag | cag | gct | tgc | tcc | ctc | acc | act | gag | acc | cac | ccc | aga | ctc | 96 |
| Ala | Ala | Gln | Gln | Ala | Cys | Ser | Leu | Thr | Thr | Glu | Thr | His | Pro | Arg | Leu | |
| | -1 | 1 | | | 5 | | | | | 10 | | | | | | |
| act | tgg | aag | cgc | tgc | acc | tct | ggc | ggc | aac | tgc | tcg | acc | gtg | aac | ggc | 144 |
| Thr | Trp | Lys | Arg | Cys | Thr | Ser | Gly | Gly | Asn | Cys | Ser | Thr | Val | Asn | Gly | |
| 15 | | | | 20 | | | | | 25 | | | | | 30 | | |
| gcc | gtc | acc | atc | gat | gcc | aac | tgg | cgc | tgg | act | cac | acc | gtt | tcc | ggc | 192 |
| Ala | Val | Thr | Ile | Asp | Ala | Asn | Trp | Arg | Trp | Thr | His | Thr | Val | Ser | Gly | |
| | | | 35 | | | | 40 | | | | | 45 | | | | |
| tcg | acc | aac | tgc | tac | acc | ggc | aac | gag | tgg | gat | acc | tcc | atc | tgc | tct | 240 |
| Ser | Thr | Asn | Cys | Tyr | Thr | Gly | Asn | Glu | Trp | Asp | Thr | Ser | Ile | Cys | Ser | |
| | | 50 | | | | | 55 | | | | | 60 | | | | |
| gat | ggc | aag | agc | tgc | gcc | cag | acc | tgc | tgc | gtc | gac | ggc | gct | gac | tac | 288 |
| Asp | Gly | Lys | Ser | Cys | Ala | Gln | Thr | Cys | Cys | Val | Asp | Gly | Ala | Asp | Tyr | |
| | 65 | | | | | 70 | | | | | 75 | | | | | |
| tct | tcg | acc | tat | ggt | atc | acc | acc | agc | ggt | gac | tcc | ctg | aac | ctc | aag | 336 |
| Ser | Ser | Thr | Tyr | Gly | Ile | Thr | Thr | Ser | Gly | Asp | Ser | Leu | Asn | Leu | Lys | |
| 80 | | | | | 85 | | | | | 90 | | | | | | |
| ttc | gtc | acc | aag | cac | cag | tac | ggc | acc | aat | gtc | ggc | tct | cgt | gtc | tac | 384 |
| Phe | Val | Thr | Lys | His | Gln | Tyr | Gly | Thr | Asn | Val | Gly | Ser | Arg | Val | Tyr | |
| 95 | | | | 100 | | | | | 105 | | | | | 110 | | |
| ctg | atg | gag | aac | gac | acc | aag | tac | cag | atg | ttc | gag | ctc | ctc | ggc | aac | 432 |
| Leu | Met | Glu | Asn | Asp | Thr | Lys | Tyr | Gln | Met | Phe | Glu | Leu | Leu | Gly | Asn | |
| | | | | 115 | | | | | 120 | | | | | 125 | | |
| gag | ttc | acc | ttc | gat | gtc | gat | gtc | tct | aac | ctg | ggc | tgc | ggt | ctc | aac | 480 |
| Glu | Phe | Thr | Phe | Asp | Val | Asp | Val | Ser | Asn | Leu | Gly | Cys | Gly | Leu | Asn | |
| | | | 130 | | | | | 135 | | | | | 140 | | | |
| ggt | gcc | ctc | tac | ttc | gtc | tcc | atg | gac | gct | gat | ggt | ggt | atg | agc | aag | 528 |
| Gly | Ala | Leu | Tyr | Phe | Val | Ser | Met | Asp | Ala | Asp | Gly | Gly | Met | Ser | Lys | |
| | | 145 | | | | | 150 | | | | | 155 | | | | |
| tac | tct | ggc | aac | aag | gct | ggc | gcc | aag | tac | ggt | acc | ggc | tac | tgc | gat | 576 |
| Tyr | Ser | Gly | Asn | Lys | Ala | Gly | Ala | Lys | Tyr | Gly | Thr | Gly | Tyr | Cys | Asp | |
| | 160 | | | | | 165 | | | | | 170 | | | | | |
| gct | cag | tgc | ccg | cgc | gac | ctt | aag | ttc | atc | aac | ggc | gag | gcc | aac | att | 624 |
| Ala | Gln | Cys | Pro | Arg | Asp | Leu | Lys | Phe | Ile | Asn | Gly | Glu | Ala | Asn | Ile | |
| 175 | | | | | 180 | | | | | 185 | | | | | 190 | |
| gag | aac | tgg | acc | cct | tcg | acc | aat | gat | gcc | aac | gcc | ggt | ttc | ggc | cgc | 672 |
| Glu | Asn | Trp | Thr | Pro | Ser | Thr | Asn | Asp | Ala | Asn | Ala | Gly | Phe | Gly | Arg | |
| | | | | 195 | | | | | 200 | | | | | 205 | | |
| tat | ggc | agc | tgc | tgc | tct | gag | atg | gat | atc | tgg | gag | gcc | aac | aac | atg | 720 |
| Tyr | Gly | Ser | Cys | Cys | Ser | Glu | Met | Asp | Ile | Trp | Glu | Ala | Asn | Asn | Met | |
| | | 210 | | | | | 215 | | | | | 220 | | | | |
| gct | act | gcc | ttc | act | cct | cac | cct | tgc | acc | att | atc | ggc | cag | agc | cgc | 768 |
| Ala | Thr | Ala | Phe | Thr | Pro | His | Pro | Cys | Thr | Ile | Ile | Gly | Gln | Ser | Arg | |
| | 225 | | | | | 230 | | | | | 235 | | | | | |
| tgc | gag | ggc | aac | agc | tgc | ggt | ggc | acc | tac | agc | tct | gag | cgc | tat | gct | 816 |
| Cys | Glu | Gly | Asn | Ser | Cys | Gly | Gly | Thr | Tyr | Ser | Ser | Glu | Arg | Tyr | Ala | |
| 240 | | | | | 245 | | | | | 250 | | | | | | |
| ggt | gtt | tgc | gat | cct | gat | ggc | tgc | gac | ttc | aac | gcc | tac | cgc | cag | ggc | 864 |
| Gly | Val | Cys | Asp | Pro | Asp | Gly | Cys | Asp | Phe | Asn | Ala | Tyr | Arg | Gln | Gly | |
| 255 | | | | | 260 | | | | | 265 | | | | | 270 | |
| gac | aag | acc | ttc | tac | ggc | aag | ggc | atg | acc | gtc | gac | acc | acc | aag | aag | 912 |

```
                Asp Lys Thr Phe Tyr Gly Lys Gly Met Thr Val Asp Thr Thr Lys Lys
                                275                 280                 285 atg acc gtc gtc acc cag ttc cac aag aac tcg gct ggc gtc ctc agc           960
Met Thr Val Val Thr Gln Phe His Lys Asn Ser Ala Gly Val Leu Ser
            290                 295                 300 gag atc aag cgc ttc tac gtt cag gac ggc aag atc att gcc aac gcc          1008
Glu Ile Lys Arg Phe Tyr Val Gln Asp Gly Lys Ile Ile Ala Asn Ala
        305                 310                 315 gag tcc aag atc ccc ggc aac ccc ggc aac tcc atc acc cag gag tgg          1056
Glu Ser Lys Ile Pro Gly Asn Pro Gly Asn Ser Ile Thr Gln Glu Trp
    320                 325                 330 tgc gat gcc cag aag gtc gcc ttc ggt gac atc gat gac ttc aac cgc          1104
Cys Asp Ala Gln Lys Val Ala Phe Gly Asp Ile Asp Asp Phe Asn Arg
335                 340                 345                 350 aag ggc ggt atg gct cag atg agc aag gcc ctc gag ggc cct atg gtc          1152
Lys Gly Gly Met Ala Gln Met Ser Lys Ala Leu Glu Gly Pro Met Val
                355                 360                 365 ctg gtc atg tcc gtc tgg gat gac cac tac gcc aac atg ctc tgg ctc          1200
Leu Val Met Ser Val Trp Asp Asp His Tyr Ala Asn Met Leu Trp Leu
            370                 375                 380 gac tcg acc tac ccc atc gac aag gcc ggc acc ccc ggc gcc gag cgc          1248
Asp Ser Thr Tyr Pro Ile Asp Lys Ala Gly Thr Pro Gly Ala Glu Arg
        385                 390                 395 ggt gct tgc ccg acc acc tcc ggt gtc cct gcc gag att gag gcc cag          1296
Gly Ala Cys Pro Thr Thr Ser Gly Val Pro Ala Glu Ile Glu Ala Gln
    400                 405                 410 gtc ccc aac agc aac gtc atc ttc tcc aac atc cgc ttc ggc ccc atc          1344
Val Pro Asn Ser Asn Val Ile Phe Ser Asn Ile Arg Phe Gly Pro Ile
415                 420                 425                 430 ggc tcg acc gtc cct ggc ctc gac ggc agc act ccc agc aac ccg acc          1392
Gly Ser Thr Val Pro Gly Leu Asp Gly Ser Thr Pro Ser Asn Pro Thr
                435                 440                 445 gcc acc gtt gct cct ccc act tct acc acc agc gtg aga agc agc act          1440
Ala Thr Val Ala Pro Pro Thr Ser Thr Thr Ser Val Arg Ser Ser Thr
            450                 455                 460 act cag att tcc acc ccg act agc cag ccc ggc ggc tgc acc acc cag          1488
Thr Gln Ile Ser Thr Pro Thr Ser Gln Pro Gly Gly Cys Thr Thr Gln
        465                 470                 475 aag tgg ggc cag tgc ggt ggt atc ggc tac acc ggc tgc act aac tgc          1536
Lys Trp Gly Gln Cys Gly Gly Ile Gly Tyr Thr Gly Cys Thr Asn Cys
    480                 485                 490 gtt gct ggc act acc tgc act gag ctc aac ccc tgg tac agc cag tgc          1584
Val Ala Gly Thr Thr Cys Thr Glu Leu Asn Pro Trp Tyr Ser Gln Cys
495                 500                 505                 510 ctg taa                                                                    1590
Leu <210> SEQ ID NO 22
<211> LENGTH: 529
<212> TYPE: PRT
<213> ORGANISM: Chaetomium thermophilum

<400> SEQUENCE: 22

Met Met Tyr Lys Lys Phe Ala Ala Leu Ala Ala Leu Val Ala Gly Ala
                -15                 -10                 -5

Ala Ala Gln Gln Ala Cys Ser Leu Thr Thr Glu Thr His Pro Arg Leu
    -1  1                   5                  10

Thr Trp Lys Arg Cys Thr Ser Gly Gly Asn Cys Ser Thr Val Asn Gly
15                  20                  25                  30
```

-continued

Ala Val Thr Ile Asp Ala Asn Trp Arg Trp Thr His Thr Val Ser Gly
                35                  40                  45
Ser Thr Asn Cys Tyr Thr Gly Asn Glu Trp Asp Thr Ser Ile Cys Ser
            50                  55                  60
Asp Gly Lys Ser Cys Ala Gln Thr Cys Cys Val Asp Gly Ala Asp Tyr
        65                  70                  75
Ser Ser Thr Tyr Gly Ile Thr Thr Ser Gly Asp Ser Leu Asn Leu Lys
    80                  85                  90
Phe Val Thr Lys His Gln Tyr Gly Thr Asn Val Gly Ser Arg Val Tyr
95                  100                 105                 110
Leu Met Glu Asn Asp Thr Lys Tyr Gln Met Phe Glu Leu Leu Gly Asn
                115                 120                 125
Glu Phe Thr Phe Asp Val Asp Val Ser Asn Leu Gly Cys Gly Leu Asn
                130                 135                 140
Gly Ala Leu Tyr Phe Val Ser Met Asp Ala Asp Gly Gly Met Ser Lys
            145                 150                 155
Tyr Ser Gly Asn Lys Ala Gly Ala Lys Tyr Gly Thr Gly Tyr Cys Asp
        160                 165                 170
Ala Gln Cys Pro Arg Asp Leu Lys Phe Ile Asn Gly Glu Ala Asn Ile
175                 180                 185                 190
Glu Asn Trp Thr Pro Ser Thr Asn Asp Ala Asn Ala Gly Phe Gly Arg
                195                 200                 205
Tyr Gly Ser Cys Cys Ser Glu Met Asp Ile Trp Glu Ala Asn Asn Met
            210                 215                 220
Ala Thr Ala Phe Thr Pro His Pro Cys Thr Ile Ile Gly Gln Ser Arg
        225                 230                 235
Cys Glu Gly Asn Ser Cys Gly Gly Thr Tyr Ser Ser Glu Arg Tyr Ala
240                 245                 250
Gly Val Cys Asp Pro Asp Gly Cys Asp Phe Asn Ala Tyr Arg Gln Gly
255                 260                 265                 270
Asp Lys Thr Phe Tyr Gly Lys Gly Met Thr Val Asp Thr Lys Lys
                275                 280                 285
Met Thr Val Val Thr Gln Phe His Lys Asn Ser Ala Gly Val Leu Ser
                290                 295                 300
Glu Ile Lys Arg Phe Tyr Val Gln Asp Gly Lys Ile Ile Ala Asn Ala
    305                 310                 315
Glu Ser Lys Ile Pro Gly Asn Pro Gly Asn Ser Ile Thr Gln Glu Trp
        320                 325                 330
Cys Asp Ala Gln Lys Val Ala Phe Gly Asp Ile Asp Asp Phe Asn Arg
335                 340                 345                 350
Lys Gly Gly Met Ala Gln Met Ser Lys Ala Leu Glu Gly Pro Met Val
                355                 360                 365
Leu Val Met Ser Val Trp Asp Asp His Tyr Ala Asn Met Leu Trp Leu
                370                 375                 380
Asp Ser Thr Tyr Pro Ile Asp Lys Ala Gly Thr Pro Gly Ala Glu Arg
                385                 390                 395
Gly Ala Cys Pro Thr Thr Ser Gly Val Pro Ala Glu Ile Glu Ala Gln
            400                 405                 410
Val Pro Asn Ser Asn Val Ile Phe Ser Asn Ile Arg Phe Gly Pro Ile
415                 420                 425                 430
Gly Ser Thr Val Pro Gly Leu Asp Gly Ser Thr Pro Ser Asn Pro Thr
            435                 440                 445
Ala Thr Val Ala Pro Pro Thr Ser Thr Thr Ser Val Arg Ser Ser Thr

```
                    450             455             460
Thr Gln Ile Ser Thr Pro Thr Ser Gln Pro Gly Gly Cys Thr Thr Gln
        465                 470                 475

Lys Trp Gly Gln Cys Gly Gly Ile Gly Tyr Thr Gly Cys Thr Asn Cys
        480                 485                 490

Val Ala Gly Thr Thr Cys Thr Glu Leu Asn Pro Trp Tyr Ser Gln Cys
495                 500                 505                 510

Leu
```

<210> SEQ ID NO 23
<211> LENGTH: 30
<212> TYPE: DNA
<213> ORGANISM: Artificial Sequence
<220> FEATURE:
<223> OTHER INFORMATION: ARTIFICIAL DNA PRIMER

<400> SEQUENCE: 23
gggaaccctc gtcggccaac gccaacaccg                              30

<210> SEQ ID NO 24
<211> LENGTH: 30
<212> TYPE: DNA
<213> ORGANISM: Artificial Sequence
<220> FEATURE:
<223> OTHER INFORMATION: ARTIFICIAL DNA PRIMER

<400> SEQUENCE: 24
cggtgttggc gttggccgac gagggttccc                              30

<210> SEQ ID NO 25
<211> LENGTH: 32
<212> TYPE: DNA
<213> ORGANISM: Artificial Sequence
<220> FEATURE:
<223> OTHER INFORMATION: ARTIFICIAL DNA PRIMER

<400> SEQUENCE: 25
tcgtcggcca acgccgccac cggcattgga gg                           32

<210> SEQ ID NO 26
<211> LENGTH: 32
<212> TYPE: DNA
<213> ORGANISM: Artificial Sequence
<220> FEATURE:
<223> OTHER INFORMATION: ARTIFICIAL DNA PRIMER

<400> SEQUENCE: 26
cctccaatgc cggtggcggc gttggccgac ga                           32

<210> SEQ ID NO 27
<211> LENGTH: 18
<212> TYPE: DNA
<213> ORGANISM: Artificial Sequence
<220> FEATURE:
<223> OTHER INFORMATION: ARTIFICIAL DNA PRIMER

<400> SEQUENCE: 27
cgttgtaaaa cgacggcc                                           18

<210> SEQ ID NO 28
<211> LENGTH: 18
<212> TYPE: DNA
<213> ORGANISM: Artificial Sequence
<220> FEATURE:

<223> OTHER INFORMATION: ARTIFICIAL DNA PRIMER

<400> SEQUENCE: 28
tgttaatgca gctggcac                                                    18

<210> SEQ ID NO 29
<211> LENGTH: 18
<212> TYPE: DNA
<213> ORGANISM: Artificial Sequence
<220> FEATURE:
<223> OTHER INFORMATION: ARTIFICIAL DNA PRIMER

<400> SEQUENCE: 29
cttgtcggag aacgacga                                                    18

<210> SEQ ID NO 30
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 30
cccttgtcga tgcgatgtat c                                                21

<210> SEQ ID NO 31
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 31
atcctcaatt ccgtcggtcg a                                                21

<210> SEQ ID NO 32
<211> LENGTH: 1713
<212> TYPE: DNA
<213> ORGANISM: Aspergillus fumigatus

<400> SEQUENCE: 32
atgaagcacc ttgcatcttc catcgcattg actctactgt tgcctgccgt gcaggcccag      60
cagaccgtat ggggccaatg tatgttctgg ctgtcactgg aataagactg tatcaactgc     120
tgatatgctt ctaggtggcg gccaaggctg gtctggcccg acgagctgtg ttgccggcgc     180
agcctgtagc acactgaatc cctgtatgtt agatatcgtc ctgagtggag acttatactg     240
acttccttag actacgctca gtgtatcccg ggagccaccg cgacgtccac caccctcacg     300
acgacgacgg cggcgacgac gacatcccag accaccacca aacctaccac gactggtcca     360
actacatccg cacccaccgt gaccgcatcc ggtaacccct tcagcggcta ccagctgtat     420
gccaaccccc tactactcctc cgaggtccat actctggcca tgccttctct gcccagctcg     480
ctgcagccca aggctagtgc tgttgctgaa gtgccctcat ttgtttggct gtaagtggcc     540
ttatcccaat actgagacca actctctgac agtcgtagcg acgttgccgc caaggtgccc     600
actatgggaa cctacctggc cgacattcag gccaagaaca aggccggcgc caaccctcct     660
atcgctggta tcttcgtggt ctacgacttg ccggaccgtg actgcgccgc tctggccagt     720
aatggcgagt actcaattgc caacaacggt gtggccaact acaaggcgta cattgacgcc     780
atccgtgctc agctggtgaa gtactctgac gttcacacca tcctcgtcat cggtaggccc     840
tacacctccg ttgcgcgccg ccttctctg acatcttgca gaacccgaca gcttggccaa     900

```
cctggtgacc aacctcaacg tcgccaaatg cgccaatgcg cagagcgcct acctggagtg    960
tgtcgactat gctctgaagc agctcaacct gcccaacgtc gccatgtacc tcgacgcagg   1020
tatgcctcac ttcccgcatt ctgtatccct tccagacact aactcatcag gccatgcggg   1080
ctggctcgga tggcccgcca acttgggccc gccgcaaca ctcttcgcca agtctacac    1140
cgacgcgggt tccccgcgg ctgttcgtgg cctggccacc aacgtcgcca actacaacgc    1200
ctggtcgctc agtacctgcc cctcctacac ccagggagac cccaactgcg acgagaagaa   1260
gtacatcaac gccatggcgc tcttctcaa ggaagccggc ttcgatgccc acttcatcat    1320
ggatacctgt aagtgcttat ccaatcgcc gatgtgtgcc gactaatcaa tgtttcagcc    1380
cggaatggcg tccagcccac gaagcaaaac gcctggggtg actggtgcaa cgtcatcggc   1440
accggcttcg gtgttcgccc ctcgactaac accggcgatc cgctccagga tgcctttgtg   1500
tggatcaagc ccggtggaga gagtgatggc acgtccaact cgacttcccc ccggtatgac   1560
gcgcactgcg gatatagtga tgctctgcag cctgctcctg aggctggtac ttggttccag   1620
gtatgtcatc cattagccag atgagggata agtgactgac ggacctaggc ctactttgag   1680
cagcttctga ccaacgctaa cccgtccttt taa                                1713

<210> SEQ ID NO 33
<211> LENGTH: 454
<212> TYPE: PRT
<213> ORGANISM: Aspergillus fumigatus

<400> SEQUENCE: 33

Met Lys His Leu Ala Ser Ser Ile Ala Leu Thr Leu Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220
```

```
Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
        435                 440                 445

Asn Ala Asn Pro Ser Phe
        450

<210> SEQ ID NO 34
<211> LENGTH: 1849
<212> TYPE: DNA
<213> ORGANISM: Trichoderma reesei

<400> SEQUENCE: 34
tgccatttct gacctggata ggttttccta tggtcattcc tataagagac acgctctttc      60
gtcggcccgt agatatcaga ttggtattca gtcgcacaga cgaaggtgag ttgatcctcc     120
aacatgagtt ctatgagccc ccccttgcc ccccccgtt caccttgacc tgcaatgaga     180
atcccacctt ttacaagagc atcaagaagt attaatggcg ctgaatagcc tctgctcgat     240
aatatctccc cgtcatcgac aatgaacaag tccgtggctc cattgctgct tgcagcgtcc     300
atactatatg gcggcgccgt cgcacagcag actgtctggg ccagtgtgg aggtattggt     360
tggagcggac ctacgaattg tgctcctggc tcagcttgtt cgaccctcaa tccttattat     420
gcgcaatgta ttccgggagc cactactatc accacttcga cccggccacc atccggtcca     480
accaccacca ccagggctac ctcaacaagc tcatcaactc cacccacgag ctctggggtc     540
cgatttgccg gcgttaacat cgcgggtttt gactttggct gtaccacaga gtgagtaccc     600
ttgtttcctg gtgttgctgg ctggttgggc gggtatacag cgaagcggac gcaagaacac     660
cgccggtccg ccaccatcaa gatgtgggtg gtaagcggcg gtgttttgta caactacctg     720
acagctcact caggaaatga gaattaatgg aagtcttgtt acagtggcac ttgcgttacc     780
```

```
tcgaaggttt atcctccgtt gaagaacttc accggctcaa acaactaccc cgatggcatc      840
ggccagatgc agcacttcgt caacgaggac gggatgacta ttttccgctt acctgtcgga      900
tggcagtacc tcgtcaacaa caatttgggc ggcaatcttg attccacgag catttccaag      960
tatgatcagc ttgttcaggg gtgcctgtct ctgggcgcat actgcatcgt cgacatccac     1020
aattatgctc gatggaacgg tgggatcatt ggtcagggcg ccctactaa tgctcaattc      1080 acgagccttt ggtcgcagtt ggcatcaaag tacgcatctc agtcgagggt gtggttcggc     1140
atcatgaatg agccccacga cgtgaacatc aacacctggg ctgccacggt ccaagaggtt     1200
gtaaccgcaa tccgcaacgc tggtgctacg tcgcaattca tctctttgcc tggaaatgat     1260
tggcaatctg ctggggcttt catatccgat ggcagtgcag ccgccctgtc tcaagtcacg     1320
aacccggatg ggtcaacaac gaatctgatt tttgacgtgc acaaatactt ggactcagac     1380
aactccggta ctcacgccga atgtactaca aataacattg acggcgcctt ttctccgctt     1440
gccacttggc tccgacagaa caatcgccag gctatcctga cagaaaccgg tggtggcaac     1500
gttcagtcct gcatacaaga catgtgccag caaatccaat atctcaacca gaactcagat     1560
gtctatcttg gctatgttgg ttggggtgcc ggatcatttg atagcacgta tgtcctgacg     1620
gaaacaccga ctggcagtgg taactcatgg acggacacat ccttggtcag ctcgtgtctc     1680
gcaagaaagt agcactctga gctgaatgca gaagcctcgc caacgtttgt atctcgctat     1740
caaacatagt agctactcta tgaggctgtc tgttctcgat ttcagcttta tatagtttca     1800
tcaaacagta catattccct ctgtggccac gcaaaaaaaa aaaaaaaa                  1849

<210> SEQ ID NO 35
<211> LENGTH: 418
<212> TYPE: PRT
<213> ORGANISM: Trichoderma reesei

<400> SEQUENCE: 35

Met Asn Lys Ser Val Ala Pro Leu Leu Ala Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190
```

Asp Ile His Asn Tyr Ala Arg Trp Asn Gly Gly Ile Ile Gly Gln Gly
            195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys

<210> SEQ ID NO 36
<211> LENGTH: 835
<212> TYPE: DNA
<213> ORGANISM: Penicillium emersonii

<400> SEQUENCE: 36
atgctgtctt cgacgactcg caccctcgcc tttacaggcc ttgcgggcct tctgtccgct      60
cccctggtca aggcccatgg ctttgtccag ggcattgtca tcggtgacca attgtaagtc     120
cctctcttgc agttctgtcg attaactgct ggactgcttg cttgactccc tgctgactcc     180
caacagctac agcgggtaca tcgtcaactc gttcccctac gaatccaacc cacccccgt      240 catcggctgg ccacgaccg ccaccgacct gggcttcgtc gacggcacag gataccaagg     300
cccggacatc atctgccacc ggaatgcgac gcccgcgccg ctgacagccc ccgtggccgc     360
cggcggcacc gtcgagctgc agtggacgcc gtggccggac agccaccacg gacccgtcat     420
cacctacctg gcgccgtgca acggcaactg ctcgaccgtc gacaagacga cgctggagtt     480
cttcaagatc gaccagcagg gcctgatcga cgacacgagc ccgccgggca cctgggcgtc     540
ggacaacctc atcgccaaca acaatagctg gaccgtcacc attcccaaca gcgtcgcccc     600
cggcaactac gtcctgcgcc acgagatcat cgccctgcac tcggccaaca acaaggacgg     660
cgcccagaac tacccccagt gcatcaacat cgaggtcacg gcggcggct ccgacgcgcc      720 tgagggtact ctgggcgagg atctctacca tgacaccgac ccgggcattc tggtcgacat     780
ttacgagccc attgcgacgt ataccattcc ggggccgcct gagccgacgt tctag    835

<210> SEQ ID NO 37
<211> LENGTH: 253
<212> TYPE: PRT
<213> ORGANISM: Penicillium emersonii

<400> SEQUENCE: 37

```
Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250
```

<210> SEQ ID NO 38
<211> LENGTH: 1415
<212> TYPE: DNA
<213> ORGANISM: Aspergillus fumigatus

<400> SEQUENCE: 38
atggtccatc tatcttcatt ggcagcagcc ctggctgctc tgcctctgta tgtttaccca    60
ctcacgagag gaggaacagc tttgacattg ctatagtgta tatggagctg gcctgaacac   120
agcagccaaa gccaaaggac taaagtactt tggttccgcc acggacaatc cagagctcac   180
ggactctgcg tatgtcgcgc aactgagcaa caccgatgat tttggtcaaa tcacacccgg   240
aaactccatg aaggttttgct tacgtctgcc tccctggagc attgcctcaa aagctaattg   300
gttgttttgt ttggatagtg ggatgccacc gagccttctc agaattcttt ttcgttcgca   360
aatggagacg ccgtggtcaa tctggcgaac aagaatggcc agctgatgcg atgccatact   420

```
ctggtctggc acagtcagct accgaactgg ggtatgtaaa cgtcttgtct attctcaaat      480
actctctaac agttgacagt ctctagcggg tcatggacca atgcgaccct tttggcggcc      540
atgaagaatc atatcaccaa tgtggttact cactacaagg ggaagtgcta cgcctgggat      600
gttgtcaatg aaggtttgtt gctccatcta tcctcaatag ttcttttgaa actgacaagc      660
ctgtcaatct agccctgaac gaggacggta cttccgtaa ctctgtcttc taccagatca       720
tcggcccagc atacattcct attgcgttcg ccacggctgc tgccgcagat ccgacgtga       780 aactctacta caacgactac aacattgaat actcaggcgc aaagcgact gctgcgcaga       840 atatcgtcaa gatgatcaag gcctacgcg cgaagatcga cggcgtcggc ctccaggcac        900
actttatcgt cggcagcact ccgagtcaat cggatctgac gaccgtcttg aagggctaca      960
ctgctctcgg cgttgaggtg gcctatacccg aacttgacat ccgcatgcag ctgccctcga     1020
ccgccgcaaa gctggcccag cagtccactg acttccaagg cgtggccgca gcatgcgtta    1080
gcaccactgg ctgcgtgggt gtcactatct gggactggac cgacaagtac tcctgggtcc    1140
ccagcgtgtt ccaaggctac ggcgccccat tgccttggga tgagaactat gtgaagaagc    1200
cagcgtacga tggcctgatg gcgggtcttg gagcaagcgg ctccggcacc acaacgacca    1260
ctactactac ttctactacg acaggaggta cggaccctac tggagtcgct cagaaatggg    1320
gacagtgtgg cggtattggc tggaccgggc caacaacttg tgtcagtggt accacttgcc    1380
aaaagctgaa tgactggtac tcacagtgcc tgtaa                                1415
```

<210> SEQ ID NO 39
<211> LENGTH: 397
<212> TYPE: PRT
<213> ORGANISM: Aspergillus fumigatus
<400> SEQUENCE: 39

```
Met Val His Leu Ser Ser Leu Ala Ala Ala Leu Ala Ala Leu Pro Leu
1               5                   10                  15

Val Tyr Gly Ala Gly Leu Asn Thr Ala Ala Lys Ala Lys Gly Leu Lys
                20                  25                  30

Tyr Phe Gly Ser Ala Thr Asp Asn Pro Glu Leu Thr Asp Ser Ala Tyr
            35                  40                  45

Val Ala Gln Leu Ser Asn Thr Asp Asp Phe Gly Gln Ile Thr Pro Gly
        50                  55                  60

Asn Ser Met Lys Trp Asp Ala Thr Glu Pro Ser Gln Asn Ser Phe Ser
65                  70                  75                  80

Phe Ala Asn Gly Asp Ala Val Val Asn Leu Ala Asn Lys Asn Gly Gln
                85                  90                  95

Leu Met Arg Cys His Thr Leu Val Trp His Ser Gln Leu Pro Asn Trp
            100                 105                 110

Val Ser Ser Gly Ser Trp Thr Asn Ala Thr Leu Leu Ala Ala Met Lys
        115                 120                 125

Asn His Ile Thr Asn Val Val Thr His Tyr Lys Gly Lys Cys Tyr Ala
    130                 135                 140

Trp Asp Val Val Asn Glu Ala Leu Asn Glu Asp Gly Thr Phe Arg Asn
145                 150                 155                 160

Ser Val Phe Tyr Gln Ile Ile Gly Pro Ala Tyr Ile Pro Ile Ala Phe
                165                 170                 175

Ala Thr Ala Ala Ala Asp Pro Asp Val Lys Leu Tyr Tyr Asn Asp
            180                 185                 190
```

```
Tyr Asn Ile Glu Tyr Ser Gly Ala Lys Ala Thr Ala Ala Gln Asn Ile
            195                 200                 205

Val Lys Met Ile Lys Ala Tyr Gly Ala Lys Ile Asp Gly Val Gly Leu
    210                 215                 220

Gln Ala His Phe Ile Val Gly Ser Thr Pro Ser Gln Ser Asp Leu Thr
225                 230                 235                 240

Thr Val Leu Lys Gly Tyr Thr Ala Leu Gly Val Glu Val Ala Tyr Thr
                245                 250                 255

Glu Leu Asp Ile Arg Met Gln Leu Pro Ser Thr Ala Ala Lys Leu Ala
            260                 265                 270

Gln Gln Ser Thr Asp Phe Gln Gly Val Ala Ala Cys Val Ser Thr
            275                 280                 285

Thr Gly Cys Val Gly Val Thr Ile Trp Asp Trp Thr Asp Lys Tyr Ser
    290                 295                 300

Trp Val Pro Ser Val Phe Gln Gly Tyr Gly Ala Pro Leu Pro Trp Asp
305                 310                 315                 320

Glu Asn Tyr Val Lys Lys Pro Ala Tyr Asp Gly Leu Met Ala Gly Leu
                325                 330                 335

Gly Ala Ser Gly Ser Gly Thr Thr Thr Thr Thr Thr Thr Thr Ser Thr
            340                 345                 350

Thr Thr Gly Gly Thr Asp Pro Thr Gly Val Ala Gln Lys Trp Gly Gln
            355                 360                 365

Cys Gly Gly Ile Gly Trp Thr Gly Pro Thr Thr Cys Val Ser Gly Thr
    370                 375                 380

Thr Cys Gln Lys Leu Asn Asp Trp Tyr Ser Gln Cys Leu
385                 390                 395

<210> SEQ ID NO 40
<211> LENGTH: 3060
<212> TYPE: DNA
<213> ORGANISM: Aspergillus fumigatus

<400> SEQUENCE: 40
atgagattcg gttggctcga ggtggccgct ctgacggccg cttctgtagc caatgcccag      60
gtttgtgatg cttccccgtc attgtttcgg atatagttga caatagtcat ggaaataatc    120
aggaattggc tttctctcca ccattctacc cttcgccttg ggctgatggc cagggagagt    180
gggcagatgc ccatcgacgc gccgtcgaga tcgtttctca gatgacactg gcggagaagg    240
ttaaccttac aacgggtact gggtgggttg cgactttttt gttgacagtg agctttcttc    300
actgaccatc tacacagatg ggaaatggac cgatgcgtcg gtcaaaccgg cagcgttccc    360
aggtaagctt gcaattctgc aacaacgtgc aagtgtagtt gctaaaacgc ggtggtgcag    420
acttggtatc aactggggtc tttgtggcca ggattcccct ttgggtatcc gtgactgtga    480 gctataccg cggagtcttt cagtccttgt attatgtgct gatgattgtc tctgtatagc    540
tgacctcaac tccgccttcc ctgctggtac taatgtcgcc gcgacatggg acaagacact    600
cgcctacctt cgtggcaagg ccatgggtga ggaattcaac gacaagggcg tggacatttt    660 gctgggcct gctgctggtc ctctcggcaa atacccggac ggcggcagaa tctgggaagg    720
cttctctcct gatccggttc tcactggtgt acttttcgcc gaaactatca agggtatcca    780
agacgcgggt gtgattgcta ctgccaagca ttacattctg aatgaacagg agcatttccg    840
acaggttggc gaggcccagg atatggttta acatcacg gagacgatca gctccaacgt    900
ggatgacaag accatgcacg agttgtacct tggtgagta gttgacactg caaatgagga    960
```

```
ccttgattga tttgactgac ctggaatgca ggcccttttgc agatgctgtg cgcggtaaga    1020
ttttccgtag acttgacctc gcgacgaaga aatcgctgac gaaccatcgt agctggcgtt    1080
ggcgctgtca tgtgttccta caatcaaatc aacaacagct acggttgtca aaacagtcaa    1140
actctcaaca agctcctcaa ggctgagctg ggcttccaag gcttcgtcat gagtgactgg    1200
ggcgctcacc acagcggtgt cggcgctgcc ctcgctgggt tggatatgtc gatgcctgga    1260
gacatttcct tcgacgacgg actctccttc tggggcacga acctaactgt cagtgttctt    1320
aacggcaccg ttccagcctg gcgtgtcgat gacatggctg ttcgtatcat gaccgcgtac    1380
tacaaggttg gtcgtgaccg tcttcgtatt ccccctaact tcagctcctg gacccgggat    1440
gagtacggct gggagcattc tgctgtctcc gagggagcct ggaccaaggt gaacgacttc    1500
gtcaatgtgc agcgcagtca ctctcagatc atccgtgaga ttggtgccgc tagtacagtg    1560
ctcttgaaga acacgggtgc tcttcctttg accggcaagg aggttaaagt gggtgttctc    1620
ggtgaagacg ctggttccaa cccgtggggt gctaacggct gccccgaccg cggctgtgat    1680
aacggcactc ttgctatggc ctggggtagt ggtactgccg agttcccctta ccttgtcacc    1740 cccgagcagg ctatccagcg agaggtcatc agcaacggcg gcaatgtctt tgctgtgact    1800
gataacgggg ctctcagcca gatggcagat gttgcatctc aatccaggtg agtgcgggct    1860
cttagaaaaa gaacgttctc tgaatgaagt ttttttaacca ttgcgaacag cgtgtctttg    1920
gtgtttgtca acgccgactc tggagagggt tacatcagtg tcgacggcaa cgagggtgac    1980
cgcaaaaatc tcactctgtg gaagaacggc gaggccgtca ttgacactgt tgtcagccac    2040
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
aatgagaccc ccatttatga gtttggccat ggcttgagct acaccacctt tggttactct    2400
caccttcggg ttcaggccct caatagttcg agttcggcat atgtcccgac tagcggagag    2460
accaagcctg cgccaaccta tggtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaacccct cctgaaggct ggcggcgctc ctggtggtaa ccctacccctt    2700 tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc ctctgccccg tgtctactag    3060
```

<210> SEQ ID NO 41
<211> LENGTH: 844
<212> TYPE: PRT
<213> ORGANISM: Aspergillus fumigatus

<400> SEQUENCE: 41

Gln Glu Leu Ala Phe Ser Pro Pro Phe Tyr Pro Ser Pro Trp Ala Asp

```
1               5                    10                   15
Gly Gln Gly Glu Trp Ala Asp Ala His Arg Arg Ala Val Glu Ile Val
            20                   25                   30
Ser Gln Met Thr Leu Ala Glu Lys Val Asn Leu Thr Thr Gly Thr Gly
            35                   40                   45
Trp Glu Met Asp Arg Cys Val Gly Gln Thr Gly Ser Val Pro Arg Leu
            50                   55                   60
Gly Ile Asn Trp Gly Leu Cys Gly Gln Asp Ser Pro Leu Gly Ile Arg
65                   70                   75                   80
Asp Ser Asp Leu Asn Ser Ala Phe Pro Ala Gly Thr Asn Val Ala Ala
                85                   90                   95
Thr Trp Asp Lys Thr Leu Ala Tyr Leu Arg Gly Lys Ala Met Gly Glu
                100                  105                  110
Glu Phe Asn Asp Lys Gly Val Asp Ile Leu Leu Gly Pro Ala Ala Gly
                115                  120                  125
Pro Leu Gly Lys Tyr Pro Asp Gly Gly Arg Ile Trp Glu Gly Phe Ser
130                  135                  140
Pro Asp Pro Val Leu Thr Gly Val Leu Phe Ala Glu Thr Ile Lys Gly
145                  150                  155                  160
Ile Gln Asp Ala Gly Val Ile Ala Thr Ala Lys His Tyr Ile Leu Asn
                165                  170                  175
Glu Gln Glu His Phe Arg Gln Val Gly Glu Ala Gln Gly Tyr Gly Tyr
                180                  185                  190
Asn Ile Thr Glu Thr Ile Ser Ser Asn Val Asp Asp Lys Thr Met His
                195                  200                  205
Glu Leu Tyr Leu Trp Pro Phe Ala Asp Ala Val Arg Ala Gly Val Gly
                210                  215                  220
Ala Val Met Cys Ser Tyr Asn Gln Ile Asn Asn Ser Tyr Gly Cys Gln
225                  230                  235                  240
Asn Ser Gln Thr Leu Asn Lys Leu Leu Lys Ala Glu Leu Gly Phe Gln
                245                  250                  255
Gly Phe Val Met Ser Asp Trp Gly Ala His His Ser Gly Val Gly Ala
                260                  265                  270
Ala Leu Ala Gly Leu Asp Met Ser Met Pro Gly Asp Ile Ser Phe Asp
                275                  280                  285
Asp Gly Leu Ser Phe Trp Gly Thr Asn Leu Thr Val Ser Val Leu Asn
                290                  295                  300
Gly Thr Val Pro Ala Trp Arg Val Asp Asp Met Ala Val Arg Ile Met
305                  310                  315                  320
Thr Ala Tyr Tyr Lys Val Gly Arg Asp Arg Leu Arg Ile Pro Pro Asn
                325                  330                  335
Phe Ser Ser Trp Thr Arg Asp Glu Tyr Gly Trp Glu His Ser Ala Val
                340                  345                  350
Ser Glu Gly Ala Trp Thr Lys Val Asn Asp Phe Val Asn Val Gln Arg
                355                  360                  365
Ser His Ser Gln Ile Ile Arg Glu Ile Gly Ala Ala Ser Thr Val Leu
                370                  375                  380
Leu Lys Asn Thr Gly Ala Leu Pro Leu Thr Gly Lys Glu Val Lys Val
385                  390                  395                  400
Gly Val Leu Gly Glu Asp Ala Gly Ser Asn Pro Trp Gly Ala Asn Gly
                405                  410                  415
Cys Pro Asp Arg Gly Cys Asp Asn Gly Thr Leu Ala Met Ala Trp Gly
                420                  425                  430
```

```
Ser Gly Thr Ala Glu Phe Pro Tyr Leu Val Thr Pro Glu Gln Ala Ile
        435                 440                 445

Gln Arg Glu Val Ile Ser Asn Gly Asn Val Phe Ala Val Thr Asp
        450                 455                 460

Asn Gly Ala Leu Ser Gln Met Ala Asp Val Ala Ser Gln Ser Ser Val
465                 470                 475                 480

Ser Leu Val Phe Val Asn Ala Asp Ser Gly Glu Gly Tyr Ile Ser Val
                485                 490                 495

Asp Gly Asn Glu Gly Asp Arg Lys Asn Leu Thr Leu Trp Lys Asn Gly
                500                 505                 510

Glu Ala Val Ile Asp Thr Val Val Ser His Cys Asn Asn Thr Ile Val
                515                 520                 525

Val Ile His Ser Val Gly Pro Val Leu Ile Asp Arg Trp Tyr Asp Asn
                530                 535                 540

Pro Asn Val Thr Ala Ile Ile Trp Ala Gly Leu Pro Gly Gln Glu Ser
545                 550                 555                 560

Gly Asn Ser Leu Val Asp Val Leu Tyr Gly Arg Val Asn Pro Ser Ala
                565                 570                 575

Lys Thr Pro Phe Thr Trp Gly Lys Thr Arg Glu Ser Tyr Gly Ala Pro
                580                 585                 590

Leu Leu Thr Glu Pro Asn Asn Gly Asn Gly Ala Pro Gln Asp Asp Phe
                595                 600                 605

Asn Glu Gly Val Phe Ile Asp Tyr Arg His Phe Asp Lys Arg Asn Glu
                610                 615                 620

Thr Pro Ile Tyr Glu Phe Gly His Gly Leu Ser Tyr Thr Thr Phe Gly
625                 630                 635                 640

Tyr Ser His Leu Arg Val Gln Ala Leu Asn Ser Ser Ser Ala Tyr
                645                 650                 655

Val Pro Thr Ser Gly Glu Thr Lys Pro Ala Pro Thr Tyr Gly Glu Ile
                660                 665                 670

Gly Ser Ala Ala Asp Tyr Leu Tyr Pro Glu Gly Leu Lys Arg Ile Thr
                675                 680                 685

Lys Phe Ile Tyr Pro Trp Leu Asn Ser Thr Asp Leu Glu Asp Ser Ser
                690                 695                 700

Asp Asp Pro Asn Tyr Gly Trp Glu Asp Ser Glu Tyr Ile Pro Glu Gly
705                 710                 715                 720

Ala Arg Asp Gly Ser Pro Gln Pro Leu Leu Lys Ala Gly Gly Ala Pro
                725                 730                 735

Gly Gly Asn Pro Thr Leu Tyr Gln Asp Leu Val Arg Val Ser Ala Thr
                740                 745                 750

Ile Thr Asn Thr Gly Asn Val Ala Gly Tyr Glu Val Pro Gln Leu Tyr
                755                 760                 765

Val Ser Leu Gly Gly Pro Asn Glu Pro Arg Val Leu Arg Lys Phe
        770                 775                 780

Asp Arg Ile Phe Leu Ala Pro Gly Glu Gln Lys Val Trp Thr Thr Thr
785                 790                 795                 800

Leu Asn Arg Arg Asp Leu Ala Asn Trp Asp Val Glu Ala Gln Asp Trp
                805                 810                 815

Val Ile Thr Lys Tyr Pro Lys Lys Val His Val Gly Ser Ser Ser Arg
                820                 825                 830

Lys Leu Pro Leu Arg Ala Pro Leu Pro Arg Val Tyr
                835                 840
```

<210> SEQ ID NO 42
<211> LENGTH: 2388
<212> TYPE: DNA
<213> ORGANISM: Talaromyces emersonii

<400> SEQUENCE: 42

| | | | | | |
|---|---|---|---|---|---|
| atgatgactc | ccacggcgat | tctcaccgca | gtggcggcgc | tcctgcccac | cgcgacatgg | 60 |
| gcacaggata | accaaaccta | tgccaattac | tcgtcgcagt | ctcagccgga | cctgtttccc | 120 |
| cggaccgtcg | cgaccatcga | cctgtccttc | cccgactgtg | agaatggccc | gctcagcacg | 180 |
| aacctggtgt | gcaacaaatc | ggccgatccc | tgggcccgag | ctgaggccct | catctcgctc | 240 |
| tttaccctcg | aagagctgat | taacaacacc | cagaacaccg | ctcctggcgt | gccccgtttg | 300 |
| ggtctgcccc | agtatcaggt | gtggaatgaa | gctctgcacg | gactggaccg | cgccaatttc | 360 |
| tcccattcgg | gcgaatacag | ctgggccacg | tccttcccca | tgccatcct | gtcgatggcg | 420 |
| tccttcaacc | ggaccctcat | caaccagatt | gcctccatca | ttgcaacgca | agcccgtgcc | 480 |
| ttcaacaacg | ccggccgtta | cggccttgac | agctatgcgc | caacatcaa | tggcttccgc | 540 |
| agtcccctct | ggggccgtgg | acaggagacg | cctggtgagg | atgcgttctt | cttgagttcc | 600 |
| acctatgcgt | acgagtacat | cacaggcctg | cagggcggtg | tcgacccaga | gcatgtcaag | 660 |
| atcgtcgcga | cggcgaagca | cttcgccggc | tatgatctgg | agaactgggg | caacgtctct | 720 |
| cggctggggt | tcaatgctat | catcacgcag | caggatctct | ccgagtacta | cacccctcag | 780 |
| ttcctggcgt | ctgctcgata | cgccaagacg | cgcagcatca | tgtgctccta | caatgcagtg | 840 |
| aatggagtcc | caagctgtgc | caactccttc | ttcctccaga | cgcttctccg | agaaaacttt | 900 |
| gacttcgttg | acgacgggta | cgtctcgtcg | gattgcgacg | ccgtctacaa | cgtcttcaac | 960 |
| ccacacggtt | acgcccttaa | ccagtcggga | gccgctgcgg | actcgctcct | agcaggtacc | 1020 |
| gatatcgact | gtggtcagac | cttgccgtgg | cacctgaatg | agtccttcgt | agaaggatac | 1080 |
| gtctcccgcg | gtgatatcga | gaatccctc | accgtctct | actcaaacct | ggtgcgtctc | 1140 |
| ggctactttg | acggcaacaa | cagcgagtac | cgcaacctca | actggaacga | cgtcgtgact | 1200 |
| acggacgcct | ggaacatctc | gtacgaggcc | gcggtggaag | gtatcaccct | gctcaagaac | 1260 |
| gacggaacgc | tgccgctgtc | caagaaggtc | cgcagcattg | cgctcatcgg | tccttgggcc | 1320 |
| aatgccacgg | tgcagatgca | gggtaactac | tatggaacgc | caccgtatct | gatcagtccg | 1380 |
| ctggaagccg | ccaaggccag | tgggttcacg | gtcaactatg | cattcggtac | caacatctcg | 1440 |
| accgattcta | cccagtggtt | cgcggaagcc | atcgcggcgg | cgaagaagtc | ggacgtgatc | 1500 |
| atctacgccg | gtggtattga | caacacgatc | gaggcagagg | acaggaccg | cacggatctc | 1560 |
| aagtggccgg | ggaaccagct | ggatctgatc | gagcagctca | gccaggtggg | caagcccttg | 1620 |
| gtcgtcctgc | agatgggcgg | tggccaggtg | gattcgtcgt | cactcaaggc | aacaagaat | 1680 |
| gtcaacgctc | tggtgtgggg | tggctatccc | ggacagtcgg | gtggtgcggc | cctgtttgac | 1740 |
| atccttacgg | gcaagcgtgc | gccggccggt | cgtctggtga | gcacgcagta | cccggccgag | 1800 |
| tatgcgacgc | agttcccggc | caacgacatg | aacctgcgtc | cgaacggcag | caacccggga | 1860 |
| cagacataca | tctggtacac | gggcacgccc | gtgtatgagt | tcggccacgg | tctgttctac | 1920 |
| acggagttcc | aggagtcggc | tgcggcgggc | acgaacaaga | cgtcgacttt | cgacattctg | 1980 |
| gaccttttct | ccacccctca | tccgggatac | gagtacatcg | agcaggttcc | gttcatcaac | 2040 |
| gtgactgtgg | acgtgaagaa | cgtcggccac | acgccatcgc | cgtacacggg | tctgttgttc | 2100 |
| gcgaacacga | cagccgggcc | caagccgtac | ccgaacaaat | ggctcgtcgg | gttcgactgg | 2160 |

```
ctgccgacga tccagccggg cgagactgcc aagttgacga tcccggtgcc gttgggcgcg    2220
attgcgtggg cggacgagaa cggcaacaag gtggtcttcc cgggcaacta cgaattggca    2280
ctgaacaatg agcgatcggt agtggtgtcg ttcacgctga cgggcgatgc ggcgactcta    2340
gagaaatggc ctttgtggga gcaggcggtt ccggggcgtgc tgcagcaa              2388
```

<210> SEQ ID NO 43
<211> LENGTH: 796
<212> TYPE: PRT
<213> ORGANISM: Talaromyces emersonii

<400> SEQUENCE: 43

```
Met Met Thr Pro Thr Ala Ile Leu Thr Ala Val Ala Ala Leu Leu Pro
1               5                   10                  15

Thr Ala Thr Trp Ala Gln Asp Asn Gln Thr Tyr Ala Asn Tyr Ser Ser
            20                  25                  30

Gln Ser Gln Pro Asp Leu Phe Pro Arg Thr Val Ala Thr Ile Asp Leu
        35                  40                  45

Ser Phe Pro Asp Cys Glu Asn Gly Pro Leu Ser Thr Asn Leu Val Cys
    50                  55                  60

Asn Lys Ser Ala Asp Pro Trp Ala Arg Ala Glu Ala Leu Ile Ser Leu
65                  70                  75                  80

Phe Thr Leu Glu Glu Leu Ile Asn Asn Thr Gln Asn Thr Ala Pro Gly
                85                  90                  95

Val Pro Arg Leu Gly Leu Pro Gln Tyr Gln Val Trp Asn Glu Ala Leu
            100                 105                 110

His Gly Leu Asp Arg Ala Asn Phe Ser His Ser Gly Glu Tyr Ser Trp
        115                 120                 125

Ala Thr Ser Phe Pro Met Pro Ile Leu Ser Met Ala Ser Phe Asn Arg
    130                 135                 140

Thr Leu Ile Asn Gln Ile Ala Ser Ile Ile Ala Thr Gln Ala Arg Ala
145                 150                 155                 160

Phe Asn Asn Ala Gly Arg Tyr Gly Leu Asp Ser Tyr Ala Pro Asn Ile
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Thr Tyr Ala Tyr Gly Tyr Ile Thr
        195                 200                 205

Gly Leu Gln Gly Gly Val Asp Pro Glu His Val Lys Ile Val Ala Thr
    210                 215                 220

Ala Lys His Phe Ala Gly Tyr Asp Leu Glu Asn Trp Gly Asn Val Ser
225                 230                 235                 240

Arg Leu Gly Phe Asn Ala Ile Ile Thr Gln Gln Asp Leu Ser Glu Tyr
                245                 250                 255

Tyr Thr Pro Gln Phe Leu Ala Ser Ala Arg Tyr Ala Lys Thr Arg Ser
            260                 265                 270

Ile Met Cys Ser Tyr Asn Ala Val Asn Gly Val Pro Ser Cys Ala Asn
        275                 280                 285

Ser Phe Phe Leu Gln Thr Leu Leu Arg Glu Asn Phe Asp Phe Val Asp
    290                 295                 300

Asp Gly Tyr Val Ser Ser Asp Cys Asp Ala Val Tyr Asn Val Phe Asn
305                 310                 315                 320

Pro His Gly Tyr Ala Leu Asn Gln Ser Gly Ala Ala Ala Asp Ser Leu
                325                 330                 335
```

```
Leu Ala Gly Thr Asp Ile Asp Cys Gly Gln Thr Leu Pro Trp His Leu
            340                 345                 350

Asn Glu Ser Phe Val Glu Gly Tyr Val Ser Arg Gly Asp Ile Glu Lys
            355                 360                 365

Ser Leu Thr Arg Leu Tyr Ser Asn Leu Val Arg Leu Gly Tyr Phe Asp
370                 375                 380

Gly Asn Ser Glu Tyr Arg Asn Leu Asn Trp Asn Asp Val Val Thr
385                 390                 395                 400

Thr Asp Ala Trp Asn Ile Ser Tyr Glu Ala Val Glu Gly Ile Thr
                405                 410                 415

Leu Leu Lys Asn Asp Gly Thr Leu Pro Leu Ser Lys Lys Val Arg Ser
            420                 425                 430

Ile Ala Leu Ile Gly Pro Trp Ala Asn Ala Thr Val Gln Met Gln Gly
            435                 440                 445

Asn Tyr Tyr Gly Thr Pro Pro Tyr Leu Ile Ser Pro Leu Glu Ala Ala
            450                 455                 460

Lys Ala Ser Gly Phe Thr Val Asn Tyr Ala Phe Gly Thr Asn Ile Ser
465                 470                 475                 480

Thr Asp Ser Thr Gln Trp Phe Ala Glu Ala Ile Ala Ala Lys Lys
                485                 490                 495

Ser Asp Val Ile Ile Tyr Ala Gly Gly Ile Asp Asn Thr Ile Glu Ala
            500                 505                 510

Glu Gly Gln Asp Arg Thr Asp Leu Lys Trp Pro Gly Asn Gln Leu Asp
            515                 520                 525

Leu Ile Glu Gln Leu Ser Gln Val Gly Lys Pro Leu Val Val Leu Gln
            530                 535                 540

Met Gly Gly Gly Gln Val Asp Ser Ser Ser Leu Lys Ala Asn Lys Asn
545                 550                 555                 560

Val Asn Ala Leu Val Trp Gly Gly Tyr Pro Gly Gln Ser Gly Gly Ala
                565                 570                 575

Ala Leu Phe Asp Ile Leu Thr Gly Lys Arg Ala Pro Ala Gly Arg Leu
            580                 585                 590

Val Ser Thr Gln Tyr Pro Ala Glu Tyr Ala Thr Gln Phe Pro Ala Asn
            595                 600                 605

Asp Met Asn Leu Arg Pro Asn Gly Ser Asn Pro Gly Gln Thr Tyr Ile
            610                 615                 620

Trp Tyr Thr Gly Thr Pro Val Tyr Glu Phe Gly His Gly Leu Phe Tyr
625                 630                 635                 640

Thr Glu Phe Gln Glu Ser Ala Ala Ala Gly Thr Asn Lys Thr Ser Thr
                645                 650                 655

Phe Asp Ile Leu Asp Leu Phe Ser Thr Pro His Pro Gly Tyr Glu Tyr
            660                 665                 670

Ile Glu Gln Val Pro Phe Ile Asn Val Thr Val Asp Val Lys Asn Val
            675                 680                 685

Gly His Thr Pro Ser Pro Tyr Thr Gly Leu Leu Phe Ala Asn Thr Thr
            690                 695                 700

Ala Gly Pro Lys Pro Tyr Pro Asn Lys Trp Leu Val Gly Phe Asp Trp
705                 710                 715                 720

Leu Pro Thr Ile Gln Pro Gly Glu Thr Ala Lys Leu Thr Ile Pro Val
                725                 730                 735

Pro Leu Gly Ala Ile Ala Trp Ala Asp Glu Asn Gly Asn Lys Val Val
            740                 745                 750
```

-continued

```
              Phe Pro Gly Asn Tyr Glu Leu Ala Leu Asn Asn Glu Arg Ser Val Val
                      755                 760                 765

Val Ser Phe Thr Leu Thr Gly Asp Ala Ala Thr Leu Glu Lys Trp Pro
                  770                 775                 780

Leu Trp Glu Gln Ala Val Pro Gly Val Leu Gln Gln
              785                 790                 795

<210> SEQ ID NO 44
<211> LENGTH: 1545
<212> TYPE: DNA
<213> ORGANISM: Trichoderma reesei
<220> FEATURE:
<221> NAME/KEY: sig_peptide
<222> LOCATION: (1)..(51)
<220> FEATURE:
<221> NAME/KEY: CDS
<222> LOCATION: (1)..(1542)
<220> FEATURE:
<221> NAME/KEY: mat_peptide
<222> LOCATION: (52)..(1542)

<400> SEQUENCE: 44 atg tat cgt aag ctc gca gtc atc tcc gcg ttc ctc gca aca gca cga      48
Met Tyr Arg Lys Leu Ala Val Ile Ser Ala Phe Leu Ala Thr Ala Arg
        -15                 -10                  -5 gcg cag tcc gcc tgt acc ttg cag tcg gaa aca cat cct ccc ctc act      96
Ala Gln Ser Ala Cys Thr Leu Gln Ser Glu Thr His Pro Pro Leu Thr
 -1   1                  5                  10                  15 tgg cag aaa tgt tcg tcc gga gga acg tgt acg cag cag act ggc tcg     144
Trp Gln Lys Cys Ser Ser Gly Gly Thr Cys Thr Gln Gln Thr Gly Ser
                 20                  25                  30 gtg gtc atc gac gcc aac tgg agg tgg acg cat gca acc aac tcc tcc     192
Val Val Ile Asp Ala Asn Trp Arg Trp Thr His Ala Thr Asn Ser Ser
             35                  40                  45 acc aac tgt tac gat ggc aac act tgg tcc tcc acc ttg tgt ccc gat     240
Thr Asn Cys Tyr Asp Gly Asn Thr Trp Ser Ser Thr Leu Cys Pro Asp
         50                  55                  60 aac gaa acc tgt gcc aag aac tgt tgt ttg gat ggt gca gcc tac gcc     288
Asn Glu Thr Cys Ala Lys Asn Cys Cys Leu Asp Gly Ala Ala Tyr Ala
     65                  70                  75 tcg aca tac gga gtc act act tcc ggc aac tcg ctc tcg atc ggc ttc     336
Ser Thr Tyr Gly Val Thr Thr Ser Gly Asn Ser Leu Ser Ile Gly Phe
 80                  85                  90                  95 gtg act cag tcc gca cag aaa aac gtc gga gcg cga ctc tac ttg atg     384
Val Thr Gln Ser Ala Gln Lys Asn Val Gly Ala Arg Leu Tyr Leu Met
                 100                 105                 110 gca tcc gat aca acc tac cag gaa ttc act ctc ttg ggc aac gag ttc     432
Ala Ser Asp Thr Thr Tyr Gln Glu Phe Thr Leu Leu Gly Asn Glu Phe
             115                 120                 125 tcc ttc gac gtc gac gtc tcc cag ctc cct tgt ggc ctc aac gga gca     480
Ser Phe Asp Val Asp Val Ser Gln Leu Pro Cys Gly Leu Asn Gly Ala
         130                 135                 140 ctc tac ttc gtg tcg atg gac gcg gat gga ggt gtc tcc aag tac ccg     528
Leu Tyr Phe Val Ser Met Asp Ala Asp Gly Gly Val Ser Lys Tyr Pro
     145                 150                 155 acc aac aca gca gga gcg aaa tac ggc acg ggt tac tgt gac tcg cag     576
Thr Asn Thr Ala Gly Ala Lys Tyr Gly Thr Gly Tyr Cys Asp Ser Gln
160                 165                 170                 175 tgt cct cgc gat ctc aag ttc atc aac ggc cag gca aac gtc gaa ggc     624
Cys Pro Arg Asp Leu Lys Phe Ile Asn Gly Gln Ala Asn Val Glu Gly
                 180                 185                 190 tgg gaa ccc tcg tcg aac gca gcc aac acc ggc att gga ggc cat ggc     672
Trp Glu Pro Ser Ser Asn Ala Ala Asn Thr Gly Ile Gly Gly His Gly
```

```
                Trp Glu Pro Ser Ser Asn Ala Ala Asn Thr Gly Ile Gly Gly His Gly
                            195                 200                 205 tcc tgt tgt tcg gaa atg gat atc tgg gag gcc aac tcg atc tcc gag        720
Ser Cys Cys Ser Glu Met Asp Ile Trp Glu Ala Asn Ser Ile Ser Glu
            210                 215                 220 gca ctc aca ccc cac ccc tgt aca acc gtc ggc cag gag att tgt gaa        768
Ala Leu Thr Pro His Pro Cys Thr Thr Val Gly Gln Glu Ile Cys Glu
225                 230                 235 gga gac ggc tgt ggc gga act tac tcc gat aac cgt tac ggt ggt acc        816
Gly Asp Gly Cys Gly Gly Thr Tyr Ser Asp Asn Arg Tyr Gly Gly Thr
240                 245                 250                 255 tgt gat ccc gat ggc tgt gac tgg aac ccc tac cgc ctc ggt aac aca        864
Cys Asp Pro Asp Gly Cys Asp Trp Asn Pro Tyr Arg Leu Gly Asn Thr
                260                 265                 270 tcg ttc tac ggt ccg ggt tcc tcc ttc acc ctc gac act acc aaa aag        912
Ser Phe Tyr Gly Pro Gly Ser Ser Phe Thr Leu Asp Thr Thr Lys Lys
            275                 280                 285 ttg acg gtg gtc acg cag ttc gag act tcc gga gcc atc aac cgg tac        960
Leu Thr Val Val Thr Gln Phe Glu Thr Ser Gly Ala Ile Asn Arg Tyr
        290                 295                 300 tac gtg cag aac gga gtc aca ttc cag cag ccc aac gca gaa ctc ggc       1008
Tyr Val Gln Asn Gly Val Thr Phe Gln Gln Pro Asn Ala Glu Leu Gly
305                 310                 315 tcg tac tcg gga aac gag ctc aac gat gat tac tgt aca gcg gaa gag       1056
Ser Tyr Ser Gly Asn Glu Leu Asn Asp Asp Tyr Cys Thr Ala Glu Glu
320                 325                 330                 335 gca gaa ttc gga gga tcg tcg ttc tcc gac aag ggt ggt ttg acc cag       1104
Ala Glu Phe Gly Gly Ser Ser Phe Ser Asp Lys Gly Gly Leu Thr Gln
                340                 345                 350 ttc aag aag gcc aca tcg gga gga atg gtg ttg gtc atg tcc ttg tgg       1152
Phe Lys Lys Ala Thr Ser Gly Gly Met Val Leu Val Met Ser Leu Trp
            355                 360                 365 gac gac tac tat gcc aac atg ctc tgg ctc gac tcc acc tac ccc acc       1200
Asp Asp Tyr Tyr Ala Asn Met Leu Trp Leu Asp Ser Thr Tyr Pro Thr
        370                 375                 380 aac gag acc tcc tcg aca cct ggc gca gtg agg ggc tcg tgt tcc act       1248
Asn Glu Thr Ser Ser Thr Pro Gly Ala Val Arg Gly Ser Cys Ser Thr
385                 390                 395 tcg tcg gga gtg cct gca cag gtg gag tcc cag tcg ccg aac gcc aag       1296
Ser Ser Gly Val Pro Ala Gln Val Glu Ser Gln Ser Pro Asn Ala Lys
400                 405                 410                 415 gtc act ttc tcc aac att aag ttc gga ccc atc ggt tcg acc ggc aac       1344
Val Thr Phe Ser Asn Ile Lys Phe Gly Pro Ile Gly Ser Thr Gly Asn
                420                 425                 430 ccc tcc ggt gga aac cct cct ggc gga aac cct cct ggc aca act aca       1392
Pro Ser Gly Gly Asn Pro Pro Gly Gly Asn Pro Pro Gly Thr Thr Thr
            435                 440                 445 aca cga cgg cct gcg act aca acg ggt tcg tcc cct gga ccg acc cag       1440
Thr Arg Arg Pro Ala Thr Thr Thr Gly Ser Ser Pro Gly Pro Thr Gln
        450                 455                 460 tcc cac tac gga cag tgt gga ggc atc ggt tat tcc ggt ccg acc gtc       1488
Ser His Tyr Gly Gln Cys Gly Gly Ile Gly Tyr Ser Gly Pro Thr Val
465                 470                 475 tgt gcg tcc ggc aca acc tgt cag gtc ttg aac cct tac tat tcg cag       1536
Cys Ala Ser Gly Thr Thr Cys Gln Val Leu Asn Pro Tyr Tyr Ser Gln
480                 485                 490                 495 tgt ctc taa                                                            1545
Cys Leu
```

<210> SEQ ID NO 45
<211> LENGTH: 514
<212> TYPE: PRT
<213> ORGANISM: Trichoderma reesei

<400> SEQUENCE: 45

```
Met Tyr Arg Lys Leu Ala Val Ile Ser Ala Phe Leu Ala Thr Ala Arg
    -15                 -10                  -5

Ala Gln Ser Ala Cys Thr Leu Gln Ser Glu Thr His Pro Pro Leu Thr
 -1   1               5                  10                  15

Trp Gln Lys Cys Ser Ser Gly Gly Thr Cys Thr Gln Gln Thr Gly Ser
             20                  25                  30

Val Val Ile Asp Ala Asn Trp Arg Trp Thr His Ala Thr Asn Ser Ser
             35                  40                  45

Thr Asn Cys Tyr Asp Gly Asn Thr Trp Ser Ser Thr Leu Cys Pro Asp
             50                  55                  60

Asn Glu Thr Cys Ala Lys Asn Cys Cys Leu Asp Gly Ala Ala Tyr Ala
             65                  70                  75

Ser Thr Tyr Gly Val Thr Thr Ser Gly Asn Ser Leu Ser Ile Gly Phe
 80                  85                  90                  95

Val Thr Gln Ser Ala Gln Lys Asn Val Gly Ala Arg Leu Tyr Leu Met
                100                 105                 110

Ala Ser Asp Thr Thr Tyr Gln Glu Phe Thr Leu Leu Gly Asn Glu Phe
                115                 120                 125

Ser Phe Asp Val Asp Val Ser Gln Leu Pro Cys Gly Leu Asn Gly Ala
                130                 135                 140

Leu Tyr Phe Val Ser Met Asp Ala Asp Gly Gly Val Ser Lys Tyr Pro
145                 150                 155

Thr Asn Thr Ala Gly Ala Lys Tyr Gly Thr Gly Tyr Cys Asp Ser Gln
160                 165                 170                 175

Cys Pro Arg Asp Leu Lys Phe Ile Asn Gly Gln Ala Asn Val Glu Gly
                180                 185                 190

Trp Glu Pro Ser Ser Asn Ala Ala Asn Thr Gly Ile Gly Gly His Gly
                195                 200                 205

Ser Cys Cys Ser Glu Met Asp Ile Trp Glu Ala Asn Ser Ile Ser Glu
                210                 215                 220

Ala Leu Thr Pro His Pro Cys Thr Thr Val Gly Gln Glu Ile Cys Glu
225                 230                 235

Gly Asp Gly Cys Gly Gly Thr Tyr Ser Asp Asn Arg Tyr Gly Gly Thr
240                 245                 250                 255

Cys Asp Pro Asp Gly Cys Asp Trp Asn Pro Tyr Arg Leu Gly Asn Thr
                260                 265                 270

Ser Phe Tyr Gly Pro Gly Ser Ser Phe Thr Leu Asp Thr Thr Lys Lys
                275                 280                 285

Leu Thr Val Val Thr Gln Phe Glu Thr Ser Gly Ala Ile Asn Arg Tyr
                290                 295                 300

Tyr Val Gln Asn Gly Val Thr Phe Gln Gln Pro Asn Ala Glu Leu Gly
                305                 310                 315

Ser Tyr Ser Gly Asn Glu Leu Asn Asp Asp Tyr Cys Thr Ala Glu Glu
320                 325                 330                 335

Ala Glu Phe Gly Gly Ser Ser Phe Ser Asp Lys Gly Gly Leu Thr Gln
                340                 345                 350

Phe Lys Lys Ala Thr Ser Gly Gly Met Val Leu Val Met Ser Leu Trp
                355                 360                 365
```

```
Asp Asp Tyr Tyr Ala Asn Met Leu Trp Leu Asp Ser Thr Tyr Pro Thr
            370                 375                 380

Asn Glu Thr Ser Ser Thr Pro Gly Ala Val Arg Gly Ser Cys Ser Thr
    385                 390                 395

Ser Ser Gly Val Pro Ala Gln Val Glu Ser Gln Ser Pro Asn Ala Lys
400                 405                 410                 415

Val Thr Phe Ser Asn Ile Lys Phe Gly Pro Ile Gly Ser Thr Gly Asn
                420                 425                 430

Pro Ser Gly Gly Asn Pro Pro Gly Gly Asn Pro Pro Gly Thr Thr Thr
            435                 440                 445

Thr Arg Arg Pro Ala Thr Thr Thr Gly Ser Ser Pro Gly Pro Thr Gln
            450                 455                 460

Ser His Tyr Gly Gln Cys Gly Gly Ile Gly Tyr Ser Gly Pro Thr Val
            465                 470                 475

Cys Ala Ser Gly Thr Thr Cys Gln Val Leu Asn Pro Tyr Tyr Ser Gln
480                 485                 490                 495

Cys Leu

<210> SEQ ID NO 46
<211> LENGTH: 1542
<212> TYPE: DNA
<213> ORGANISM: Trichoderma reesei
<220> FEATURE:
<221> NAME/KEY: sig_peptide
<222> LOCATION: (1)..(51)
<220> FEATURE:
<221> NAME/KEY: CDS
<222> LOCATION: (1)..(1539)
<220> FEATURE:
<221> NAME/KEY: mat_peptide
<222> LOCATION: (52)..(1539)

<400> SEQUENCE: 46 atg tat cgt aag ctc gca gtc atc tcc gcg ttc ctc gca aca gca cga     48
Met Tyr Arg Lys Leu Ala Val Ile Ser Ala Phe Leu Ala Thr Ala Arg
        -15                 -10                  -5 gcg cag tcc gcc tgt acc ttg cag tcg gaa aca cat cct ccc ctc act     96
Ala Gln Ser Ala Cys Thr Leu Gln Ser Glu Thr His Pro Pro Leu Thr
 -1   1               5                  10                  15 tgg cag aaa tgt tcg tcc gga gga acg tgt acg cag cag act ggc tcg    144
Trp Gln Lys Cys Ser Ser Gly Gly Thr Cys Thr Gln Gln Thr Gly Ser
             20                  25                  30 gtg gtc atc gac gcc aac tgg agg tgg acg cat gca acc aac tcc tcc    192
Val Val Ile Asp Ala Asn Trp Arg Trp Thr His Ala Thr Asn Ser Ser
         35                  40                  45 acc aac tgt tac gat ggc aac act tgg tcc tcc acc ttg tgt ccc gat    240
Thr Asn Cys Tyr Asp Gly Asn Thr Trp Ser Ser Thr Leu Cys Pro Asp
     50                  55                  60 aac gaa acc tgt gcc aag aac tgt tgt ttg gat ggt gca gcc tac gcc    288
Asn Glu Thr Cys Ala Lys Asn Cys Cys Leu Asp Gly Ala Ala Tyr Ala
 65                  70                  75 tcg aca tac gga gtc act act tcc ggc aac tcg ctc tcg atc ggc ttc    336
Ser Thr Tyr Gly Val Thr Thr Ser Gly Asn Ser Leu Ser Ile Gly Phe
 80                  85                  90                  95 gtg act cag tcc gca cag aaa aac gtc gga gcg cga ctc tac ttg atg    384
Val Thr Gln Ser Ala Gln Lys Asn Val Gly Ala Arg Leu Tyr Leu Met
                100                 105                 110 gca tcc gat aca acc tac cag gaa ttc act ctc ttg ggc aac gag ttc    432
Ala Ser Asp Thr Thr Tyr Gln Glu Phe Thr Leu Leu Gly Asn Glu Phe
            115                 120                 125
```

```
tcc ttc gac gtc gac gtc tcc cag ctc cct tgt ggc ctc aac gga gca     480
Ser Phe Asp Val Asp Val Ser Gln Leu Pro Cys Gly Leu Asn Gly Ala
    130             135             140 ctc tac ttc gtg tcg atg gac gcg gat gga ggt gtc tcc aag tac ccg     528
Leu Tyr Phe Val Ser Met Asp Ala Asp Gly Gly Val Ser Lys Tyr Pro
145             150             155 acc aac aca gca gga gcg aaa tac ggc acg ggt tac tgt gac tcg cag     576
Thr Asn Thr Ala Gly Ala Lys Tyr Gly Thr Gly Tyr Cys Asp Ser Gln
160             165             170             175 tgt cct cgc gat ctc aag ttc atc aac ggc cag gca aac gtc gaa ggc     624
Cys Pro Arg Asp Leu Lys Phe Ile Asn Gly Gln Ala Asn Val Glu Gly
        180             185             190 tgg gaa ccc tcg tcg aac aac aac acc ggc att gga ggc cat ggc tcc     672
Trp Glu Pro Ser Ser Asn Asn Asn Thr Gly Ile Gly Gly His Gly Ser
        195             200             205 tgt tgt tcg gaa atg gat atc tgg gag gcc aac tcg atc tcg gag gca     720
Cys Cys Ser Glu Met Asp Ile Trp Glu Ala Asn Ser Ile Ser Glu Ala
210             215             220 ctc aca ccc cac ccc tgt aca acc gtc ggc cag gag att tgt gaa gga     768
Leu Thr Pro His Pro Cys Thr Thr Val Gly Gln Glu Ile Cys Glu Gly
    225             230             235 gac ggc tgt ggc gga act tac tcc gat aac cgt tac ggt ggt acc tgt     816
Asp Gly Cys Gly Gly Thr Tyr Ser Asp Asn Arg Tyr Gly Gly Thr Cys
240             245             250             255 gat ccc gat ggc tgt gac tgg aac ccc tac cgc ctc ggt aac aca tcg     864
Asp Pro Asp Gly Cys Asp Trp Asn Pro Tyr Arg Leu Gly Asn Thr Ser
        260             265             270 ttc tac ggt ccg ggt tcc tcc ttc acc ctc gac act acc aaa aag ttg     912
Phe Tyr Gly Pro Gly Ser Ser Phe Thr Leu Asp Thr Thr Lys Lys Leu
        275             280             285 acg gtg gtc acg cag ttc gag act tcc gga gcc atc aac cgg tac tac     960
Thr Val Val Thr Gln Phe Glu Thr Ser Gly Ala Ile Asn Arg Tyr Tyr
            290             295             300 gtg cag aac gga gtc aca ttc cag cag ccc aac gca gaa ctc ggc tcg    1008
Val Gln Asn Gly Val Thr Phe Gln Gln Pro Asn Ala Glu Leu Gly Ser
305             310             315 tac tcg gga aac gag ctc aac gat gat tac tgt aca gcg gaa gag gca    1056
Tyr Ser Gly Asn Glu Leu Asn Asp Asp Tyr Cys Thr Ala Glu Glu Ala
320             325             330             335 gaa ttc gga gga tcg tcg ttc tcc gac aag ggt ggt ttg acc cag ttc    1104
Glu Phe Gly Gly Ser Ser Phe Ser Asp Lys Gly Gly Leu Thr Gln Phe
        340             345             350 aag aag gcc aca tcg gga gga atg gtg ttg gtc atg tcc ttg tgg gac    1152
Lys Lys Ala Thr Ser Gly Gly Met Val Leu Val Met Ser Leu Trp Asp
            355             360             365 gac tac tat gcc aac atg ctc tgg ctc gac tcc acc tac ccc acc aac    1200
Asp Tyr Tyr Ala Asn Met Leu Trp Leu Asp Ser Thr Tyr Pro Thr Asn
        370             375             380 gag acc tcc tcg aca cct ggc gca gtg agg ggc tcg tgt tcc act tcg    1248
Glu Thr Ser Ser Thr Pro Gly Ala Val Arg Gly Ser Cys Ser Thr Ser
385             390             395 tcg gga gtg cct gca cag gtg gag tcc cag tcg ccg aac gcc aag gtc    1296
Ser Gly Val Pro Ala Gln Val Glu Ser Gln Ser Pro Asn Ala Lys Val
400             405             410             415 act ttc tcc aac att aag ttc gga ccc atc ggt tcg acc ggc aac ccc    1344
Thr Phe Ser Asn Ile Lys Phe Gly Pro Ile Gly Ser Thr Gly Asn Pro
            420             425             430 tcc ggt gga aac cct cct ggc gga aac cct cct ggc aca act aca aca    1392
Ser Gly Gly Asn Pro Pro Gly Gly Asn Pro Pro Gly Thr Thr Thr Thr
            435             440             445
```

```
cga cgg cct gcg act aca acg ggt tcg tcc cct gga ccg acc cag tcc      1440
Arg Arg Pro Ala Thr Thr Thr Gly Ser Ser Pro Gly Pro Thr Gln Ser
        450                 455                 460 cac tac gga cag tgt gga ggc atc ggt tat tcc ggt ccg acc gtc tgt      1488
His Tyr Gly Gln Cys Gly Gly Ile Gly Tyr Ser Gly Pro Thr Val Cys
465                 470                 475 gcg tcc ggc aca acc tgt cag gtc ttg aac cct tac tat tcg cag tgt      1536
Ala Ser Gly Thr Thr Cys Gln Val Leu Asn Pro Tyr Tyr Ser Gln Cys
480                 485                 490                 495 ctc taa                                                               1542
Leu

<210> SEQ ID NO 47
<211> LENGTH: 513
<212> TYPE: PRT
<213> ORGANISM: Trichoderma reesei

<400> SEQUENCE: 47

Met Tyr Arg Lys Leu Ala Val Ile Ser Ala Phe Leu Ala Thr Ala Arg
         -15                 -10                  -5

Ala Gln Ser Ala Cys Thr Leu Gln Ser Glu Thr His Pro Pro Leu Thr
 -1   1               5                  10                  15

Trp Gln Lys Cys Ser Ser Gly Gly Thr Cys Thr Gln Thr Gly Ser
                 20                  25                  30

Val Val Ile Asp Ala Asn Trp Arg Trp Thr His Ala Thr Asn Ser Ser
             35                  40                  45

Thr Asn Cys Tyr Asp Gly Asn Thr Trp Ser Ser Thr Leu Cys Pro Asp
         50                  55                  60

Asn Glu Thr Cys Ala Lys Asn Cys Cys Leu Asp Gly Ala Ala Tyr Ala
 65                  70                  75

Ser Thr Tyr Gly Val Thr Thr Ser Gly Asn Ser Leu Ser Ile Gly Phe
 80                  85                  90                  95

Val Thr Gln Ser Ala Gln Lys Asn Val Gly Ala Arg Leu Tyr Leu Met
                100                 105                 110

Ala Ser Asp Thr Thr Tyr Gln Glu Phe Thr Leu Leu Gly Asn Glu Phe
            115                 120                 125

Ser Phe Asp Val Asp Val Ser Gln Leu Pro Cys Gly Leu Asn Gly Ala
        130                 135                 140

Leu Tyr Phe Val Ser Met Asp Ala Asp Gly Gly Val Ser Lys Tyr Pro
145                 150                 155

Thr Asn Thr Ala Gly Ala Lys Tyr Gly Thr Gly Tyr Cys Asp Ser Gln
160                 165                 170                 175

Cys Pro Arg Asp Leu Lys Phe Ile Asn Gly Gln Ala Asn Val Glu Gly
                180                 185                 190

Trp Glu Pro Ser Ser Asn Asn Thr Gly Ile Gly Gly His Gly Ser
            195                 200                 205

Cys Cys Ser Glu Met Asp Ile Trp Glu Ala Asn Ser Ile Ser Glu Ala
        210                 215                 220

Leu Thr Pro His Pro Cys Thr Thr Val Gly Gln Glu Ile Cys Glu Gly
225                 230                 235

Asp Gly Cys Gly Gly Thr Tyr Ser Asp Asn Arg Tyr Gly Gly Thr Cys
240                 245                 250                 255

Asp Pro Asp Gly Cys Asp Trp Asn Pro Tyr Arg Leu Gly Asn Thr Ser
                260                 265                 270

Phe Tyr Gly Pro Gly Ser Ser Phe Thr Leu Asp Thr Thr Lys Lys Leu
```

```
                    275                 280                 285
Thr Val Val Thr Gln Phe Glu Thr Ser Gly Ala Ile Asn Arg Tyr Tyr
            290                 295                 300

Val Gln Asn Gly Val Thr Phe Gln Gln Pro Asn Ala Glu Leu Gly Ser
            305                 310                 315

Tyr Ser Gly Asn Glu Leu Asn Asp Asp Tyr Cys Thr Ala Glu Glu Ala
320                 325                 330                 335

Glu Phe Gly Gly Ser Ser Phe Ser Asp Lys Gly Gly Leu Thr Gln Phe
                340                 345                 350

Lys Lys Ala Thr Ser Gly Gly Met Val Leu Val Met Ser Leu Trp Asp
                355                 360                 365

Asp Tyr Tyr Ala Asn Met Leu Trp Leu Asp Ser Thr Tyr Pro Thr Asn
                370                 375                 380

Glu Thr Ser Ser Thr Pro Gly Ala Val Arg Gly Ser Cys Ser Thr Ser
            385                 390                 395

Ser Gly Val Pro Ala Gln Val Glu Ser Gln Ser Pro Asn Ala Lys Val
400                 405                 410                 415

Thr Phe Ser Asn Ile Lys Phe Gly Pro Ile Gly Ser Thr Gly Asn Pro
                420                 425                 430

Ser Gly Gly Asn Pro Pro Gly Gly Asn Pro Pro Gly Thr Thr Thr Thr
                435                 440                 445

Arg Arg Pro Ala Thr Thr Thr Gly Ser Ser Pro Gly Pro Thr Gln Ser
            450                 455                 460

His Tyr Gly Gln Cys Gly Gly Ile Gly Tyr Ser Gly Pro Thr Val Cys
            465                 470                 475

Ala Ser Gly Thr Thr Cys Gln Val Leu Asn Pro Tyr Tyr Ser Gln Cys
480                 485                 490                 495

Leu

<210> SEQ ID NO 48
<211> LENGTH: 1545
<212> TYPE: DNA
<213> ORGANISM: Trichoderma reesei
<220> FEATURE:
<221> NAME/KEY: sig_peptide
<222> LOCATION: (1)..(51)
<220> FEATURE:
<221> NAME/KEY: CDS
<222> LOCATION: (1)..(1542)
<220> FEATURE:
<221> NAME/KEY: mat_peptide
<222> LOCATION: (52)..(1542)

<400> SEQUENCE: 48 atg tat cgt aag ctc gca gtc atc tcc gcg ttc ctc gca aca gca cga     48
Met Tyr Arg Lys Leu Ala Val Ile Ser Ala Phe Leu Ala Thr Ala Arg
        -15                 -10                  -5 gcg cag tcc gcc tgt acc ttg cag tcg gaa aca cat cct ccc ctc act     96
Ala Gln Ser Ala Cys Thr Leu Gln Ser Glu Thr His Pro Pro Leu Thr
 -1   1               5                  10                  15 tgg cag aaa tgt tcg tcc gga gga acg tgt acg cag cag act ggc tcg    144
Trp Gln Lys Cys Ser Ser Gly Gly Thr Cys Thr Gln Gln Thr Gly Ser
                    20                  25                  30 gtg gtc atc gac gcc aac tgg agg tgg acg cat gca acc aac tcc tcc    192
Val Val Ile Asp Ala Asn Trp Arg Trp Thr His Ala Thr Asn Ser Ser
                35                  40                  45 acc aac tgt tac gat ggc aac act tgg tcc tcc acc ttg tgt ccc gat    240
Thr Asn Cys Tyr Asp Gly Asn Thr Trp Ser Ser Thr Leu Cys Pro Asp
        50                  55                  60
```

-continued

| | |
|---|---|
| aac gaa acc tgt gcc aag aac tgt tgt ttg gat ggt gca gcc tac gcc<br>Asn Glu Thr Cys Ala Lys Asn Cys Cys Leu Asp Gly Ala Ala Tyr Ala<br>65                     70                          75 | 288 |
| tcg aca tac gga gtc act act tcc ggc aac tcg ctc tcg atc ggc ttc<br>Ser Thr Tyr Gly Val Thr Thr Ser Gly Asn Ser Leu Ser Ile Gly Phe<br>80                     85                     90                         95 | 336 |
| gtg act cag tcc gca cag aaa aac gtc gga gcg cga ctc tac ttg atg<br>Val Thr Gln Ser Ala Gln Lys Asn Val Gly Ala Arg Leu Tyr Leu Met<br>                  100                     105                     110 | 384 |
| gca tcc gat aca acc tac cag gaa ttc act ctc ttg ggc aac gag ttc<br>Ala Ser Asp Thr Thr Tyr Gln Glu Phe Thr Leu Leu Gly Asn Glu Phe<br>               115                     120                     125 | 432 |
| tcc ttc gac gtc gac gtc tcc cag ctc cct tgt ggc ctc aac gga gca<br>Ser Phe Asp Val Asp Val Ser Gln Leu Pro Cys Gly Leu Asn Gly Ala<br>130                     135                     140 | 480 |
| ctc tac ttc gtg tcg atg gac gcg gat gga ggt gtc tcc aag tac ccg<br>Leu Tyr Phe Val Ser Met Asp Ala Asp Gly Gly Val Ser Lys Tyr Pro<br>               145                     150                     155 | 528 |
| acc aac aca gca gga gcg aaa tac ggc acg ggt tac tgt gac tcg cag<br>Thr Asn Thr Ala Gly Ala Lys Tyr Gly Thr Gly Tyr Cys Asp Ser Gln<br>160                     165                     170                     175 | 576 |
| tgt cct cgc gat ctc aag ttc atc aac ggc cag gca aac gtc gaa ggc<br>Cys Pro Arg Asp Leu Lys Phe Ile Asn Gly Gln Ala Asn Val Glu Gly<br>                  180                     185                     190 | 624 |
| tgg gaa ccc tcg tcg aac aac gcc tgg acc ggc att gga ggc cat ggc<br>Trp Glu Pro Ser Ser Asn Asn Ala Trp Thr Gly Ile Gly Gly His Gly<br>               195                     200                     205 | 672 |
| tcc tgt tgt tcg gaa atg gat atc tgg gag gcc aac tcg atc tcc gag<br>Ser Cys Cys Ser Glu Met Asp Ile Trp Glu Ala Asn Ser Ile Ser Glu<br>210                     215                     220 | 720 |
| gca ctc aca ccc cac ccc tgt aca acc gtc ggc cag gag att tgt gaa<br>Ala Leu Thr Pro His Pro Cys Thr Thr Val Gly Gln Glu Ile Cys Glu<br>               225                     230                     235 | 768 |
| gga gac ggc tgt ggc gga act tac tcc gat aac cgt tac ggt ggt acc<br>Gly Asp Gly Cys Gly Gly Thr Tyr Ser Asp Asn Arg Tyr Gly Gly Thr<br>240                     245                     250                     255 | 816 |
| tgt gat ccc gat ggc tgt gac tgg aac ccc tac cgc ctc ggt aac aca<br>Cys Asp Pro Asp Gly Cys Asp Trp Asn Pro Tyr Arg Leu Gly Asn Thr<br>                  260                     265                     270 | 864 |
| tcg ttc tac ggt ccg ggt tcc tcc ttc acc ctc gac act acc aaa aag<br>Ser Phe Tyr Gly Pro Gly Ser Ser Phe Thr Leu Asp Thr Thr Lys Lys<br>                     275                     280                     285 | 912 |
| ttg acg gtg gtc acg cag ttc gag act tcc gga gcc atc aac cgg tac<br>Leu Thr Val Val Thr Gln Phe Glu Thr Ser Gly Ala Ile Asn Arg Tyr<br>               290                     295                     300 | 960 |
| tac gtg cag aac gga gtc aca ttc cag cag ccc aac gca gaa ctc ggc<br>Tyr Val Gln Asn Gly Val Thr Phe Gln Gln Pro Asn Ala Glu Leu Gly<br>305                     310                     315 | 1008 |
| tcg tac tcg gga aac gag ctc aac gat gat tac tgt aca gcg gaa gag<br>Ser Tyr Ser Gly Asn Glu Leu Asn Asp Asp Tyr Cys Thr Ala Glu Glu<br>320                     325                     330                     335 | 1056 |
| gca gaa ttc gga gga tcg tcg ttc tcc gac aag ggt ggt ttg acc cag<br>Ala Glu Phe Gly Gly Ser Ser Phe Ser Asp Lys Gly Gly Leu Thr Gln<br>                  340                     345                     350 | 1104 |
| ttc aag aag gcc aca tcg gga gga atg gtg ttg gtc atg tcc ttg tgg<br>Phe Lys Lys Ala Thr Ser Gly Gly Met Val Leu Val Met Ser Leu Trp<br>               355                     360                     365 | 1152 |
| gac gac tac tat gcc aac atg ctc tgg ctc gac tcc acc tac ccc acc<br>Asp Asp Tyr Tyr Ala Asn Met Leu Trp Leu Asp Ser Thr Tyr Pro Thr | 1200 |

```
                    370                 375                 380
aac gag acc tcc tcg aca cct ggc gca gtg agg ggc tcg tgt tcc act       1248
Asn Glu Thr Ser Ser Thr Pro Gly Ala Val Arg Gly Ser Cys Ser Thr
    385                 390                 395 tcg tcg gga gtg cct gca cag gtg gag tcc cag tcg ccg aac gcc aag       1296
Ser Ser Gly Val Pro Ala Gln Val Glu Ser Gln Ser Pro Asn Ala Lys
400                 405                 410                 415 gtc act ttc tcc aac att aag ttc gga ccc atc ggt tcg acc ggc aac       1344
Val Thr Phe Ser Asn Ile Lys Phe Gly Pro Ile Gly Ser Thr Gly Asn
                420                 425                 430 ccc tcc ggt gga aac cct cct ggc gga aac cct cct ggc aca act aca       1392
Pro Ser Gly Gly Asn Pro Pro Gly Gly Asn Pro Pro Gly Thr Thr Thr
            435                 440                 445 aca cga cgg cct gcg act aca acg ggt tcg tcc cct gga ccg acc cag       1440
Thr Arg Arg Pro Ala Thr Thr Thr Gly Ser Ser Pro Gly Pro Thr Gln
        450                 455                 460 tcc cac tac gga cag tgt gga ggc atc ggt tat tcc ggt ccg acc gtc       1488
Ser His Tyr Gly Gln Cys Gly Gly Ile Gly Tyr Ser Gly Pro Thr Val
    465                 470                 475 tgt gcg tcc ggc aca acc tgt cag gtc ttg aac cct tac tat tcg cag       1536
Cys Ala Ser Gly Thr Thr Cys Gln Val Leu Asn Pro Tyr Tyr Ser Gln
480                 485                 490                 495 tgt ctc taa                                                            1545
Cys Leu <210> SEQ ID NO 49
<211> LENGTH: 514
<212> TYPE: PRT
<213> ORGANISM: Trichoderma reesei

<400> SEQUENCE: 49

Met Tyr Arg Lys Leu Ala Val Ile Ser Ala Phe Leu Ala Thr Ala Arg
        -15                 -10                  -5

Ala Gln Ser Ala Cys Thr Leu Gln Ser Glu Thr His Pro Pro Leu Thr
 -1  1               5                  10                  15

Trp Gln Lys Cys Ser Ser Gly Gly Thr Cys Thr Gln Gln Thr Gly Ser
                20                  25                  30

Val Val Ile Asp Ala Asn Trp Arg Trp Thr His Ala Thr Asn Ser Ser
            35                  40                  45

Thr Asn Cys Tyr Asp Gly Asn Thr Trp Ser Ser Thr Leu Cys Pro Asp
        50                  55                  60

Asn Glu Thr Cys Ala Lys Asn Cys Cys Leu Asp Gly Ala Ala Tyr Ala
    65                  70                  75

Ser Thr Tyr Gly Val Thr Thr Ser Gly Asn Ser Leu Ser Ile Gly Phe
80                  85                  90                  95

Val Thr Gln Ser Ala Gln Lys Asn Val Gly Ala Arg Leu Tyr Leu Met
                100                 105                 110

Ala Ser Asp Thr Thr Tyr Gln Glu Phe Thr Leu Leu Gly Asn Glu Phe
            115                 120                 125

Ser Phe Asp Val Asp Val Ser Gln Leu Pro Cys Gly Leu Asn Gly Ala
        130                 135                 140

Leu Tyr Phe Val Ser Met Asp Ala Asp Gly Gly Val Ser Lys Tyr Pro
    145                 150                 155

Thr Asn Thr Ala Gly Ala Lys Tyr Gly Thr Gly Tyr Cys Asp Ser Gln
160                 165                 170                 175

Cys Pro Arg Asp Leu Lys Phe Ile Asn Gly Gln Ala Asn Val Glu Gly
                180                 185                 190
```

Trp Glu Pro Ser Ser Asn Asn Ala Trp Thr Gly Ile Gly Gly His Gly
                195                 200                 205

Ser Cys Cys Ser Glu Met Asp Ile Trp Glu Ala Asn Ser Ile Ser Glu
            210                 215                 220

Ala Leu Thr Pro His Pro Cys Thr Thr Val Gly Gln Glu Ile Cys Glu
        225                 230                 235

Gly Asp Gly Cys Gly Gly Thr Tyr Ser Asp Asn Arg Tyr Gly Gly Thr
240                 245                 250                 255

Cys Asp Pro Asp Gly Cys Asp Trp Asn Pro Tyr Arg Leu Gly Asn Thr
                260                 265                 270

Ser Phe Tyr Gly Pro Gly Ser Ser Phe Thr Leu Asp Thr Lys Lys
            275                 280                 285

Leu Thr Val Val Thr Gln Phe Glu Thr Ser Gly Ala Ile Asn Arg Tyr
        290                 295                 300

Tyr Val Gln Asn Gly Val Thr Phe Gln Gln Pro Asn Ala Glu Leu Gly
305                 310                 315

Ser Tyr Ser Gly Asn Glu Leu Asn Asp Asp Tyr Cys Thr Ala Glu Glu
320                 325                 330                 335

Ala Glu Phe Gly Gly Ser Ser Phe Ser Asp Lys Gly Gly Leu Thr Gln
                340                 345                 350

Phe Lys Lys Ala Thr Ser Gly Gly Met Val Leu Val Met Ser Leu Trp
            355                 360                 365

Asp Asp Tyr Tyr Ala Asn Met Leu Trp Leu Asp Ser Thr Tyr Pro Thr
        370                 375                 380

Asn Glu Thr Ser Ser Thr Pro Gly Ala Val Arg Gly Ser Cys Ser Thr
385                 390                 395

Ser Ser Gly Val Pro Ala Gln Val Glu Ser Gln Ser Pro Asn Ala Lys
400                 405                 410                 415

Val Thr Phe Ser Asn Ile Lys Phe Gly Pro Ile Gly Ser Thr Gly Asn
                420                 425                 430

Pro Ser Gly Gly Asn Pro Pro Gly Gly Asn Pro Pro Gly Thr Thr Thr
            435                 440                 445

Thr Arg Arg Pro Ala Thr Thr Thr Gly Ser Ser Pro Gly Pro Thr Gln
        450                 455                 460

Ser His Tyr Gly Gln Cys Gly Gly Ile Gly Tyr Ser Gly Pro Thr Val
465                 470                 475

Cys Ala Ser Gly Thr Thr Cys Gln Val Leu Asn Pro Tyr Tyr Ser Gln
480                 485                 490                 495

Cys Leu

<210> SEQ ID NO 50
<211> LENGTH: 1545
<212> TYPE: DNA
<213> ORGANISM: Trichoderma reesei
<220> FEATURE:
<221> NAME/KEY: sig_peptide
<222> LOCATION: (1)..(51)
<220> FEATURE:
<221> NAME/KEY: CDS
<222> LOCATION: (1)..(1542)
<220> FEATURE:
<221> NAME/KEY: mat_peptide
<222> LOCATION: (52)..(1542)

<400> SEQUENCE: 50 atg tat cgt aag ctc gca gtc atc tcc gcg ttc ctc gca aca gca cga    48
Met Tyr Arg Lys Leu Ala Val Ile Ser Ala Phe Leu Ala Thr Ala Arg -continued

```
                -15                  -10                   -5
gcg cag tcc gcc tgt acc ttg cag tcg gaa aca cat cct ccc ctc act        96
Ala Gln Ser Ala Cys Thr Leu Gln Ser Glu Thr His Pro Pro Leu Thr
 -1   1              5                  10                  15 tgg cag aaa tgt tcg tcc gga gga acg tgt acg cag cag act ggc tcg       144
Trp Gln Lys Cys Ser Ser Gly Gly Thr Cys Thr Gln Gln Thr Gly Ser
                 20                  25                  30 gtg gtc atc gac gcc aac tgg agg tgg acg cat gca acc aac tcc tcc       192
Val Val Ile Asp Ala Asn Trp Arg Trp Thr His Ala Thr Asn Ser Ser
             35                  40                  45 acc aac tgt tac gat ggc aac act tgg tcc tcc acc ttg tgt ccc gat       240
Thr Asn Cys Tyr Asp Gly Asn Thr Trp Ser Ser Thr Leu Cys Pro Asp
         50                  55                  60 aac gaa acc tgt gcc aag aac tgt tgt ttg gat ggt gca gcc tac gcc       288
Asn Glu Thr Cys Ala Lys Asn Cys Cys Leu Asp Gly Ala Ala Tyr Ala
     65                  70                  75 tcg aca tac gga gtc act act tcc ggc aac tcg ctc tcg atc ggc ttc       336
Ser Thr Tyr Gly Val Thr Thr Ser Gly Asn Ser Leu Ser Ile Gly Phe
 80                  85                  90                  95 gtg act cag tcc gca cag aaa aac gtc gga gcg cga ctc tac ttg atg       384
Val Thr Gln Ser Ala Gln Lys Asn Val Gly Ala Arg Leu Tyr Leu Met
                100                 105                 110 gca tcc gat aca acc tac cag gaa ttc act ctc ttg ggc aac gag ttc       432
Ala Ser Asp Thr Thr Tyr Gln Glu Phe Thr Leu Leu Gly Asn Glu Phe
            115                 120                 125 tcc ttc gac gtc gac gtc tcc cag ctc cct tgt ggc ctc aac gga gca       480
Ser Phe Asp Val Asp Val Ser Gln Leu Pro Cys Gly Leu Asn Gly Ala
        130                 135                 140 ctc tac ttc gtg tcg atg gac gcg gat gga ggt gtc tcc aag tac ccg       528
Leu Tyr Phe Val Ser Met Asp Ala Asp Gly Gly Val Ser Lys Tyr Pro
    145                 150                 155 acc aac aca gca gga gcg aaa tac ggc acg ggt tac tgt gac tcg cag       576
Thr Asn Thr Ala Gly Ala Lys Tyr Gly Thr Gly Tyr Cys Asp Ser Gln
160                 165                 170                 175 tgt cct cgc gat ctc aag ttc atc aac ggc cag gca aac gtc gaa ggc       624
Cys Pro Arg Asp Leu Lys Phe Ile Asn Gly Gln Ala Asn Val Glu Gly
                180                 185                 190 tgg gaa ccc tcg tcg aac aac gcc gga acc ggc att gga ggc cat ggc       672
Trp Glu Pro Ser Ser Asn Asn Ala Gly Thr Gly Ile Gly Gly His Gly
            195                 200                 205 tcc tgt tgt tcg gaa atg gat atc tgg gag gcc aac tcg atc tcc gag       720
Ser Cys Cys Ser Glu Met Asp Ile Trp Glu Ala Asn Ser Ile Ser Glu
        210                 215                 220 gca ctc aca ccc cac ccc tgt aca acc gtc ggc cag gag att tgt gaa       768
Ala Leu Thr Pro His Pro Cys Thr Thr Val Gly Gln Glu Ile Cys Glu
    225                 230                 235 gga gac ggc tgt ggc gga act tac tcc gat aac cgt tac ggt ggt acc       816
Gly Asp Gly Cys Gly Gly Thr Tyr Ser Asp Asn Arg Tyr Gly Gly Thr
240                 245                 250                 255 tgt gat ccc gat ggc tgt gac tgg aac ccc tac cgc ctc ggt aac aca       864
Cys Asp Pro Asp Gly Cys Asp Trp Asn Pro Tyr Arg Leu Gly Asn Thr
                260                 265                 270 tcg ttc tac ggt ccg ggt tcc tcc ttc acc ctc gac act acc aaa aag       912
Ser Phe Tyr Gly Pro Gly Ser Ser Phe Thr Leu Asp Thr Thr Lys Lys
            275                 280                 285 ttg acg gtg gtc acg cag ttc gag act tcc gga gcc atc aac cgg tac       960
Leu Thr Val Val Thr Gln Phe Glu Thr Ser Gly Ala Ile Asn Arg Tyr
        290                 295                 300 tac gtg cag aac gga gtc aca ttc cag cag ccc aac gca gaa ctc ggc      1008
Tyr Val Gln Asn Gly Val Thr Phe Gln Gln Pro Asn Ala Glu Leu Gly
```

| | | | | | | | | | | | | |
|---|---|---|---|---|---|---|---|---|---|---|---|---|
| Tyr | Val | Gln | Asn | Gly | Val | Thr | Phe | Gln | Gln | Pro | Asn | Ala Glu Leu Gly |
| | | 305 | | | 310 | | | | 315 | | | |

| tcg | tac | tcg | gga | aac | gag | ctc | aac | gat | gat | tac | tgt | aca | gcg | gaa | gag | 1056 |
|---|---|---|---|---|---|---|---|---|---|---|---|---|---|---|---|---|
| Ser | Tyr | Ser | Gly | Asn | Glu | Leu | Asn | Asp | Asp | Tyr | Cys | Thr | Ala | Glu | Glu | |
| 320 | | | | | 325 | | | | 330 | | | | | 335 | | |

| gca | gaa | ttc | gga | gga | tcg | tcg | ttc | tcc | gac | aag | ggt | ggt | ttg | acc | cag | 1104 |
|---|---|---|---|---|---|---|---|---|---|---|---|---|---|---|---|---|
| Ala | Glu | Phe | Gly | Gly | Ser | Ser | Phe | Ser | Asp | Lys | Gly | Gly | Leu | Thr | Gln | |
| | | | | 340 | | | | | 345 | | | | | 350 | | |

| ttc | aag | aag | gcc | aca | tcg | gga | gga | atg | gtg | ttg | gtc | atg | tcc | ttg | tgg | 1152 |
|---|---|---|---|---|---|---|---|---|---|---|---|---|---|---|---|---|
| Phe | Lys | Lys | Ala | Thr | Ser | Gly | Gly | Met | Val | Leu | Val | Met | Ser | Leu | Trp | |
| | | | | 355 | | | | | 360 | | | | | 365 | | |

| gac | gac | tac | tat | gcc | aac | atg | ctc | tgg | ctc | gac | tcc | acc | tac | ccc | acc | 1200 |
|---|---|---|---|---|---|---|---|---|---|---|---|---|---|---|---|---|
| Asp | Asp | Tyr | Tyr | Ala | Asn | Met | Leu | Trp | Leu | Asp | Ser | Thr | Tyr | Pro | Thr | |
| | | 370 | | | | | 375 | | | | | 380 | | | | |

| aac | gag | acc | tcc | tcg | aca | cct | ggc | gca | gtg | agg | ggc | tcg | tgt | tcc | act | 1248 |
|---|---|---|---|---|---|---|---|---|---|---|---|---|---|---|---|---|
| Asn | Glu | Thr | Ser | Ser | Thr | Pro | Gly | Ala | Val | Arg | Gly | Ser | Cys | Ser | Thr | |
| 385 | | | | | 390 | | | | | 395 | | | | | | |

| tcg | tcg | gga | gtg | cct | gca | cag | gtg | gag | tcc | cag | tcg | ccg | aac | gcc | aag | 1296 |
|---|---|---|---|---|---|---|---|---|---|---|---|---|---|---|---|---|
| Ser | Ser | Gly | Val | Pro | Ala | Gln | Val | Glu | Ser | Gln | Ser | Pro | Asn | Ala | Lys | |
| 400 | | | | | 405 | | | | | 410 | | | | | 415 | |

| gtc | act | ttc | tcc | aac | att | aag | ttc | gga | ccc | atc | ggt | tcg | acc | ggc | aac | 1344 |
|---|---|---|---|---|---|---|---|---|---|---|---|---|---|---|---|---|
| Val | Thr | Phe | Ser | Asn | Ile | Lys | Phe | Gly | Pro | Ile | Gly | Ser | Thr | Gly | Asn | |
| | | | | 420 | | | | | 425 | | | | | 430 | | |

| ccc | tcc | ggt | gga | aac | cct | cct | ggc | gga | aac | cct | cct | ggc | aca | act | aca | 1392 |
|---|---|---|---|---|---|---|---|---|---|---|---|---|---|---|---|---|
| Pro | Ser | Gly | Gly | Asn | Pro | Pro | Gly | Gly | Asn | Pro | Pro | Gly | Thr | Thr | Thr | |
| | | | | 435 | | | | | 440 | | | | | 445 | | |

| aca | cga | cgg | cct | gcg | act | aca | acg | ggt | tcg | tcc | cct | gga | ccg | acc | cag | 1440 |
|---|---|---|---|---|---|---|---|---|---|---|---|---|---|---|---|---|
| Thr | Arg | Arg | Pro | Ala | Thr | Thr | Thr | Gly | Ser | Ser | Pro | Gly | Pro | Thr | Gln | |
| | | 450 | | | | | 455 | | | | | 460 | | | | |

| tcc | cac | tac | gga | cag | tgt | gga | ggc | atc | ggt | tat | tcc | ggt | ccg | acc | gtc | 1488 |
|---|---|---|---|---|---|---|---|---|---|---|---|---|---|---|---|---|
| Ser | His | Tyr | Gly | Gln | Cys | Gly | Gly | Ile | Gly | Tyr | Ser | Gly | Pro | Thr | Val | |
| 465 | | | | | 470 | | | | | 475 | | | | | | |

| tgt | gcg | tcc | ggc | aca | acc | tgt | cag | gtc | ttg | aac | cct | tac | tat | tcg | cag | 1536 |
|---|---|---|---|---|---|---|---|---|---|---|---|---|---|---|---|---|
| Cys | Ala | Ser | Gly | Thr | Thr | Cys | Gln | Val | Leu | Asn | Pro | Tyr | Tyr | Ser | Gln | |
| 480 | | | | | 485 | | | | | 490 | | | | | 495 | |

| tgt | ctc | taa | 1545 |
|---|---|---|---|
| Cys | Leu | | |

<210> SEQ ID NO 51
<211> LENGTH: 514
<212> TYPE: PRT
<213> ORGANISM: Trichoderma reesei

<400> SEQUENCE: 51

| Met | Tyr | Arg | Lys | Leu | Ala | Val | Ile | Ser | Ala | Phe | Leu | Ala | Thr | Ala | Arg |
|---|---|---|---|---|---|---|---|---|---|---|---|---|---|---|---|
| | | | -15 | | | | | -10 | | | | | -5 | | |

| Ala | Gln | Ser | Ala | Cys | Thr | Leu | Gln | Ser | Glu | Thr | His | Pro | Pro | Leu | Thr |
|---|---|---|---|---|---|---|---|---|---|---|---|---|---|---|---|
| -1 | 1 | | | | 5 | | | | | 10 | | | | | 15 |

| Trp | Gln | Lys | Cys | Ser | Ser | Gly | Gly | Thr | Cys | Thr | Gln | Gln | Thr | Gly | Ser |
|---|---|---|---|---|---|---|---|---|---|---|---|---|---|---|---|
| | | | 20 | | | | | 25 | | | | | 30 | | |

| Val | Val | Ile | Asp | Ala | Asn | Trp | Arg | Trp | Thr | His | Ala | Thr | Asn | Ser | Ser |
|---|---|---|---|---|---|---|---|---|---|---|---|---|---|---|---|
| | | | 35 | | | | | 40 | | | | | 45 | | |

| Thr | Asn | Cys | Tyr | Asp | Gly | Asn | Thr | Trp | Ser | Ser | Thr | Leu | Cys | Pro | Asp |
|---|---|---|---|---|---|---|---|---|---|---|---|---|---|---|---|
| | | 50 | | | | | 55 | | | | | 60 | | | |

| Asn | Glu | Thr | Cys | Ala | Lys | Asn | Cys | Cys | Leu | Asp | Gly | Ala | Ala | Tyr | Ala |
|---|---|---|---|---|---|---|---|---|---|---|---|---|---|---|---|
| | 65 | | | | | 70 | | | | | 75 | | | | |

| Ser | Thr | Tyr | Gly | Val | Thr | Thr | Ser | Gly | Asn | Ser | Leu | Ser | Ile | Gly | Phe |
|---|---|---|---|---|---|---|---|---|---|---|---|---|---|---|---|
| 80 | | | | | 85 | | | | | 90 | | | | | 95 |

```
Val Thr Gln Ser Ala Gln Lys Asn Val Gly Ala Arg Leu Tyr Leu Met
                100                 105                 110
Ala Ser Asp Thr Thr Tyr Gln Glu Phe Thr Leu Leu Gly Asn Glu Phe
            115                 120                 125
Ser Phe Asp Val Asp Val Ser Gln Leu Pro Cys Gly Leu Asn Gly Ala
        130                 135                 140
Leu Tyr Phe Val Ser Met Asp Ala Asp Gly Gly Val Ser Lys Tyr Pro
    145                 150                 155
Thr Asn Thr Ala Gly Ala Lys Tyr Gly Thr Gly Tyr Cys Asp Ser Gln
160                 165                 170                 175
Cys Pro Arg Asp Leu Lys Phe Ile Asn Gly Gln Ala Asn Val Glu Gly
            180                 185                 190
Trp Glu Pro Ser Ser Asn Asn Ala Gly Thr Gly Ile Gly Gly His Gly
        195                 200                 205
Ser Cys Cys Ser Glu Met Asp Ile Trp Glu Ala Asn Ser Ile Ser Glu
        210                 215                 220
Ala Leu Thr Pro His Pro Cys Thr Thr Val Gly Gln Glu Ile Cys Glu
    225                 230                 235
Gly Asp Gly Cys Gly Gly Thr Tyr Ser Asp Asn Arg Tyr Gly Gly Thr
240                 245                 250                 255
Cys Asp Pro Asp Gly Cys Asp Trp Asn Pro Tyr Arg Leu Gly Asn Thr
            260                 265                 270
Ser Phe Tyr Gly Pro Gly Ser Ser Phe Thr Leu Asp Thr Thr Lys Lys
        275                 280                 285
Leu Thr Val Val Thr Gln Phe Glu Thr Ser Gly Ala Ile Asn Arg Tyr
    290                 295                 300
Tyr Val Gln Asn Gly Val Thr Phe Gln Gln Pro Asn Ala Glu Leu Gly
    305                 310                 315
Ser Tyr Ser Gly Asn Glu Leu Asn Asp Asp Tyr Cys Thr Ala Glu Glu
320                 325                 330                 335
Ala Glu Phe Gly Gly Ser Ser Phe Ser Asp Lys Gly Gly Leu Thr Gln
            340                 345                 350
Phe Lys Lys Ala Thr Ser Gly Gly Met Val Leu Val Met Ser Leu Trp
        355                 360                 365
Asp Asp Tyr Tyr Ala Asn Met Leu Trp Leu Asp Ser Thr Tyr Pro Thr
        370                 375                 380
Asn Glu Thr Ser Ser Thr Pro Gly Ala Val Arg Gly Ser Cys Ser Thr
    385                 390                 395
Ser Ser Gly Val Pro Ala Gln Val Glu Ser Gln Ser Pro Asn Ala Lys
400                 405                 410                 415
Val Thr Phe Ser Asn Ile Lys Phe Gly Pro Ile Gly Ser Thr Gly Asn
            420                 425                 430
Pro Ser Gly Gly Asn Pro Gly Gly Asn Pro Gly Thr Thr Thr
        435                 440                 445
Thr Arg Arg Pro Ala Thr Thr Thr Gly Ser Ser Pro Gly Pro Thr Gln
    450                 455                 460
Ser His Tyr Gly Gln Cys Gly Gly Ile Gly Tyr Ser Gly Pro Thr Val
    465                 470                 475
Cys Ala Ser Gly Thr Thr Cys Gln Val Leu Asn Pro Tyr Tyr Ser Gln
480                 485                 490                 495
Cys Leu

<210> SEQ ID NO 52
```

<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 52
gctgggaacc ctcgtcgaac gcagccaaca ccggcattgg a                41

<210> SEQ ID NO 53
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 53
gttcgacgag ggttcccagc cttcgacgtt tg                          32

<210> SEQ ID NO 54
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 54
tgggaacccT cgtcgaacaa caacaccggc attggaggcc at               42

<210> SEQ ID NO 55
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 55
gttgttcgac gagggttccc agccttcgac g                           31

<210> SEQ ID NO 56
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 56
gaaccctcgt cgaacaacgc ctggaccggc attggaggcc atgg             44

<210> SEQ ID NO 57
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 57
ggcgttgttc gacgagggtt cccagccttc g                           31

<210> SEQ ID NO 58
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 58
gaaccctcgt cgaacaacgc cggaaccggc attggaggcc at             42

<210> SEQ ID NO 59
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 59
ggcgttgttc gacgagggtt cccagccttc g             31

<210> SEQ ID NO 60
<211> LENGTH: 28
<212> TYPE: DNA
<213> ORGANISM: Artificial Sequence
<220> FEATURE:
<223> OTHER INFORMATION: Artificial DNA Primer

<400> SEQUENCE: 60
catgtatcgt aagctcgcag tcatctcc             28

<210> SEQ ID NO 61
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 61
cttcgtgtcg atggacgcgg             20

<210> SEQ ID NO 62
<211> LENGTH: 20
<212> TYPE: DNA
<213> ORGANISM: Artificial Sequence
<220> FEATURE:
<223> OTHER INFORMATION: Artificial DNA Primer

<400> SEQUENCE: 62
gaacacgagc ccctcactgc             20

<210> SEQ ID NO 63
<211> LENGTH: 1368
<212> TYPE: DNA
<213> ORGANISM: Rasamsonia emersonii

<400> SEQUENCE: 63
atgcttcgac gggctcttct tctatcctct tccgccatcc ttgctgtcaa ggcacagcag     60
gccggcacgg cgacggcaga gaaccacccg ccctgacat ggcaggaatg caccgccct    120
gggagctgca ccacccagaa cggggcggtc gttcttgatg cgaactggcg ttgggtgcac    180
gatgtgaacg gataccacca ctgctacacg ggcaatacct ggaaccccac gtactgccct    240
gacgacgaaa cctgcgccca gaactgtgcg ctggacggcg cggattacga gggcacctac    300
ggcgtgactt cgtcgggcag ctccttgaag ctcaatttcg tcaccgggtc gaacgtcgga    360
tcccgtctct acctgctgca ggacgactcg acctatcaga tcttcaagct tctgaaccgc    420
gagtttacct tgacgtcga tgtctccaat cttccgtgcg gattgaacgg cgctctgtac    480
tttgtcgcca tggacgccga cggcggcgtg tccaagtacc cgaacaacaa ggctggtgcc    540
aagtacggaa ccgggtattg cgactcccaa tgcccacggg acctcaagtt catcgacggc    600

```
gaggccaacg tcgagggctg gcagccgtct tcgaacaacg ccaacaccgg aattggcgac      660
catggctcct gctgtgcgga gatggatgtc tgggaagcca acagcatctc caatgcggtc      720
actccgcacc cgtgcgacac gccaggccag acgatgtgct ctggcgatga ctgcggtggc      780
acatactcta acgatcgcta cgcgggaacc tgcgatcctg acggctgtga cttcaaccct      840
taccgcatgg gcaacacttc tttctacggg cctggcaaga tcatcgatac caccaagcct      900
ttcactgtcg tgacgcagtt cctcactgat gatggtacgg atactggaac tctcagcgag      960
atcaagcgct tctacgtcca gaacggcaac gtcattccgc agcccaactc ggacatcagt     1020
ggcgtgaccg gcaactcgat cacgacggag ttctgtactg ctcagaagca ggccttggc      1080 gacacggacg acttctctca gcacggtggc ctggccaaga tgggagcggc catgcagcag     1140
ggtatggtcc tggtgatgag tttgtgggac gactacgccg cgcagatgct gtggctggat     1200
tccgactacc cgacggatgc ggaccccacg acccctggta ttgcccgtgg aacgtgtccg     1260
acggactcgg gcgtcccatc ggatgtcgag tcgcagagcc ccaactccta cgtgacctac     1320
tcgaacatca agtttggtcc gatcaactcg accttcaccg cttcgtga                  1368
```

<210> SEQ ID NO 64  
<211> LENGTH: 1368  
<212> TYPE: DNA  
<213> ORGANISM: Rasamsonia emersonii

<400> SEQUENCE: 64

```
atgttgcgaa gggccttgtt gctctcgtcc tccgcaatct tggcggtcaa ggcacagcag       60
gcaggcaccg caaccgcaga gaaccatcct ccgctcactt ggcaggaatg tacagcacct      120
ggctcctgta caacccagaa cggagcggtc gtgctcgatg cgaactggcg ctgggtgcac      180
gatgtcaacg gatacacaaa ctgttataca ggtaacacgt ggaaccctac gtattgtccc      240
gacgacgaaa cgtgtgccca gaactgtgcg ttggatggag cagactacga gggaacgtat      300
ggcgtgacct cgtccggctc ctccttgaag ctcaacttcg tcacgggctc gaacgtcggc      360
tcccgcttgt acctcctcca ggacgactcg acctaccaga tcttcaagct cctcaacagg      420
gagttcacct tcgacgtcga tgtctccaac ttgccctgtg gtctcaacgg agccttgtac      480
ttcgtcgcga tggatgcaga cggaggtgtc tcgaagtacc caacaacaa ggcaggtgcc      540 aagtatggta ctggctactg tgattcgcag tgtcctcgcg atctcaagtt cattgacggt      600
gaggcgaacg tggaaggatg gcagccctcg tccaacaacg cgaacactgg catcggtgat      660
cacggttcgt gttgtgccga gatggacgtc tgggaagcca actccatctc gaacgcggtc      720
acaccgcacc cgtgtgatac tcctggccag actatgtgtt ccggagatga ttgtggaggc      780
acctattcga cgaccggta tgcaggcacg tgtgacccgg atggctgtga cttcaacccg      840
taccgcatgg gcaacaccct cttctatgga ccgggtaaga tcatcgatac aactaagccc      900
ttcaccgtcg tcacgcagtt cctcacagat gacggcacgg acacaggtac tttgtcggag      960
atcaaacgct tctacgtcca gaacggaaac gtcatccccc agccgaactc cgacatttcg     1020
ggagtcacag gcaactcgat tacgaccgag ttctgtacag cccagaaaca ggcattcggt     1080
gacacggatg atttctccca gcacggagga ttggcgaaaa tgggagccgc aatgcagcag     1140
ggaatggtcc tcgtgatgtc gctctgggac gactatgcag cccagatgtt gtggctcgac     1200
tcggactacc ccacagacgc cgatcccacg acacccggta tcgcacgagg cacttgtccg     1260
acagattccg gagtccgtc ggacgtcgag tcccagtccc ccaactcgta cgtcacctat     1320
tcgaacatca aattcggtcc catcaactcg acattcacag cctcgtaa                  1368
```

```
<210> SEQ ID NO 65
<211> LENGTH: 1368
<212> TYPE: DNA
<213> ORGANISM: Rasamsonia emersonii
<220> FEATURE:
<221> NAME/KEY: sig_peptide
<222> LOCATION: (1)..(54)
<220> FEATURE:
<221> NAME/KEY: CDS
<222> LOCATION: (1)..(1365)
<220> FEATURE:
<221> NAME/KEY: mat_peptide
<222> LOCATION: (55)..(1635)

<400> SEQUENCE: 65
```

| | | | | | | | | | | | | | | | | |
|---|---|---|---|---|---|---|---|---|---|---|---|---|---|---|---|---|
| atg | ttg | cga | agg | gcc | ttg | ttg | ctc | tcg | tcc | tcc | gca | atc | ttg | gcg | gtc | 48 |
| Met | Leu | Arg | Arg | Ala | Leu | Leu | Leu | Ser | Ser | Ser | Ala | Ile | Leu | Ala | Val | |
| | | | -15 | | | | -10 | | | | | -5 | | | | |
| aag | gca | cag | cag | gca | ggc | acc | gca | acc | gca | gag | aac | cat | cct | ccg | ctc | 96 |
| Lys | Ala | Gln | Gln | Ala | Gly | Thr | Ala | Thr | Ala | Glu | Asn | His | Pro | Pro | Leu | |
| | -1 | 1 | | | 5 | | | | | 10 | | | | | | |
| act | tgg | cag | gaa | tgt | aca | gca | cct | ggc | tcc | tgt | aca | acc | cag | aac | gga | 144 |
| Thr | Trp | Gln | Glu | Cys | Thr | Ala | Pro | Gly | Ser | Cys | Thr | Thr | Gln | Asn | Gly | |
| 15 | | | | | 20 | | | | | 25 | | | | | 30 | |
| gcg | gtc | gtg | ctc | gat | gcg | aac | tgg | cgc | tgg | gtg | cac | gat | gtc | aac | gga | 192 |
| Ala | Val | Val | Leu | Asp | Ala | Asn | Trp | Arg | Trp | Val | His | Asp | Val | Asn | Gly | |
| | | | 35 | | | | | 40 | | | | | 45 | | | |
| tac | aca | aac | tgt | tat | aca | ggt | aac | acg | tgg | aac | cct | acg | tat | tgt | ccc | 240 |
| Tyr | Thr | Asn | Cys | Tyr | Thr | Gly | Asn | Thr | Trp | Asn | Pro | Thr | Tyr | Cys | Pro | |
| | | 50 | | | | | 55 | | | | | 60 | | | | |
| gac | gac | gaa | acg | tgt | gcc | cag | aac | tgt | gcg | ttg | gat | gga | gca | gac | tac | 288 |
| Asp | Asp | Glu | Thr | Cys | Ala | Gln | Asn | Cys | Ala | Leu | Asp | Gly | Ala | Asp | Tyr | |
| 65 | | | | | 70 | | | | | 75 | | | | | | |
| gag | gga | acg | tat | ggc | gtg | acc | tcg | tcc | ggc | tcc | tcc | ttg | aag | ctc | aac | 336 |
| Glu | Gly | Thr | Tyr | Gly | Val | Thr | Ser | Ser | Gly | Ser | Ser | Leu | Lys | Leu | Asn | |
| | 80 | | | | | 85 | | | | | 90 | | | | | |
| ttc | gtc | acg | ggc | tcg | aac | gtc | ggc | tcc | cgc | ttg | tac | ctc | ctc | cag | gac | 384 |
| Phe | Val | Thr | Gly | Ser | Asn | Val | Gly | Ser | Arg | Leu | Tyr | Leu | Leu | Gln | Asp | |
| 95 | | | | | 100 | | | | | 105 | | | | | 110 | |
| gac | tcg | acc | tac | cag | atc | ttc | aag | ctc | ctc | aac | agg | gag | ttc | acc | ttc | 432 |
| Asp | Ser | Thr | Tyr | Gln | Ile | Phe | Lys | Leu | Leu | Asn | Arg | Glu | Phe | Thr | Phe | |
| | | | 115 | | | | | 120 | | | | | 125 | | | |
| gac | gtc | gat | gtc | tcc | aac | ttg | ccc | tgt | ggt | ctc | aac | gga | gcc | ttg | tac | 480 |
| Asp | Val | Asp | Val | Ser | Asn | Leu | Pro | Cys | Gly | Leu | Asn | Gly | Ala | Leu | Tyr | |
| | | 130 | | | | | 135 | | | | | 140 | | | | |
| ttc | gtc | gcg | atg | gat | gca | gac | gga | ggt | gtc | tcg | aag | tac | ccc | aac | aac | 528 |
| Phe | Val | Ala | Met | Asp | Ala | Asp | Gly | Gly | Val | Ser | Lys | Tyr | Pro | Asn | Asn | |
| | 145 | | | | | 150 | | | | | 155 | | | | | |
| aag | gca | ggt | gcc | aag | tat | ggt | act | ggc | tac | tgt | gat | tcg | cag | tgt | cct | 576 |
| Lys | Ala | Gly | Ala | Lys | Tyr | Gly | Thr | Gly | Tyr | Cys | Asp | Ser | Gln | Cys | Pro | |
| 160 | | | | | 165 | | | | | 170 | | | | | | |
| cgc | gat | ctc | aag | ttc | att | gac | ggt | gag | gcg | aac | gtg | gaa | gga | tgg | cag | 624 |
| Arg | Asp | Leu | Lys | Phe | Ile | Asp | Gly | Glu | Ala | Asn | Val | Glu | Gly | Trp | Gln | |
| 175 | | | | | 180 | | | | | 185 | | | | | 190 | |
| ccc | tcg | tcc | gca | aac | gcg | gca | act | ggc | atc | ggt | gat | cac | ggt | tcg | tgt | 672 |
| Pro | Ser | Ser | Ala | Asn | Ala | Ala | Thr | Gly | Ile | Gly | Asp | His | Gly | Ser | Cys | |
| | | | 195 | | | | | 200 | | | | | 205 | | | |
| tgt | gcc | gag | atg | gac | gtc | tgg | gaa | gcc | aac | tcc | atc | tcg | aac | gcg | gtc | 720 |
| Cys | Ala | Glu | Met | Asp | Val | Trp | Glu | Ala | Asn | Ser | Ile | Ser | Asn | Ala | Val | |
| | | 210 | | | | | 215 | | | | | 220 | | | | |
| aca | ccg | cac | ccg | tgt | gat | act | cct | ggc | cag | act | atg | tgt | tcc | gga | gat | 768 |

| | | | | | | | | | | | | | | |
|---|---|---|---|---|---|---|---|---|---|---|---|---|---|---|
| Thr | Pro | His | Pro | Cys | Asp | Thr | Pro | Gly | Gln | Thr | Met | Cys | Ser | Gly Asp |
| | | 225 | | | | | 230 | | | | | 235 | | |

```
gat tgt gga ggc acc tat tcg aac gac cgg tat gca ggc acg tgt gac      816
Asp Cys Gly Gly Thr Tyr Ser Asn Asp Arg Tyr Ala Gly Thr Cys Asp
240                 245                 250 ccg gat ggc tgt gac ttc aac ccg tac cgc atg ggc aac acc tcc ttc      864
Pro Asp Gly Cys Asp Phe Asn Pro Tyr Arg Met Gly Asn Thr Ser Phe
255                 260                 265                 270 tat gga ccg ggt aag atc atc gat aca act aag ccc ttc acc gtc gtc      912
Tyr Gly Pro Gly Lys Ile Ile Asp Thr Thr Lys Pro Phe Thr Val Val
                275                 280                 285 acg cag ttc ctc aca gat gac ggc acg gac aca ggt act ttg tcg gag      960
Thr Gln Phe Leu Thr Asp Asp Gly Thr Asp Thr Gly Thr Leu Ser Glu
        290                 295                 300 atc aaa cgc ttc tac gtc cag aac gga aac gtc atc ccc cag ccg aac     1008
Ile Lys Arg Phe Tyr Val Gln Asn Gly Asn Val Ile Pro Gln Pro Asn
            305                 310                 315 tcc gac att tcg gga gtc aca ggc aac tcg att acg acc gag ttc tgt     1056
Ser Asp Ile Ser Gly Val Thr Gly Asn Ser Ile Thr Thr Glu Phe Cys
320                 325                 330 aca gcc cag aaa cag gca ttc ggt gac acg gat gat ttc tcc cag cac     1104
Thr Ala Gln Lys Gln Ala Phe Gly Asp Thr Asp Asp Phe Ser Gln His
335                 340                 345                 350 gga gga ttg gcg aaa atg gga gcc gca atg cag cag gga atg gtc ctc     1152
Gly Gly Leu Ala Lys Met Gly Ala Ala Met Gln Gln Gly Met Val Leu
                355                 360                 365 gtg atg tcg ctc tgg gac gac tat gca gcc cag atg ttg tgg ctc gac     1200
Val Met Ser Leu Trp Asp Asp Tyr Ala Ala Gln Met Leu Trp Leu Asp
        370                 375                 380 tcg gac tac ccc aca gac gcc gat ccc acg aca ccc ggt atc gca cga     1248
Ser Asp Tyr Pro Thr Asp Ala Asp Pro Thr Thr Pro Gly Ile Ala Arg
            385                 390                 395 ggc act tgt ccg aca gat tcc gga gtc ccg tcg gac gtc gag tcc cag     1296
Gly Thr Cys Pro Thr Asp Ser Gly Val Pro Ser Asp Val Glu Ser Gln
400                 405                 410 tcc ccc aac tcg tac gtc acc tat tcg aac atc aaa ttc ggt ccc atc     1344
Ser Pro Asn Ser Tyr Val Thr Tyr Ser Asn Ile Lys Phe Gly Pro Ile
415                 420                 425                 430 aac tcg aca ttc aca gcc tcg taa                                     1368
Asn Ser Thr Phe Thr Ala Ser
                435
```

<210> SEQ ID NO 66
<211> LENGTH: 455
<212> TYPE: PRT
<213> ORGANISM: Rasamsonia emersonii

<400> SEQUENCE: 66

| | | | | | | | | | | | | | | |
|---|---|---|---|---|---|---|---|---|---|---|---|---|---|---|
| Met | Leu | Arg | Arg | Ala | Leu | Leu | Leu | Ser | Ser | Ala | Ile | Leu | Ala | Val |
| | | | -15 | | | | -10 | | | | | -5 | | |

| | | | | | | | | | | | | | | |
|---|---|---|---|---|---|---|---|---|---|---|---|---|---|---|
| Lys | Ala | Gln | Gln | Ala | Gly | Thr | Ala | Thr | Ala | Glu | Asn | His | Pro | Pro Leu |
| -1 | 1 | | | | | 5 | | | | | 10 | | | |

| | | | | | | | | | | | | | | |
|---|---|---|---|---|---|---|---|---|---|---|---|---|---|---|
| Thr | Trp | Gln | Glu | Cys | Thr | Ala | Pro | Gly | Ser | Cys | Thr | Thr | Gln | Asn Gly |
| 15 | | | | | 20 | | | | | 25 | | | | | 30 |

| | | | | | | | | | | | | | | |
|---|---|---|---|---|---|---|---|---|---|---|---|---|---|---|
| Ala | Val | Val | Leu | Asp | Ala | Asn | Trp | Arg | Trp | Val | His | Asp | Val | Asn Gly |
| | | | | 35 | | | | | 40 | | | | | 45 |

| | | | | | | | | | | | | | | |
|---|---|---|---|---|---|---|---|---|---|---|---|---|---|---|
| Tyr | Thr | Asn | Cys | Tyr | Thr | Gly | Asn | Thr | Trp | Asn | Pro | Thr | Tyr | Cys Pro |
| | | 50 | | | | | 55 | | | | | 60 | | |

| | | | | | | | | | | | | | | |
|---|---|---|---|---|---|---|---|---|---|---|---|---|---|---|
| Asp | Asp | Glu | Thr | Cys | Ala | Gln | Asn | Cys | Ala | Leu | Asp | Gly | Ala | Asp Tyr |

```
            65                  70                  75
Glu Gly Thr Tyr Gly Val Thr Ser Ser Gly Ser Ser Leu Lys Leu Asn
         80                  85                  90

Phe Val Thr Gly Ser Asn Val Gly Ser Arg Leu Tyr Leu Leu Gln Asp
 95                 100                 105                 110

Asp Ser Thr Tyr Gln Ile Phe Lys Leu Leu Asn Arg Glu Phe Thr Phe
                115                 120                 125

Asp Val Asp Val Ser Asn Leu Pro Cys Gly Leu Asn Gly Ala Leu Tyr
            130                 135                 140

Phe Val Ala Met Asp Ala Asp Gly Gly Val Ser Lys Tyr Pro Asn Asn
            145                 150                 155

Lys Ala Gly Ala Lys Tyr Gly Thr Gly Tyr Cys Asp Ser Gln Cys Pro
            160                 165                 170

Arg Asp Leu Lys Phe Ile Asp Gly Glu Ala Asn Val Glu Gly Trp Gln
175                 180                 185                 190

Pro Ser Ser Ala Asn Ala Ala Thr Gly Ile Gly Asp His Gly Ser Cys
                195                 200                 205

Cys Ala Glu Met Asp Val Trp Glu Ala Asn Ser Ile Ser Asn Ala Val
            210                 215                 220

Thr Pro His Pro Cys Asp Thr Pro Gly Gln Thr Met Cys Ser Gly Asp
            225                 230                 235

Asp Cys Gly Gly Thr Tyr Ser Asn Asp Arg Tyr Ala Gly Thr Cys Asp
240                 245                 250

Pro Asp Gly Cys Asp Phe Asn Pro Tyr Arg Met Gly Asn Thr Ser Phe
255                 260                 265                 270

Tyr Gly Pro Gly Lys Ile Ile Asp Thr Thr Lys Pro Phe Thr Val Val
                275                 280                 285

Thr Gln Phe Leu Thr Asp Asp Gly Thr Asp Thr Gly Thr Leu Ser Glu
            290                 295                 300

Ile Lys Arg Phe Tyr Val Gln Asn Gly Asn Val Ile Pro Gln Pro Asn
            305                 310                 315

Ser Asp Ile Ser Gly Val Thr Gly Asn Ser Ile Thr Thr Glu Phe Cys
            320                 325                 330

Thr Ala Gln Lys Gln Ala Phe Gly Asp Thr Asp Asp Phe Ser Gln His
335                 340                 345                 350

Gly Gly Leu Ala Lys Met Gly Ala Ala Met Gln Gln Gly Met Val Leu
                355                 360                 365

Val Met Ser Leu Trp Asp Asp Tyr Ala Ala Gln Met Leu Trp Leu Asp
            370                 375                 380

Ser Asp Tyr Pro Thr Asp Ala Asp Pro Thr Thr Pro Gly Ile Ala Arg
            385                 390                 395

Gly Thr Cys Pro Thr Asp Ser Gly Val Pro Ser Asp Val Glu Ser Gln
            400                 405                 410

Ser Pro Asn Ser Tyr Val Thr Tyr Ser Asn Ile Lys Phe Gly Pro Ile
415                 420                 425                 430

Asn Ser Thr Phe Thr Ala Ser
                435

<210> SEQ ID NO 67
<211> LENGTH: 50
<212> TYPE: DNA
<213> ORGANISM: Artificial Sequence
<220> FEATURE:
<223> OTHER INFORMATION: Artificial DNA Primer
```

<400> SEQUENCE: 67
aaggatggca gccctcgtcc gcaaacgcgg caactggcat cggtgatcac          50

<210> SEQ ID NO 68
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 68
ggacgagggc tgccatcctt ccacgttcgc                               30

<210> SEQ ID NO 69
<211> LENGTH: 28
<212> TYPE: DNA
<213> ORGANISM: Artificial Sequence
<220> FEATURE:
<223> OTHER INFORMATION: Artificial DNA Primer

<400> SEQUENCE: 69
ccacacttct cttccttcct caatcctc                                 28

<210> SEQ ID NO 70
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 70
gtgaggcgaa cgtggaagga tg                                       22

<210> SEQ ID NO 71
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 71
gtacctgtgt ccgtgccgtc atctg                                    25

<210> SEQ ID NO 72
<211> LENGTH: 1560
<212> TYPE: DNA
<213> ORGANISM: Rasamsonia emersonii
<220> FEATURE:
<221> NAME/KEY: sig_peptide
<222> LOCATION: (1)..(54)
<220> FEATURE:
<221> NAME/KEY: CDS
<222> LOCATION: (1)..(1557)
<220> FEATURE:
<221> NAME/KEY: mat_peptide
<222> LOCATION: (55)..(1557)

<400> SEQUENCE: 72

```
atg ttg cga agg gcc ttg ttg ctc tcg tcc tcc gca atc ttg gcg gtc        48
Met Leu Arg Arg Ala Leu Leu Leu Ser Ser Ser Ala Ile Leu Ala Val
        -15                 -10                 -5 aag gca cag cag gca ggc acc gca acc gca gag aac cat cct ccg ctc        96
Lys Ala Gln Gln Ala Gly Thr Ala Thr Ala Glu Asn His Pro Pro Leu
 -1   1               5                  10 act tgg cag gaa tgt aca gca cct ggc tcc tgt aca acc cag aac gga       144
Thr Trp Gln Glu Cys Thr Ala Pro Gly Ser Cys Thr Thr Gln Asn Gly
```

```
              15                  20                  25                  30 gcg gtc gtg ctc gat gcg aac tgg cgc tgg gtg cac gat gtc aac gga      192
Ala Val Val Leu Asp Ala Asn Trp Arg Trp Val His Asp Val Asn Gly
                 35                  40                  45 tac aca aac tgt tat aca ggt aac acg tgg aac cct acg tat tgt ccc      240
Tyr Thr Asn Cys Tyr Thr Gly Asn Thr Trp Asn Pro Thr Tyr Cys Pro
             50                  55                  60 gac gac gaa acg tgt gcc cag aac tgt gcg ttg gat gga gca gac tac      288
Asp Asp Glu Thr Cys Ala Gln Asn Cys Ala Leu Asp Gly Ala Asp Tyr
         65                  70                  75 gag gga acg tat ggc gtg acc tcg tcc ggc tcc tcc ttg aag ctc aac      336
Glu Gly Thr Tyr Gly Val Thr Ser Ser Gly Ser Ser Leu Lys Leu Asn
     80                  85                  90 ttc gtc acg ggc tcg aac gtc ggc tcc cgc ttg tac ctc ctc cag gac      384
Phe Val Thr Gly Ser Asn Val Gly Ser Arg Leu Tyr Leu Leu Gln Asp
 95                 100                 105                 110 gac tcg acc tac cag atc ttc aag ctc ctc aac agg gag ttc acc ttc      432
Asp Ser Thr Tyr Gln Ile Phe Lys Leu Leu Asn Arg Glu Phe Thr Phe
                115                 120                 125 gac gtc gat gtc tcc aac ttg ccc tgt ggt ctc aac gga gcc ttg tac      480
Asp Val Asp Val Ser Asn Leu Pro Cys Gly Leu Asn Gly Ala Leu Tyr
            130                 135                 140 ttc gtc gcg atg gat gca gac gga ggt gtc tcg aag tac ccc aac aac      528
Phe Val Ala Met Asp Ala Asp Gly Gly Val Ser Lys Tyr Pro Asn Asn
        145                 150                 155 aag gca ggt gcc aag tat ggt act ggc tac tgt gat tcg cag tgt cct      576
Lys Ala Gly Ala Lys Tyr Gly Thr Gly Tyr Cys Asp Ser Gln Cys Pro
    160                 165                 170 cgc gat ctc aag ttc att gac ggt gag gcg aac gtg gaa gga tgg cag      624
Arg Asp Leu Lys Phe Ile Asp Gly Glu Ala Asn Val Glu Gly Trp Gln
175                 180                 185                 190 ccc tcg tcc aac aac gcg aac act ggc atc ggt gat cac ggt tcg tgt      672
Pro Ser Ser Asn Asn Ala Asn Thr Gly Ile Gly Asp His Gly Ser Cys
                195                 200                 205 tgt gcc gag atg gac gtc tgg gaa gcc aac tcc atc tcg aac gcg gtc      720
Cys Ala Glu Met Asp Val Trp Glu Ala Asn Ser Ile Ser Asn Ala Val
            210                 215                 220 aca ccg cac ccg tgt gat act cct ggc cag act atg tgt tcc gga gat      768
Thr Pro His Pro Cys Asp Thr Pro Gly Gln Thr Met Cys Ser Gly Asp
        225                 230                 235 gat tgt gga ggc acc tat tcg aac gac cgg tat gca ggc acg tgt gac      816
Asp Cys Gly Gly Thr Tyr Ser Asn Asp Arg Tyr Ala Gly Thr Cys Asp
    240                 245                 250 ccg gat ggc tgt gac ttc aac ccg tac cgc atg ggc aac acc tcc ttc      864
Pro Asp Gly Cys Asp Phe Asn Pro Tyr Arg Met Gly Asn Thr Ser Phe
255                 260                 265                 270 tat gga ccg ggt aag atc atc gat aca act aag ccc ttc acc gtc gtc      912
Tyr Gly Pro Gly Lys Ile Ile Asp Thr Thr Lys Pro Phe Thr Val Val
                275                 280                 285 acg cag ttc ctc aca gat gac ggc acg gac aca ggt act ttg tcg gag      960
Thr Gln Phe Leu Thr Asp Asp Gly Thr Asp Thr Gly Thr Leu Ser Glu
            290                 295                 300 atc aaa cgc ttc tac gtc cag aac gga aac gtc atc ccc cag ccg aac     1008
Ile Lys Arg Phe Tyr Val Gln Asn Gly Asn Val Ile Pro Gln Pro Asn
        305                 310                 315 tcc gac att tcg gga gtc aca ggc aac tcg att acg acc gag ttc tgt     1056
Ser Asp Ile Ser Gly Val Thr Gly Asn Ser Ile Thr Thr Glu Phe Cys
    320                 325                 330 aca gcc cag aaa cag gca ttc ggt gac acg gat gat ttc tcc cag cac     1104
```

```
Thr Ala Gln Lys Gln Ala Phe Gly Asp Thr Asp Phe Ser Gln His
335                 340                 345                 350 gga gga ttg gcg aaa atg gga gcc gca atg cag cag gga atg gtc ctc      1152
Gly Gly Leu Ala Lys Met Gly Ala Ala Met Gln Gln Gly Met Val Leu
                355                 360                 365 gtg atg tcg ctc tgg gac gac tat gca gcc cag atg ttg tgg ctc gac      1200
Val Met Ser Leu Trp Asp Asp Tyr Ala Ala Gln Met Leu Trp Leu Asp
            370                 375                 380 tcg gac tac ccc aca gac gcc gat ccc acg aca ccc ggt atc gca cga      1248
Ser Asp Tyr Pro Thr Asp Ala Asp Pro Thr Thr Pro Gly Ile Ala Arg
        385                 390                 395 ggc act tgt ccg aca gat tcc gga gtc ccg tcg gac gtc gag tcc cag      1296
Gly Thr Cys Pro Thr Asp Ser Gly Val Pro Ser Asp Val Glu Ser Gln
    400                 405                 410 tcc ccc aac tcg tac gtc acc tat tcg aac atc aaa ttc ggt ccc atc      1344
Ser Pro Asn Ser Tyr Val Thr Tyr Ser Asn Ile Lys Phe Gly Pro Ile
415                 420                 425                 430 aac tcg aca ttc aca gcc tcg ggt gga aac cct cct ggc gga aac cct      1392
Asn Ser Thr Phe Thr Ala Ser Gly Gly Asn Pro Pro Gly Gly Asn Pro
                435                 440                 445 cct ggc aca act aca aca cga cgg cct gcg act aca acg ggt tcg tcc      1440
Pro Gly Thr Thr Thr Thr Arg Arg Pro Ala Thr Thr Thr Gly Ser Ser
            450                 455                 460 cct gga ccg acc cag tcc cac tac gga cag tgt gga ggc atc ggt tat      1488
Pro Gly Pro Thr Gln Ser His Tyr Gly Gln Cys Gly Gly Ile Gly Tyr
        465                 470                 475 tcc ggt ccg acc gtc tgt gcg tcc ggc aca acc tgt cag gtc ttg aac      1536
Ser Gly Pro Thr Val Cys Ala Ser Gly Thr Thr Cys Gln Val Leu Asn
    480                 485                 490 cct tac tat tcg cag tgt ctc taa                                      1560
Pro Tyr Tyr Ser Gln Cys Leu
495                 500

<210> SEQ ID NO 73
<211> LENGTH: 519
<212> TYPE: PRT
<213> ORGANISM: Rasamsonia emersonii

<400> SEQUENCE: 73

Met Leu Arg Arg Ala Leu Leu Leu Ser Ser Ala Ile Leu Ala Val
            -15                 -10                 -5

Lys Ala Gln Gln Ala Gly Thr Ala Thr Ala Glu Asn His Pro Leu
    -1  1               5                   10

Thr Trp Gln Glu Cys Thr Ala Pro Gly Ser Cys Thr Thr Gln Asn Gly
15                  20                  25                  30

Ala Val Val Leu Asp Ala Asn Trp Arg Trp Val His Asp Val Asn Gly
                35                  40                  45

Tyr Thr Asn Cys Tyr Thr Gly Asn Thr Trp Asn Pro Thr Tyr Cys Pro
            50                  55                  60

Asp Asp Glu Thr Cys Ala Gln Asn Cys Ala Leu Asp Gly Ala Asp Tyr
        65                  70                  75

Glu Gly Thr Tyr Gly Val Thr Ser Ser Gly Ser Ser Leu Lys Leu Asn
    80                  85                  90

Phe Val Thr Gly Ser Asn Val Gly Ser Arg Leu Tyr Leu Leu Gln Asp
95                  100                 105                 110

Asp Ser Thr Tyr Gln Ile Phe Lys Leu Leu Asn Arg Glu Phe Thr Phe
                115                 120                 125

Asp Val Asp Val Ser Asn Leu Pro Cys Gly Leu Asn Gly Ala Leu Tyr
```

130                 135                 140
Phe Val Ala Met Asp Ala Asp Gly Gly Val Ser Lys Tyr Pro Asn Asn
            145                 150                 155

Lys Ala Gly Ala Lys Tyr Gly Thr Gly Tyr Cys Asp Ser Gln Cys Pro
160                 165                 170

Arg Asp Leu Lys Phe Ile Asp Gly Glu Ala Asn Val Glu Gly Trp Gln
175                 180                 185                 190

Pro Ser Ser Asn Asn Ala Asn Thr Gly Ile Gly Asp His Gly Ser Cys
                195                 200                 205

Cys Ala Glu Met Asp Val Trp Glu Ala Asn Ser Ile Ser Asn Ala Val
            210                 215                 220

Thr Pro His Pro Cys Asp Thr Pro Gly Gln Thr Met Cys Ser Gly Asp
        225                 230                 235

Asp Cys Gly Gly Thr Tyr Ser Asn Asp Arg Tyr Ala Gly Thr Cys Asp
240                 245                 250

Pro Asp Gly Cys Asp Phe Asn Pro Tyr Arg Met Gly Asn Thr Ser Phe
255                 260                 265                 270

Tyr Gly Pro Gly Lys Ile Ile Asp Thr Thr Lys Pro Phe Thr Val Val
                275                 280                 285

Thr Gln Phe Leu Thr Asp Asp Gly Thr Asp Thr Gly Thr Leu Ser Glu
            290                 295                 300

Ile Lys Arg Phe Tyr Val Gln Asn Gly Asn Val Ile Pro Gln Pro Asn
        305                 310                 315

Ser Asp Ile Ser Gly Val Thr Gly Asn Ser Ile Thr Thr Glu Phe Cys
320                 325                 330

Thr Ala Gln Lys Gln Ala Phe Gly Asp Thr Asp Asp Phe Ser Gln His
335                 340                 345                 350

Gly Gly Leu Ala Lys Met Gly Ala Ala Met Gln Gln Gly Met Val Leu
                355                 360                 365

Val Met Ser Leu Trp Asp Asp Tyr Ala Ala Gln Met Leu Trp Leu Asp
            370                 375                 380

Ser Asp Tyr Pro Thr Asp Ala Asp Pro Thr Thr Pro Gly Ile Ala Arg
        385                 390                 395

Gly Thr Cys Pro Thr Asp Ser Gly Val Pro Ser Asp Val Glu Ser Gln
400                 405                 410

Ser Pro Asn Ser Tyr Val Thr Tyr Ser Asn Ile Lys Phe Gly Pro Ile
415                 420                 425                 430

Asn Ser Thr Phe Thr Ala Ser Gly Gly Asn Pro Pro Gly Gly Asn Pro
                435                 440                 445

Pro Gly Thr Thr Thr Thr Arg Arg Pro Ala Thr Thr Thr Gly Ser Ser
            450                 455                 460

Pro Gly Pro Thr Gln Ser His Tyr Gly Gln Cys Gly Gly Ile Gly Tyr
        465                 470                 475

Ser Gly Pro Thr Val Cys Ala Ser Gly Thr Thr Cys Gln Val Leu Asn
480                 485                 490

Pro Tyr Tyr Ser Gln Cys Leu
495                 500

<210> SEQ ID NO 74
<211> LENGTH: 58
<212> TYPE: DNA
<213> ORGANISM: Artificial Sequence
<220> FEATURE:
<223> OTHER INFORMATION: Artificial DNA Primer -continued

```
<400> SEQUENCE: 74
ggtcccatca actcgacatt cacagcctcg ggtggaaacc ctcctggcgg aaaccctc          58

<210> SEQ ID NO 75
<211> LENGTH: 1560
<212> TYPE: DNA
<213> ORGANISM: Rasamsonia emersonii
<220> FEATURE:
<221> NAME/KEY: sig_peptide
<222> LOCATION: (1)..(54)
<220> FEATURE:
<221> NAME/KEY: CDS
<222> LOCATION: (1)..(1557)
<220> FEATURE:
<221> NAME/KEY: mat_peptide
<222> LOCATION: (55)..(1557)

<400> SEQUENCE: 75 atg ttg cga agg gcc ttg ttg ctc tcg tcc tcc gca atc ttg gcg gtc          48
Met Leu Arg Arg Ala Leu Leu Leu Ser Ser Ser Ala Ile Leu Ala Val
            -15                 -10                  -5 aag gca cag cag gca ggc acc gca acc gca gag aac cat cct ccg ctc          96
Lys Ala Gln Gln Ala Gly Thr Ala Thr Ala Glu Asn His Pro Pro Leu
 -1   1               5                  10 act tgg cag gaa tgt aca gca cct ggc tcc tgt aca acc cag aac gga         144
Thr Trp Gln Glu Cys Thr Ala Pro Gly Ser Cys Thr Thr Gln Asn Gly
 15                  20                  25                  30 gcg gtc gtg ctc gat gcg aac tgg cgc tgg gtg cac gat gtc aac gga         192
Ala Val Val Leu Asp Ala Asn Trp Arg Trp Val His Asp Val Asn Gly
                 35                  40                  45 tac aca aac tgt tat aca ggt aac acg tgg aac cct acg tat tgt ccc         240
Tyr Thr Asn Cys Tyr Thr Gly Asn Thr Trp Asn Pro Thr Tyr Cys Pro
             50                  55                  60 gac gac gaa acg tgt gcc cag aac tgt gcg ttg gat gga gca gac tac         288
Asp Asp Glu Thr Cys Ala Gln Asn Cys Ala Leu Asp Gly Ala Asp Tyr
 65                  70                  75 gag gga acg tat ggc gtg acc tcg tcc ggc tcc tcc ttg aag ctc aac         336
Glu Gly Thr Tyr Gly Val Thr Ser Ser Gly Ser Ser Leu Lys Leu Asn
         80                  85                  90 ttc gtc acg ggc tcg aac gtc ggc tcc cgc ttg tac ctc ctc cag gac         384
Phe Val Thr Gly Ser Asn Val Gly Ser Arg Leu Tyr Leu Leu Gln Asp
 95                 100                 105                 110 gac tcg acc tac cag atc ttc aag ctc ctc aac agg gag ttc acc ttc         432
Asp Ser Thr Tyr Gln Ile Phe Lys Leu Leu Asn Arg Glu Phe Thr Phe
                115                 120                 125 gac gtc gat gtc tcc aac ttg ccc tgt ggt ctc aac gga gcc ttg tac         480
Asp Val Asp Val Ser Asn Leu Pro Cys Gly Leu Asn Gly Ala Leu Tyr
            130                 135                 140 ttc gtc gcg atg gat gca gac gga ggt gtc tcg aag tac ccc aac aac         528
Phe Val Ala Met Asp Ala Asp Gly Gly Val Ser Lys Tyr Pro Asn Asn
        145                 150                 155 aag gca ggt gcc aag tat ggt act ggc tac tgt gat tcg cag tgt cct         576
Lys Ala Gly Ala Lys Tyr Gly Thr Gly Tyr Cys Asp Ser Gln Cys Pro
    160                 165                 170 cgc gat ctc aag ttc att gac ggt gag gcg aac gtg gaa gga tgg cag         624
Arg Asp Leu Lys Phe Ile Asp Gly Glu Ala Asn Val Glu Gly Trp Gln
175                 180                 185                 190 ccc tcg tcc gca aac gcg gca act ggc atc ggt gat cac ggt tcg tgt         672
Pro Ser Ser Ala Asn Ala Ala Thr Gly Ile Gly Asp His Gly Ser Cys
                195                 200                 205 tgt gcc gag atg gac gtc tgg gaa gcc aac tcc atc tcg aac gcg gtc         720
Cys Ala Glu Met Asp Val Trp Glu Ala Asn Ser Ile Ser Asn Ala Val
```

```
aca ccg cac ccg tgt gat act cct ggc cag act atg tgt tcc gga gat    768
Thr Pro His Pro Cys Asp Thr Pro Gly Gln Thr Met Cys Ser Gly Asp
            225                 230                 235 gat tgt gga ggc acc tat tcg aac gac cgg tat gca ggc acg tgt gac    816
Asp Cys Gly Gly Thr Tyr Ser Asn Asp Arg Tyr Ala Gly Thr Cys Asp
        240                 245                 250 ccg gat ggc tgt gac ttc aac ccg tac cgc atg ggc aac acc tcc ttc    864
Pro Asp Gly Cys Asp Phe Asn Pro Tyr Arg Met Gly Asn Thr Ser Phe
255                 260                 265                 270 tat gga ccg ggt aag atc atc gat aca act aag ccc ttc acc gtc gtc    912
Tyr Gly Pro Gly Lys Ile Ile Asp Thr Thr Lys Pro Phe Thr Val Val
                275                 280                 285 acg cag ttc ctc aca gat gac ggc acg gac aca ggt act ttg tcg gag    960
Thr Gln Phe Leu Thr Asp Asp Gly Thr Asp Thr Gly Thr Leu Ser Glu
            290                 295                 300 atc aaa cgc ttc tac gtc cag aac gga aac gtc atc ccc cag ccg aac   1008
Ile Lys Arg Phe Tyr Val Gln Asn Gly Asn Val Ile Pro Gln Pro Asn
        305                 310                 315 tcc gac att tcg gga gtc aca ggc aac tcg att acg acc gag ttc tgt   1056
Ser Asp Ile Ser Gly Val Thr Gly Asn Ser Ile Thr Thr Glu Phe Cys
320                 325                 330 aca gcc cag aaa cag gca ttc ggt gac acg gat gat ttc tcc cag cac   1104
Thr Ala Gln Lys Gln Ala Phe Gly Asp Thr Asp Asp Phe Ser Gln His
335                 340                 345                 350 gga gga ttg gcg aaa atg gga gcc gca atg cag cag gga atg gtc ctc   1152
Gly Gly Leu Ala Lys Met Gly Ala Ala Met Gln Gln Gly Met Val Leu
                355                 360                 365 gtg atg tcg ctc tgg gac gac tat gca gcc cag atg ttg tgg ctc gac   1200
Val Met Ser Leu Trp Asp Asp Tyr Ala Ala Gln Met Leu Trp Leu Asp
            370                 375                 380 tcg gac tac ccc aca gac gcc gat ccc acg aca ccc ggt atc gca cga   1248
Ser Asp Tyr Pro Thr Asp Ala Asp Pro Thr Thr Pro Gly Ile Ala Arg
        385                 390                 395 ggc act tgt ccg aca gat tcc gga gtc ccg tcg gac gtc gag tcc cag   1296
Gly Thr Cys Pro Thr Asp Ser Gly Val Pro Ser Asp Val Glu Ser Gln
400                 405                 410 tcc ccc aac tcg tac gtc acc tat tcg aac atc aaa ttc ggt ccc atc   1344
Ser Pro Asn Ser Tyr Val Thr Tyr Ser Asn Ile Lys Phe Gly Pro Ile
415                 420                 425                 430 aac tcg aca ttc aca gcc tcg ggt gga aac cct cct ggc gga aac cct   1392
Asn Ser Thr Phe Thr Ala Ser Gly Gly Asn Pro Pro Gly Gly Asn Pro
                435                 440                 445 cct ggc aca act aca aca cga cgg cct gcg act aca acg ggt tcg tcc   1440
Pro Gly Thr Thr Thr Thr Arg Arg Pro Ala Thr Thr Thr Gly Ser Ser
            450                 455                 460 cct gga ccg acc cag tcc cac tac gga cag tgt gga ggc atc ggt tat   1488
Pro Gly Pro Thr Gln Ser His Tyr Gly Gln Cys Gly Gly Ile Gly Tyr
        465                 470                 475 tcc ggt ccg acc gtc tgt gcg tcc ggc aca acc tgt cag gtc ttg aac   1536
Ser Gly Pro Thr Val Cys Ala Ser Gly Thr Thr Cys Gln Val Leu Asn
480                 485                 490 cct tac tat tcg cag tgt ctc taa                                    1560
Pro Tyr Tyr Ser Gln Cys Leu
495                 500

<210> SEQ ID NO 76
<211> LENGTH: 519
<212> TYPE: PRT
<213> ORGANISM: Rasamsonia emersonii
```

<400> SEQUENCE: 76

```
Met Leu Arg Arg Ala Leu Leu Leu Ser Ser Ala Ile Leu Ala Val
            -15                 -10                  -5
Lys Ala Gln Gln Ala Gly Thr Ala Thr Ala Glu Asn His Pro Pro Leu
 -1   1               5                  10
Thr Trp Gln Glu Cys Thr Ala Pro Gly Ser Cys Thr Thr Gln Asn Gly
 15              20                  25                  30
Ala Val Val Leu Asp Ala Asn Trp Arg Trp Val His Asp Val Asn Gly
                 35                  40                  45
Tyr Thr Asn Cys Tyr Thr Gly Asn Thr Trp Asn Pro Thr Tyr Cys Pro
             50                  55                  60
Asp Asp Glu Thr Cys Ala Gln Asn Cys Ala Leu Asp Gly Ala Asp Tyr
             65                  70                  75
Glu Gly Thr Tyr Gly Val Thr Ser Ser Gly Ser Ser Leu Lys Leu Asn
         80                  85                  90
Phe Val Thr Gly Ser Asn Val Gly Ser Arg Leu Tyr Leu Leu Gln Asp
 95                 100                 105                 110
Asp Ser Thr Tyr Gln Ile Phe Lys Leu Leu Asn Arg Glu Phe Thr Phe
                115                 120                 125
Asp Val Asp Val Ser Asn Leu Pro Cys Gly Leu Asn Gly Ala Leu Tyr
            130                 135                 140
Phe Val Ala Met Asp Ala Asp Gly Gly Val Ser Lys Tyr Pro Asn Asn
                145                 150                 155
Lys Ala Gly Ala Lys Tyr Gly Thr Gly Tyr Cys Asp Ser Gln Cys Pro
160                 165                 170
Arg Asp Leu Lys Phe Ile Asp Gly Glu Ala Asn Val Glu Gly Trp Gln
175                 180                 185                 190
Pro Ser Ser Ala Asn Ala Ala Thr Gly Ile Gly Asp His Gly Ser Cys
                195                 200                 205
Cys Ala Glu Met Asp Val Trp Glu Ala Asn Ser Ile Ser Asn Ala Val
            210                 215                 220
Thr Pro His Pro Cys Asp Thr Pro Gly Gln Thr Met Cys Ser Gly Asp
            225                 230                 235
Asp Cys Gly Gly Thr Tyr Ser Asn Asp Arg Tyr Ala Gly Thr Cys Asp
240                 245                 250
Pro Asp Gly Cys Asp Phe Asn Pro Tyr Arg Met Gly Asn Thr Ser Phe
255                 260                 265                 270
Tyr Gly Pro Gly Lys Ile Ile Asp Thr Thr Lys Pro Phe Thr Val Val
                275                 280                 285
Thr Gln Phe Leu Thr Asp Asp Gly Thr Asp Thr Gly Thr Leu Ser Glu
            290                 295                 300
Ile Lys Arg Phe Tyr Val Gln Asn Gly Asn Val Ile Pro Gln Pro Asn
        305                 310                 315
Ser Asp Ile Ser Gly Val Thr Gly Asn Ser Ile Thr Thr Glu Phe Cys
        320                 325                 330
Thr Ala Gln Lys Gln Ala Phe Gly Asp Thr Asp Asp Phe Ser Gln His
335                 340                 345                 350
Gly Gly Leu Ala Lys Met Gly Ala Ala Met Gln Gln Gly Met Val Leu
                355                 360                 365
Val Met Ser Leu Trp Asp Asp Tyr Ala Ala Gln Met Leu Trp Leu Asp
            370                 375                 380
Ser Asp Tyr Pro Thr Asp Ala Asp Pro Thr Thr Pro Gly Ile Ala Arg
```

```
                    385                 390                 395
Gly Thr Cys Pro Thr Asp Ser Gly Val Pro Ser Asp Val Glu Ser Gln
400                 405                 410

Ser Pro Asn Ser Tyr Val Thr Tyr Ser Asn Ile Lys Phe Gly Pro Ile
415                 420                 425                 430

Asn Ser Thr Phe Thr Ala Ser Gly Gly Asn Pro Pro Gly Gly Asn Pro
                435                 440                 445

Pro Gly Thr Thr Thr Thr Arg Arg Pro Ala Thr Thr Thr Gly Ser Ser
            450                 455                 460

Pro Gly Pro Thr Gln Ser His Tyr Gly Gln Cys Gly Gly Ile Gly Tyr
        465                 470                 475

Ser Gly Pro Thr Val Cys Ala Ser Gly Thr Thr Cys Gln Val Leu Asn
    480                 485                 490

Pro Tyr Tyr Ser Gln Cys Leu
495                 500

<210> SEQ ID NO 77
<211> LENGTH: 1551
<212> TYPE: DNA
<213> ORGANISM: Penicillium emersonii
<220> FEATURE:
<221> NAME/KEY: sig_peptide
<222> LOCATION: (1)..(54)
<220> FEATURE:
<221> NAME/KEY: CDS
<222> LOCATION: (1)..(1548)
<220> FEATURE:
<221> NAME/KEY: mat_peptide
<222> LOCATION: (55)..(1548)

<400> SEQUENCE: 77 atg ttg cga agg gcc ttg ttg ctc tcg tcc tcc gca atc ttg gcg gtc         48
Met Leu Arg Arg Ala Leu Leu Leu Ser Ser Ser Ala Ile Leu Ala Val
            -15                 -10                  -5 aag gca cag cag gca ggc acc gca acc gca gag aac cat cct ccg ctc         96
Lys Ala Gln Gln Ala Gly Thr Ala Thr Ala Glu Asn His Pro Pro Leu
    -1   1                   5                  10 act tgg cag gaa tgt aca gca cct ggc tcc tgt aca acc cag aac gga        144
Thr Trp Gln Glu Cys Thr Ala Pro Gly Ser Cys Thr Thr Gln Asn Gly
 15                  20                  25                  30 gcg gtc gtg ctc gat gcg aac tgg cgc tgg gtg cac gat gtc aac gga        192
Ala Val Val Leu Asp Ala Asn Trp Arg Trp Val His Asp Val Asn Gly
                 35                  40                  45 tac aca aac tgt tat aca ggt aac acg tgg aac cct acg tat tgt ccc        240
Tyr Thr Asn Cys Tyr Thr Gly Asn Thr Trp Asn Pro Thr Tyr Cys Pro
             50                  55                  60 gac gac gaa acg tgt gcc cag aac tgt gcg ttg gat gga gca gac tac        288
Asp Asp Glu Thr Cys Ala Gln Asn Cys Ala Leu Asp Gly Ala Asp Tyr
         65                  70                  75 gag gga acg tat ggc gtg acc tcg tcc ggc tcc tcc ttg aag ctc aac        336
Glu Gly Thr Tyr Gly Val Thr Ser Ser Gly Ser Ser Leu Lys Leu Asn
 80                  85                  90 ttc gtc acg ggc tcg aac gtc ggc tcc cgc ttg tac ctc ctc cag gac        384
Phe Val Thr Gly Ser Asn Val Gly Ser Arg Leu Tyr Leu Leu Gln Asp
 95                 100                 105                 110 gac tcg acc tac cag atc ttc aag ctc ctc aac agg gag ttc acc ttc        432
Asp Ser Thr Tyr Gln Ile Phe Lys Leu Leu Asn Arg Glu Phe Thr Phe
                 115                 120                 125 gac gtc gat gtc tcc aac ttg ccc tgt ggt ctc aac gga gcc ttg tac        480
Asp Val Asp Val Ser Asn Leu Pro Cys Gly Leu Asn Gly Ala Leu Tyr
             130                 135                 140
```

```
ttc gtc gcg atg gat gca gac gga ggt gtc tcg aag tac ccc aac aac      528
Phe Val Ala Met Asp Ala Asp Gly Gly Val Ser Lys Tyr Pro Asn Asn
            145                 150                 155 aag gca ggt gcc aag tat ggt act ggc tac tgt gat tcg cag tgt cct      576
Lys Ala Gly Ala Lys Tyr Gly Thr Gly Tyr Cys Asp Ser Gln Cys Pro
    160                 165                 170 cgc gat ctc aag ttc att gac ggt gag gcg aac gtg gaa gga tgg cag      624
Arg Asp Leu Lys Phe Ile Asp Gly Glu Ala Asn Val Glu Gly Trp Gln
175                 180                 185                 190 ccc tcg gcg aac act ggc atc ggt gat cac ggt tcg tgt tgt gcc gag      672
Pro Ser Ala Asn Thr Gly Ile Gly Asp His Gly Ser Cys Cys Ala Glu
                195                 200                 205 atg gac gtc tgg gaa gcc aac tcc atc tcg aac gcg gtc aca ccg cac      720
Met Asp Val Trp Glu Ala Asn Ser Ile Ser Asn Ala Val Thr Pro His
            210                 215                 220 ccg tgt gat act cct ggc cag act atg tgt tcc gga gat gat tgt gga      768
Pro Cys Asp Thr Pro Gly Gln Thr Met Cys Ser Gly Asp Asp Cys Gly
        225                 230                 235 ggc acc tat tcg aac gac cgg tat gca ggc acg tgt gac ccg gat ggc      816
Gly Thr Tyr Ser Asn Asp Arg Tyr Ala Gly Thr Cys Asp Pro Asp Gly
    240                 245                 250 tgt gac ttc aac ccg tac cgc atg ggc aac acc tcc ttc tat gga ccg      864
Cys Asp Phe Asn Pro Tyr Arg Met Gly Asn Thr Ser Phe Tyr Gly Pro
255                 260                 265                 270 ggt aag atc atc gat aca act aag ccc ttc acc gtc gtc acg cag ttc      912
Gly Lys Ile Ile Asp Thr Thr Lys Pro Phe Thr Val Val Thr Gln Phe
                275                 280                 285 ctc aca gat gac ggc acg gac aca ggt act ttg tcg gag atc aaa cgc      960
Leu Thr Asp Asp Gly Thr Asp Thr Gly Thr Leu Ser Glu Ile Lys Arg
            290                 295                 300 ttc tac gtc cag aac gga aac gtc atc ccc cag ccg aac tcc gac att     1008
Phe Tyr Val Gln Asn Gly Asn Val Ile Pro Gln Pro Asn Ser Asp Ile
        305                 310                 315 tcg gga gtc aca ggc aac tcg att acg acc gag ttc tgt aca gcc cag     1056
Ser Gly Val Thr Gly Asn Ser Ile Thr Thr Glu Phe Cys Thr Ala Gln
    320                 325                 330 aaa cag gca ttc ggt gac acg gat gat ttc tcc cag cac gga gga ttg     1104
Lys Gln Ala Phe Gly Asp Thr Asp Asp Phe Ser Gln His Gly Gly Leu
335                 340                 345                 350 gcg aaa atg gga gcc gca atg cag cag gga atg gtc ctc gtg atg tcg     1152
Ala Lys Met Gly Ala Ala Met Gln Gln Gly Met Val Leu Val Met Ser
                355                 360                 365 ctc tgg gac gac tat gca gcc cag atg ttg tgg ctc gac tcg gac tac     1200
Leu Trp Asp Asp Tyr Ala Ala Gln Met Leu Trp Leu Asp Ser Asp Tyr
            370                 375                 380 ccc aca gac gcc gat ccc acg aca ccc ggt atc gca cga ggc act tgt     1248
Pro Thr Asp Ala Asp Pro Thr Thr Pro Gly Ile Ala Arg Gly Thr Cys
        385                 390                 395 ccg aca gat tcc gga gtc ccg tcg gac gtc gag tcc cag tcc ccc aac     1296
Pro Thr Asp Ser Gly Val Pro Ser Asp Val Glu Ser Gln Ser Pro Asn
    400                 405                 410 tcg tac gtc acc tat tcg aac atc aaa ttc ggt ccc atc aac tcg aca     1344
Ser Tyr Val Thr Tyr Ser Asn Ile Lys Phe Gly Pro Ile Asn Ser Thr
415                 420                 425                 430 ttc aca gcc tcg ggt gga aac cct cct ggc gga aac cct cct ggc aca     1392
Phe Thr Ala Ser Gly Gly Asn Pro Pro Gly Gly Asn Pro Pro Gly Thr
                435                 440                 445 act aca aca cga cgg cct gcg act aca acg ggt tcg tcc cct gga ccg     1440
Thr Thr Thr Arg Arg Pro Ala Thr Thr Thr Gly Ser Ser Pro Gly Pro
```

```
                     450                 455                 460
acc cag tcc cac tac gga cag tgt gga ggc atc ggt tat tcc ggt ccg          1488
Thr Gln Ser His Tyr Gly Gln Cys Gly Gly Ile Gly Tyr Ser Gly Pro
        465                 470                 475 acc gtc tgt gcg tcc ggc aca acc tgt cag gtc ttg aac cct tac tat          1536
Thr Val Cys Ala Ser Gly Thr Thr Cys Gln Val Leu Asn Pro Tyr Tyr
    480                 485                 490 tcg cag tgt ctc taa                                                      1551
Ser Gln Cys Leu
495

<210> SEQ ID NO 78
<211> LENGTH: 516
<212> TYPE: PRT
<213> ORGANISM: Penicillium emersonii

<400> SEQUENCE: 78

Met Leu Arg Arg Ala Leu Leu Leu Ser Ser Ala Ile Leu Ala Val
                -15                 -10                 -5

Lys Ala Gln Gln Ala Gly Thr Ala Thr Ala Glu Asn His Pro Pro Leu
 -1   1                   5                  10

Thr Trp Gln Glu Cys Thr Ala Pro Gly Ser Cys Thr Thr Gln Asn Gly
 15                  20                  25                  30

Ala Val Val Leu Asp Ala Asn Trp Arg Trp Val His Asp Val Asn Gly
                 35                  40                  45

Tyr Thr Asn Cys Tyr Thr Gly Asn Thr Trp Asn Pro Thr Tyr Cys Pro
                 50                  55                  60

Asp Asp Glu Thr Cys Ala Gln Asn Cys Ala Leu Asp Gly Ala Asp Tyr
                 65                  70                  75

Glu Gly Thr Tyr Gly Val Thr Ser Ser Gly Ser Ser Leu Lys Leu Asn
 80                  85                  90

Phe Val Thr Gly Ser Asn Val Gly Ser Arg Leu Tyr Leu Leu Gln Asp
 95                 100                 105                 110

Asp Ser Thr Tyr Gln Ile Phe Lys Leu Leu Asn Arg Glu Phe Thr Phe
                115                 120                 125

Asp Val Asp Val Ser Asn Leu Pro Cys Gly Leu Asn Gly Ala Leu Tyr
                130                 135                 140

Phe Val Ala Met Asp Ala Asp Gly Gly Val Ser Lys Tyr Pro Asn Asn
                145                 150                 155

Lys Ala Gly Ala Lys Tyr Gly Thr Gly Tyr Cys Asp Ser Gln Cys Pro
160                 165                 170

Arg Asp Leu Lys Phe Ile Asp Gly Glu Ala Asn Val Glu Gly Trp Gln
175                 180                 185                 190

Pro Ser Ala Asn Thr Gly Ile Gly Asp His Gly Ser Cys Cys Ala Glu
                195                 200                 205

Met Asp Val Trp Glu Ala Asn Ser Ile Ser Asn Ala Val Thr Pro His
                210                 215                 220

Pro Cys Asp Thr Pro Gly Gln Thr Met Cys Ser Gly Asp Cys Gly
                225                 230                 235

Gly Thr Tyr Ser Asn Asp Arg Tyr Ala Gly Thr Cys Asp Pro Asp Gly
240                 245                 250

Cys Asp Phe Asn Pro Tyr Arg Met Gly Asn Thr Ser Phe Tyr Gly Pro
255                 260                 265                 270

Gly Lys Ile Ile Asp Thr Thr Lys Pro Phe Thr Val Val Thr Gln Phe
                275                 280                 285
```

```
Leu Thr Asp Asp Gly Thr Asp Thr Gly Thr Leu Ser Glu Ile Lys Arg
        290                 295                 300

Phe Tyr Val Gln Asn Gly Asn Val Ile Pro Gln Pro Asn Ser Asp Ile
            305                 310                 315

Ser Gly Val Thr Gly Asn Ser Ile Thr Thr Glu Phe Cys Thr Ala Gln
        320                 325                 330

Lys Gln Ala Phe Gly Asp Thr Asp Phe Ser Gln His Gly Gly Leu
335                 340                 345                 350

Ala Lys Met Gly Ala Met Gln Gln Gly Met Val Leu Val Met Ser
                355                 360                 365

Leu Trp Asp Asp Tyr Ala Ala Gln Met Leu Trp Leu Asp Ser Asp Tyr
        370                 375                 380

Pro Thr Asp Ala Asp Pro Thr Thr Pro Gly Ile Ala Arg Gly Thr Cys
            385                 390                 395

Pro Thr Asp Ser Gly Val Pro Ser Asp Val Glu Ser Gln Ser Pro Asn
        400                 405                 410

Ser Tyr Val Thr Tyr Ser Asn Ile Lys Phe Gly Pro Ile Asn Ser Thr
415                 420                 425                 430

Phe Thr Ala Ser Gly Gly Asn Pro Pro Gly Gly Asn Pro Pro Gly Thr
                435                 440                 445

Thr Thr Thr Arg Arg Pro Ala Thr Thr Thr Gly Ser Ser Pro Gly Pro
            450                 455                 460

Thr Gln Ser His Tyr Gly Gln Cys Gly Gly Ile Gly Tyr Ser Gly Pro
                465                 470                 475

Thr Val Cys Ala Ser Gly Thr Thr Cys Gln Val Leu Asn Pro Tyr Tyr
        480                 485                 490

Ser Gln Cys Leu
495

<210> SEQ ID NO 79
<211> LENGTH: 1539
<212> TYPE: DNA
<213> ORGANISM: Trichoderma reesei
<220> FEATURE:
<221> NAME/KEY: sig_peptide
<222> LOCATION: (1)..(17)
<220> FEATURE:
<221> NAME/KEY: CDS
<222> LOCATION: (1)..(1536)
<220> FEATURE:
<221> NAME/KEY: mat_peptide
<222> LOCATION: (52)..(1536)

<400> SEQUENCE: 79 atg tat cgt aag ctc gca gtc atc tcc gcg ttc ctc gca aca gca cga      48
Met Tyr Arg Lys Leu Ala Val Ile Ser Ala Phe Leu Ala Thr Ala Arg
        -15                 -10                  -5 gcg cag tcc gcc tgt acc ttg cag tcg gaa aca cat cct ccc ctc act      96
Ala Gln Ser Ala Cys Thr Leu Gln Ser Glu Thr His Pro Pro Leu Thr
 -1  1               5                  10                  15 tgg cag aaa tgt tcg tcc gga gga acg tgt acg cag cag act ggc tcg     144
Trp Gln Lys Cys Ser Ser Gly Gly Thr Cys Thr Gln Gln Thr Gly Ser
                20                  25                  30 gtg gtc atc gac gcc aac tgg agg tgg acg cat gca acc aac tcc tcc     192
Val Val Ile Asp Ala Asn Trp Arg Trp Thr His Ala Thr Asn Ser Ser
            35                  40                  45 acc aac tgt tac gat ggc aac act tgg tcc tcc acc ttg tgt ccc gat     240
Thr Asn Cys Tyr Asp Gly Asn Thr Trp Ser Ser Thr Leu Cys Pro Asp
        50                  55                  60
```

-continued

| | | | | | | | | | | | | | | | | |
|---|---|---|---|---|---|---|---|---|---|---|---|---|---|---|---|---|
| aac | gaa | acc | tgt | gcc | aag | aac | tgt | tgt | ttg | gat | ggt | gca | gcc | tac | gcc | 288 |
| Asn | Glu | Thr | Cys | Ala | Lys | Asn | Cys | Cys | Leu | Asp | Gly | Ala | Ala | Tyr | Ala | |
| 65 | | | | 70 | | | | | 75 | | | | | | | |

| tcg | aca | tac | gga | gtc | act | act | tcc | ggc | aac | tcg | ctc | tcg | atc | ggc | ttc | 336 |
| Ser | Thr | Tyr | Gly | Val | Thr | Thr | Ser | Gly | Asn | Ser | Leu | Ser | Ile | Gly | Phe | |
| 80 | | | | | 85 | | | | | 90 | | | | | 95 | |

| gtg | act | cag | tcc | gca | cag | aaa | aac | gtc | gga | gcg | cga | ctc | tac | ttg | atg | 384 |
| Val | Thr | Gln | Ser | Ala | Gln | Lys | Asn | Val | Gly | Ala | Arg | Leu | Tyr | Leu | Met | |
| | | | | 100 | | | | | 105 | | | | | 110 | | |

| gca | tcc | gat | aca | acc | tac | cag | gaa | ttc | act | ctc | ttg | ggc | aac | gag | ttc | 432 |
| Ala | Ser | Asp | Thr | Thr | Tyr | Gln | Glu | Phe | Thr | Leu | Leu | Gly | Asn | Glu | Phe | |
| | | | 115 | | | | | 120 | | | | | 125 | | | |

| tcc | ttc | gac | gtc | gac | gtc | tcc | cag | ctc | cct | tgt | ggc | ctc | aac | gga | gca | 480 |
| Ser | Phe | Asp | Val | Asp | Val | Ser | Gln | Leu | Pro | Cys | Gly | Leu | Asn | Gly | Ala | |
| | | | 130 | | | | | 135 | | | | | 140 | | | |

| ctc | tac | ttc | gtg | tcg | atg | gac | gcg | gat | gga | ggt | gtc | tcc | aag | tac | ccg | 528 |
| Leu | Tyr | Phe | Val | Ser | Met | Asp | Ala | Asp | Gly | Gly | Val | Ser | Lys | Tyr | Pro | |
| | 145 | | | | | 150 | | | | | 155 | | | | | |

| acc | aac | aca | gca | gga | gcg | aaa | tac | ggc | acg | ggt | tac | tgt | gac | tcg | cag | 576 |
| Thr | Asn | Thr | Ala | Gly | Ala | Lys | Tyr | Gly | Thr | Gly | Tyr | Cys | Asp | Ser | Gln | |
| 160 | | | | | 165 | | | | | 170 | | | | | 175 | |

| tgt | cct | cgc | gat | ctc | aag | ttc | atc | aac | ggc | cag | gca | aac | gtc | gaa | ggc | 624 |
| Cys | Pro | Arg | Asp | Leu | Lys | Phe | Ile | Asn | Gly | Gln | Ala | Asn | Val | Glu | Gly | |
| | | | | 180 | | | | | 185 | | | | | 190 | | |

| tgg | gaa | ccc | tcg | tcg | gcc | aac | acc | ggc | att | gga | ggc | cat | ggc | tcc | tgt | 672 |
| Trp | Glu | Pro | Ser | Ser | Ala | Asn | Thr | Gly | Ile | Gly | Gly | His | Gly | Ser | Cys | |
| | | | 195 | | | | | 200 | | | | | 205 | | | |

| tgt | tcg | gaa | atg | gat | atc | tgg | gag | gcc | aac | tcg | atc | tcc | gag | gca | ctc | 720 |
| Cys | Ser | Glu | Met | Asp | Ile | Trp | Glu | Ala | Asn | Ser | Ile | Ser | Glu | Ala | Leu | |
| | | | 210 | | | | | 215 | | | | | 220 | | | |

| aca | ccc | cac | ccc | tgt | aca | acc | gtc | ggc | cag | gag | att | tgt | gaa | gga | gac | 768 |
| Thr | Pro | His | Pro | Cys | Thr | Thr | Val | Gly | Gln | Glu | Ile | Cys | Glu | Gly | Asp | |
| | 225 | | | | | 230 | | | | | 235 | | | | | |

| ggc | tgt | ggc | gga | act | tac | tcc | gat | aac | cgt | tac | ggt | ggt | acc | tgt | gat | 816 |
| Gly | Cys | Gly | Gly | Thr | Tyr | Ser | Asp | Asn | Arg | Tyr | Gly | Gly | Thr | Cys | Asp | |
| 240 | | | | | 245 | | | | | 250 | | | | | 255 | |

| ccc | gat | ggc | tgt | gac | tgg | aac | ccc | tac | cgc | ctc | ggt | aac | aca | tcg | ttc | 864 |
| Pro | Asp | Gly | Cys | Asp | Trp | Asn | Pro | Tyr | Arg | Leu | Gly | Asn | Thr | Ser | Phe | |
| | | | | 260 | | | | | 265 | | | | | 270 | | |

| tac | ggt | ccg | ggt | tcc | tcc | ttc | acc | ctc | gac | act | acc | aaa | aag | ttg | acg | 912 |
| Tyr | Gly | Pro | Gly | Ser | Ser | Phe | Thr | Leu | Asp | Thr | Thr | Lys | Lys | Leu | Thr | |
| | | | 275 | | | | | 280 | | | | | 285 | | | |

| gtg | gtc | acg | cag | ttc | gag | act | tcc | gga | gcc | atc | aac | cgg | tac | tac | gtg | 960 |
| Val | Val | Thr | Gln | Phe | Glu | Thr | Ser | Gly | Ala | Ile | Asn | Arg | Tyr | Tyr | Val | |
| | | 290 | | | | | 295 | | | | | 300 | | | | |

| cag | aac | gga | gtc | aca | ttc | cag | cag | ccc | aac | gca | gaa | ctc | ggc | tcg | tac | 1008 |
| Gln | Asn | Gly | Val | Thr | Phe | Gln | Gln | Pro | Asn | Ala | Glu | Leu | Gly | Ser | Tyr | |
| | 305 | | | | | 310 | | | | | 315 | | | | | |

| tcg | gga | aac | gag | ctc | aac | gat | gat | tac | tgt | aca | gcg | gaa | gag | gca | gaa | 1056 |
| Ser | Gly | Asn | Glu | Leu | Asn | Asp | Asp | Tyr | Cys | Thr | Ala | Glu | Glu | Ala | Glu | |
| 320 | | | | | 325 | | | | | 330 | | | | | 335 | |

| ttc | gga | gga | tcg | tcg | ttc | tcc | gac | aag | ggt | ggt | ttg | acc | cag | ttc | aag | 1104 |
| Phe | Gly | Gly | Ser | Ser | Phe | Ser | Asp | Lys | Gly | Gly | Leu | Thr | Gln | Phe | Lys | |
| | | | | 340 | | | | | 345 | | | | | 350 | | |

| aag | gcc | aca | tcg | gga | gga | atg | gtg | ttg | gtc | atg | tcc | ttg | tgg | gac | gac | 1152 |
| Lys | Ala | Thr | Ser | Gly | Gly | Met | Val | Leu | Val | Met | Ser | Leu | Trp | Asp | Asp | |
| | | | 355 | | | | | 360 | | | | | 365 | | | |

| tac | tat | gcc | aac | atg | ctc | tgg | ctc | gac | tcc | acc | tac | ccc | acc | aac | gag | 1200 |
| Tyr | Tyr | Ala | Asn | Met | Leu | Trp | Leu | Asp | Ser | Thr | Tyr | Pro | Thr | Asn | Glu | |
| | | | 370 | | | | | 375 | | | | | 380 | | | |

```
acc tcc tcg aca cct ggc gca gtg agg ggc tcg tgt tcc act tcg tcg      1248
Thr Ser Ser Thr Pro Gly Ala Val Arg Gly Ser Cys Ser Thr Ser Ser
385                 390                 395 gga gtg cct gca cag gtg gag tcc cag tcg ccg aac gcc aag gtc act      1296
Gly Val Pro Ala Gln Val Glu Ser Gln Ser Pro Asn Ala Lys Val Thr
400                 405                 410                 415 ttc tcc aac att aag ttc gga ccc atc ggt tcg acc ggc aac ccc tcc      1344
Phe Ser Asn Ile Lys Phe Gly Pro Ile Gly Ser Thr Gly Asn Pro Ser
                420                 425                 430 ggt gga aac cct cct ggc gga aac cct cct ggc aca act aca aca cga      1392
Gly Gly Asn Pro Pro Gly Gly Asn Pro Pro Gly Thr Thr Thr Thr Arg
            435                 440                 445 cgg cct gcg act aca acg ggt tcg tcc cct gga ccg acc cag tcc cac      1440
Arg Pro Ala Thr Thr Thr Gly Ser Ser Pro Gly Pro Thr Gln Ser His
        450                 455                 460 tac gga cag tgt gga ggc atc ggt tat tcc ggt ccg acc gtc tgt gcg      1488
Tyr Gly Gln Cys Gly Gly Ile Gly Tyr Ser Gly Pro Thr Val Cys Ala
    465                 470                 475 tcc ggc aca acc tgt cag gtc ttg aac cct tac tat tcg cag tgt ctc      1536
Ser Gly Thr Thr Cys Gln Val Leu Asn Pro Tyr Tyr Ser Gln Cys Leu
480                 485                 490                 495 taa                                                                  1539

<210> SEQ ID NO 80
<211> LENGTH: 512
<212> TYPE: PRT
<213> ORGANISM: Trichoderma reesei

<400> SEQUENCE: 80

Met Tyr Arg Lys Leu Ala Val Ile Ser Ala Phe Leu Ala Thr Ala Arg
        -15                 -10                  -5

Ala Gln Ser Ala Cys Thr Leu Gln Ser Glu Thr His Pro Pro Leu Thr
 -1   1               5                  10                  15

Trp Gln Lys Cys Ser Ser Gly Gly Thr Cys Thr Gln Gln Thr Gly Ser
                20                  25                  30

Val Val Ile Asp Ala Asn Trp Arg Trp Thr His Ala Thr Asn Ser Ser
            35                  40                  45

Thr Asn Cys Tyr Asp Gly Asn Thr Trp Ser Ser Thr Leu Cys Pro Asp
        50                  55                  60

Asn Glu Thr Cys Ala Lys Asn Cys Cys Leu Asp Gly Ala Ala Tyr Ala
 65                  70                  75

Ser Thr Tyr Gly Val Thr Thr Ser Gly Asn Ser Leu Ser Ile Gly Phe
 80                  85                  90                  95

Val Thr Gln Ser Ala Gln Lys Asn Val Gly Ala Arg Leu Tyr Leu Met
                100                 105                 110

Ala Ser Asp Thr Thr Tyr Gln Glu Phe Thr Leu Leu Gly Asn Glu Phe
            115                 120                 125

Ser Phe Asp Val Asp Val Ser Gln Leu Pro Cys Gly Leu Asn Gly Ala
        130                 135                 140

Leu Tyr Phe Val Ser Met Asp Ala Asp Gly Gly Val Ser Lys Tyr Pro
    145                 150                 155

Thr Asn Thr Ala Gly Ala Lys Tyr Gly Thr Gly Tyr Cys Asp Ser Gln
160                 165                 170                 175

Cys Pro Arg Asp Leu Lys Phe Ile Asn Gly Gln Ala Asn Val Glu Gly
                180                 185                 190

Trp Glu Pro Ser Ser Ala Asn Thr Gly Ile Gly Gly His Gly Ser Cys
```

```
                   195                 200                 205
       Cys Ser Glu Met Asp Ile Trp Glu Ala Asn Ser Ile Ser Glu Ala Leu
               210                 215                 220

Thr Pro His Pro Cys Thr Thr Val Gly Gln Glu Ile Cys Glu Gly Asp
                   225                 230                 235

Gly Cys Gly Gly Thr Tyr Ser Asp Asn Arg Tyr Gly Gly Thr Cys Asp
       240                 245                 250                 255

Pro Asp Gly Cys Asp Trp Asn Pro Tyr Arg Leu Gly Asn Thr Ser Phe
                       260                 265                 270

Tyr Gly Pro Gly Ser Ser Phe Thr Leu Asp Thr Thr Lys Lys Leu Thr
                   275                 280                 285

Val Val Thr Gln Phe Glu Thr Ser Gly Ala Ile Asn Arg Tyr Tyr Val
                   290                 295                 300

Gln Asn Gly Val Thr Phe Gln Gln Pro Asn Ala Glu Leu Gly Ser Tyr
                   305                 310                 315

Ser Gly Asn Glu Leu Asn Asp Asp Tyr Cys Thr Ala Glu Glu Ala Glu
       320                 325                 330                 335

Phe Gly Gly Ser Ser Phe Ser Asp Lys Gly Gly Leu Thr Gln Phe Lys
                       340                 345                 350

Lys Ala Thr Ser Gly Gly Met Val Leu Val Met Ser Leu Trp Asp Asp
                   355                 360                 365

Tyr Tyr Ala Asn Met Leu Trp Leu Asp Ser Thr Tyr Pro Thr Asn Glu
                   370                 375                 380

Thr Ser Ser Thr Pro Gly Ala Val Arg Gly Ser Cys Ser Thr Ser Ser
                   385                 390                 395

Gly Val Pro Ala Gln Val Glu Ser Gln Ser Pro Asn Ala Lys Val Thr
       400                 405                 410                 415

Phe Ser Asn Ile Lys Phe Gly Pro Ile Gly Ser Thr Gly Asn Pro Ser
                       420                 425                 430

Gly Gly Asn Pro Pro Gly Gly Asn Pro Pro Gly Thr Thr Thr Thr Arg
                   435                 440                 445

Arg Pro Ala Thr Thr Thr Gly Ser Ser Pro Gly Pro Thr Gln Ser His
                   450                 455                 460

Tyr Gly Gln Cys Gly Gly Ile Gly Tyr Ser Gly Pro Thr Val Cys Ala
                   465                 470                 475

Ser Gly Thr Thr Cys Gln Val Leu Asn Pro Tyr Tyr Ser Gln Cys Leu
       480                 485                 490                 495

<210> SEQ ID NO 81
<211> LENGTH: 1539
<212> TYPE: DNA
<213> ORGANISM: Trichoderma reesei
<220> FEATURE:
<221> NAME/KEY: sig_peptide
<222> LOCATION: (1)..(17)
<220> FEATURE:
<221> NAME/KEY: CDS
<222> LOCATION: (1)..(1536)
<220> FEATURE:
<221> NAME/KEY: mat_peptide
<222> LOCATION: (52)..(1536)

<400> SEQUENCE: 81 atg tat cgt aag ctc gca gtc atc tcc gcg ttc ctc gca aca gca cga      48
Met Tyr Arg Lys Leu Ala Val Ile Ser Ala Phe Leu Ala Thr Ala Arg
        -15                 -10                  -5 gcg cag tcc gcc tgt acc ttg cag tcg gaa aca cat cct ccc ctc act      96
Ala Gln Ser Ala Cys Thr Leu Gln Ser Glu Thr His Pro Pro Leu Thr
```

```
      -1    1                   5                       10                          15
      tgg   cag   aaa   tgt   tcg   tcc   gga   gga   acg   tgt   acg   cag   cag   act   ggc   tcg         144
      Trp   Gln   Lys   Cys   Ser   Ser   Gly   Gly   Thr   Cys   Thr   Gln   Gln   Thr   Gly   Ser
                              20                        25                          30 gtg   gtc   atc   gac   gcc   aac   tgg   agg   tgg   acg   cat   gca   acc   aac   tcc   tcc         192
      Val   Val   Ile   Asp   Ala   Asn   Trp   Arg   Trp   Thr   His   Ala   Thr   Asn   Ser   Ser
                                    35                        40                        45 acc   aac   tgt   tac   gat   ggc   aac   act   tgg   tcc   tcc   acc   ttg   tgt   ccc   gat         240
      Thr   Asn   Cys   Tyr   Asp   Gly   Asn   Thr   Trp   Ser   Ser   Thr   Leu   Cys   Pro   Asp
                        50                        55                        60 aac   gaa   acc   tgt   gcc   aag   aac   tgt   tgt   ttg   gat   ggt   gca   gcc   tac   gcc         288
      Asn   Glu   Thr   Cys   Ala   Lys   Asn   Cys   Cys   Leu   Asp   Gly   Ala   Ala   Tyr   Ala
                  65                        70                        75 tcg   aca   tac   gga   gtc   act   act   tcc   ggc   aac   tcg   ctc   tcg   atc   ggc   ttc         336
      Ser   Thr   Tyr   Gly   Val   Thr   Thr   Ser   Gly   Asn   Ser   Leu   Ser   Ile   Gly   Phe
      80                        85                        90                        95 gtg   act   cag   tcc   gca   cag   aaa   aac   gtc   gga   gcg   cga   ctc   tac   ttg   atg         384
      Val   Thr   Gln   Ser   Ala   Gln   Lys   Asn   Val   Gly   Ala   Arg   Leu   Tyr   Leu   Met
                              100                       105                         110 gca   tcc   gat   aca   acc   tac   cag   gaa   ttc   act   ctc   ttg   ggc   aac   gag   ttc         432
      Ala   Ser   Asp   Thr   Thr   Tyr   Gln   Glu   Phe   Thr   Leu   Leu   Gly   Asn   Glu   Phe
                        115                       120                       125 tcc   ttc   gac   gtc   gac   gtc   tcc   cag   ctc   cct   tgt   ggc   ctc   aac   gga   gca         480
      Ser   Phe   Asp   Val   Asp   Val   Ser   Gln   Leu   Pro   Cys   Gly   Leu   Asn   Gly   Ala
                  130                       135                       140 ctc   tac   ttc   gtg   tcg   atg   gac   gcg   gat   gga   ggt   gtc   tcc   aag   tac   ccg         528
      Leu   Tyr   Phe   Val   Ser   Met   Asp   Ala   Asp   Gly   Gly   Val   Ser   Lys   Tyr   Pro
            145                       150                       155 acc   aac   aca   gca   gga   gcg   aaa   tac   ggc   acg   ggt   tac   tgt   gac   tcg   cag         576
      Thr   Asn   Thr   Ala   Gly   Ala   Lys   Tyr   Gly   Thr   Gly   Tyr   Cys   Asp   Ser   Gln
      160                       165                       170                       175 tgt   cct   cgc   gat   ctc   aag   ttc   atc   aac   ggc   cag   gca   aac   gtc   gaa   ggc         624
      Cys   Pro   Arg   Asp   Leu   Lys   Phe   Ile   Asn   Gly   Gln   Ala   Asn   Val   Glu   Gly
                              180                       185                       190 tgg   gaa   ccc   aac   aac   gcc   aac   acc   ggc   att   gga   ggc   cat   ggc   tcc   tgt         672
      Trp   Glu   Pro   Asn   Asn   Ala   Asn   Thr   Gly   Ile   Gly   Gly   His   Gly   Ser   Cys
                        195                       200                       205 tgt   tcg   gaa   atg   gat   atc   tgg   gag   gcc   aac   tcg   atc   tcc   gag   gca   ctc         720
      Cys   Ser   Glu   Met   Asp   Ile   Trp   Glu   Ala   Asn   Ser   Ile   Ser   Glu   Ala   Leu
                  210                       215                       220 aca   ccc   cac   ccc   tgt   aca   acc   gtc   ggc   cag   gag   att   tgt   gaa   gga   gac         768
      Thr   Pro   His   Pro   Cys   Thr   Thr   Val   Gly   Gln   Glu   Ile   Cys   Glu   Gly   Asp
            225                       230                       235 ggc   tgt   ggc   gga   act   tac   tcc   gat   aac   cgt   tac   ggt   ggt   acc   tgt   gat         816
      Gly   Cys   Gly   Gly   Thr   Tyr   Ser   Asp   Asn   Arg   Tyr   Gly   Gly   Thr   Cys   Asp
      240                       245                       250                       255 ccc   gat   ggc   tgt   gac   tgg   aac   ccc   tac   cgc   ctc   ggt   aac   aca   tcg   ttc         864
      Pro   Asp   Gly   Cys   Asp   Trp   Asn   Pro   Tyr   Arg   Leu   Gly   Asn   Thr   Ser   Phe
                              260                       265                       270 tac   ggt   ccg   ggt   tcc   tcc   ttc   acc   ctc   gac   act   acc   aaa   aag   ttg   acg         912
      Tyr   Gly   Pro   Gly   Ser   Ser   Phe   Thr   Leu   Asp   Thr   Thr   Lys   Lys   Leu   Thr
                        275                       280                       285 gtg   gtc   acg   cag   ttc   gag   act   tcc   gga   gcc   atc   aac   cgg   tac   tac   gtg         960
      Val   Val   Thr   Gln   Phe   Glu   Thr   Ser   Gly   Ala   Ile   Asn   Arg   Tyr   Tyr   Val
                  290                       295                       300 cag   aac   gga   gtc   aca   ttc   cag   cag   ccc   aac   gca   gaa   ctc   ggc   tcg   tac        1008
      Gln   Asn   Gly   Val   Thr   Phe   Gln   Gln   Pro   Asn   Ala   Glu   Leu   Gly   Ser   Tyr
            305                       310                       315 tcg   gga   aac   gag   ctc   aac   gat   gat   tac   tgt   aca   gcg   gaa   gag   gca   gaa        1056
```

| | | | | | | | | | | | | | |
|---|---|---|---|---|---|---|---|---|---|---|---|---|---|
|Ser|Gly|Asn|Glu|Leu|Asn|Asp|Asp|Tyr|Cys|Thr|Ala|Glu|Glu|Ala|Glu|
|320| | | | |325| | | |330| | | | |335| |

```
ttc gga gga tcg tcg ttc tcc gac aag ggt ggt ttg acc cag ttc aag      1104
Phe Gly Gly Ser Ser Phe Ser Asp Lys Gly Gly Leu Thr Gln Phe Lys
                340                 345                 350 aag gcc aca tcg gga gga atg gtg ttg gtc atg tcc ttg tgg gac gac      1152
Lys Ala Thr Ser Gly Gly Met Val Leu Val Met Ser Leu Trp Asp Asp
                355                 360                 365 tac tat gcc aac atg ctc tgg ctc gac tcc acc tac ccc acc aac gag      1200
Tyr Tyr Ala Asn Met Leu Trp Leu Asp Ser Thr Tyr Pro Thr Asn Glu
                370                 375                 380 acc tcc tcg aca cct ggc gca gtg agg ggc tcg tgt tcc act tcg tcg      1248
Thr Ser Ser Thr Pro Gly Ala Val Arg Gly Ser Cys Ser Thr Ser Ser
385                 390                 395 gga gtg cct gca cag gtg gag tcc cag tcg ccg aac gcc aag gtc act      1296
Gly Val Pro Ala Gln Val Glu Ser Gln Ser Pro Asn Ala Lys Val Thr
400                 405                 410                 415 ttc tcc aac att aag ttc gga ccc atc ggt tcg acc ggc aac ccc tcc      1344
Phe Ser Asn Ile Lys Phe Gly Pro Ile Gly Ser Thr Gly Asn Pro Ser
                420                 425                 430 ggt gga aac cct cct ggc gga aac cct cct ggc aca act aca aca cga      1392
Gly Gly Asn Pro Pro Gly Gly Asn Pro Pro Gly Thr Thr Thr Thr Arg
                435                 440                 445 cgg cct gcg act aca acg ggt tcg tcc cct gga ccg acc cag tcc cac      1440
Arg Pro Ala Thr Thr Thr Gly Ser Ser Pro Gly Pro Thr Gln Ser His
                450                 455                 460 tac gga cag tgt gga ggc atc ggt tat tcc ggt ccg acc gtc tgt gcg      1488
Tyr Gly Gln Cys Gly Gly Ile Gly Tyr Ser Gly Pro Thr Val Cys Ala
465                 470                 475 tcc ggc aca acc tgt cag gtc ttg aac cct tac tat tcg cag tgt ctc      1536
Ser Gly Thr Thr Cys Gln Val Leu Asn Pro Tyr Tyr Ser Gln Cys Leu
480                 485                 490                 495 taa                                                                  1539

<210> SEQ ID NO 82
<211> LENGTH: 512
<212> TYPE: PRT
<213> ORGANISM: Trichoderma reesei

<400> SEQUENCE: 82

Met Tyr Arg Lys Leu Ala Val Ile Ser Ala Phe Leu Ala Thr Ala Arg
        -15                 -10                  -5

Ala Gln Ser Ala Cys Thr Leu Gln Ser Glu Thr His Pro Pro Leu Thr
 -1   1               5                  10                  15

Trp Gln Lys Cys Ser Ser Gly Gly Thr Cys Thr Gln Gln Thr Gly Ser
                 20                  25                  30

Val Val Ile Asp Ala Asn Trp Arg Trp Thr His Ala Thr Asn Ser Ser
             35                  40                  45

Thr Asn Cys Tyr Asp Gly Asn Thr Trp Ser Ser Thr Leu Cys Pro Asp
         50                  55                  60

Asn Glu Thr Cys Ala Lys Asn Cys Cys Leu Asp Gly Ala Ala Tyr Ala
 65                  70                  75

Ser Thr Tyr Gly Val Thr Thr Ser Gly Asn Ser Leu Ser Ile Gly Phe
 80                  85                  90                  95

Val Thr Gln Ser Ala Gln Lys Asn Val Gly Ala Arg Leu Tyr Leu Met
                100                 105                 110

Ala Ser Asp Thr Thr Tyr Gln Glu Phe Thr Leu Leu Gly Asn Glu Phe
            115                 120                 125
```

Ser Phe Asp Val Asp Val Ser Gln Leu Pro Cys Gly Leu Asn Gly Ala
        130                 135                 140

Leu Tyr Phe Val Ser Met Asp Ala Asp Gly Gly Val Ser Lys Tyr Pro
    145                 150                 155

Thr Asn Thr Ala Gly Ala Lys Tyr Gly Thr Gly Tyr Cys Asp Ser Gln
160                 165                 170                 175

Cys Pro Arg Asp Leu Lys Phe Ile Asn Gly Gln Ala Asn Val Glu Gly
            180                 185                 190

Trp Glu Pro Asn Asn Ala Asn Thr Gly Ile Gly Gly His Gly Ser Cys
                195                 200                 205

Cys Ser Glu Met Asp Ile Trp Glu Ala Asn Ser Ile Ser Glu Ala Leu
            210                 215                 220

Thr Pro His Pro Cys Thr Thr Val Gly Gln Glu Ile Cys Glu Gly Asp
    225                 230                 235

Gly Cys Gly Gly Thr Tyr Ser Asp Asn Arg Tyr Gly Gly Thr Cys Asp
240                 245                 250                 255

Pro Asp Gly Cys Asp Trp Asn Pro Tyr Arg Leu Gly Asn Thr Ser Phe
                260                 265                 270

Tyr Gly Pro Gly Ser Ser Phe Thr Leu Asp Thr Thr Lys Lys Leu Thr
            275                 280                 285

Val Val Thr Gln Phe Glu Thr Ser Gly Ala Ile Asn Arg Tyr Tyr Val
    290                 295                 300

Gln Asn Gly Val Thr Phe Gln Gln Pro Asn Ala Glu Leu Gly Ser Tyr
305                 310                 315

Ser Gly Asn Glu Leu Asn Asp Asp Tyr Cys Thr Ala Glu Glu Ala Glu
320                 325                 330                 335

Phe Gly Gly Ser Ser Phe Ser Asp Lys Gly Gly Leu Thr Gln Phe Lys
                340                 345                 350

Lys Ala Thr Ser Gly Gly Met Val Leu Val Met Ser Leu Trp Asp Asp
            355                 360                 365

Tyr Tyr Ala Asn Met Leu Trp Leu Asp Ser Thr Tyr Pro Thr Asn Glu
    370                 375                 380

Thr Ser Ser Thr Pro Gly Ala Val Arg Gly Ser Cys Ser Thr Ser Ser
385                 390                 395

Gly Val Pro Ala Gln Val Glu Ser Gln Ser Pro Asn Ala Lys Val Thr
400                 405                 410                 415

Phe Ser Asn Ile Lys Phe Gly Pro Ile Gly Ser Thr Gly Asn Pro Ser
                420                 425                 430

Gly Gly Asn Pro Pro Gly Gly Asn Pro Pro Gly Thr Thr Thr Thr Arg
            435                 440                 445

Arg Pro Ala Thr Thr Thr Gly Ser Ser Pro Gly Pro Thr Gln Ser His
    450                 455                 460

Tyr Gly Gln Cys Gly Gly Ile Gly Tyr Ser Gly Pro Thr Val Cys Ala
465                 470                 475

Ser Gly Thr Thr Cys Gln Val Leu Asn Pro Tyr Tyr Ser Gln Cys Leu
480                 485                 490                 495

<210> SEQ ID NO 83
<211> LENGTH: 40
<212> TYPE: DNA
<213> ORGANISM: Artificial Sequence
<220> FEATURE:
<223> OTHER INFORMATION: Artificial DNA Primer

<400> SEQUENCE: 83

```
aaggctggga accctcgtcg gccaacaccg gcattggagg                              40

<210> SEQ ID NO 84
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 84
cgacgagggt tcccagcctt cgacgtttgc c                                      31

<210> SEQ ID NO 85
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 85
acgtcgaagg ctgggaaccc aacaacgcca acaccggcat tg                          42

<210> SEQ ID NO 86
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 86
gggttcccag ccttcgacgt ttgcctggcc                                        30

<210> SEQ ID NO 87
<211> LENGTH: 1599
<212> TYPE: DNA
<213> ORGANISM: Aspergillus fumigatus

<400> SEQUENCE: 87
atgctggcct ccaccttctc ctaccgcatg tacaagaccg cgctcatcct ggccgccctt       60
ctgggctctg gccaggctca gcaggtcggt acttcccagg cggaagtgca tccgtccatg      120
acctggcaga gctgcacggc tggcggcagc tgcaccacca acaacggcaa ggtggtcatc      180
gacgcgaact ggcgttgggt gcacaaagtc ggcgactaca ccaactgcta caccggcaac      240
acctgggaca cgactatctg ccctgacgat gcgacctgcg catccaactg cgcccttgag      300
ggtgccaact acgaatccac ctatggtgtg accgccagcg gcaattccct ccgcctcaac      360
ttcgtcacca ccagccagca gaagaacatt ggctcgcgtc tgtacatgat gaaggacgac      420
tcgacctacg agatgtttaa gctgctgaac caggagttca ccttcgatgt cgatgtctcc      480
aacctcccct gcggtctcaa cggtgctctg tactttgtcg ccatggacgc cgacggtggc      540
atgtccaagt acccaaccaa caaggccggt gccaagtacg gtactggata ctgtgactcg      600
cagtgccctc gcgacctcaa gttcatcaac ggtcaggcca cgttgaaggg gtggcagccc      660
tcctccaacg atgccaatgc gggtaccggc aaccacgggt cctgctgcgc ggagatggat      720
atctgggagg ccaacagcat ctccacggcc ttcacccccc atccgtgcga cacgcccggc      780
caggtgatgt gcaccggtga tgcctgcggt ggcacctaca gctccgaccg ctacggcggc      840
acctgcgacc ccgacggatg tgatttcaac tccttccgcc agggcaacaa gaccttctac      900
ggccctggca tgaccgtcga caccaagagc aagtttacgg tcgtcaccca gttcatcacc      960
```

```
gacgacggca cctccagcgg caccctcaag gagatcaagc gcttctacgt gcagaacggc   1020
aaggtgatcc ccaactcgga gtcgacctgg accggcgtca gcggcaactc catcaccacc   1080
gagtactgca ccgcccagaa aagcctgttc caggaccaga acgtcttcga aaagcacggc   1140
ggcctcgagg gcatgggtgc tgccctcgcc cagggcatgg ttctcgtcat gtccctgtgg   1200
gatgatcact cggccaacat gctctggctc gacagcaact acccgaccac tgcctcttcc   1260
accactcccg gcgtcgcccg tggtacctgc gacatctcct ccggcgtccc tgcggatgtc   1320
gaggcgaacc accccgacgc ctacgtcgtc tactccaaca tcaaggtcgg ccccatcggc   1380
tcgaccttca cagcggtgg ctcgaaccccg gtggcggaa ccaccacgac aactaccacc   1440
```

```
gacgacggca cctccagcgg caccctcaag gagatcaagc gcttctacgt gcagaacggc   1020
aaggtgatcc ccaactcgga gtcgacctgg accggcgtca gcggcaactc catcaccacc   1080
gagtactgca ccgcccagaa aagcctgttc caggaccaga acgtcttcga aaagcacggc   1140
ggcctcgagg gcatgggtgc tgccctcgcc cagggcatgg ttctcgtcat gtccctgtgg   1200
gatgatcact cggccaacat gctctggctc gacagcaact acccgaccac tgcctcttcc   1260
accactcccg gcgtcgcccg tggtacctgc gacatctcct ccggcgtccc tgcggatgtc   1320
gaggcgaacc accccgacgc ctacgtcgtc tactccaaca tcaaggtcgg ccccatcggc   1380
tcgaccttca cagcggtgg ctcgaacccc ggtggcggaa ccaccacgac aactaccacc   1440
cagcctacta ccaccacgac cacggctgga aaccctggcg gcaccggagt cgcacagcac   1500
tatggccagt gtggtggaat cggatggacc ggacccacaa cctgtgccag cccttatacc   1560
tgccagaagc tgaatgatta ttactctcag tgcctgtag                          1599
```

<210> SEQ ID NO 88
<211> LENGTH: 1599
<212> TYPE: DNA
<213> ORGANISM: Aspergillus fumigatus

<400> SEQUENCE: 88

```
atgctggcct ccaccttctc ctaccgcatg tacaagaccg cgctcatcct ggccgccctt     60
ctgggctctg gccaggctca gcaggtcggt acttcccagg cggaagtgca tccgtccatg    120
acctggcaga gctgcacggc tggcggcagc tgcaccacca caacggcaa ggtggtcatc     180 gacgcgaact ggcgttgggt gcacaaagtc ggcgactaca ccaactgcta caccggcaac    240
acctgggaca cgactatctg ccctgacgat gcgacctgcg catccaactg cgcccttgag    300
ggtgccaact acgaatccac ctatggtgtg accgccagcg gcaattccct ccgcctcaac    360
ttcgtcacca ccagccagca gaagaacatt ggctcgcgtc tgtacatgat gaaggacgac    420
tcgacctacg agatgtttaa gctgctgaac caggagttca ccttcgatgt cgatgtctcc    480 aacctccccct gcggtctcaa cggtgctctg tactttgtcg ccatggacgc cgacggtggc    540
atgtccaagt acccaaccaa caaggccggt gccaagtacg gtactggata ctgtgactcg    600
cagtgccctc gcgacctcaa gttcatcaac ggtcaggcca cgttgaagg gtggcagccc    660 tcctccaacg atgccaatgc gggtaccggc aaccacgggt cctgctgcgc ggagatggat    720
atctgggagg ccaacagcat ctccacggcc ttcacccccc atccgtgcga cacgcccggc    780
caggtgatgt gcaccggtga tgcctgcggt ggcacctaca gctccgaccg ctacggcggc    840
acctgcgacc ccgacggatg tgatttcaac tccttccgcc agggcaacaa gaccttctac    900
ggccctggca tgaccgtcga caccaagagc aagtttaccg tcgtcaccca gttcatcacc    960
gacgacggca cctccagcgg caccctcaag gagatcaagc gcttctacgt gcagaacggc   1020
aaggtgatcc ccaactcgga gtcgacctgg accggcgtca gcggcaactc catcaccacc   1080
gagtactgca ccgcccagaa aagcctgttc caggaccaga acgtcttcga aaagcacggc   1140
ggcctcgagg gcatgggtgc tgccctcgcc cagggcatgg ttctcgtcat gtccctgtgg   1200
gatgatcact cggccaacat gctctggctc gacagcaact acccgaccac tgcctcttcc   1260
accactcccg gcgtcgcccg tggtacctgc gacatctcct ccggcgtccc tgcggatgtc   1320
gaggcgaacc accccgacgc ctacgtcgtc tactccaaca tcaaggtcgg ccccatcggc   1380
tcgaccttca cagcggtgg ctcgaacccc ggtggcggaa ccaccacgac aactaccacc   1440
cagcctacta ccaccacgac cacggctgga aaccctggcg gcaccggagt cgcacagcac   1500
```

```
tatggccagt gtggtggaat cggatggacc ggacccacaa cctgtgccag cccttatacc    1560
tgccagaagc tgaatgatta ttactctcag tgcctgtag                            1599

<210> SEQ ID NO 89
<211> LENGTH: 1599
<212> TYPE: DNA
<213> ORGANISM: Aspergillus fumigatus

<400> SEQUENCE: 89
atgttggcct ccacgttctc ctatcgcatg tacaaaacag cgctcatctt ggcagccctc      60
ttgggctcgg acaggcaca gcaggtcgga acctcgcagg ccgaggtcca tccttccatg     120
acgtggcagt cgtgtacagc gggtggttcg tgtaccacaa caacggtaa agtcgtgatc     180 gatgcaaact ggaggtgggt gcacaaggtc ggcgactaca ccaactgtta cacaggcaac     240
acatgggata caaccatctg tcccgacgat gccacttgtg catccaactg tgcactcgag     300
ggtgccaact atgagtcgac gtacggagtg accgcctccg gaaactcgct caggctcaac     360
ttcgtcacaa cttcccagca gaagaacatc ggctcgcggt tgtatatgat gaaagacgat     420
tccacttacg agatgttcaa gctcctcaac caggaattca ctttcgatgt cgacgtctcc     480
aacctccctt gtggcttgaa cggagcgctc tacttcgtcg ccatggatgc ggatggaggc     540
atgtccaagt atcctaccaa caaagcagga gccaagtatg gtacaggtta ctgtgattcc     600
cagtgtccca gggatctcaa gttcatcaac ggtcaggcca acgtcgaggg ttggcagcct     660
tcgtcgaacg atgccaacgc aggtaccggc aaccacggtt cctgttgtgc cgaaatggac     720
atttgggaag cgaactcgat ctcgacggcg ttcactcctc acccgtgtga tacacccgga     780
caggtgatgt gtacaggcga cgcctgtggc ggaacctact cgtcggatcg atatggcggt     840
acgtgtgacc ccgacggctg tgacttcaac tccttcaggc agggcaacaa acattctat      900 ggacctggca tgacggtgga tacaaagtcg aaattcacag tcgtcactca gttcatcacc     960
gacgatggta cgtcctcggg taccttgaag gagatcaaaa ggttctatgt ccagaacgga    1020
aaggtcatcc cgaactcgga gtccacgtgg acaggagtgt cgggtaactc catcactacg    1080
gagtattgta cagcccagaa gtcgctcttc caggatcaga acgtcttcga gaaacatgga    1140
ggcttggaag gaatgggtgc cgcattggcc cagggtatgg tcctcgtcat gtccttgtgg    1200
gacgaccact cggccaacat gctctggttg gattccaact accccaccac tgcctcgtcc    1260
acgacaccgg tgtcgcacg cggaacttgt gatatctcct cgggagtgcc tgcagacgtc     1320
gaggcgaacc atcccgacgc ctacgtggtc tactcgaaca ttaaggtggg acccatcggt    1380
tcgacattca actccggagg ctcgaaccct ggaggcggaa cgaccactac tacaacgact    1440
cagccgacaa caacaactac cacagcaggc aaccctggag gtacaggtgt ggcccagcac    1500
tacggacagt gtggcggtat cggatggaca ggacctacta cttgtgcatc gccttatacc    1560
tgtcagaaat tgaacgacta ctactcgcag tgtttgtaa                            1599

<210> SEQ ID NO 90
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 90
cccttgtcga tgcgatgtat c                                                21
```

```
<210> SEQ ID NO 91
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 91
atcctcaatt ccgtcggtcg a                                        21

<210> SEQ ID NO 92
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 92
gtgatacacc cggacaggtg atgtg                                    25

<210> SEQ ID NO 93
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 93
ccatatcgat ccgacgagta ggttc                                    25

<210> SEQ ID NO 94
<211> LENGTH: 1590
<212> TYPE: DNA
<213> ORGANISM: Aspergillus fumigatus
<220> FEATURE:
<221> NAME/KEY: sig_peptide
<222> LOCATION: (1)..(26)
<220> FEATURE:
<221> NAME/KEY: CDS
<222> LOCATION: (1)..(1587)
<220> FEATURE:
<221> NAME/KEY: mat_peptide
<222> LOCATION: (79)..(1587)

<400> SEQUENCE: 94
```

| | | | | | | | | | | | | | | | | |
|---|---|---|---|---|---|---|---|---|---|---|---|---|---|---|---|---|
| atg | ttg | gcc | tcc | acg | ttc | tcc | tat | cgc | atg | tac | aaa | aca | gcg | ctc | atc | 48 |
| Met | Leu | Ala | Ser | Thr | Phe | Ser | Tyr | Arg | Met | Tyr | Lys | Thr | Ala | Leu | Ile | |
| | -25 | | | | -20 | | | | | -15 | | | | | | |
| ttg | gca | gcc | ctc | ttg | ggc | tcg | gga | cag | gca | cag | cag | gtc | gga | acc | tcg | 96 |
| Leu | Ala | Ala | Leu | Leu | Gly | Ser | Gly | Gln | Ala | Gln | Gln | Val | Gly | Thr | Ser | |
| -10 | | | | | -5 | | | | -1 | 1 | | | | 5 | | |
| cag | gcc | gag | gtc | cat | cct | tcc | atg | acg | tgg | cag | tcg | tgt | aca | gcg | ggt | 144 |
| Gln | Ala | Glu | Val | His | Pro | Ser | Met | Thr | Trp | Gln | Ser | Cys | Thr | Ala | Gly | |
| | | | | 10 | | | | | 15 | | | | | 20 | | |
| ggt | tcg | tgt | acc | aca | aac | aac | ggt | aaa | gtc | gtg | atc | gat | gca | aac | tgg | 192 |
| Gly | Ser | Cys | Thr | Thr | Asn | Asn | Gly | Lys | Val | Val | Ile | Asp | Ala | Asn | Trp | |
| | | 25 | | | | | 30 | | | | | 35 | | | | |
| agg | tgg | gtg | cac | aag | gtc | ggc | gac | tac | acc | aac | tgt | tac | aca | ggc | aac | 240 |
| Arg | Trp | Val | His | Lys | Val | Gly | Asp | Tyr | Thr | Asn | Cys | Tyr | Thr | Gly | Asn | |
| | 40 | | | | | 45 | | | | | 50 | | | | | |
| aca | tgg | gat | aca | acc | atc | tgt | ccc | gac | gat | gcc | act | tgt | gca | tcc | aac | 288 |
| Thr | Trp | Asp | Thr | Thr | Ile | Cys | Pro | Asp | Asp | Ala | Thr | Cys | Ala | Ser | Asn | |
| 55 | | | | | 60 | | | | | 65 | | | | | 70 | |
| tgt | gca | ctc | gag | ggt | gcc | aac | tat | gag | tcg | acg | tac | gga | gtg | acc | gcc | 336 |
| Cys | Ala | Leu | Glu | Gly | Ala | Asn | Tyr | Glu | Ser | Thr | Tyr | Gly | Val | Thr | Ala | |

```
                    75                  80                  85
tcc gga aac tcg ctc agg ctc aac ttc gtc aca act tcc cag cag aag      384
Ser Gly Asn Ser Leu Arg Leu Asn Phe Val Thr Thr Ser Gln Gln Lys
         90                  95                 100 aac atc ggc tcg cgg ttg tat atg atg aaa gac gat tcc act tac gag      432
Asn Ile Gly Ser Arg Leu Tyr Met Met Lys Asp Asp Ser Thr Tyr Glu
            105                 110                 115 atg ttc aag ctc ctc aac cag gaa ttc act ttc gat gtc gac gtc tcc      480
Met Phe Lys Leu Leu Asn Gln Glu Phe Thr Phe Asp Val Asp Val Ser
        120                 125                 130 aac ctc cct tgt ggc ttg aac gga gcg ctc tac ttc gtc gcc atg gat      528
Asn Leu Pro Cys Gly Leu Asn Gly Ala Leu Tyr Phe Val Ala Met Asp
135                 140                 145                 150 gcg gat gga ggc atg tcc aag tat cct acc aac aaa gca gga gcc aag      576
Ala Asp Gly Gly Met Ser Lys Tyr Pro Thr Asn Lys Ala Gly Ala Lys
                    155                 160                 165 tat ggt aca ggt tac tgt gat tcc cag tgt ccc agg gat ctc aag ttc      624
Tyr Gly Thr Gly Tyr Cys Asp Ser Gln Cys Pro Arg Asp Leu Lys Phe
                170                 175                 180 atc aac ggt cag gcc aac gtc gag ggt tgg cag cct tcg gcc aac gca      672
Ile Asn Gly Gln Ala Asn Val Glu Gly Trp Gln Pro Ser Ala Asn Ala
            185                 190                 195 ggt acc ggc aac cac ggt tcc tgt tgt gcc gaa atg gac att tgg gaa      720
Gly Thr Gly Asn His Gly Ser Cys Cys Ala Glu Met Asp Ile Trp Glu
200                 205                 210 gcg aac tcg atc tcg acg gcg ttc act cct cac ccg tgt gat aca ccc      768
Ala Asn Ser Ile Ser Thr Ala Phe Thr Pro His Pro Cys Asp Thr Pro
215                 220                 225                 230 gga cag gtg atg tgt aca ggc gac gcc tgt ggc gga acc tac tcg tcg      816
Gly Gln Val Met Cys Thr Gly Asp Ala Cys Gly Gly Thr Tyr Ser Ser
                    235                 240                 245 gat cga tat ggc ggt acg tgt gac ccc gac ggc tgt gac ttc aac tcc      864
Asp Arg Tyr Gly Gly Thr Cys Asp Pro Asp Gly Cys Asp Phe Asn Ser
                250                 255                 260 ttc agg cag ggc aac aaa aca ttc tat gga cct ggc atg acg gtg gat      912
Phe Arg Gln Gly Asn Lys Thr Phe Tyr Gly Pro Gly Met Thr Val Asp
            265                 270                 275 aca aag tcg aaa ttc aca gtc gtc act cag ttc atc acc gac gat ggt      960
Thr Lys Ser Lys Phe Thr Val Val Thr Gln Phe Ile Thr Asp Asp Gly
280                 285                 290 acg tcc tcg ggt acc ttg aag gag atc aaa agg ttc tat gtc cag aac     1008
Thr Ser Ser Gly Thr Leu Lys Glu Ile Lys Arg Phe Tyr Val Gln Asn
295                 300                 305                 310 gga aag gtc atc ccg aac tcg gag tcc acg tgg aca gga gtg tcg ggt     1056
Gly Lys Val Ile Pro Asn Ser Glu Ser Thr Trp Thr Gly Val Ser Gly
                    315                 320                 325 aac tcc atc act acg gag tat tgt aca gcc cag aag tcg ctc ttc cag     1104
Asn Ser Ile Thr Thr Glu Tyr Cys Thr Ala Gln Lys Ser Leu Phe Gln
                330                 335                 340 gat cag aac gtc ttc gag aaa cat gga ggc ttg gaa gga atg ggt gcc     1152
Asp Gln Asn Val Phe Glu Lys His Gly Gly Leu Glu Gly Met Gly Ala
            345                 350                 355 gca ttg gcc cag ggt atg gtc ctc gtc atg tcc ttg tgg gac gac cac     1200
Ala Leu Ala Gln Gly Met Val Leu Val Met Ser Leu Trp Asp Asp His
        360                 365                 370 tcg gcc aac atg ctc tgg ttg gat tcc aac tac ccc acc act gcc tcg     1248
Ser Ala Asn Met Leu Trp Leu Asp Ser Asn Tyr Pro Thr Thr Ala Ser
375                 380                 385                 390 tcc acg aca ccg ggt gtc gca cgc gga act tgt gat atc tcc tcg gga     1296
```

-continued

```
Ser Thr Thr Pro Gly Val Ala Arg Gly Thr Cys Asp Ile Ser Ser Gly
            395                 400                 405 gtg cct gca gac gtc gag gcg aac cat ccc gac gcc tac gtg gtc tac    1344
Val Pro Ala Asp Val Glu Ala Asn His Pro Asp Ala Tyr Val Val Tyr
            410                 415                 420 tcg aac att aag gtg gga ccc atc ggt tcg aca ttc aac tcc gga ggc    1392
Ser Asn Ile Lys Val Gly Pro Ile Gly Ser Thr Phe Asn Ser Gly Gly
            425                 430                 435 tcg aac cct gga ggc gga acg acc act act aca acg act cag ccg aca    1440
Ser Asn Pro Gly Gly Gly Thr Thr Thr Thr Thr Thr Thr Gln Pro Thr
            440                 445                 450 aca aca act acc aca gca ggc aac cct gga ggt aca ggt gtg gcc cag    1488
Thr Thr Thr Thr Thr Ala Gly Asn Pro Gly Gly Thr Gly Val Ala Gln
455                 460                 465                 470 cac tac gga cag tgt ggc ggt atc gga tgg aca gga cct act act tgt    1536
His Tyr Gly Gln Cys Gly Gly Ile Gly Trp Thr Gly Pro Thr Thr Cys
            475                 480                 485 gca tcg cct tat acc tgt cag aaa ttg aac gac tac tac tcg cag tgt    1584
Ala Ser Pro Tyr Thr Cys Gln Lys Leu Asn Asp Tyr Tyr Ser Gln Cys
            490                 495                 500 ttg taa                                                             1590
Leu
```

<210> SEQ ID NO 95
<211> LENGTH: 529
<212> TYPE: PRT
<213> ORGANISM: Aspergillus fumigatus

<400> SEQUENCE: 95

```
Met Leu Ala Ser Thr Phe Ser Tyr Arg Met Tyr Lys Thr Ala Leu Ile
    -25                 -20                 -15

Leu Ala Ala Leu Leu Gly Ser Gly Gln Ala Gln Val Gly Thr Ser
-10                  -5             -1   1               5

Gln Ala Glu Val His Pro Ser Met Thr Trp Gln Ser Cys Thr Ala Gly
                10                  15                  20

Gly Ser Cys Thr Thr Asn Asn Gly Lys Val Val Ile Asp Ala Asn Trp
            25                  30                  35

Arg Trp Val His Lys Val Gly Asp Tyr Thr Asn Cys Tyr Thr Gly Asn
40                  45                  50

Thr Trp Asp Thr Thr Ile Cys Pro Asp Asp Ala Thr Cys Ala Ser Asn
55                  60                  65                  70

Cys Ala Leu Glu Gly Ala Asn Tyr Glu Ser Thr Tyr Gly Val Thr Ala
            75                  80                  85

Ser Gly Asn Ser Leu Arg Leu Asn Phe Val Thr Thr Ser Gln Gln Lys
            90                  95                  100

Asn Ile Gly Ser Arg Leu Tyr Met Met Lys Asp Asp Ser Thr Tyr Glu
            105                 110                 115

Met Phe Lys Leu Leu Asn Gln Glu Phe Thr Phe Asp Val Asp Val Ser
    120                 125                 130

Asn Leu Pro Cys Gly Leu Asn Gly Ala Leu Tyr Phe Val Ala Met Asp
135                 140                 145                 150

Ala Asp Gly Gly Met Ser Lys Tyr Pro Thr Asn Lys Ala Gly Ala Lys
                155                 160                 165

Tyr Gly Thr Gly Tyr Cys Asp Ser Gln Cys Pro Arg Asp Leu Lys Phe
            170                 175                 180

Ile Asn Gly Gln Ala Asn Val Glu Gly Trp Gln Pro Ser Ala Asn Ala
            185                 190                 195
```

-continued

Gly Thr Gly Asn His Gly Ser Cys Cys Ala Glu Met Asp Ile Trp Glu
200                 205                 210

Ala Asn Ser Ile Ser Thr Ala Phe Thr Pro His Pro Cys Asp Thr Pro
215                 220                 225                 230

Gly Gln Val Met Cys Thr Gly Asp Ala Cys Gly Gly Thr Tyr Ser Ser
            235                 240                 245

Asp Arg Tyr Gly Gly Thr Cys Asp Pro Asp Gly Cys Asp Phe Asn Ser
        250                 255                 260

Phe Arg Gln Gly Asn Lys Thr Phe Tyr Gly Pro Gly Met Thr Val Asp
    265                 270                 275

Thr Lys Ser Lys Phe Thr Val Val Thr Gln Phe Ile Thr Asp Asp Gly
280                 285                 290

Thr Ser Ser Gly Thr Leu Lys Glu Ile Lys Arg Phe Tyr Val Gln Asn
295                 300                 305                 310

Gly Lys Val Ile Pro Asn Ser Glu Ser Thr Trp Thr Gly Val Ser Gly
            315                 320                 325

Asn Ser Ile Thr Thr Glu Tyr Cys Thr Ala Gln Lys Ser Leu Phe Gln
                330                 335                 340

Asp Gln Asn Val Phe Glu Lys His Gly Gly Leu Glu Gly Met Gly Ala
            345                 350                 355

Ala Leu Ala Gln Gly Met Val Leu Val Met Ser Leu Trp Asp Asp His
360                 365                 370

Ser Ala Asn Met Leu Trp Leu Asp Ser Asn Tyr Pro Thr Thr Ala Ser
375                 380                 385                 390

Ser Thr Thr Pro Gly Val Ala Arg Gly Thr Cys Asp Ile Ser Ser Gly
            395                 400                 405

Val Pro Ala Asp Val Glu Ala Asn His Pro Asp Ala Tyr Val Val Tyr
            410                 415                 420

Ser Asn Ile Lys Val Gly Pro Ile Gly Ser Thr Phe Asn Ser Gly Gly
            425                 430                 435

Ser Asn Pro Gly Gly Gly Thr Thr Thr Thr Thr Thr Gln Pro Thr
            440                 445                 450

Thr Thr Thr Thr Thr Ala Gly Asn Pro Gly Gly Thr Gly Val Ala Gln
455                 460                 465                 470

His Tyr Gly Gln Cys Gly Gly Ile Gly Trp Thr Gly Pro Thr Cys
                475                 480                 485

Ala Ser Pro Tyr Thr Cys Gln Lys Leu Asn Asp Tyr Tyr Ser Gln Cys
            490                 495                 500

Leu

<210> SEQ ID NO 96
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 96
tcgagggttg gcagccttcg gccaacgcag gtaccggcaa c         41

<210> SEQ ID NO 97
<211> LENGTH: 30
<212> TYPE: DNA
<213> ORGANISM: Artificial Sequence
<220> FEATURE:
<223> OTHER INFORMATION: Artificial DNA Primer

```
<400> SEQUENCE: 97
cgaaggctgc caaccctcga cgttggcctg                              30
```